US012595494B2

(12) United States Patent
Coleman et al.

(10) Patent No.: US 12,595,494 B2
(45) Date of Patent: *Apr. 7, 2026

(54) BIOLOGICAL PRODUCTION OF MULTI-CARBON COMPOUNDS FROM METHANE

(71) Applicant: BioVerde Tech LLC, Houston, TX (US)

(72) Inventors: William J. Coleman, Redwood City, CA (US); Genevieve M. Vidanes, San Francisco, CA (US); Guillaume Cottarel, Mountain View, CA (US); Sheela Muley, Fremont, CA (US); Roy Kamimura, Daly City, CA (US); Akbar F. Javan, Chapel Hill, NC (US); Jianping Sun, Belmont, CA (US); Eli S. Groban, San Francisco, CA (US)

(73) Assignee: BioVerde Tech LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,079

(22) Filed: Oct. 11, 2023

(65) Prior Publication Data

US 2024/0368638 A1 Nov. 7, 2024

Related U.S. Application Data

(60) Continuation of application No. 17/103,516, filed on Nov. 24, 2020, now Pat. No. 11,821,019, which is a continuation of application No. 15/648,920, filed on Jul. 13, 2017, now Pat. No. 10,876,137, which is a continuation of application No. 15/192,290, filed on Jun. 24, 2016, now Pat. No. 9,745,603, which is a division of application No. 14/989,859, filed on Jan. 7, 2016, now Pat. No. 9,399,783, which is a division of application No. 14/206,835, filed on Mar. 12, 2014, now Pat. No. 9,267,158.

(60) Provisional application No. 61/782,830, filed on Mar. 14, 2013.

(51) Int. Cl.
| | |
|---|---|
| *C12P 7/16* | (2006.01) |
| *C12N 9/04* | (2006.01) |
| *C12N 9/10* | (2006.01) |
| *C12N 9/88* | (2006.01) |
| *C12N 15/52* | (2006.01) |

(52) U.S. Cl.
CPC .............. *C12P 7/16* (2013.01); *C12N 9/0006* (2013.01); *C12N 9/1022* (2013.01); *C12N 9/1025* (2013.01); *C12N 9/88* (2013.01); *C12N 15/52* (2013.01); *C12Y 101/01001* (2013.01); *C12Y 101/01004* (2013.01); *C12Y 101/01086* (2013.01); *C12Y 202/01006* (2013.01); *C12Y 203/03006* (2013.01); *C12Y 401/01072* (2013.01); *C12Y 402/01009*
(2013.01); *C12Y 402/01033* (2013.01); *C12Y 403/01019* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 4,594,324 | A | 6/1986 | Dalton et al. |
| 4,982,023 | A | 1/1991 | Han et al. |
| 6,576,449 | B2 | 6/2003 | Clark et al. |
| 6,660,507 | B2 | 12/2003 | Cheng et al. |
| 6,767,744 | B2 | 7/2004 | Koffas et al. |
| 6,818,424 | B2 | 11/2004 | Dicosimo et al. |

(Continued)

FOREIGN PATENT DOCUMENTS

| | | |
|---|---|---|
| EP | 0306466 A2 | 3/1989 |
| EP | 0418187 A1 | 3/1991 |

(Continued)

OTHER PUBLICATIONS

Nguyen, et al., "Systematic metabolic engineering of Methylomicrobium alcaliphilum 20Z for 2,3-butanediol production from methane", Metabolic Engineering 47, pp. 323-333, (2018).
Vecherskaya, et al., "Microaerobic and anaerobic metabolism of a Methylocystis parvus strain isolated from a denitrifying bioreactor", Environmental Microbiology Reports, vol. 1, Issue 5, pp. 442-449, (Oct. 8, 2009).
Ward, et al., Genomic Insights into Methanotrophy: The Complete Genome Sequence of Methylococcus Capsulates (Bath) PLoS Biol, vol. 2, Issue 10, e303 (Oct. 2004).
Anthony, C. and Williams, P., "The structure and mechanism of methnal dehydrogenase", Biochimica et Biophysica Acta 1647: 18-23, Elsevier Pub. Co., Netherlands (2003).

(Continued)

*Primary Examiner* — Manjunath N Rao
*Assistant Examiner* — Jae W Lee
(74) *Attorney, Agent, or Firm* — The Marbury Law Group, PLLC

(57) ABSTRACT

Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications. The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

20 Claims, 9 Drawing Sheets

Specification includes a Sequence Listing.

(56)                    References Cited

U.S. PATENT DOCUMENTS

| | | | |
|---|---|---|---|
| 6,969,595 | B2 | 11/2005 | Brzostowicz et al. |
| 7,026,464 | B2 | 4/2006 | Dicosimo et al. |
| 7,851,188 | B2 | 12/2010 | Donaldson et al. |
| 7,910,342 | B2 | 3/2011 | Liao et al. |
| 7,943,362 | B2 | 5/2011 | Frost |
| 7,977,084 | B2 | 7/2011 | Sun et al. |
| 7,993,889 | B1 | 8/2011 | Donaldson et al. |
| 8,017,375 | B2 | 9/2011 | Feldman et al. |
| 8,030,021 | B2 | 10/2011 | Criddle et al. |
| 8,101,808 | B2 | 1/2012 | Evanko et al. |
| 8,158,404 | B2 | 4/2012 | Lies et al. |
| 8,232,089 | B2 | 7/2012 | Urano et al. |
| 8,263,373 | B2 | 9/2012 | Herrema et al. |
| 8,268,599 | B2 | 9/2012 | Schirmer et al. |
| 8,283,143 | B2 | 10/2012 | Hu et al. |
| 8,349,587 | B2 | 1/2013 | Fischer et al. |
| 9,267,158 | B2 | 2/2016 | Coleman et al. |
| 9,399,783 | B2 | 7/2016 | Coleman et al. |
| 9,611,487 | B2 | 4/2017 | Blake et al. |
| 9,745,603 | B2 | 8/2017 | Coleman et al. |
| 10,876,137 | B2 | 12/2020 | Coleman et al. |
| 2006/0057726 | A1 | 3/2006 | Sharpe |
| 2007/0251141 | A1 | 11/2007 | Bist et al. |
| 2009/0263877 | A1 | 10/2009 | Eriksen et al. |
| 2010/0274033 | A1 | 10/2010 | Sanchez-Riera et al. |
| 2011/0301388 | A1 | 12/2011 | Donaldson et al. |
| 2012/0009640 | A1 | 1/2012 | Behrouzian et al. |
| 2013/0344553 | A1 | 12/2013 | Lee |
| 2014/0193869 | A1* | 7/2014 | Blake ............. C12Y 503/01027 |
| | | | 435/189 |
| 2014/0273128 | A1 | 9/2014 | Coleman et al. |

FOREIGN PATENT DOCUMENTS

| | | | | |
|---|---|---|---|---|
| WO | 2003015534 | A1 | 2/2003 | |
| WO | 2003016460 | A1 | 2/2003 | |
| WO | 2004104180 | A2 | 12/2004 | |
| WO | 2005062867 | A2 | 7/2005 | |
| WO | WO-2006069610 | A2 * | 7/2006 | ........... C07K 14/245 |
| WO | 2011019858 | A1 | 2/2011 | |
| WO | 200218617 | A2 | 3/2022 | |

OTHER PUBLICATIONS

Atsumi, S., et al., "Engineering the isobutanol biosynthetic pathway in *Escherichia coli* by comparison of three aldehyde reductase/ alcohol dehydrogenase genes," Appl. Microbial Biotechnol 85: 651-657, Springer-Verlag GmbH, Germany (2010).

Avalos, J.L., et al., "Compartmentalization of metabolic pathways in yeast mitochondria improves the production of branched-chain alcohols," Nature Biotechnology 31 (4): 335-341, Nature Publishing Group, England (2013).

Bastian, S., et al., "Engineered ketol-acid reductoisomerase and alcohol dehydrogenase enable anaerobic 2-methylpropan-1-ol production at theoretical yield in *Escherichia coli*," Metabolic Engineering 13:345-352, Elsevier Inc., United States (2011).

Chistoserdova, L., et al., "A genomic view of methane oxidation by aerobic bacteria and anaerobic archaea," Genome Biology 6:203. 1-208.6, BioMed Central Ltd., England (2005).

Chistoserdova, L., et al., "The Expanding World of Methyltrophic Metabolism," Ann. Rev Microbiol 63:477-499, Annual Reviews, United States (2009).

Chistoserdova, L., et al., "Modularity of methylotrophy, revisited," Environmental Microbiology 13(10):2603-2622, Society for Applied Microbiology and Blackwell, Publishing Ltd., England (2011).

Culpepper, M.A. and Rosenzweig, A.C., "Architecture and active site of particulate methane monooxygenase," Grit Rev Mol Biol 47(6):483-492, CRC Press, England (2012).

Duan, Y., et al., "De novo Biosynthesis of Biodiesel by *Escherichia coli* in Optimized Fed-Batch Cultivation," PLOS ONE 6(5): 1-7, Public Library of Science, U.S.A. (2011).

Dunfield, P.F., et al., "*Methylocella silvestris* sp. nov . . . , a novel methanotroph isolated from an acidic forest cambisol," International Journal of Systemic and Evolutionary Microbiology 53: 1231-1239, IUMS, England (2003).

Energy Policy Act of 2005, Pub. L. No. 109-58, 119 Stal. 594 (2005).

Gellissen, G., et al., "New yeast expression platforms based on methylotrophic Hansenula polymorpha and Pichia pastoris and on dimorphic Arxula adeninivorans and Yarrowia lipolytica—A comparison," FEMS Yeast Research 5: 1 079• 1 096, Elsevier Science B.V., Netherlands (2005).

Hakemian, A.S. and Rosenzweig, A.C., "The Biochemistry of Methane Oxidation," Annu Rev Biochem 76:223-241, Annual Reviews, United States (2007).

Hanson, R.S., and Hanson, T.E., "Methanotrophic Bacteria," Microbiological Reviews 60(2):439-471, American Society for Microbiology, United States (1996).

Jaeger, W.K. and Egelkraut, T.M., "Biofuel Economics in a Setting of Multiple Objectives & Unintended Consequences," Renewable and Sustainable Energy Reviews 15(9):4320-4333, Elsevier Ltd., England (2011).

Jang, Y.-S. et al., "Enhanced Butanol Production Obtained by Reinforcing the Direct Butanol•Forming Route in Clostridium acetobutylicum," mBio 3(5):e00314-12, American Society for Microbiology, United States (2012).

Kidnay, A.J. and Parris, W.R., Fundamentals of Natural Gas Processing, Faulkner, L.L., ed., Taylor and Francis Group, LLC, England (2006).

Kim, S., et al., "Cellulosic ethanol production using a yeast consortium displaying a minicellulosome and β-glucosidase," Microbial Cell Factories 12:14, BioMed Central Ltd., England (2013).

Klett, T. R. et al., "An Evaluation of the USGS World Petroleum Assessment 2000—Supporting Data," U.S. Geological Survey Open-File Report 2007-1021.

Murrell, J.C., et al., "Molecular biology and regulation of methane monooxygenase," Arch Microbiol 173:325-332, Springer-Verlag GmbH, Germany (2000).

Patras, L.E. and Tang, A., "Bioconversion of methane to methanol by Methylobacterium organophilum," Unocal Science and Technology Division, Brea, California, pp. 462-468.

Phillips, R.B., et al., "Integration of pulp and paper technology with bioethanol production," Biotechnology for Biofuels 6: 13-25, BioMed Central Ltd., England (2013).

Rudolf, A. et al., "Ethanol Production from Traditional and Emerging Raw Materials," in Yeast Biotechnology: Diversity and Applications, Satyanarayana, T., ed., pp. 489-513, Springer-Verlag GmbH, Gennany (2009).

Saka, S., and Kusdiana, D., "Biodiesel fuel from rapeseed oil as prepared in supercritical methanol," Fuel 80:225-231, Elsevier Ltd., England (2001).

Schrader, J., et al., "Methanol-based industrial biotechnology: current status and future perspectives of methylotrophic bacteria," Trends in Biotechnology 27(2): 1 07-115, Elsevier Ltd., England (2009).

Semrau, J.D., et ai., "Facultative methanotrophy: false leads, true results, and suggestions for future research," FEMS Microbial. Lett. 323:1-12, Blackwell Publishing Ltd., England (2011).

Stanley, S.H. and Dalton, 1-1., "Role of Ribulose-1,5-biphosphate Carboxylase/Oxygenase in Methylococcus capsulatus (Bath)," Journal of General Microbiology 28:2927-2935, Society for General Microbiology, England (1982).

Tinberg, C.E. and Lippard, S.J., "Dioxygen Activation in Soluble Methane Monooxygenase," Ace Chem Res 44 (4):280-288, American Chemical Society, United States (2011).

Trotsenko, Y.A. and Murrell, IC., "Metabolic Aspects of Aerobic Obligate Methanotrophy," Advances in Applied Microbiology 63: 183-229, Elsevier Inc., United States (2008).

Veazey, M.V., "GTL Tech Converts Methane to Ethylene without Fischer Tropsch," Rigzone.com., accessed at https ://www.rigzone. com/news/oil_gas/ a/ 14 9438/gtl_ tech_ converts _methane_to_ ethylene_ with o ut_fisch er_tropsch/, made available on Apr. 10, 2012,2 pages.

(56)         References Cited

OTHER PUBLICATIONS

Wright, C.K. and Wimberly, M.C., "Recent land use change in the Western Corn Belt threatens grasslands and wetlands," Proc Natl Acad Sci USA. J 10(10):4134-4139, National Academy of Sciences, United States (2012).

Yu, X. et al., "In vitro reconstitution and steady-state analysis of the fatty acid synthase from *Escherichia coli*," Proc Natl Acad Sci U.S.A. 108(46): 18643-18648, National Academy of Sciences, United States (2011).

Alayon, E.M.C., "Catalytic Conversion of Methane to Methanol Using Cu-Zeolites," Chimia 66(9):668-674, Schweizerische Chemische Gesellschaft, Switzerland (2012).

Arakawa, et al., "Catalysis Research of Relevance to Carbon Management: Progress, Challenges, and Opportunities," Chem. Rev. 101(4): 953-966, American Chemical Society, United States (2001).

Yurimoto, R, et al., "Assimilation, Dissimilation, and Detoxification of Formaldehyde, a Central Metabolic Intermediate of Methylotrophic Metabolism," The Chemical Record 5:367-375, The Japan Chemical Journal Forum and Wiley Periodicals, Inc., Japan (2005).

Yurimoto, R, et al., "Genomic organization and biochemistry of the ribulose monophosphate pathway and its application in biotechnology," App/ Microbial Biotechnol 84:407-416, Springer-Verlag, Germany (2009).

* cited by examiner

1. Fermentative pathway:

2. Fermentative pathway with NADPH:

3. Thiobutanoate pathway:

4. Ketoacid pathway:

5. Methylmalate pathway:

6. Isobutanol pathway:

SEQUENCE LISTING

```
Sequence total quantity: 175
SEQ ID NO: 1          moltype = DNA  length = 1662
FEATURE               Location/Qualifiers
source                1..1662
                      mol_type = other DNA
                      organism = Methylococcus capsulatus
SEQUENCE: 1
atgcgtgaaa cgatacctcc ccgcaccggc gccgacctgc tggtcgactc cctccaggcg  60
ctgggcgtcg aatacgtctt cggcgtgccc ggcggcgcga tactcccgat cctgaacgtg  120
ctggccgacc gcggcccgcg cttcatcgtt tgccgggacg aaaccggcgc cgccttcatg  180
gcccagtcct ggggccggat caccggccgg cccggcgtgg tgctcaccac ctccggcccc  240
ggcctcatca acgccgtctg tggcgtcgct accgccacag aggaccgcga cccgctggtc  300
gtcatcaccg gccaggtgcc gcgggccgtg caattcaagc agagccacat gaacctggat  360
tcggtcggcc tgttcgcgcc gatcaccaaa tggagcgtcg aggtcgagga accgaatact  420
gtatcggaaa tcctggtcaa cgccttccgc accgcgcaga cgccgtgcgc cggagccgtc  480
cacgtctcgg taccgaacga catgctcacc gcgccggtca ccgcgcaggc cctggcgccg  540
gccgaacccg ccgtctgggg aacggccccg gccgccgtcg tcgaacgcgc ggcgtccctg  600
ctgaacgatg ccaaagcccc ggccatcctg ctcggattgc gggccgacgc acctggagcg  660
gcggcggcgg tccggcgttt cctggagcgg catccgctgc cggtggcgat gaccttcgaa  720
gccgccggca ccctgtcccg cgatctggtc gatcagttcg tcggccgggt cggctacgtg  780
ctcaaccagc cgggcgacga ggtgctgcgc caagccgatc tggtactcac gatcggctac  840
gacccgatcg aatacgaacc ttccgcctgg atctcaccgc agtcgcaggc gatccacctg  900
gatgccctgc ccgccgccgt cgaccgggcc taccaccctg ccgccgaact ggtcggcgac  960
atcgccgcca acctggccgc gctcggccagc ctgctccgaa tcgaggatcg agccggacgc  1020
cccgccgtcg ccgcggcgcg gcggcgtctg ctggaggagc aagcccgcgg cgcagcactg  1080
accggtatgc cgatccaccc cttgcgcttc attcacgacc ttcgggccac gctggacgac  1140
gaggcgacgg tgacctgcga cgtcggcgcc cacgagatct ggatggcccg ctacttcttc  1200
tgctacgccc cgcgtcacct gctgttcagc atgggccacc agaccatggg cgtcgccctg  1260
ccctgggcca tcggcgcggc cctggcccgg cccggcaaga aagtggtttc ggtatccggc  1320
gacggctcct tcctcatgac ctgcatggaa ctggaaaccg cggtgcgcct caaactgccg  1380
atcgtgcaca tcgtctggaa agacggcggc tacaacctga tccacagcct gcagatgcgc  1440
gactatgggc gcagcttcgg cgccgagttc ggccccaccg acttcgtcaa actggcggag  1500
gccttcggcg cgatcgggta ccggatcgag tccgcggacg ggatcgtccc tgtgctgaac  1560
cgggcgctcg cggccgacgc gccggtgctg atcgaagtgc ccatcgacta cagcgacaac  1620
gtccacctgg tcgaggcgat cgacgcctcg gcgcagcact ga                     1662

SEQ ID NO: 2          moltype = AA  length = 553
FEATURE               Location/Qualifiers
source                1..553
                      mol_type = protein
                      organism = Methylococcus capsulatus
SEQUENCE: 2
```

-continued

```
MRETIPPRTG ADLLVDSLQA LGVEYVFGVP GGAILPILNV LADRGPRFIV CRDETGAAFM  60
AQSWGRITGR PGVVLTTSGP GLINAVCGVA TATEDRDPLV VITGQVPRAV QFKQSHMNLD  120
SVGLFAPITK WSVEVEEPNT VSEILVNAFR TAQTPCAGAV HVSVPNDMLT APVTAQALAP  180
AEPAVWGTAP AAVVERAASL LNDAKAPAIL LGLRASTPGA AAAVRRFLER HPLPVAMTFE  240
AAGTLSRDLV DQFVGRVGYV LNQPGDEVLR QADLVLTIGY DPIEYEPSAW ISPQSQAIHL  300
DALPAAVDRA YHPAAELVGD IAANLAALGS LLRIEDRAGR PAVAAARRRL LEEQARGAAL  360
TGMPIHPLRF IHDLRATLDD EATVTCDVGA HEIWMARYFF CYAPRHLLFS MGHQTMGVAL  420
PWAIGAALAR PGKKVVSVSG DGSFLMTCME LETAVRLKLP IVHIVWKDGG YNLIHSLQMR  480
DYGRSFGAEF GPTDFVKLAE AFGAIGYRIE SADGIVPVLN RALAADAPVL IEVPIDYSDN  540
VHLVEAIDAS AQH                                                     553

SEQ ID NO: 3         moltype = DNA   length = 1017
FEATURE              Location/Qualifiers
source               1..1017
                     mol_type = other DNA
                     organism = Methylococcus capsulatus
SEQUENCE: 3
atgcagattt actacgacaa agacgccgac ctttccatca tccagggaaa gaaggttgcc  60
atcatcggct acggctcgca gggccacgcc cacgccaaca acctcaagga ttccggagtg  120
caggtcgtgg tggggctgcg tccgggttcg gcttccgcca agaaggccga gaacgccggc  180
ctcgcggtcc cctcggtcga ggatgcggtc aaacaggcgg acgtcatcat gatcctggcg  240
ccggacgagc atcaggcccg cctctacaat gaacagatcg caagcaggcc  300
gccgccctcg ccttcgccca cggcttcaac atccacttcg agcagatcac cccgcgcgcc  360
gacctcgacg tgatcatgat cgcgcccaag ggtcccggcc atctggtacg ttccacctac  420
acccaggggc gcggcgtgcc ctcgctgatc gccgtgtacc agaatgccag cggggcgcc  480
aaggaactcg cgctgtccta tgcttcggcc aatggcggcg gtcgggcgg tatcatcgag  540
accaccttcc gcgaagagac cgaaaccgat ctgttcggcg aacaggccgt cctgtgtggc  600
ggcgccaccg cactggtgca ggcgggtttc gagacgctgg tcgaagccgg ttatgcgccc  660
gagatggcct atttcgagtg tctgcacgaa ctcaagctga tcgtcgacct gatgtacgaa  720
ggcggcatcg ccaacatgcg ttattcgatc tccaatacgg cagagtacgg cgacctgacc  780
cgtggtccgc gcatcgtcac cgagcagacc aagcaggaaa tgaagaaaat cctgcgcgag  840
atccagaccg gcgaattcgc ccgtgagttc attttggaaa accaggccgg agccgccacc  900
ctgaaagcga aacgccgtct cggccgagag catctcatcg agagcgtggg cgccaggctg  960
cgcgacatga tgccgtggat caaggccaac cgcattgtgg acacgagcaa gaactga    1017

SEQ ID NO: 4         moltype = AA   length = 338
FEATURE              Location/Qualifiers
source               1..338
                     mol_type = protein
                     organism = Methylococcus capsulatus
SEQUENCE: 4
MQIYYDKDAD LSIIQGKKVA IIGYGSQGHA HANNLKDSGV QVVVGLRPGS ASAKKAENAG  60
LAVASVEDAV KQADVIMILA PDEHQARLYN EQIAPNIKQG AALAFAHGFN IHFEQITPRA  120
DLDVIMIAPK GPGHLVRSTY TQGGGVPSLI AVYQNASGRA KELALSYASA NGGGRAGIIE  180
TTFREETETD LFGEQAVLCG GATALVQAGF ETLVEAGYAP EMAYFECLHE LKLIVDLMYE  240
GGIANMRYSI SNTAEYGDLT RGPRIVTEQT KQEMKKILRE IQTGEFAREF ILENQAGAAT  300
LKAKRRLGRE HLIESVGARL RDMMPWIKAN RIVDTSKN                          338

SEQ ID NO: 5         moltype = DNA   length = 1689
FEATURE              Location/Qualifiers
source               1..1689
                     mol_type = other DNA
                     organism = Methylococcus capsulatus
SEQUENCE: 5
atgaccgaca agcacccccg tccccattcg tcccaggtcg tcgacggcat ggagcgcgcc  60
ccgagccgcg cgatgctgca cgccgtcggc ttcgccgatg ccgacttcgc caaaccgcag  120
atcggcatcg cttccacctg ggcgatggtg acgccgtgca acatgcacat caacaagctc  180
gccgaggacg cagcacgcgg cgtcgacggc ggcggcggca aggcagtgat cttcaacacc  240
atcaccattt ccgacggcat ctcgatgggc accgaaggaa tgaaatactc cctcgtgtcg  300
cgggaagtca tcgccgactc gatcgaaacc gtggtggcct gtcagggtta tgacggcgtg  360
gtcgccatcg gcggctgcga caagaacatg cccggctgcc tgatcgccct cgccgcctc  420
aaccgtccgg cggtgttcgt ctatggcggc accatcctgc cggggctgcca cgacggcaag  480
aagctggacg tggtgtcggt gttcgaagcg gtcggcgccc gcgccaacca ccgcatcgac  540
gatgcgaac tgcacgccat cgaatccaat gccatccccg gtccgggctc ctgcggtggc  600
atgtataccg ccaacaccat ggcctccgcc atcgaggcat tagggatgag cctgccgggc  660
agttcggccc aggtggccat ttccgcgcc aaggaactgg attgcgagcg ggccggcgcg  720
caggtcctca agctcctgga cctggggctc aaaccccgcg acatcatgac caagaaggcg  780
ttcgagaacg ccatcacggt ggtgatcgcc ctgggcggct ccaccaacgc cgtgctgcac  840
ctcctggcca tggccaacgc ctgcgccgtc gacctgaagc tcgacgattt caccgccatc  900
gggcgcaaag tgccgatgct ggcggatctg aaacccagcg gcagatactc catggccgaa  960
ctggtggaaa tcgcgcggcat ccagccgctg atgaagacct tgctggacgc gggactcctg  1020
cacggcgact gcatgaccgt aaccggcaag acctggaag aaaacctggc cgacgcgccc  1080
gactacccgg ccggacaaga catgatccgg tcgctggaca accccatcaa aaaggacagc  1140
catctggtga tcctcaaggg caacctggcg cggaaggcg gatcaccggt gatcaccgtc  1200
aaggaaggac tgagcttcac cggcaccgcc cgcgtattcg actgcgagga agcggcgctc  1260
acggccatcc tcgacggcac gatcgtgaaa ggcgacgtca tcgtcatccg ctatgaaggc  1320
cccaagggcg gccccggcat gcgcgagatg ctctcgccga cctcggcggt catgggcaag  1380
ggattgggca aggaggtcgc cctcatcacc gacggccgct tttccggcgg cacccacggc  1440
ttcgtggtcg gccacatcac gccggaagcc tacaccggcg gcccctggc gatcgtccgg  1500
```

-continued

```
gacggcgata ccatcaccat cgacgccgag acccgcgaat tgagcctgca cgtcaccgac    1560
gatgaaatcg gccggcgcct ggcgcagtgg actcaaccgg cgccgcgcta caccaagggc    1620
gtgctggcca aatacgccag gttggtgagc ccggcctcgg aaggcgccgt caccgacgac    1680
ggcctctga                                                            1689

SEQ ID NO: 6                moltype = AA   length = 562
FEATURE                     Location/Qualifiers
source                      1..562
                            mol_type = protein
                            organism = Methylococcus capsulatus
SEQUENCE: 6
MTDKHPRPHS SQVVDGMERA PSRAMLHAVG FADADFAKPQ IGIASTWAMV TPCNMHINKL    60
AEDAARGVDG GGGKAVIFNT ITISDGISMG TEGMKYSLVS REVIADSIET VVACQGYDGV    120
VAIGGCDKNM PGCLIALARL NRPAVFVYGG TILPGCHDGK KLDVVSVFEA VGARANHRID    180
DAELHAIESN AIPGPGSCGG MYTANTMASA IEALGMSLPG SSAQVAISRA KELDCERAGA    240
QVLKLLDLGL KPRDIMTKKA FENAITVVIA LGGSTNAVLH LLAMANACGV DLKLDDFTRI    300
GRKVPMLADL KPSGRYSMAE LVEIGGIQPL MKTLLDAGLL HGDCMTVTGK TLEENLADGA    360
DYPAGQDMIR SLDNPIKKDS HLVILKGNLA PEGAVAKITG KEGLSFTGTA RVFDCEEAAL    420
TAILDGTIVK GDVIVIRYEG PKGGPGMREM LSPTSAVMGK GLGKEVALIT DGRFSGGTHG    480
FVVGHITPEA YTGGPLAIVR DGDTITIDAE TRELSLHVTD DEIGRRLAQW TQPAPRYTKG    540
VLAKYARLVS PASEGAVTDD GL                                             562

SEQ ID NO: 7                moltype = DNA   length = 1650
FEATURE                     Location/Qualifiers
source                      1..1650
                            mol_type = other DNA
                            organism = Methylococcus capsulatus
SEQUENCE: 7
atgggcacgg ttgagcctgg cgctatcgga caacatctgc tcgcctgcct ttaccaggcg    60
ggcgtcgggc acatcttcgg cgttcccggc gattacgtgc tgggcttcta tgatctgatg    120
gccaaaggtc ccgtccggca tatcgggacc acgcgggagg acaccgccgc cttcgccgcc    180
gacggctatg cccgctgccg gggcatgggc gcgctggcgg tgacttacgg ggtcggtgcg    240
ctcaacaccg tcaacgccgt cgccggcgcc tatgcggaat cctcgccggt ggtggtcatc    300
agcggtgcgc cggggggtgcg cgagcaaagg gaagacccgt tgatccacca ccgcttcggg    360
ccgttccggt tccagcgcga gatattcgaa cggatcacct gcgccgccgt ggtgctggac    420
gatccggtga tcgccttccg gcaggtggag cgtgcgctcg cggccgcccg tcagcactgc    480
aagccggtgt acatcgagat tcccgccgac cgggtgatgg cgccgggata tccgattcca    540
caggaaaccc cggaaacgcc ttccagcgac gattcggccc tggcggaggc ggtcgccgag    600
gccgcgaagc tcctgggccg tgcggtgtcg ccggtgatcg cttgcaggcgt cgagttgcac    660
cggcgagggc tccaggacgc cctcgtcggc ctcgtcgagc aggcgcgcct gccggtggcg    720
gcgaccttga ccggcaagtc ggtgttcgcc gagcgccatc ccgcctatct gggggtgtac    780
gagggtgcga tgagcacgga aaacgcgcgc tacatggtcg agcagtccga cctcctgctg    840
atgctcgggg tcacgctgaa cgatgtcgac acgggcatct acacgcgcct gtctcgatccg    900
cagcgcatcg tccgcgcagc ccagaacgag gtcgtgattc gccatcaccg ctatcccgc     960
gtcctgctcg cggacttcgt cacggccctg gcgcggtccg tcaaggcccg gggcgaggcg    1020
tttccgatgc cggcggggcc ggaaccgtgg gactttcccg cgccggaccg gccgatgacg    1080
atcgcccggc tggtggagcg gctcgaccgc gcgctgacct cggacatgat cgtagtgtgc    1140
gacgtcggcg actgcctgtt cgcagccacc gacctgcgcg tgcacgagcg cagcgaattc    1200
ctggcgtccg ccttctatac ctcgatgggg ttcgcggtgc ccgccgccct cggggcccag    1260
atcgcccgtc cggaccaccg ggcgctgatc ctggtcggcg acggtgcctt ccagatgacc    1320
ggaacggagc tgtcgaccca tgcccgtctc ggcctgccg ccatcgtggt ggtgctcgac    1380
aatcgcggtt acagcaccga gcgcttcatc ctcgacggag ccttcaacga catcgccgac    1440
tggcgcttcc accggctggg cgaggtgttc ggcccctac agggctacga cgcgcccgac    1500
gaagcggcgt tcgaaaacgc gctcagcgaa gcgctggtca accgaaacat gccgagcctc    1560
atcaacgtcc gtctttcccc cggcgatgcc tcgatagcca tgaagcgtct cgccgggcat    1620
ctgcagtgcc gggtcaaggg cgagggctga                                     1650

SEQ ID NO: 8                moltype = AA   length = 549
FEATURE                     Location/Qualifiers
source                      1..549
                            mol_type = protein
                            organism = Methylococcus capsulatus
SEQUENCE: 8
MGTVEPGAIG QHLLACLYQA GVGHIFGVPG DYVLGFYDLM AKGPVRHIGT TREDTAAFAA    60
DGYARCRGMG ALAVTYGVGA LNTVNAVAGA YAESSPVVVI SGAPGVREQR EDPLIHHRFG    120
PFRFQREIFE RITCAAVVLD DPVIAFRQVE RALAAARQHC KPVYIEIPAD RVMAPGYPIP    180
QETPETPSSD DSALAEAVAE AAELLGRAVS PVILAGVELH RRGLQDALVG LVEQARLPVA    240
ATLTGKSVFA ERHPAYLGVY EGAMSTENAR YMVEQSDLLL MLGVTLNDVD TGIYTARLDP    300
QRIVRAAQNE VVIRHHRYPR VLLADFVTAL ARSVKARGEA FPMPAGPEPW DFPAPDRPMT    360
IARLVERLDR ALTSDMIVVC DVGDCLFAAT DLRVHERSEF LASAFYTSMG FAVPAALGAQ    420
IARPDHRALI LVGDGAFQMT GTELSTHARL GLAPIVVVLD NRGYSTERFI LDGAFNDIAD    480
WRFHRLGEVF GPLQGYDAPD EAAFENALSE ALVNRNMPSL INVRLSPGDA SIAMKRLAGH    540
LQCRVKGEG                                                            549

SEQ ID NO: 9                moltype = DNA   length = 1083
FEATURE                     Location/Qualifiers
source                      1..1083
                            mol_type = other DNA
                            organism = Saccharomyces cerevisiae
```

-continued

```
SEQUENCE: 9
atgtcttatc ctgagaaatt tgaaggtatc gctattcaat cacacgaaga ttggaaaaac    60
ccaaagaaga caaagtatga cccaaaacca ttttacgatc atgacattga cattaagatc   120
gaagcatgtg gtgtctgcgg tagtgatatt cattgtgcag ctggtcattg gggcaatatg   180
aagatgccgc tagtcgttgg tcatgaaatc gttggtaagg ttgtcaagct agggcccaag   240
tcaaacagtg ggttgaaagt cggtcaacgt gttggtgtag gtgctcaagt cttttcatgc   300
ttggaatgtg accgttgtaa gaatgataat gaaccatact gcaccaagtt tgttaccaca   360
tacagtcagc cttatgaaga cggctatgtg tcgcagggtg gctatgcaaa ctacgtcaga   420
gttcatgaac attttgtggt gcctatccca gagaatattc catcacattt ggctgctcca   480
ctattatgtg gtggtttgac tgtgtactct ccattggttc gtaacggttg cggtccaggt   540
aaaaaagttg gtatagttgg tcttggtggt atcggcagta tgggtacatt gatttccaaa   600
gccatggggg cagagacgta tgttatttct cgttcttcga gaaaaagaga agatgcaatg   660
aagatggggcg ccgatcacta cattgctaca ttagaagaag gtgattgggg tgaaaagtac   720
tttgacacct tcgacctgat tgtagtctgt gcttcctccc ttaccgacat tgacttcaac   780
attatgccaa aggctatgaa ggttggtggt agaattgtct caatctctat accagaacaa   840
cacgaaatgt tatcgctaaa gccatatggc ttaaaggctg tctccatttc ttacagtgct   900
ttaggttcca tcaaagaatt gaaccaactc ttgaaattag tctctgaaaa agatatcaaa   960
atttgggtgg aaacattacc tgttggtgaa gccggcgtcc atgaagcctt cgaaaggatg  1020
gaaaagggtg acgttagata tagatttacc ttagtcggct acgacaaaga attttcagac  1080
tag                                                                 1083

SEQ ID NO: 10          moltype = AA   length = 360
FEATURE                Location/Qualifiers
source                 1..360
                       mol_type = protein
                       organism = Saccharomyces cerevisiae
SEQUENCE: 10
MSYPEKFEGI AIQSHEDWKN PKKTKYDPKP FYDHDIDIKI EACGVCGSDI HCAAGHWGNM    60
KMPLVVGHEI VGKVVKLGPK SNSGLKVGQR VGVGAQVFSC LECDRCKNDN EPYCTKFVTT   120
YSQPYEDGYV SQGGYANYVR VHEHPVVPIP ENIPSHLAAP LLCGGLTVYS PLVRNGCGPG   180
KKVGIVGLGG IGSMGTLISK AMGAETYVIS RSSRKREDAM KMGADHYIAT LEEGDWGEKY   240
FDTFDLIVVC ASSLTDIDFN IMPKAMKVGG RIVSISIPEQ HEMLSLKPYG LKAVSISYSA   300
LGSIKELNQL LKLVSEKDIK IWVETLPVGE AGVHEAFERM EKGDVRYRFT LVGYDKEFSD   360

SEQ ID NO: 11          moltype = DNA   length = 783
FEATURE                Location/Qualifiers
source                 1..783
                       mol_type = other DNA
                       organism = Methylococcus capsulatus
SEQUENCE: 11
atggcagcaa caaccattgg tggtgcagct gcggcggaag cgccgctgct ggacaagaag    60
tggctcacgt tcgcactggc gatttacacc gtgttctacc tgtgggtgcg gtggtacgaa   120
ggtgtctatg gctggtccgc cggactggac tcgttcgcgc cggagttcga gacctactgg   180
atgaatttcc tgtacaccga gatcgtcctg gagatcgtga cggcttcgat cctgtggggc   240
tatctctgga gacccgcga ccgcaacctg gccgcgctga ccccgcgtga agagctgcgc   300
cgcaacttca cccacctggt gtggctggtg gcctacgcct gggccatcta ctggggcgca   360
tcctacttca ccgagcagga cggcacctgg catcagacga tcgtgcgga caccgacttc   420
acgccgtcgc acatcatcga gttctatctg agctacccga tctacatcat caccggtttt   480
gcggcgttca tctacgccaa gacgcgtctg ccgttcttcg cgaagggcat ctcgctgccg   540
tacctggtgc tggtggtggg tccgttcatg attctgccga acgtgggtct gaacgaatgg   600
ggccacacct tctggttcat ggaagagctg ttcgtgccgc tgcactacgg cttcgtg      660
atcttcggct ggctggcact ggccgtcatg ggcaccctga cccagacctt ctacagcttc   720
gctcagggcg ggctggggca gtcgctctgt gaagccgtgg acgaaggctt gatcgcgaaa   780
taa                                                                  783

SEQ ID NO: 12          moltype = AA   length = 260
FEATURE                Location/Qualifiers
source                 1..260
                       mol_type = protein
                       organism = Methylococcus capsulatus
SEQUENCE: 12
MAATTIGGAA AAEAPLLDKK WLTFALAIYT VFYLWVRWYE GVYGWSAGLD SFAPEFETYW    60
MNFLYTEIVL EIVTASILWG YLWKTRDRNL AALTPREELR RNFTHLVWLV AYAWAIYWGA   120
SYFTEQDGTW HQTIVRDTDF TPSHIIEFYL SYPIYIITGF AAFIYAKTRL PFFAKGISLP   180
YLVLVVGPFM ILPNVGLNEW GHTFWFMEEL FVAPLHYGFV IFGWLALAVM GTLTQTFYSF   240
AQGGLGQSLC EAVDEGLIAK                                                260

SEQ ID NO: 13          moltype = DNA   length = 744
FEATURE                Location/Qualifiers
source                 1..744
                       mol_type = other DNA
                       organism = Methylococcus capsulatus
SEQUENCE: 13
atgagtgctg cgcaatctgc ggttcgttcg cacgccgaag cggtccaggt atcccggacc    60
atcgactgga tggcgttgtt cgtggtgttt ttcgtgatcg tgggctcgta ccacattcat   120
gccatgctca ccatgggtga ctgggacttc tggtcggact ggaaagaccg tcgactgtgg   180
gtcacggtga ccccgatcgt actggtcacc ttccggcgg ccgtacaatc ctacctgtgg   240
gagcggtatc gtctgccctg gggagccacc gtgtgcgtcc tgggtctgct gctgggcgag   300
tggatcaacc gttatttcaa cttctggggc tggacctact tcccgatcaa cttcgtgttc   360
```

```
cctgcctcgc tggtgccggg cgccatcatc ctggacaccg tgctgatgct gtcgggcagc  420
tacctgttca ccgcgatcgt cggtgcgatg ggctggggtc tgatcttcta cccgggcaac  480
tggccgatca tcgcgccgct gcacgtgccg gtggaataca acggcatgct gatgtcgatc  540
gccgacatcc agggttacaa ctatgtgcgt acgggtacgc ctgagtacat ccgcatggta  600
gagaagggca ccctgcgtac cttcggtaag gactggcgc cggtatcggc attcttctcc  660
gcgttcatgt cgatcctgat ctacttcatg tggcacttca tcggtcgctg gttctccaac  720
gaacggttcc tgcagagcac ctga                                          744
```

SEQ ID NO: 14              moltype = AA   length = 247
FEATURE                    Location/Qualifiers
source                     1..247
                           mol_type = protein
                           organism = Methylococcus capsulatus
SEQUENCE: 14
```
MSAAQSAVRS HAEAVQVSRT IDWMALFVVF FVIVGSYHIH AMLTMGDWDF WSDWKDRRLW  60
VTVTPIVLVT FPAAVQSYLW ERYRLPWGAT VCVLGLLLGE WINRYFNFWG WTYFPINFVF  120
PASLVPGAII LDTVLMLSGS YLFTAIVGAM GWGLIFYPGN WPIIAPLHVP VEYNGMLMSI  180
ADIQGYNYVR TGTPEYIRMV EKGTLRTFGK DVAPVSAFFS AFMSILIYFM WHFIGRWFSN  240
ERFLQST                                                             247
```

SEQ ID NO: 15              moltype = DNA   length = 1245
FEATURE                    Location/Qualifiers
source                     1..1245
                           mol_type = other DNA
                           organism = Methylococcus capsulatus
SEQUENCE: 15
```
atgaaaacaa taaaggaccg gattgcaaaa tggtctgcaa tcggactgct gtccgccgtg  60
gcagcgaccg ccttctatgc gccgagcgcc agcgcccacg gtgagaaatc gcaggccgcg  120
ttcatgcgta tgcgtaccat ccactggtac gacctgagct ggtcgaaaga aaagtcaag   180
atcaacgaga ccgtggaaat caaaggcaag ttccacgtgt tcgaaggctg gccggaaacg  240
gtcgacgaac cggatgtggc gttcctgaac gtcggcatgc cgggtccggt gttcatccgc  300
aaggaatcgt acatcggcgg tcagctggtg ccgcgttccg tacgtctgga aatcggcaag  360
acctatgact tccgggttgt cctcaaagcc cgtcgtccgg gtgactggca cgttcacacc  420
atgatgaacg tccagggcgg tggaccgatc atcggtccag gcaaatggat caccgtggaa  480
ggctccatga gtgaattccg caaccccgtc accaccctga ccggtcagac ggtggacctg  540
gagaactaca cgaaggcaa cacctatttc tggcacgcct tctggttcgc catcggagtt  600
gcctggatcg gctactggtc gcgtcgaccg atcttcatcc ccgtctgct gatggtggat  660
gccggtcgtg cggatgaact ggtgtccgcc accgaccgca aggtggcgat gggcttcctg  720
gccgccacca tcctgatcgt ggtcatggcc atgtccagcg ccaacagcaa gtacccgatc  780
accatcccgc tgcaggccgg caccatgcgt ggcatgaagc cgctggaact gccggcgccg  840
acggtatcgg tgaaagtgga agacgccacc taccgggtac cgggccgcgc catgcggatg  900
aagctgacca tcaccaacca cggcaacagc ccgatccggc tgggtgagtt ctacaccgcc  960
tcggtcgtt tcctggattc cgacgtgtac aaggacacca ccggctatcc ggaagacctg  1020
ctggccgaag acggcctgag cgtcagcgac aacagcccgc tggctccggg tgagacgcgc  1080
acggtcgacg tgacggcgtc cgacgcggcg tgggaagtgt accgtctgtc cgacatcatc  1140
tacgatccgc acagccgttt cgccggtctg ctgttcttct tcgacgccac tggcaaccgc  1200
caggtcgtcc agatcgacgc accgctgatc ccgtcgttca tgtaa            1245
```

SEQ ID NO: 16              moltype = AA   length = 414
FEATURE                    Location/Qualifiers
source                     1..414
                           mol_type = protein
                           organism = Methylococcus capsulatus
SEQUENCE: 16
```
MKTIKDRIAK WSAIGLLSAV AATAFYAPSA SAHGEKSQAA FMRMRTIHWY DLSWSKEKVK  60
INETVEIKGK FHVFEGWPET VDEPDVAFLN VGMPGPVFIR KESYIGGQLV PRSVRLEIGK  120
TYDFRVVLKA RRPGDWHVHT MMNVQGGGPI IGPGKWITVE GSMSEFRNPV TTLTGQTVDL  180
ENYNEGNTYF WHAFWFAIGV AWIGYWSRRP IFIPRLLMVD AGRADELVSA TDRKVAMGFL  240
AATILIVVMA MSSANSKYPI TIPLQAGTMR GMKPLELPAP SVKVEDAT YRVPGRAMRM  300
KLTITNHGNS PIRLGEFYTA SVRFLDSDVY KDTTGYPEDL LAEDGLSVSD NSPLAPGETR  360
TVDVTASDAA WEVYRLSDII YDPDSRFAGL LFFFDATGNR QVVQIDAPLI PSFM      414
```

SEQ ID NO: 17              moltype = DNA   length = 783
FEATURE                    Location/Qualifiers
source                     1..783
                           mol_type = other DNA
                           organism = Methylococcus capsulatus
SEQUENCE: 17
```
atggcagcaa caaccattgg tggtgcagct gcggcggaag cgccgctgct ggacaagaag  60
tggctcacgt tcgcactggc gatttacacc gtgttctacc tgtgggtgcg gtggtacgaa  120
ggtgtctatg gctggtccgc cggactggac tcgttcgcgc cggagttcga gacctactgg  180
atgaatttcc tgtacaccga gatcgtcctg agatcgtga cggcttcgat cctgggggc  240
tatctctgga gacccgcga ccgcaacctg gccgcgctga ccccgcgtga agagctgcgc  300
gcaacttca cccacctggt gtggctggtg gcctacgcct ggcgccatca ctgggggcgca  360
tcctacttca ccgagcagga cggcacctgg catcagacga tcgtgcgcga caccgacttc  420
acgccgtcgc acatcatcga gttctatctg agctacccga tctacatcat caccggtttt  480
gcggcgttca tctacgccaa gacgcgtctg ccgttcttcg cgaagggcat ctcgctgccg  540
tacctggtgc tggtggtggg tccgttcatg attctgccga acgtgggtct gaacgaatgg  600
ggccacacct tctggttcat ggaagagctg ttcgtggcgc cgctgcacta cggcttcgtg  660
```

-continued

```
atcttcggct ggctggcact ggccgtcatg ggcaccctga cccagaccct ctacagcttc  720
gctcagggcg ggctggggca gtcgctctgt gaagccgtgg acgaaggctt gatcgcgaaa  780
taa                                                                 783

SEQ ID NO: 18            moltype = AA   length = 260
FEATURE                  Location/Qualifiers
source                   1..260
                         mol_type = protein
                         organism = Methylococcus capsulatus
SEQUENCE: 18
MAATTIGGAA AAEAPLLDKK WLTFALAIYT VFYLWVRWYE GVYGWSAGLD SFAPEFETYW    60
MNFLYTEIVL EIVTASILWG YLWKTRDRNL AALTPREELR RNFTHLVWLV AYAWAIYWGA   120
SYFTEQDGTW HQTIVRDTDF TPSHIIEFYL SYPIYIITGF AAFIYAKTRL PFFAKGISLP   180
YLVLVVGPFM ILPNVGLNEW GHTFWFMEEL FVAPLHYGFV IFGWLALAVM GTLTQTFYSF   240
AQGGLGQSLC EAVDEGLIAK                                               260

SEQ ID NO: 19            moltype = DNA   length = 744
FEATURE                  Location/Qualifiers
source                   1..744
                         mol_type = other DNA
                         organism = Methylococcus capsulatus
SEQUENCE: 19
atgagtgctg cgcaatctgc ggttcgttcg cacgccgaag cggtccaggt atcccggacc    60
atcgactgga tggcgttgtt cgtggtgttt ttcgtgatcg tgggctcgta ccacattcac   120
gccatgctca ccatgggtga ctgggacttc tggtcggact ggaaagaccg tcgactgtgg   180
gtcacggtga ccccgatcgt actggtcacc ttcccggcag ccgtacaatc ctacctgtgg   240
gagcggtatc gtctgccctg gggagccacc gtgtgcgtcc tgggtctgct gctgggcgag   300
tggatcaacc gttatttcaa cttctggggc tggacctact tcccgatcaa cttcgtgttc   360
cctgcctcgc tggtgccggg cgccatcatc ctggacaccg tgctgatgct gtcgggcagc   420
tacctgttca ccgcgatcgt cggtgcgatg ggctggggtc tgatcttcta cccgggcaac   480
tggccgatca tcgcgccgct gcacgtgccg gtggaataca acggcatgct gatgtcgatc   540
gccgacatcc agggttacaa ctatgtgcgt acgggtacgc ctgagtacat ccgcatggta   600
gagaagggca ccctgcgtac cttcggtaag gacgtggcgc cggtatcggc attcttctcc   660
gcgttcatgt cgatcctgat ctacttcatg tggcacttca tcggtcgctg gttctccaac   720
gaacggttcc tgcagagcac ctga                                          744

SEQ ID NO: 20            moltype = AA   length = 247
FEATURE                  Location/Qualifiers
source                   1..247
                         mol_type = protein
                         organism = Methylococcus capsulatus
SEQUENCE: 20
MSAAQSAVRS HAEAVQVSRT IDWMALFVVF FVIVGSYHIH AMLTMGDWDF WSDWKDRRLW    60
VTVTPIVLVT FPAAVQSYLW ERYRLPWGAT VCVLGLLLGE WINRYFNFWG WTYFPINFVF   120
PASLVPGAII LDTVLMLSGS YLFTAIVGAM GWGLIFYPGN WPIIAPLHVP VEYNGMLMSI   180
ADIQGYNYVR TGTPEYIRMV EKGTLRTFGK DVAPVSAFFS AFMSILIYFM WHFIGRWFSN   240
ERFLQST                                                             247

SEQ ID NO: 21            moltype = DNA   length = 1245
FEATURE                  Location/Qualifiers
source                   1..1245
                         mol_type = other DNA
                         organism = Methylococcus capsulatus
SEQUENCE: 21
atgaaaacaa taaaggaccg gattgcaaaa tggtctgcaa tcggactgct gtccgccgtg    60
gcagcgaccg ccttctatgc gccgagcgcc agcgcccacg gtgagaaatc gcaggccgcg   120
ttcatgcgta tgcgtaccat ccactggtac gacctgagct ggtcgaaaga gaaagtcaag   180
atcaacgaga ccgtggaaat caaaggcaag ttccacgtgt cgaaggctg ccggaaacg   240
gtcgacgaac cggatgtggc gttcctgaac gtcggcatgc cgggtccggt gttcatccgc   300
aaggaatcgt acatcggcgg tcagctggtg ccgcgttccg tacgtctgga aatcggcaag   360
acctatgact tccgggttgt cctcaaagcc cgtcgtccgg gtgactggca cgttcacacc   420
atgatgaacg tccagggcgg tggaccgatc atcggtcccg gcaaatggat caccgtggaa   480
ggctccatga gtgaattccg caaccccgtc accaccctga ccggtcagac ggtggacctg   540
gagaactaca acgaaggcaa cacctatttc tggcacgcct tctggttcgc catcggagtt   600
gcctggatcg gctactggtc gcgtcgaccg atcttcatcc ccgtctgct gatggtggat   660
gccggtcgtg cggacgaact ggtgtccgcc accaccgca aggtggcgat gggcttcctg   720
gccgccacca tcctgatcgt ggtcatggcc atgtccagcg ccaacagcaa gtacccgatc   780
accatcccgc tgcaggccgg caccatgcgt ggcatgaagc cgctggaact gccggcgccg   840
acggtatcgg tgaaagtgga agacgccacc taccgggtac cggccgcgc catgcggatg   900
aagctgacca tcaccaacca cggcaacagc ccgatccggc tgggtgagtt ctacaccgcc   960
tcggtgcgtt cctggattc cgacgtgtac aaggacacca ccggctatcc ggaagacctg  1020
ctggccgaag acgcctgag cgtcagcgac aacagcccgc tggctccggg tgagaccgc  1080
acggtcgacg tgacggcgtc cgacgcgcg tgggaagtgt accgtctgtc cgacatcatc  1140
tacgatccgg acagccgttt cgccggtctg ctgttcttct tcgacgccac tggcaaccgc  1200
caggtcgtcc agatcgacgc accgctgatc ccgtcgttca tgtaa                  1245

SEQ ID NO: 22            moltype = AA   length = 414
FEATURE                  Location/Qualifiers
source                   1..414
```

```
                      mol_type = protein
                      organism = Methylococcus capsulatus
SEQUENCE: 22
MKTIKDRIAK WSAIGLLSAV AATAFYAPSA SAHGEKSQAA FMRMRTIHWY DLSWSKEKVK   60
INETVEIKGK FHVFEGWPET VDEPDVAFLN VGMPGPVFIR KESYIGGQLV PRSVRLEIGK  120
TYDFRVVLKA RRPGDWHVHT MMNVQGGGPI IGPGKWITVE GSMSEFRNPV TTLTGQTVDL  180
ENYNEGNTYF WHAFWFAIGV AWIGYWSRRP IFIPRLLMVD AGRADELVSA TDRKVAMGFL  240
AATILIVVMA MSSANSKYPI TIPLQAGTMR GMKPLELPAP TVSVKVEDAT YRVPGRAMRM  300
KLTITNHGNS PIRLGEFYTA SVRFLDSDVY KDTTGYPEDL LAEDGLSVSD NSPLAPGETR  360
TVDVTASDAA WEVYRLSDII YDPDSRFAGL LFFFDATGNR QVVQIDAPLI PSFM         414

SEQ ID NO: 23         moltype = DNA   length = 1584
FEATURE               Location/Qualifiers
source                1..1584
                      mol_type = other DNA
                      organism = Methylococcus capsulatus
SEQUENCE: 23
atggcactta gcaccgcaac caaggccgcg acggacgcgc tggctgccaa tcgggcaccc   60
accagcgtga atgcacagga agtgcaccgt tggctccaga gcttcaactg ggatttcaag  120
aacaaccgga ccaagtacgc caccaagtac aagatggcga acgagaccaa ggaacagttc  180
aagctgatcg ccaaggaata tgcgcgcatg gaggcagtca aggacgaaag gcagttcggt  240
agcctgcagg atgcgctgac ccgcctcaac gccggtgttc gcgttcatcc gaagtggaac  300
gagaccatga aagtggtttc gaacttcctg gaagtgggcg aatacaacgc catcgccgct  360
accgggatgc tgtgggattc cgcccaggcg gcggaacaga agaacggcta tctggcccag  420
gtgttggatg aaatccgcca cacccaccag tgtgcctacg tcaactacta cttcgcgaag  480
aacggccagg acccggccgg tcacaacgat gctcgccgca cccgtaccat cggtccgctg  540
tggaagggca tgaagcgcgt gttttccgac ggcttcattt ccggcgacgc cgtggaatgc  600
tccctcaacc tgcagctggt gggtgaggcc tgcttcacca tccgctgat cgtcgcagtg   660
accgaatggg ctgccgccaa cggcgatgaa atcaccccga cggtgttcct gtcgatcgag  720
accgacgaac tgcgccacat ggccaacggt taccagaccg tcgtttccat cgccaacgat  780
ccggcttccg ccaagtatct caacacggac ctgaacaacg ccttctggac ccagcagaag  840
tacttcacgc cggtgttggg catgctgttc gagtatggct ccaagttcaa ggtcgagccg  900
tgggtcaaga cgtggaaccg ctgggtgtac gaggactggg gcggcatctg gatcggccgt  960
ctgggcaagt acggggtgga gtcgccgcgc agcctcaagg acgccaagca ggacgcttac 1020
tgggctcacc acgacctgta tctgctggct tatgcgctgt ggccgaccgg cttcttccgt 1080
ctggcgctgc cggatcagga agaaatggag tggttcgagg ccaactaccc cggctggtac 1140
gaccactacg gcaagatcta cgaggaatgg cgcgcccgcg gttgcgagga tccgtcctcg 1200
ggcttcatcc cgctgatgtg gttcatcgaa aacaaccatc ccatctacat cgatcgcgtg 1260
tcgcaagtgc cgttctgccc gagcttggcc aagggcgcca gcacctcgc gcgtcgacgag 1320
tacaacggcc agatgcacac cttcagcgac cagtggggcg agcgcatgtg gctggccgag 1380
ccggagcgct acgagtgcca gaacatcttc gaacagtacg aaggacgcga actgtcggaa 1440
gtgatcgccg aactgcacgg gctgcgcagt gatggcaaga ccctgatcgc ccagccgcat 1500
gtccgtggcg acaagctgtg gacgttggac gatatcaaac gcctgaactg cgtcttcaag 1560
aacccggtga aggcattcaa ttga                                        1584

SEQ ID NO: 24         moltype = AA   length = 527
FEATURE               Location/Qualifiers
source                1..527
                      mol_type = protein
                      organism = Methylococcus capsulatus
SEQUENCE: 24
MALSTATKAA TDALAANRAP TSVNAQEVHR WLQSFNWDFK NNRTKYATKY KMANETKEQF   60
KLIAKEYARM EAVKDERQFG SLQDALTRLN AGVRVHPKWN ETMKVVSNFL EVGEYNAIAA  120
TGMLWDSAQA AEQKNGYLAQ VLDEIRHTHQ CAYVNYYFAK NGQDPAGHND ARRTRTIGPL  180
WKGMKRVFSD GFISGDAVEC SLNLQLVGEA CFTNPLIVAV TEWAAANGDE ITPTVFLSIE  240
TDELRHMANG YQTVVSIAND PASAKYLNTD LNNAFWTQQK YFTPVLGMLF EYGSKFKVEP  300
WVKTWNRWVY EDWGGIWIGR LGKYGVESPR SLKDAKQDAY WAHHDLYLLA YALWPTGFFR  360
LALPDQEEME WFEANYPGWY DHYGKIYEEW RARGCEDPSS GFIPLMWFIE NNHPIYIDRV  420
SQVPFCPSLA KGASTLRVHE YNGQMHTFSD QWGERMWLAE PERYECQNIF EQYEGRELSE  480
VIAELHGLRS DGKTLIAQPH VRGDKLWTLD DIKRLNCVFK NPVKAFN               527

SEQ ID NO: 25         moltype = DNA   length = 1170
FEATURE               Location/Qualifiers
source                1..1170
                      mol_type = other DNA
                      organism = Methylococcus capsulatus
SEQUENCE: 25
atgagcatgt taggagaaag acgccgcggt ctgaccgatc cggaaatggc ggccgtcatt   60
ttgaaggcgc ttcctgaagc tccgctggac ggcaacaaca agatgggtta tttcgtcacc  120
ccccgctgga aacgcttgac ggaatatgaa gccctgaccg tttatgcgca gcccaacgcc  180
gactggatcg ccggcggcct ggactggggc gactggaccc agaaattcca cggcggccgc  240
ccttcctggg gcaacgagac cacggagctg cgcaccgtcg actggttcaa gcaccgtgac  300
ccgctccgcc gttggcatgc gccgtacgtc aaggacaagg ccgaggaatg cgcgctacacc  360
gaccgttcc tgcagggtta ctccgccgac ggtcagatcc cggcgatgaa cccgacctgg  420
cgggacgagt tcatcaaccg gtattgggc gccttcctgt tcaacgaata cggattgttc  480
aacgctcatt cgcagggcgc ccgggaggcg ctgtcggacg taaccgcgt cagcctggct  540
ttctggggct cgacaagat cgacatcgcc cagatgatcc aactcgaacg gggtttcctc  600
gccaagatcg tacccggttt cgacgagtcc acagcggtgc cgaaggccga atggacgaac  660
ggggaggtct acaagagcgc ccgtctggcc gtggaagggc tgtggcagga ggtgttcgac  720
```

```
tggaacgaga gcgctttctc ggtgcacgcc gtctatgacg cgctgttcgg tcagttcgtc    780
cgccgcgagt tctttcagcg gctggctccc cgcttcggcg acaatctgac gccattcttc    840
atcaaccagg cccagacata cttccagatc gccaagcagg gcgtacagga tctgtattac    900
aactgtctgg gtgacgatcc ggagttcagc gattacaacc gtaccgtgat gcgcaactgg    960
accggcaagt ggctggagcc cacgatcgcc gctctgcgca acttcatggg gctgtttgcg   1020
aagctgccgg cgggcaccac tgacaaggaa gaaatcaccg cgtccctgta ccgggtggtc   1080
gacgactgga tcgaggacta cgccagcagg atcgacttca aggcggaccg cgatcagatc   1140
gttaaagcgg ttctggcagg attgaaataa                                    1170
```

```
SEQ ID NO: 26              moltype = AA   length = 389
FEATURE                    Location/Qualifiers
source                     1..389
                           mol_type = protein
                           organism = Methylococcus capsulatus
SEQUENCE: 26
MSMLGERRRG LTDPEMAAVI LKALPEAPLD GNNKMGYFVT PRWKRLTEYE ALTVYAQPNA    60
DWIAGGLDWG DWTQKFHGGR PSWGNETTEL RTVDWFKHRD PLRRWHAPYV KDKAEEWRYT   120
DRFLQGYSAD GQIRAMNPTW RDEFINRYWG AFLFNEYGLF NAHSQGAREA LSDVTRVSLA   180
FWGFDKIDIA QMIQLERGFL AKIVPGFDES TAVPKAEWTN GEVYKSARLA VEGLWQEVFD   240
WNESAFSVHA VYDALFGQFV RREFFQRLAP RFGDNLTPFF INQAQTYFQI AKQGVQDLYY   300
NCLGDDPEFS DYNRTVMRNW TGKWLEPTIA ALRDFMGLFA KLPAGTTDKE EITASLYRVV   360
DDWIEDYASR IDFKADRDQI VKAVLAGLK                                     389
```

```
SEQ ID NO: 27              moltype = DNA   length = 426
FEATURE                    Location/Qualifiers
source                     1..426
                           mol_type = other DNA
                           organism = Methylococcus capsulatus
SEQUENCE: 27
atgagcgtaa acagcaacgc atacgacgcc ggcatcatgg gcctgaaagg caaggacttc    60
gccgatcagt tctttgccga cgaaaaccaa gtggtccatg aaagcgacac ggtcgttctg   120
gtcctcaaga agtcggacga gatcaatacc tttatcgagg agatccttct gacggactac   180
aagaagaacg tcaatccgac ggtaaacgtg aagaccgcg cgggttactg gtggatcaag    240
gccaacggca agatcgaggt cgattgcgac gagatttccg agctgttggg gcggcagttc   300
aacgtctacg acttcctcgt cgacgtttcc tccaccatcg gccgggccta taccctgggc   360
aacaagttca ccattaccag tgagctgatg ggcctggacc gcaagctcga agactatcac   420
gcttaa                                                              426
```

```
SEQ ID NO: 28              moltype = AA   length = 138
FEATURE                    Location/Qualifiers
source                     1..138
                           mol_type = protein
                           organism = Methylococcus capsulatus
SEQUENCE: 28
MSVNSNAYDA GIMGLKGKDF ADQFFADENQ VVHESDTVVL VLKKSDEINT FIEEILLTDY    60
KKNVNPTVNV EDRAGYWWIK ANGKIEVDCD EISELLGRQF NVYDFLVDVS STIGRAYTLG   120
NKFTITSELM GLDRKLED                                                 138
```

```
SEQ ID NO: 29              moltype = DNA   length = 513
FEATURE                    Location/Qualifiers
source                     1..513
                           mol_type = other DNA
                           organism = Methylococcus capsulatus
SEQUENCE: 29
atggcgaaac tgggtataca cagcaacgac acccgcgacg cctgggtgaa caagatcgcg    60
cagctcaaca ccctggaaaa agcggccgag atgctgaagc agttccggat ggaccacacc   120
acgccgttcc gcaacagcta cgaactggac aacgactacc tctggatcga ggccaagctc   180
gaagagaagg tcgccgtcct caaggcacgc gccttcaacg aggtggactt ccgtcataag   240
accgctttcg gcgaggatgc caagtccgtt ctggacggca ccgtcgcgaa gatgaacgcg   300
gccaaggaca agtgggaggc ggagaagatc catatcggtt tccgccaggc ctacaagccg   360
ccgatcatgc cggtgaacta tttcctggac ggcgagcgtc agttggggac ccggctgatg   420
gaactgcgca acctcaacta ctacgacacg ccgctggaag aactgcgcaa acagcgcggt   480
gtgcgggtgg tgcatctgca gtcgccgcac tga                               513
```

```
SEQ ID NO: 30              moltype = AA   length = 170
FEATURE                    Location/Qualifiers
source                     1..170
                           mol_type = protein
                           organism = Methylococcus capsulatus
SEQUENCE: 30
MAKLGIHSND TRDAWVNKIA QLNTLEKAAE MLKQFRMDHT TPFRNSYELD NDYLWIEAKL    60
EEKVAVLKAR AFNEVDFRHK TAFGEDAKSV LDGTVAKMNA AKDKWEAEKI HIGFRQAYKP   120
PIMPVNYFLD GERQLGTRLM ELRNLNYYDT PLEELRKQRG VRVVHLQSPH             170
```

```
SEQ ID NO: 31              moltype = DNA   length = 312
FEATURE                    Location/Qualifiers
source                     1..312
                           mol_type = other DNA
                           organism = Methylococcus capsulatus
```

```
SEQUENCE: 31
atggtcgaat cggcatttca gccattttcg ggcgacgcag acgaatggtt cgaggaacca   60
cggccccagg ccggtttctt cccttccgcg gactggcatc tgctcaaacg ggacgagacc  120
tacgcagcct atgccaagga tctcgatttc atgtggcggt gggtcatcgt ccgggaagaa  180
aggatcgtcc aggagggttg ctcgatcagc ctggagtcgt cgatccgcgc cgtgacgcac  240
gtactgaatt attttggtat gaccgaacaa cgcgccccgg cagaggaccg gaccggcgga  300
gttcaacatt ga                                                       312

SEQ ID NO: 32             moltype = AA   length = 103
FEATURE                   Location/Qualifiers
source                    1..103
                          mol_type = protein
                          organism = Methylococcus capsulatus
SEQUENCE: 32
MVESAFQPFS GDADEWFEEP RPQAGFFPSA DWHLLKRDET YAAYAKDLDF MWRWVIVREE   60
RIVQEGCSIS LESSIRAVTH VLNYFGMTEQ RAPAEDRTGG VQH                     103

SEQ ID NO: 33             moltype = DNA   length = 1047
FEATURE                   Location/Qualifiers
source                    1..1047
                          mol_type = other DNA
                          organism = Methylococcus capsulatus
SEQUENCE: 33
atgcagcgag ttcacactat cacggcggtg acggaggatg gcgaatcgct ccgcttcgaa   60
tgccgttcgg acgaggacgt catcaccgcc gccctgcgcc agaacatctt tctgatgtcg  120
tcctgcgggg agggcggctg tgcgacctgc aaggccttgt gcagcgaagg ggactacgac  180
ctcaagggct gcagcgttca ggcgctgccg ccggaagagg aggaggaagg gttggtgttg  240
ttgtgccgga cctacccgaa gaccgacctg gaaatcgaac tgccctatac ccattgccgc  300
atcagttttg gtgaggtcgg cagtttcgag gcggaggtcg tcggcctcaa ctgggtttcg  360
agcaacaccg tccagtttct tttgcagaag cggcccgacg agtgcggcaa ccgtggcgtg  420
aaattcgaac ccggtcagtt catggacctg accatccccg gcaccgatgt ctcccgctcc  480
tactcgccgg cgaaccttcc taatcccgaa ggccgcctgg agttcctgat ccgcgtgtta  540
ccggagggac ggttttcgga ctacctgcgc aatgacgcgc gtgtcggaca ggtcctctcg  600
gtcaaagggc cactgggcgt gttcggtctc aaggagcggg gcatggcgcc gcgctatttc  660
gtggccggcg gcaccgggtt ggcgcccgtg tctctgatgg tgcggcagat gcaggagtgg  720
accgcgccga acgagacccg catctatttc ggtgtgaaca ccgagccgga attgttctac  780
atcgacgagc tcaaatccct ggaacgatcg atgcgcaatc tcaccgtgaa ggcctgtgtc  840
tggcaccga gcgggactg ggaaggcgag cagggctcgc ccatcgatgc gttgcgggaa  900
gacctggagt cctccgacgc caacccggac atttatttgt gcggtccgcc gggcatgatc  960
gatgccgcct gcgagctggt acgcagccgc ggtatccccg gcgaacaggt cttcttcgaa 1020
aaattcctgc cgtccggggc ggcctga                                     1047

SEQ ID NO: 34             moltype = AA   length = 348
FEATURE                   Location/Qualifiers
source                    1..348
                          mol_type = protein
                          organism = Methylococcus capsulatus
SEQUENCE: 34
MQRVHTITAV TEDGESLRFE CRSDEDVITA ALRQNIFLMS SCREGGCATC KALCSEGDYD   60
LKGCSVQALP PEEEEGLVL LCRTYPKTDL EIELPYTHCR ISFGEVGSFE AEVVGLNWVS   120
SNTVQFLLQK RPDECGNRGV KFEPGQFMDL TIPGTDVSRS YSPANLPNPE GRLEFLIRVL  180
PEGRFSDYLR NDARVGQVLS VKGPLGVFGL KERGMAPRYF VAGGTGLAPV VSMVRQMQEW  240
TAPNETRIYF GVNTEPELFY IDELKSLERS MRNLTVKACV WHPSGDWEGE QGSPIDALRE  300
DLESSDANPD IYLCGPPGMI DAACELVRSR GIPGEQVFFE KFLPSGAA               348

SEQ ID NO: 35             moltype = DNA   length = 1806
FEATURE                   Location/Qualifiers
source                    1..1806
                          mol_type = other DNA
                          organism = Methylococcus capsulatus
SEQUENCE: 35
atgcaaattt gcaaactggc aagtggctgc ggcgggtcga tgctggcgat ggccgccgtg   60
ctagccgcgc aatccacgca cgccaattcg gagctggacc ggctgtcgaa ggacgaccgg  120
aactgggtca tgcagaccaa ggactacagc gccacccact tcagccggct gacggaaatc  180
aatagccaca acgtcaagaa cctgaaggtg gcctggaccc tgtccaccgg cacgttgcat  240
ggccacgaag gtgcgccgtt ggtggtggac ggcatcatgt acatccacac gccgttcccc  300
aacaacgtct atgcagtcga cctgaacgac acccgcaaga tgctgtggca gtacaagccc  360
aagcagaatc cggcggcccg cgcggtggct tgctgcgacg tggtcaaccg cggtctggcc  420
tacgtgccgg ccggcgagca cggtccggcg aagatcttcc tcaaccagct tgacggccac  480
atcgtcgcac tcaacgccaa gaccggcgaa gagatatgga agatggaaaa ttccgacatc  540
gccatgggct ccaccctcac cggcgcgcct ttcgtggtga aggacaaggt actggtaggt  600
tcggccgggg ccgagctggg cgtgcgtggc tacgtcacgg cctataacat caaggacggc  660
aagcaggagt ggcgggccta tgccaccggt cccgacgaag acttgttgct ggacaaggac  720
ttcaacaagg acaacccgac ttacggtcag ttcggcgtca actgggaggg t          780
gatgcctgga gatcggcgg ggcaccaat tgggctggt atgcctatga tcccaagttg   840
gacatgatct actacggttc cggcaatccg gcacctgga acgagaccat gcggcccggc   900
gacaacaaat ggaccatgac catctggggc gcgacgccg acaccggccg cgccaagttc   960
ggctaccaga gacgccgca cgacgagtgg gattacgccg tgtcaacta catgggtctg  1020
tccgaacagg aagtggacgg caagctgacg ccgctgctga cccatcccga ccgcaacggt  1080
```

```
ctggtgtata cgctgaaccg ggaaaccggc gccctggtca atgccttcaa gatcgatgac    1140
accgtcaact gggtgaaaaa ggtcgatctg aagaccggcc tgccgatccg cgatccggag    1200
tacagcaccc gcatggacca caatgccaaa ggcatctgtc cctcggccat gggctatcac    1260
aaccagggca tcgagtccta cgatccggac aagaagctgt tcttcatggg cgtgaaccac    1320
atctgcatgg actgggagcc gttcatgctg ccctaccgtg ccggccagtt ctttgtgggg    1380
gcgaccctca acatgtatcc gggacccaag gggatgctgg gtcaggtcaa ggcgatgaac    1440
gcggtcaccg gcaagatgga atgggaagtg ccggagaagt ttgcggtctg gggtggcacc    1500
ttggcgaccg ccggcgacct cgtgttctac ggtaccctcg acggcttcat caaggcccgc    1560
gacacccgta ccggcgagct gaagtggcag ttccagttgc cctccggccgt gatcggccat    1620
cccatcacct atcagcacaa cggcaagcaa tacattgcca tctactccgg cgtcggcggc    1680
tggccaggag tagggctggt attcgacctg aaggacccga ccgcaggtct gggagctgtg    1740
ggtgcgttca gggaactggc gcattacacc cagatgggtg gatcggtgtt cgtgttctcg    1800
ctttga                                                                1806
```

SEQ ID NO: 36                     moltype = AA   length = 601
FEATURE                           Location/Qualifiers
source                            1..601
                                  mol_type = protein
                                  organism = Methylococcus capsulatus
SEQUENCE: 36
```
MQICKLASGC GGSMLAMAAV LAAQSTHANS ELDRLSKDDR NWVMQTKDYS ATHFSRLTEI    60
NSHNVKNLKV AWTLSTGTLH GHEGAPLVVD GIMYIHTPFP NNVYAVDLND TRKMLWQYKP   120
KQNPAARAVA CCDVVNRGLA YVPAGEHGPA KIFLNQLDGH IVALNAKTGE EIWKMENSDI   180
AMGSTLTGAP FVVKDKVLVG SAGAELGVRG YVTAYNIKDG KQEWRAYATG PDEDLLLDKD   240
FNKDNPHYGQ FGLGLSTWEG DAWKIGGGTN WGWYAYDPKL DMIYYGSGNP APWNETMRPG   300
DNKWTMTIWG RDADTGRAKF GYQKTPHDEW DYAGVNYMGL SEQEVDGKLT PLLTHPDRNG   360
LVYTLNRETG ALVNAFKIDD TVNWVKKVDL KTGLPIRDPE YSTRMDHNAK GICPSAMGYH   420
NQGIESYDPD KKLFFMGVNH ICMDWEPFML PYRAGQFFVG ATLNMYPGPK GMLGQVKAMN   480
AVTGKMEWEV PEKFAVWGGT LATAGDLVFY GTLDGFIKAR DTRTGELKWQ FQLPSGVIGH   540
PITYQHNGKQ YIAIYSGVGG WPGVGLVFDL KDPTAGLGAV GAFRELAHYT QMGGSVFVFS   600
L                                                                    601
```

SEQ ID NO: 37                     moltype = DNA   length = 573
FEATURE                           Location/Qualifiers
source                            1..573
                                  mol_type = other DNA
                                  organism = Methylococcus capsulatus
SEQUENCE: 37
```
atgctcacca gcagtcctta ttaccggtcc ggctacgtat tcgtctaccg caaggcacg    60
ggactgagca tccaagattg gaacagcgcg gcactgaaga ccgtgaagcg gatcgcattc   120
atgccggata ccccggctga gacgatgatc cgcaccatcg gccgctacaa cgacatgttc   180
aactacatgc actctctggt cggtttcaag tcgcggcgta accagtacgt gcgctacgac   240
ccggccaagc tggtggcgga agtcgccgac ggcaacgcgg tggccgtgct gttgtggggca  300
ccggcggcgg cgcgctatgt cagagggggc gggctggcca tgaccgtcat ccccgacgac   360
aaccggcggt ccgacggcga aaagtgccc caccactatt cgacttccgt cggcgtgcgc    420
aagggcgagg aggccctgct caagcagatc gaccaggttc tggcccgctt cggcaaggaa   480
gtgaatgcgg tgctggaggc ggaaggcatt ccgctgttgc ccatggatga aaaaccggcc   540
aggacggctt cccatgatcg aaggaaaggc tag                                 573
```

SEQ ID NO: 38                     moltype = AA   length = 190
FEATURE                           Location/Qualifiers
source                            1..190
                                  mol_type = protein
                                  organism = Methylococcus capsulatus
SEQUENCE: 38
```
MLTSSPYYRS GYVFVYRKDT GLSIQDWNSA ALKTVKRIAF MPDTPAETMI RTIGRYNDMF    60
NYMHSLVGFK SRRNQYVRYD PAKLVAEVAD GNAEVAVLWG PAAARYVRGA GLAMTVIPDD   120
NRRSDGEKVP HHYSTSVGVR KGEEALLKQI DQVLARFGKE VNAVLEAEGI PLLPMDEKPA   180
RTASHDRRKG                                                           190
```

SEQ ID NO: 39                     moltype = DNA   length = 480
FEATURE                           Location/Qualifiers
source                            1..480
                                  mol_type = other DNA
                                  organism = Methylococcus capsulatus
SEQUENCE: 39
```
atgaagctga agaatgcgag gttcgacgtg gctggcatgt gtgtcgccgg gttgttggcg    60
ctgcccgcgc aggccgacat taccctgcgg catgccgtca ccggcgagac gctggagttg   120
tcctacgcca aggcggggcgg cgacacgcaa gccgtcaagc agttcctgca gaccggcaag   180
aacccttaca cggcaacaa ggaggtagtg gaacagggac atagtctgta tctgtcagcc    240
tgttccggct gccacggcca tgaggccgaa ggcaagctcg tccgggatt ggcggacgac    300
tattggacct atccccgcgc ggccaccgac gtcggtttgt tcgaaatcct gttcggcggc   360
gcgcagggca tgatggggcc gcagtacgtc aacctcaaca atgacgaaat gctcaagatc   420
atggcctgga tccgcagcct ttaccggggc gatccagcca aggccgaatg ctgaaatga    480
```

SEQ ID NO: 40                     moltype = AA   length = 159
FEATURE                           Location/Qualifiers
source                            1..159
                                  mol_type = protein

```
                            organism = Methylococcus capsulatus
SEQUENCE: 40
MKLKNARFDV AGMCVAGLLA LPAQADITLR HAVTGETLEL SYAKAGGDTQ AVKQFLQTGK   60
NPYNGNKEVV EQGHSLYLSA CSGCHGHEAE GKLGPGLADD YWTYPRAATD VGLFEILFGG  120
AQGMMGPQYV NLNNDEMLKI MAWIRSLYRG DPAKAEWLK                          159

SEQ ID NO: 41              moltype = DNA   length = 285
FEATURE                    Location/Qualifiers
source                     1..285
                           mol_type = other DNA
                           organism = Methylococcus capsulatus
SEQUENCE: 41
atgatgcaga aaacgagttt cgtcgcggcc gccatggccg tttcgttcgc ggcgggtgtc   60
caggcctatg acggtaccca ctgcaaggcg cccggaaact gctgggagcc caagcccggt  120
tatccggaca aggtcgccgg cagcaagtac gaccccaagc atgacccgaa cgagctcaac  180
aagcaggcgg agtcgatcaa ggcgatggaa gcccgcaacc agaagcgcgt ggagaactac  240
gccaagaccg gcaagttcgt ctacaaggtc gaagacatca aatga                  285

SEQ ID NO: 42              moltype = AA   length = 94
FEATURE                    Location/Qualifiers
source                     1..94
                           mol_type = protein
                           organism = Methylococcus capsulatus
SEQUENCE: 42
MMQKTSFVAA AMAVSFAAGV QAYDGTHCKA PGNCWEPKPG YPDKVAGSKY DPKHDPNELN   60
KQAESIKAME ARNQKRVENY AKTGKFVYKV EDIK                               94

SEQ ID NO: 43              moltype = DNA   length = 1020
FEATURE                    Location/Qualifiers
source                     1..1020
                           mol_type = other DNA
                           organism = Methylococcus capsulatus
SEQUENCE: 43
atgaatctag acacccccct tgccgacggc ctggaacgcg ccaaacgctt cgaacagggg   60
ctgcagcaag tcgtgctcgg gcaggagcgc ccgatccgcc tgctgaccct ggccgtgttc  120
gcccgcggtc atgcgctgct cgaaggcggc gtcggcgtcg ggaagaccac cttgctccgt  180
gcggtggcgc gcggcatcgg cggcgattac gagcggatcg agggcaccat cgacctgatg  240
ccgaacgatc tggtctatta cacctacctg gacgagcaag gtaggccggg cgtcgcgccg  300
gggcctttgc tcaagcacgg ggagcagctt tccatttttt tcttcaacga gatcaaccgc  360
gcccggcccc aggtgcattc cctcctgcta cgggtcatgg ccgagcgcag cgtgtcggct  420
ttcaaccgcg agtaccggtt tccgtacctg caggtgttcg ccgaccgcaa ccgggtggaa  480
aaggaggaga ctttcgaatt gcccgcggcg gcgcgcgacc gcttcatgct cgaaatcgcc  540
atcgagcccg cggccgatcc tgcgcatatc gaccaaatcc tgttcgaccc gcgtttctac  600
gatcccgacc ggctggtcgc gtccgcgccg gccgatacgc tctcgttccg tgaactcaac  660
ggcattgccg aagccctgca aggcggcatc cacgtcagcg cccgtctcag atcctatgtc  720
caggatctgt ggcgcgcgac ccggcggccg gaggatttcg gcatcgctct ccacgaggcg  780
gattccggcg acatgatcga ggccggttcc agtccccgcg gcatgagcta cttggtccgg  840
ctggcgcggg tgcaggcgtg gctcagtggc cgggaccggg tcgagccgga ggacgttcaa  900
tacgtgttcg ctccggcggt cggccaccgc atcttcctca agccggtcta cgaataccgc  960
cgcgccgagc tgatcccgga gctggtcggc aagctgatcc gccggatcgc ggcgccatga 1020

SEQ ID NO: 44              moltype = AA   length = 339
FEATURE                    Location/Qualifiers
source                     1..339
                           mol_type = protein
                           organism = Methylococcus capsulatus
SEQUENCE: 44
MNLDTPLADG LERAKRFEQG LQQVVLGQER PIRLLTLAVF ARGHALLEGG VGVGKTTLLR   60
AVARGIGGDY ERIEGTIDLM PNDLVYYTYL DEQGRPGVAP GPLLKHGEQL SIFFFNEINR  120
ARPQVHSLLL RVMAERSVSA FNREYRFPYL QVFADRNRVE KEETFELPAA ARDRFMLEIA  180
IEPPADPAHI DQILFDPRFY DPDRLVASAP ADTLSFRELN GIAEALQGGI HVSARLRSYV  240
QDLWRATRRP EDFGIALHEA DSGDMIEAGS SPRGMSYLVR LARVQAWLSG RDRVEPEDVQ  300
YVFAPAVGHR IFLKPVYEYR RAELIPELVG KLIRRIAAP                         339

SEQ ID NO: 45              moltype = DNA   length = 873
FEATURE                    Location/Qualifiers
source                     1..873
                           mol_type = other DNA
                           organism = Methylococcus capsulatus
SEQUENCE: 45
gtggtttggt ctctcctgcc ggtcgcggcc ttggtatcgg ttccacttca tggcgccact   60
tcgctctcgt tcgacacgcc ccgcgccttc ggctacgtca tcggtgatct catccgccac  120
gaggttcggg tcgaaaccga tgcggggcag ggaatagagc tgcgtccct gcccaaggaa  180
ggctggatca accgctggct gctgctgcgg cgggtcgaag tccgccgcga gggcaggcac  240
cggatactga cgctggaata ccagactttc tacgccccgt tggaagtgaa gaacctcacg  300
attcccggct tcgagctgca actggccggt tcgggcgaac ggttggcggt cccggactgg  360
actttcacca ccgcgccgat ccgggagctg tcggtgctgc gcgccgaagg cccgtcgatg  420
cgtccggacg ccgcaccggc gccgctgccg actctcggcc ccgccgccgc gagcgtcggt  480
tccggcctcg cagccacggg cgcgctggcc tggtgggcct atctgagcgc ctggctgccg  540
```

-continued

```
ttcgtgtcgc gcggccgtca tttcgccgag gcccgccggg tgctgcggga tctgcgcggc  600
ctgggagaca gccgggaggc attgcgcaga ggttttttcct gtctgcacca ggctttcaat  660
cggacttcgg gtgagccgct gttcatcgaa gggctggacg agttcttccg gagccatccg  720
gcctacgatc tcttgcggga cgagatccag gacttcttcc tggcctcgta tgaagtcttt  780
ttcggagagg gcgcaccggc gccgtcgttc gacctggcgc gcatggaggc gttggcccgt  840
tcgtgccagc ttgccgaaag gaggcggcca tga                                873
```

```
SEQ ID NO: 46            moltype = AA   length = 290
FEATURE                  Location/Qualifiers
source                   1..290
                         mol_type = protein
                         organism = Methylococcus capsulatus
SEQUENCE: 46
VVWSLLPVAA LVSVPLHGAT SLSFDTPRAF GYVIGDLIRH EVRVETDAGQ GIEAASLPKE   60
GWINRWLLLR RVEVRREGRH RILTLEYQTF YAPLEVKNLT IPGFELQLAG SGERLAVPDW  120
TFTTAPIREL SVLRAEGPSM RPDAAPAPLP TLGPAAASVG SGLAATGALA WWAYLSAWLP  180
FVSRGRHFAE ARRVLRDLRG LGDSREALRR GFSCLHQAFN RTSGEPLFIE GLDEFFRSHP  240
AYDLLRDEIQ DFFLASYEVF FGEGAPAPSF DLARMEALAR SCQLAERRRP             290
```

```
SEQ ID NO: 47            moltype = DNA   length = 984
FEATURE                  Location/Qualifiers
source                   1..984
                         mol_type = other DNA
                         organism = Methylococcus capsulatus
SEQUENCE: 47
atgaccgatt gggcgctgga cacgccgtac ttgctgtggg gcctgccgct ggcgctgctt   60
ccgttgtggc ggttgccgct gcgccctgcc ccgtgttcct ggcatgcatt gttgcccgcc  120
gatactgcgt cgcgggccgt cgacctgagt ctgcgcctcg ccggtgccgg cgccatcctg  180
gcgctgctgc tgggcagtgc cggtctgcat cggcgcgagt acaccgtcga acgcaccggc  240
tacggccgcc acatggtgct gctgctggac cgcagccgca gcatggatga cagcttcgca  300
gggcgtactc ccacgggcgg cgaggaatcc aagtccgccg cggcggagcg cctcctgagc  360
ggtttcgtct cgagcggacg caacgatctg gtcggggtcg ccgccttcag cacctccccg  420
ttgttcgtgc tgccgctgac cgacaacaag gctgcggtgc tggcggcggt ccacgccatg  480
aagctgccgg gtctggcgca gacgcatgtg agcaaggggc tggcgatggc gctttcgtat  540
ttcggcgacg attcgaccgc gggttcgcgt atcgtcctgc tggtgtccga cggtgccgcc  600
gaggtggacc cggacagcga gctgaagctg cgccgctggt tcaaggagaa gggcgtacgg  660
ctgtactgga tattcctgcg caccgcgggc agccacggta tcttcgaaac tccggacaac  720
ccggaggaag acaacgccca ggcgcggccc gagcgctatc tgcatctgtt tttcaacagt  780
ctgggcatcc cctaccgcgc ctacgaggcg gaagacgccg acgccctcaa gcgcgccatc  840
gccgacgtcg accgcgagga gcagcggccg ctgcgctatg ccgagcgggt gccgcggcgg  900
gatctgcaag ccttttgtta tctggcggcg gcgctggctc tggcctggct ggtcgccgcg  960
aagggcatgg aggtggcgcg atga                                          984
```

```
SEQ ID NO: 48            moltype = AA   length = 327
FEATURE                  Location/Qualifiers
source                   1..327
                         mol_type = protein
                         organism = Methylococcus capsulatus
SEQUENCE: 48
MTDWALDTPY LLWGLPLALL PLWRLPLRPA PCSWHALLPA DTASRAVDLS LRLAGAGAIL   60
ALLLGSAGLH RREYTVERTG YGAHMVLLLD RSRSMDDSFA GRTPTGGEES KSAAAERLLS  120
GFVSSGRNDL VGVAAFSTSP LFVLPLTDNK AAVLAAVHAM KLPGLAQTHV SKGLAMALSY  180
FGDDSTAGSR IVLLVSDGAA EVDPDSELKL RRWFKEKGVR LYWIFLRTAG SHGIFETPDN  240
PEEDNAQARP ERYLHLFFNS LGIPYRAYEA EDADALKRAI ADVDREEQRP LRYAERVPRR  300
DLQAFCYLAA ALALAWLVAA KGMEVAR                                       327
```

```
SEQ ID NO: 49            moltype = DNA   length = 519
FEATURE                  Location/Qualifiers
source                   1..519
                         mol_type = other DNA
                         organism = Methylococcus capsulatus
SEQUENCE: 49
atgctggcct tgtcggcgtt gctggagctc aggcaatggc ggaaggccgc ggcggccaat   60
gccgatatcg ccgagctgct ggggggggcac gacatcgccc cggaacggct ggcggcggca  120
tcgcccaag tcctgttggc gcgggccgtg tatttcgtgc ggcacgagcg ctacggcgac  180
gcgctggagc tgctgaacct gctggagacc cggggcgatg gcgccttccg cgccgacgtg  240
tattacaacc agggcaatct gcagcttgcc caggctctgg accgcgtcga aaatcggaa  300
atggaccagg cccgggtctt cgccgaactg gccaaggaag cctaccggcg tgccttgtcc  360
ctggcacccg gccactggga cgccaaatac aacctggaag cggccatgac cctcatgccc  420
gaaatggacc gggtcagccc tgccgatgac gaggcgcccg cggctgaatc caaacggctg  480
tggacaggtt tgcccggact cccgcgaggc ctgccttga                          519
```

```
SEQ ID NO: 50            moltype = AA   length = 172
FEATURE                  Location/Qualifiers
source                   1..172
                         mol_type = protein
                         organism = Methylococcus capsulatus
SEQUENCE: 50
MLALSALLEL RQWRKAAAAN ADIAELLGGH DIAPERLAAA SPQVLLARAV YFVRHERYGD   60
```

```
ALELLNLLET RGDGAFRADV YYNQGNLQLA QALDRVEKSE MDQARVFAEL AKEAYRRALS  120
LAPGHWDAKY NLEVAMRLMP EMDRVSPADD EAPAAESKRL WTGLPGLPRG LP           172

SEQ ID NO: 51             moltype = DNA   length = 972
FEATURE                   Location/Qualifiers
source                    1..972
                          mol_type = other DNA
                          organism = Methylococcus capsulatus
SEQUENCE: 51
ttgagcatct ggcggcagcg cgttgccgat ccggtttttg ccggcctgat tgtagccctc  60
cttctggcgg tagccgcctg tttcccgctc cggctggtgc tggagcggct ggtgttcagc  120
cacatcgtcg tcgtcgacat cacccgcagc atgaacgtcg aggactaccg gcgaggcgcg  180
cgcgccgtgt cgcggctgga attcgtcagg cagagcctga tcggcgccgt ggccgacctg  240
ccctgcgggct ccgctgtggg ggtgggcgtt ttcaccgaac gcgagccggc gctactgttc  300
gagccgatcg aaacctgcgc cggcttttcc gccatcagcg ccgccatcga acagctcgac  360
tggcgcatgg cctgggctgc cgacagtctg atcgccgcag gtctgcacaa caccctggat  420
ttgctggggc gcgcgatgc ggacgtgatt ttcgtcaccg acggccatga ggcgccgcca  480
ctcaatcccc gctactgccc ggacttcagc gacctcagag gcaaggtccg ggggctgatc  540
gtcggagtgg gaggactgag cctctcgccc atccccaagt acgacgagtc ggggcggcgt  600
tcgggcgttt atggcgagga cgaagtcccg cagcgctcga gcttcggcct gtcggagctg  660
ccgcccgagc agatcgaggg ctaccacgcc cgcaacgctc ccttcggcag cgagagagcc  720
ggggcacgg aacatctgtc ccagctcaag gaaggatatt tgcgccagct cgccgaagcc  780
gccggcctgg gctaccaccg cctggaatcc cccgaaggac tgggccgcgc tctcacggca  840
ccggccttgg cgcggcgcca gcggatcgcc acagacgtcc gctggattcc cgccgccctg  900
gcgctcgccg tactgatggc ggtgtatctg cgggtgctgc tgccgcgtcc tggatttca  960
acctcaaact ga                                                     972

SEQ ID NO: 52             moltype = AA   length = 323
FEATURE                   Location/Qualifiers
source                    1..323
                          mol_type = protein
                          organism = Methylococcus capsulatus
SEQUENCE: 52
LSIWRQRVAD PVFAGLIVAL LLAVAACFPL RLVLERLVFS HIVVVDITRS MNVEDYRRGA  60
RAVSRLEFVR QSLIGAVADL PCGSAVGVGV FTEREPALLF EPIETCAGFS AISAAIEQLD  120
WRMAWAADSL IAAGLHNTLD LLGRGDADVI FVTDGHEAPP LNPRYCPDFS DLRGKVRGLI  180
VGVGGLSLSP IPKYDESGRR SGVYGEDEVP QRSSFGLSEL PPEQIEGYHA RNAPFGSERA  240
GGTEHLSQLK EGYLRQLAEA AGLGYHRLES PEGLGRALTA PALARRQRIA TDVRWIPAAL  300
ALAVLMAVYL RVLLPRPGFS TSN                                          323

SEQ ID NO: 53             moltype = DNA   length = 525
FEATURE                   Location/Qualifiers
source                    1..525
                          mol_type = other DNA
                          organism = Methylococcus capsulatus
SEQUENCE: 53
atgaaaccga tgctcatcct gaccgcgttg ctgttcgcct ccgtttcgtt ggcgcacgga  60
cccaccccc aaaaggtcgt cgagaccgtg gagatcgcgg ctcccgtgga ccgggtctgg  120
aacgccgtga aggatttcgg tgccatcgcg cagtggaatc ccgctctggc caagagcgaa  180
agcaccggcg gcaacaccac cggcgagaag cgcatcctcc attttcccaa cggcgagcag  240
ctcaccgagg aactcgatgc ctacgacccg gcagcccacg aatacaccta ccggctgggc  300
aaggacaacg tcaaggcgct gccggccagt tcctactccg ccgtgctcaa ggtcaaggcc  360
accgagacgg gcagccagat cgaatggaag agtcggctct atcgcggcga taccggaaac  420
ttcccgccgg acgagctgaa cgacgaggcc gccgttgcgg cgatgcagag gttttttccgc  480
gccgggctgg acaatctcaa gaaaagtctt gggcccctcg aatga                 525

SEQ ID NO: 54             moltype = AA   length = 174
FEATURE                   Location/Qualifiers
source                    1..174
                          mol_type = protein
                          organism = Methylococcus capsulatus
SEQUENCE: 54
MKPMLILTAL LFASVSLAHG PTPQKVVETV EIAAPVDRVW NAVKDFGAIA QWNPALAKSE  60
STGGNTTGEK RILHFPNGEQ LTEELDAYDP AAHEYTYRLG KDNVKALPAS SYSAVLKVKA  120
TETGSQIEWK SRLYRGDTGN FPPDELNDEA AVAAMQRFFR AGLDNLKKSL GPLE         174

SEQ ID NO: 55             moltype = DNA   length = 1530
FEATURE                   Location/Qualifiers
source                    1..1530
                          mol_type = other DNA
                          organism = Methylococcus capsulatus
SEQUENCE: 55
atgctgcaaa aatacataga gaagattctg cgcgcccgtg tctacgacgt tgcccaggag  60
accccgctgg acccggcgcc cggcctgtcg cggcggctgg acaacacggt gctgatcaag  120
cgcgaggacc tgcagccggt gttctcgttc aagctgcgcg cgcctacaa caagatcgcc  180
tcgctcacac ccgaggcgcg cgcggccggc gtgatcgcgg cctccgccgg caaccacgcc  240
cagggcgtgg cactggcggc gcagcggctg ggcatccgcg ccgtgatcgt gatgccttgc  300
accacccgc atatcaaggt cgatgcggtg cgcaaccgag gcggtgaggt cgtactgcat  360
ggcgacgcct atgacgaagc ctacgaacat gcgctggaac tggcccgcga ccagtgcctg  420
```

```
accttcgtcc acccctacga cgatccggaa gtcatcgccg ggcaaggcac catcggcatg   480
gaaatcctgc gccagcacca ggacgccatc cacgccatct tcgtgcctgt gggcggcggc   540
ggattgatcg ccggcatcgc cgcctacgtc aagttcgtgc gcccggacat ccgcgtcatc   600
ggcgtggaac cagtggactc cgactgcctg caccgggcgc tgaaagccaa gcggcgggtg   660
atcctgaagc aggtggggcct gttcgccgac ggcgtcggca tgaagcaggt ggcgcaaggaa   720
ccgttccatc tcgcccacca gtgggtggac gaggtcgtga ccgtcgacac cgacgaaatc   780
tgcgccgcca tcaaggacat cttcgacgac acccgctcca tcgccgagcc ggcgggcgcg   840
ctgggcatcg ccgggctcaa gaaatacgtg gccgaaacag gaatcaagaa cgcgtgcctg   900
gtggcgatcg aaagcggcgc caacatcaac ttcgaccggc tgcgccacgt cgctgagcgc   960
gccgagatcg gcgaaaagcg cgaactgctg ctggcagtga cgatccccga gcggcccggc  1020
agcttcctcg aattctgccg ggtgctgggc cgccgcaaca tcaccgaatt caactaccgc  1080
ttcttcgacg aaaaggccgc ccaggtgttc gtcggcctcc cggtggcgag cggcgcgatc  1140
gaccgcgaaa gcctggtccg cgaattcgaa cgccagggtt tcggcgtgct cgacctgacc  1200
ggcaacgaac tcgccatcga acacatccgc tacatggtcg gcggccacgc gccgaaactg  1260
ctggacgaac aggtctacag cttcgaattc cccgagcgac ccggcgcgct gctgcgcttc  1320
ctgtccatca tgggcgggcg ctggaacatc agcctgttcc attaccgcaa ccacggcgcc  1380
gccttcggcc gggtactgat gggcatccag gtgccgaaac cggaacgcaa ggccttccgg  1440
gaattcctcg aagccatcgg ctacgccttc aaggaggaaa cccaaaatcc cgcctaccgg  1500
ctgttcgcgg gggcagcgcga gcgggggtga                                    1530
```

```
SEQ ID NO: 56           moltype = AA  length = 509
FEATURE                 Location/Qualifiers
source                  1..509
                        mol_type = protein
                        organism = Methylococcus capsulatus
SEQUENCE: 56
MLQKYIEKIL RARVYDVAQE TPLDPAPGLS RRLDNTVLIK REDLQPVFSF KLRGAYNKIA   60
SLTPEARAAG VIAASAGNHA QGVALAAQRL GIRAVIVMPC TTPHIKVDAV RNRGGEVVLH  120
GDAYDEAYEH ALELARDQCL TFVHPYDDPE VIAGQGTIGM EILRQHQDAI HAIFVPVGGG  180
GLIAGIAAYV KFVRPDIRVI GVEPVDSDCL HRALKAKRRV ILKQVGLFAD GVAVKQVGKE  240
PFHLAHQWVD EVVTVDTDEI CAAIKDIFDD TRSIAEPAGA LGIAGLKKYV AETGIKNACL  300
VAIESGANIN FDRLRHVAER AEIGEKRELL LAVTIPERPG SPLEFCRVLG RRNITEFNYR  360
FFDEKAAQVF VGLPVASGAI DRESLVREFE RQGFGVLDLT GNELAIEHIR YMVGGHAPKL  420
LDEQVYSFEF PERPGALLRF LSIMGGRWNI SLFHYRNHGA AFGRVLMGIQ VPKPERKAFR  480
EFLEAIGYAF KEETQNPAYR LFAGGSERG                                     509
```

```
SEQ ID NO: 57           moltype = DNA  length = 1545
FEATURE                 Location/Qualifiers
source                  1..1545
                        mol_type = other DNA
                        organism = Methylococcus capsulatus
SEQUENCE: 57
atgcacgaca gactgatcat tttcgacacg accttgcgcg acggagagca gagcccggc     60
gcgtccatga cccgcgatga aaaggtccgc atcgcccggg cgctggagcg tctgaaggtc  120
gacgtcatcg aggcgggctt tccgccgccc agccccggcg atttcgaggc cgtccaggcc  180
gtggcccgga ccatcaagga cagcagggtc tgcggcctgg cccgcgccct cgaccgcgac  240
atcgacgccg ccggcgaagc cctcaaggac gcccagcggc cccgcatcca caccttcatc  300
gccacctcgc ccatccacat gcggcacaag ctgcagatgt cgcccgacca ggtggtggaa  360
tacgcggtca aggccgtcaa gcgggcccgc cagtacaccg acgacgtgga attctcgccc  420
gaggacgccg gacgctccga ggaggatttc ctctgccgca tcctggaagc cgtgatcgat  480
gcggggggca ccacgctgaa catccccgac accgtcggct acgccttccc ggaacagttc  540
gggcacatga tcggccggct gatcgagcgg attccgaact ccgacaaggc cgtgttctcg  600
gttcactgcc acaacgacct gggactggcg gtcgccaatt cgctggccgc cgtgctgcac  660
ggcgcgcgcc aggtggaatg caccatcaac gggctgggcg agcgggccgg caacgccgcg  720
ctggaagaga tcgtcatggc ggtgcgcacc cgtaaagaca tcttccctg cacacaccgac  780
atcgagacac gggaaatcgt ggcctgctcc aaactggtct ccagcatcac cggtttcccg  840
atccagccca acaaggccat cgtcggcgcc aacgccttcg cccacgagtc gggcatccac  900
caggacggtg tgctcaagag ccgggaaacc tacgagatca tgagcgccga ggacgtgggg  960
tggagcacca accgcatggt gctgggcaaa cattccggcc gcaacgcgtt cgtgtacccgg  1020
atgcaggaac tcggcatcga gttcgcctcg gaagaggaac tgaactcggt gttccagcgc  1080
ttcaaggtgc tggccgacaa gaagcacgag atcttcgacg aggacctcca ggccctcatc  1140
accgaagccg cgcagaagc cgaagacgaa cgggtcaagc tggtcgcgct gcgggtctgc  1200
tcggaaacgg gcgagattcc ccacgcccag gtcaccatca aggtggacaa cgaggaacgc  1260
accggcacat cgagcggcgg cggcgccgtg gacgccagcc tcaaggccat cgaatcgctg  1320
ctgcacacgg acaccgcgct gacgctgtac tcggtcaaca acatcaccag cggcaccgac  1380
gcccagggcg aggtcaccgt gcggctcgag aaaggcgggc gcatcgtcaa cggccagggc  1440
gccgataccg acatcgtgat cgcctcggcc aaggcctacg tcaacgccgt gaacaagctg  1500
ctggcgccca tccagcgcac ccacccgcaa gtcgggggatg tgtga                  1545
```

```
SEQ ID NO: 58           moltype = AA  length = 514
FEATURE                 Location/Qualifiers
source                  1..514
                        mol_type = protein
                        organism = Methylococcus capsulatus
SEQUENCE: 58
MHDRLIIFDT TLRDGEQSPG ASMTRDEKVR IARALERLKV DVIEAGFPAA SPGDFEAVQA   60
VARTIKDSRV CGLARALDRD IDRAGEALKD AQRARIHTFI ATSPIHMRHK LQMSPDQVVE  120
YAVKAVKRAR QYTDDVEFSP EDAGRSEEDF LCRILEAVID AGATTLNIPD TVGYAFPEQF  180
GHMIGRLIER IPNSDKAVFS VHCHNDLGLA VANSLAAVLH GARQVECTIN GLGERAGNAA  240
```

```
LEEIVMAVRT RKDIFPCHTD IETREIVACS KLVSSITGFP IQPNKAIVGA NAFAHESGIH  300
QDGVLKSRET YEIMSAEDVG WSTNRMVLGK HSGRNAFRTR MQELGIEFAS EEELNSVFQR  360
FKVLADKKHE IFDEDLQALI TEAGAEAEDE RVKLVALRVC SETGEIPHAQ VTIKVDNEER  420
TGTSSGGGAV DASLKAIESL LHTDTALTLY SVNNITSGTD AQGEVTVRLE KGGRIVNGQG  480
ADTDIVIASA KAYVNAVNKL LAPIQRTHPQ VGDV                              514

SEQ ID NO: 59            moltype = DNA   length = 1413
FEATURE                  Location/Qualifiers
source                   1..1413
                         mol_type = other DNA
                         organism = Methylococcus capsulatus
SEQUENCE: 59
atgagcggaa aaacccttta cgacaagctg tgggacgacc acgtcgtgca tgtcgatgcg   60
gacggatcgt gcctgatcta catcgatcgt catctaatcc acgaggtgac ctcgcctcag  120
gcattcgaag ggctgcggat ggcggggcgt gtacctggc gggtggatgc caatcttgcg  180
gtggccgacc acaacgtccc caccgccgac cgcgacaggg gtatcgccga tccggtgtcg  240
cgcctgcagg tggaaaccct ggacaagaac tgcgccgatt tcggcatcac cgaattcgcg  300
atggacgacg tgcgccaggg tatcgtgcat gtgatcggcc ccgagcaggg cgcgaccctg  360
ccgggcatga ccatcgtttg cggcgattcg catacttcga ctcacggtgc tttcgggcgc  420
ctcgccttcg ggatcggcac ttccgaggtc gagcacgtac tggccacgca atgcctggtg  480
cagcgcaagg cgaagaacat gctggtccgc gtccagggca agctggcgcc gggcgtgacg  540
gcgaaagatc tggtactggc ggtcatcggc cgtatcggaa cgccggcgg caccggctac  600
accatcgaat tcgctggcga agccattcgc ggcctgtcga tggaaggccg gatgacggtc  660
tgcaacatgg cgatcgaggc gggcgcacgt gccggcctgg tggcggtgga cgaagtcacg  720
ctcgactatc tcgagggccg cccgttcgct ccggcgggcg cgttgtggga gcgggcggtc  780
gaggcatgga aagacctgca cagcgatccg gatgcggtat tcgacaaggt cgtcgagatc  840
gatgccgcca gcatcaagcc gcaggtgacc tggggaactt cgccggaaca ggtcgtgccg  900
gtggatgccg aggtgcccga cccggccacg gaagccgatc ccgtgcggcg ggaaaagcatg  960
gagcgggcgc tgcagtacat ggatctcctg ccgggcacgc caatcggcgc gatccggggtc 1020
gatcgggtgt tcatcggctc ctgcaccaat gccaggatcg aggatctgcg cgccgcggcg 1080
gaagtcgtcc gggggcacaa gcgcgctgcc agcgtgaagc aggcactggt ggtgcccggc 1140
tcgggtttgg tcaagcggca ggcggagcag gaggggctgg acaaggtgtt cctcgaggcc 1200
ggtttcgaat ggcgcgaccc gggttgttcc atgtgtctgg cgatgaacgc cgaccgcctg 1260
gaacccggcg agcgttgcgc ctcgacctcc aaccggaatt ttgaggggcg ccagggctat 1320
ggcgggcgta cccatctggt gagtccggcc atggcgggctg cggcggccat tcacgggcat 1380
ttcgtcgaca tcaccgaagg agggcgcgca tga                              1413

SEQ ID NO: 60            moltype = AA   length = 470
FEATURE                  Location/Qualifiers
source                   1..470
                         mol_type = protein
                         organism = Methylococcus capsulatus
SEQUENCE: 60
MSGKTLYDKL WDDHVVHVDA DGSCLIYIDR HLIHEVTSPQ AFEGLRMAGR VPWRVDANLA   60
VADHNVPTAD RDRGIADPVS RLQVETLDKN CADFGITEFA MDDVRQGIVH VIGPEQGATL  120
PGMTIVCGDS HTSTHGAFGA LAFGIGTSEV EHVLATQCLV QRKAKNMLVR VQGKLAPGVT  180
AKDLVLAVIG RIGTAGGTGY TIEFAGEAIR GLSMEGRMTV CNMAIEAGAR AGLVAVDEVT  240
LDYLEGRPFA PAGALWERAV EAWKDLHSDP DAVFDKVVEI DAASIKPQVT WGTSPEQVVP  300
VDAEVPDPAT EADPVRRESM ERALQYMDLL PGTPIGAIRV DRVFIGSCTN ARIEDLRAAA  360
EVVRGHKRAA SVKQALVVPG SGLVKRQAEQ EGLDKVFLEA GFEWRDPGCS MCLAMNADRL  420
EPGERCASTS NRNFEGRQGY GGRTHLVSPA MAAAAIHGH FVDITEGGRA              470

SEQ ID NO: 61            moltype = DNA   length = 639
FEATURE                  Location/Qualifiers
source                   1..639
                         mol_type = other DNA
                         organism = Methylococcus capsulatus
SEQUENCE: 61
atgaagcctt tcaagaaatt cacttcgcga gtcgtgccgt tggaccgcgc caatgtcgac   60
accgacgcca tcattcccaa gcagttcctg aagtccatcc gccgcagcgg gttcggtccc  120
tatctgttcg acgagtggcg ttacctggac cgtggcgagc ccgacatgga ttgcagccac  180
cgtccgctca acccggagtt cgtgctcaac ctgccctgtt acgccggcgc caggatattg  240
ctggcccgca agaacttcgg ctgtggctcc tcgcgcgagc atgcgccctg ggcgctggag  300
gattacggct tccgcgccat catcgcgccg agtttcgccg atatcttcta caacaactgc  360
ttcaagaacg gcatcctgcc catcgtgctc gacgaggcca cggtcgaccg gctgtttagc  420
gaggccgggc ccggcttcga gctcaccgtc gacctggagt cgcagaccgt ggcgacgccg  480
ttcggcgaga ccttccattt cgacgtggat gcctcccgca agcatcgtct gctgaacggc  540
ctggacgaca tcggtctgac ccttcagcat gccgatgcca tccgcgccta cgaagccgcc  600
cgcaggaagt ccgcaccctg gctgtttgcc gtcccttga                        639

SEQ ID NO: 62            moltype = AA   length = 212
FEATURE                  Location/Qualifiers
source                   1..212
                         mol_type = protein
                         organism = Methylococcus capsulatus
SEQUENCE: 62
MKPFKKFTSR VVPLDRANVD TDAIIPKQFL KSIRRSGFGP YLFDEWRYLD RGEPDMDCSH   60
RPLNPEFVLN LPCYAGARIL LARKNFGCGS SREHAPWALE DYGFRAIIAP SFADIFYNNC  120
FKNGILPIVL DEATVDRLFS EAGPGFELTV DLESQTVATP FGETFHFDVD ASRKHRLLNG  180
```

-continued

```
LDDIGLTLQH ADAIRAYEAA RRKSAPWLFA VP                            212

SEQ ID NO: 63             moltype = DNA  length = 1083
FEATURE                   Location/Qualifiers
source                    1..1083
                          mol_type = other DNA
                          organism = Methylococcus capsulatus
SEQUENCE: 63
atgactatca aaatcgctgt cttgcccggt gacggcatcg gtcccgaaat cgtcgccgag   60
gccctgaagg ttctggactg cctgcggtcc gacttcggcc tcgcggtcga aaccgaacac  120
gccctgatcg gcggcgcagc ctatgatgcg cacggcacgc cgttccccaa ggaaaccctg  180
gagctgtgcc gggctgccga ttcgatcctg cttggagcgg tcggcggtcc caaatgggaa  240
ccgttggatt attcgctgcg gcccgagcgg gggctcctgg gcttgcgttc ggagctggaa  300
ctgtttttcca acctgcgccc ggcggtgctc taccctcagc tggtgtcggc ttcgaccctc  360
aagcccgagg tggtcgccgg cctcgacatc atgatcgtgc gggagctgac cggcggcata  420
tatttcggca gccgcgcggg tcgtcgcatc aacgaggacg gagagcggga gggctacaac  480
accctggtat acagcgaatc ggaaatccgc cgcatagccc atagcgcgtt ccagatcgcc  540
cggaagcgta acaggcgcct gtgcagcatc gacaaggcca atgtgctgga atgcacggaa  600
ctgtggcgcg aggtggtgat cgaggtcggc aaggactatc ccgacgtggc gctgagccac  660
atgtacgtgg acaacgccgc gatgcagctg gtccgtaacc cgaagcagtt cgacgtgatg  720
ctgaccgaca acatgttcgg cgacatcctg tccgactgtg ccgccatgct gaccggctcg  780
atcggcatgc tgccttcggc ttccctcgcc gagagcggca aggggatgta cgagcccatc  840
cacggttcgg ccccggatat cgccggccgc ggcatccaca acccgatcgc caccatcctg  900
tcgctggcca tgatgttgcg ctacagcttc gatgacgcgg tctcggcaga gcggatcggg  960
aaggcggtgc agacggcgct ggatcagggt ttccgcacgg cggacatcgc ctcggaaggc 1020
accgtcgagg tcggtaccgc tgcgatgggc gatgccatcg tcgccgcctt gcgcgccgtc 1080
tga                                                              1083

SEQ ID NO: 64             moltype = AA  length = 360
FEATURE                   Location/Qualifiers
source                    1..360
                          mol_type = protein
                          organism = Methylococcus capsulatus
SEQUENCE: 64
MTIKIAVLPG DGIGPEIVAE ALKVLDCLRS DFGLAVETEH ALIGGAAYDA HGTPFPKETL   60
ELCRAADSIL LGAVGGPKWE PLDYSLRPER GLLGLRSELE LFSNLRPAVL YPQLVSASTL  120
KPEVVAGLDI MIVRELTGGI YFGKPRGRRI NEDGEREGYN TLVYSESEIR RIAHSAFQIA  180
RKRNRRLCSI DKANVLECTE LWREVVIEVG KDYPDVALSH MYVDNAAMQL VRNPKQFDVM  240
LTDNMFGDIL SDCAAMLTGS IGMLPSASLA ESGKGMYEPI HGSAPDIAGR GIANPIATIL  300
SLAMMLRYSF DDAVSAERIG KAVQTALDQG FRTADIASEG TVEVGTAAMG DAIVAALRAV  360

SEQ ID NO: 65             moltype = DNA  length = 1477
FEATURE                   Location/Qualifiers
source                    1..1477
                          mol_type = other DNA
                          organism = Marinobacter algicola
SEQUENCE: 65
atggcgaccc agcagcagca gaacggcgcc tcggcgagcg gcgtcctgga acagttgcgc   60
gggaagcatg tcctgataac cggtaccacc ggtttccttg gcaaggtagt cctggaaaag  120
ctgatccgca cagtcccgga catcggcggc atccacctcc tgatccgggg caacaagagg  180
catccggccg cccgtgaacg gttcttgaac gagatcgcca gcagttcggt cttcgagcgt  240
ctgcgccacg acgacaacga ggccttcgaa accttcctgg aagaaagggt gcactgtata  300
accggagagg tcaccgagag tcgtttcggc cttaccccgg agcgcttccg cgcgctggcg  360
ggtcaggtgg acgccttcat caattcggcc gcctccgtca acttccgcga ggaactggac  420
aaggcgctga agatcaatac gctgtgcctg gagaatgtcg cggcccttgc tgaactcaac  480
agtgcgatgg cggtcatcca ggtttcgacc tgctacgtta acggcaagaa tagcgggcag  540
atcaccgaat cggtcatcaa gcccgcgggg gagtccatcc cgcgtagcac cgatgggtac  600
tatgaaatcg aagaattggt gcacctgctg caggacaaaa tcagcgatgt gaaggcccga  660
tactccggga aggttctgga aaaaaaattg gtggacctag gcatccggga agccaataac  720
tacgggtgga gcgatacata taccttcacc aagtggctgg gcgaacagct cctcatgaag  780
gccctgagcg gcagatcgct gaccatcgtg cggccgtcga tcatcgagtc ggcattggaa  840
gagcccagcc cggggtggat tgaaggcgtc aaggtcgccg atgccatcat actggcctac  900
gcgagggaga aggtatcgct ctttcctggc aagcggagcg gcatcatcga cgtcatccca  960
gtggatctgg tggccaattc gatcattctg tccctgggag aggcgctctc cggttcgggc 1020
cagcggcgta tctatcagtg ctgcagcggc ggctcgaacc ccatctccct cgggaagttc 1080
atcgactatc tgatggcgga ggcgaagacc aactacgcgg cctacgatca gctgttctac 1140
cgccgcccca ccaagccgtt cgtggccgtc aaccgcaaac tcttcgacgt cgtcgtgggc 1200
ggcatgcggg tcccgctctc gatcgcgggc aaagccatgc gcctggcggg acaaaaccgc 1260
gaactgaagg tcctgaagaa tctggatacg acccggtccc tggccaccat tttcgggttc 1320
tacaccgctc cggactacat cttttcgcaat gacagcctga tggccctggc ctcgcgcatg 1380
ggcgagctgg accgcgtgtt gttccccgtt gacgcccgtc agatcgactg gcagctgtat 1440
ctgtgcaaaa tccacctcgg cgggctgaat cggtacg                          1477

SEQ ID NO: 66             moltype = AA  length = 511
FEATURE                   Location/Qualifiers
source                    1..511
                          mol_type = protein
                          organism = Marinobacter algicola
SEQUENCE: 66
```

```
MATQQQQNGA SASGVLEQLR GKHVLITGTT GFLGKVVLEK LIRTVPDIGG IHLLIRGNKR  60
HPAARERFLN EIASSSVFER LRHDDNEAFE TFLEERVHCI TGEVTESRFG LTPERFRALA  120
GQVDAFINSA ASVNFREELD KALKINTLCL ENVAALAELN SAMAVIQVST CYVNGKNSGQ  180
ITESVIKPAG ESIPRSTDGY YEIEELVHLL QDKISDVKAR YSGKVLEKKL VDLGIREANN  240
YGWSDTYTFT KWLGEQLLMK ALSGRSLTIV RPSIIESALE EPSPGWIEGV KVADAIILAY  300
AREKVSLFPG KRSGIIDVIP VDLVANSIIL SLAEALSGSG QRRIYQCCSG GSNPISLGKF  360
IDYLMAEAKT NYAAYDQLFY RRPTKPFVAV NRKLFDVVVG GMRVPLSIAG KAMRLAGQNR  420
ELKVLKNLDT TRSLATIFGF YTAPDYIFRN DSLMALASRM GELDRVLFPV DARQIDWQLY  480
LCKIHLGGLN RYALKERKLY SLRAADTRKK A                                 511

SEQ ID NO: 67          moltype = DNA  length = 1377
FEATURE                Location/Qualifiers
source                 1..1377
                       mol_type = other DNA
                       organism = Acinetobacter baylyi
SEQUENCE: 67
atgcgccccc tgcaccccat cgacttcatc ttcctgagcc tggaaaagcg gcagcagccc  60
atgcacgtcg gcggcctgtt cctgttccag atcccggaca acgcccccga caccttcatc  120
caggacctgg tcaacgacat ccgcatcctc aagagcatcc cggtgccgcc cttcaacaac  180
aagctgaacg gcctgttctg ggacgaagac gaggagttcg acctggacca ccatttccgg  240
cacatcgccc tgccgcatcc cggccgcatc cgggaactgc tgatctacat ctcccaggag  300
cacagcaccc tgctggaccg cgcgaagccg ctgtggacct gcaacatcat cgaaggcatc  360
gagggcaacc ggttcgccat gtatttcaag atccaccatg cgatggtcga cggcgtggcc  420
ggcatgcgcc tgatcgaaaa gtcgctgtcc catgacgtca ccgagaagag catcgtcccg  480
ccctggtgcg tggaaggcaa gcgggcgaag cgcctgcggg agccgaagac cggcaagatc  540
aagaagatca tgtcgggcat caagtcccag ctgcaggcca ccccaccgt catccaggaa  600
ctgtcgcaga ccgtgttcaa ggacatcggc cgcaacccgg accacgtcag ctcgttccag  660
gcccctgct ccatcctgaa ccagcgggtg tccagctcgc gccggttcgc cgcgcagtcg  720
ttcgacctgg accgcttccg gaacatcgcg aagtccctga acgtcaccat caacgacgtc  780
gtgctggcgt gtgcagcggg cgccctgcgc gcgtacctga tgagccacaa ctcgctgccg  840
tccaagcccc tgatcgcgat ggtcccggcg tcgatccgca acgacgacag cgacgtgtcg  900
aaccggatca ccatgatcct ggccaacctg gcgacccata aggacgaccc gctgcagcgc  960
ctggagatca tccgccggag cgtccagaac tcgaagcagc gcttcaagcg gatgacctcc  1020
gaccagatcc tgaactacag cgcggtcgtg tatggcccgg ccgggctgaa catcatcagc  1080
ggcatgatgc ccaagcgcca ggccttcaac ctggtcatct cgaacgtgcc gggcccgcgc  1140
gagccgctgt actggaacgg cgccaagctg gacgcgctgt atcccgcctc catcgtcctg  1200
gacggccagg ccctgaacat caccatgacc agctacctgg acaagctgga ggtcggcctg  1260
atcgcgtgcc gcaacgccct gccgcggatg cagaacctgc tgacccatct ggaggaagag  1320
atccagctgt tcgaaggcgt gatcgcgaag caggaggaca tcaagacccg caactga     1377

SEQ ID NO: 68          moltype = AA  length = 458
FEATURE                Location/Qualifiers
source                 1..458
                       mol_type = protein
                       organism = Acinetobacter baylyi
SEQUENCE: 68
MRPLHPIDFI FLSLEKRQQP MHVGGLFLFQ IPDNAPDTFI QDLVNDIRIS KSIPVPPFNN  60
KLNGLFWDED EEFDLDHHFR HIALPHPGRI RELLIYISQE HSTLLDRAKP LWTCNIIEGI  120
EGNRFAMYFK IHHAMVDGVA GMRLIEKSLS HDVTEKSIVP PWCVEGKRAK RLREPKTGKI  180
KKIMSGIKSQ LQATPTVIQE LSQTVFKDIG RNPDHVSSFQ APCSILNQRV SSSRRFAAQS  240
FDLDRFRNIA KSLNVTINDV VLAVCSGALR AYLMSHNSLP SKPLIAMVPA SIRNDDSDVS  300
NRITMILANL ATHKDDPLQR LEIIRRSVQN SKQRFKRMTS DQILNYSAVV YGPAGLNIIS  360
GMMPKRQAFN LVISNVPGPR EPLYWNGAKL DALYPASIVL DGQALNITMT SYLDKLEVGL  420
IACRNALPRM QNLLTHLEEE IQLFEGVIAK QEDIKTAN                          458

SEQ ID NO: 69          moltype = DNA  length = 1428
FEATURE                Location/Qualifiers
source                 1..1428
                       mol_type = other DNA
                       organism = Psychrobacter articus
SEQUENCE: 69
atgcgcctgc tgaccgccgt cgaccagctg ttcctgctgc tggagtcccg caagcacccg  60
atgcacgtgg gcggcctgtt cctgttcgaa ctgccggaga cgccgacat ctcgttcgtc  120
caccagctgg tgaagcagat gcaggactcc gacgtcccgc ccaccttccc cttcaaccag  180
gtgctggaac acatgatgtt ctggaaggag gacaagaact cgacgtcga acaccatctg  240
caccatgtgg ccctgccgaa gcccgcgcgc gtccgggagc tgctgatgta cgtgtcccgc  300
gaacacggcc ggctgctgga ccgcgcgatg ccgctgtggg aatgccatgt catcgagggc  360
atccagccgg aaaccgaggg cagccccgag cggttcgccc tgtatttcaa gatccaccat  420
tcgctggtcg acggcatcgc cgcgatgcgc ctggtgaaga gagcctgtc gcagtcgccg  480
aacgaacccg tgaccctgcc gatctggagc ctgatggccc accatcggaa ccagatcgac  540
gcgatcttcc ccaaggagcg gagcgccctg cgcatcctga aggaacaggt ctcgaccatc  600
aagccggtgt tcaccgagct gctgaacaac ttcaagaact acaacgacga ctcgtatgtc  660
tccaccttcg acgcgccccg cagcatcctg aaccgccgga tcagcgcctc gcgccggatc  720
gccgcagt cgtacgacat caacggttc aacgacatcg caacatctcc  780
aagaacgacg tcgtgctggc cgtgtgcagc ggcgcgatcc gccgctacct gatcagcatg  840
gacgcgctgc cgagcaagcc cctgatcgcc ttcgtcccga tgtcgctgcg caccgacgac  900
tccatcgcgg gcaaccagct gtcgttcgtg ctggccaacc tgggcaccca cctggacgac  960
cccctgtccc ggatcaagct gatccatcgc tccatgaaca acagcaagcg ccggttccgc  1020
cggatgaacc aggcccaggt catcaactac agcatcgtgt cgtatgcctg ggagggcatc  1080
```

-continued

```
aacctggcga ccgacctgtt cccgaagaag caggccttca acctgatcat ctcgaacgtg  1140
ccgggcagcg agaagcccct gtactggaac ggcgcgcgcc tggaaagcct gtatccggcc  1200
tcgatcgtgt tcaacggcca ggccatgaac atcaccctgg cgtcctacct ggacaagatg  1260
gagttcggca tcaccgcctg cagcaaggcg ctgccgcacg tccaggacat gctgatgctg  1320
atcgaggaag agctgcagct gctggagtcc gtcagcaagg aactggagtt caacggcatc  1380
accgtgaagg acaagtcgga aaagaagctg aagaagctgg ccccgtga             1428
```

```
SEQ ID NO: 70          moltype = AA  length = 475
FEATURE                Location/Qualifiers
source                 1..475
                       mol_type = protein
                       organism = Psychrobacter articus
SEQUENCE: 70
MRLLTAVDQL FLLLESRKHP MHVGGLFLFE LPENADISFV HQLVKQMQDS DVPPTFPFNQ  60
VLEHMMFWKE DKNFDVEHHL HHVALPKPAR VRELLMYVSR EHGRLLDRAM PLWECHVIEG  120
IQPETEGSPE RFALYFKIHH SLVDGIAAMR LVKKSLSQSP NEPVTLPIWS LMAHHRNQID  180
AIFPKERSAL RILKEQVSTI KPVFTELLNN FKNYNDDSYV STFDAPRSIL NRRISASRRI  240
AAQSYDIKRF NDIAERINIS KNDVVLAVCS GAIRRYLISM DALPSKPLIA FVPMSLRTDD  300
SIAGNQLSFV LANLGTHLDD PLSRIKLIHR SMNNSKRRFR RMNQAQVINY SIVSYAWEGI  360
NLATDLFPKK QAFNLIISNV PGSEKPLYWN GARLESLYPA SIVFNGQAMN ITLASYLDKM  420
EFGITACSKA LPHVQDMLML IEEELQLLES VSKELEFNGI TVKDKSEKKL KKLAP        475
```

```
SEQ ID NO: 71          moltype = DNA  length = 1386
FEATURE                Location/Qualifiers
source                 1..1386
                       mol_type = other DNA
                       organism = Rhodococcus opacus
SEQUENCE: 71
atgtccgtga tgtccccgac cgaggcgatg ttcgtcctgt tcgagacccc gagccacccg  60
atgcacatgg gcgcgctgga gctgttcgag ccgccgcgcg agtcgggccc ggaccacgcc  120
cgcctgatgt tcgaggcgct gatctcccag gaaggcgcca gcgacacctt ccgccggcgc  180
gccgtccggc cgctgcgcgg cgcgtcgtac ccctggtggt ccgtcgacga ccgggtggac  240
ctgggctatc acgtccgcca taccgccgtg ccgggccggg gccgcatgga ggacctgctg  300
tcgctggtgt cccagatgca cggcatgccc ctggacccgc agcaccccat gtgggagatc  360
catgtcatcg aaggcctggc cgacggccgc accgcggtgt tcagcaagat ccatctgtcg  420
ctgatggacg gcccggccgg cctgcggctg ctgcaccatg cgctgagcac cgacccggac  480
gcccgcgact gccccgcgcc gtggacccc ggcgtcagcg gcacctcgcg cgcggaatcg  540
gccctgccgg tcgccgcggt gcgggcgggc gtgcgcgccg cgacctccat cgtcggcgtg  600
ctgcccgacc tggcgaaggt cgcctacgac ggcgtgcggg accagcacct gaccctgccg  660
ctgcagagcc cgcccaccat gctgaacgtc cccgtgggcc gggcccgcaa gctggccgcg  720
cggagctggc cgatccggcg cctggtctcg gtggccgcgg ccgcgcgcac caccatcaac  780
gccgtcgtgc tggcgatgtg ctcgggcgcc ctgcgccact acctggtcga gcagtatgcc  840
ctgccggaag cgcccctgac cgccatgctg cccgtgcccg tggacctggg cggcaccatg  900
atcggcccgc gtggccgcga ccacggcgtc ggcgcgatgg tcgtgggcct ggcgaccgac  960
gaggccgacc ccgccgcgcg gctggcccgc atcagcgagt cggtcgaaca caccaaccgc  1020
gtgttcggcg cgctgtccca tacccagttc caggtcatgt ccgccctggc gatcagcccg  1080
atcctgctgg aacccgtccg gcgcttcgtg gacgacaccc cgcccccgtt caacgtgatg  1140
atctcgtaca tgccgggtcc gtcccggccg cgctattgga acggcgcgcg gctggacgcc  1200
gtctacccgg cgccgaccgt gctgggcggc caggccctga gcatcaccct gacctcccgc  1260
agcggccagc tggacgtcgg cgtcgtgggc gaccggcagg ccgtgccgca cctgcagcgc  1320
atcatcaccc atctggagac ctccctgacc gacctggaaa acgccgtggc cgcgagcggc  1380
acctga                                                            1386
```

```
SEQ ID NO: 72          moltype = AA  length = 461
FEATURE                Location/Qualifiers
source                 1..461
                       mol_type = protein
                       organism = Rhodococcus opacus
SEQUENCE: 72
MSVMSPTEAM FVLFETPSHP MHMGALELFE PPRESGPDHA RLMFEALISQ EGASDTFRRR  60
AVRPLRGASY PWWSVDDRVD LGYHVRHTAV PGRGRMEDLL SLVSQMHGMP LDPQHPMWEI  120
HVIEGLADGR TAVFSKIHLS LMDGPAGLRL LHHALSTDPD ARDCPAPWTP GVSGTSRRES  180
ALPVAAVRAG VRAATSIVGV LPALAKVAYD GVRDQHLTLP LQSPPTMLNV PVGRARKLAA  240
RSWPIRRLVS VAAAARTTIN AVVLAMCSGA LRHYLVEQYA LPEAPLTAML PVPLDLGGTM  300
IGPRGRDHGV GAMVVGLATD EADPAARLAR ISESVEHTNR VFGALSHTQF QVMSALAISP  360
ILLEPVRRFV DDTPPPFNVM ISYMPGPSRP RYWNGARLDA VYPAPTVLGG QALSITLTSR  420
SGQLDVGVVG DRQAVPHLQR IITHLETSLT DLENAVAASG T                     461
```

```
SEQ ID NO: 73          moltype = DNA  length = 1356
FEATURE                Location/Qualifiers
source                 1..1356
                       mol_type = other DNA
                       organism = Rhodococcus opacus
SEQUENCE: 73
atgccggtca ccgactccat cttcctgctg ggcgaaagcc gcgagcaccc gatgcacgtg  60
ggctccctgg aactgttcac cccccccgac gacgccggcc ggactacgt caagtcgatg  120
cacgagaccc tgctgaagca taccgacgtg gaccccacct tccgcaagaa gccggcgggc  180
cccgtcggct cgctgggcaa cgtgtggtgg gccgacgagt ccgacgtcga cctggaatac  240
cacgtgcgcc atagcgcgct gccggccccc tatcgcgtcc gggaactgct gaccctgacc  300
```

```
tcgcggctgc acggcaccct gctggaccgc catcggccgc tgtgggagat gtacctgatc  360
gaaggcctga gcgacggccg cttcgccatc tataccaagc tgcaccatag cctgatggac  420
ggcgtctcgg gcctgcgcct gctgatgcgg accctgtcga ccgacccgga cgtgcgcgac  480
gccccgcccc cgtggaacct gccgcggccc gccgcggcca acggcgcggc cccggacctg  540
tggtcggtcg tgaacggcgt ccgccggacc gtcggcgacg tggccggcct ggcgcccgcc  600
tccctgcgca tcgcgcggac cgcgatgggc cagcacgaca tgcgcttccc gtacgaggcg  660
ccccggacca tgctgaacgt gccgatcggc ggcgcccgcc ggttcgcggc ccagtcctgg  720
cccctggaac gcgtccatgc cgtgcggaag cgggccggcg tcagcgtgaa cgacgtcgtg  780
atggccatgt gcgcgggcgc cctgcgcggc tatctggagg aacagaacgc gctgcgcggac  840
gagccctga tcgcgatggt cccggtgtcc ctgcgggacg aacagcaggc ggacgccggc  900
ggcaacgccg tcggcgtgac cctgtgcaac ctggcgaccg acgtcgacga ccccgccgag  960
cgcctgaccg cgatcagcgc ctcgatgtcc caggcaagg aactgttcgg cagcctgacc  1020
tcgatgcagg cgctggcctg gtcggcggtg aacatgtccc cgatcgccct gaccccggtc  1080
ccggcttcg tgcggttcac cccccgccc ttcaacgtca tcatcagcaa cgtgccgggc  1140
ccccgcaaga ccatgtactg gaacggctcc cggctggacg gcatctatcc gaccagcgtc  1200
gtgctgacg gccaggccct gaacatcacc ctgaccacca acggcggcaa cctggacttc  1260
ggcgtcatcg gctgccgccg gtccgtgccg agcctgcagc gcatcctgtt ctacctggaa  1320
gcggccctgg gcgagctgga agcggccctg ctgtga  1356
```

SEQ ID NO: 74          moltype = AA  length = 451
FEATURE                Location/Qualifiers
source                 1..451
                         mol_type = protein
                         organism = Rhodococcus opacus

```
SEQUENCE: 74
MPVTDSIFLL GESREHPMHV GSLELFTPPD DAGPDYVKSM HETLLKHTDV DPTFRKKPAG  60
PVGSLGNVWW ADESDVDLEY HVRHSALPAP YRVRELLTLT SRLHGTLLDR HRPLWEMYLI  120
EGLSDGRFAI YTKLHHSLMD GVSGLRLLMR TLSTDPDVRD APPPWNLPRP AAANGAAPDL  180
WSVVNGVRRT VGDVAGLAPA SLRIARTAMG QHDMRFPYEA PRTMLNVPIG GARRFAAQSW  240
PLERVHAVRK AAGVSVNDVV MAMCAGALRG YLEEQNALPD EPLIAMVPVS LRDEQQADAG  300
GNAVGVTLCN LATDVDDPAE RLTAISASMS QGKELFGSLT SMQALAWSAV NMSPIALTPV  360
PGFVRFTPPP FNVIISNVPG PRKTMYWNGS RLDGIYPTSV VLDGQALNIT LTTNGGNLDF  420
GVIGCRRSVP SLQRILFYLE AALGELEAAL L  451
```

SEQ ID NO: 75          moltype = DNA  length = 1395
FEATURE                Location/Qualifiers
source                 1..1395
                         mol_type = other DNA
                         organism = Rhodococcus opacus

```
SEQUENCE: 75
atgcccctgc cgatgtcccc cctggactcc atgttcctgc tgggcgaaag ccgcgagcac  60
ccgatgcacg tgggcggcgt cgaaatcttc cagctgcccg agggcgccga cacctacgac  120
atgcggcgga tgctggaccg cgccctggcg gacggcgacg gcatcgtcac cccgcggctg  180
gccaagcgcg cgcgccggtc gttcagctcg ctgggccagt ggtcctggga aaccgtggac  240
gacatcgacc tgggccacca tatccggcac gacgccctgc cggccctgg cggcgaggcc  300
gaactgatgg cgctgtgctc gcgcctgcac ggctccctgc tggaccgcag ccggccgctg  360
tgggagatgc atctgatcga aggcctgagc gacggccgct tcgccgtcta taccaagatc  420
caccatgccg tcgcggacgg cgtgaccgcc atgaagatgc tgcggaacgc gctgagcgag  480
aactcggacg accgcgacgt gccggccccc tggcagcgc gtggcccgcg gccccagcgc  540
accccctcca gcaagggctt ctccctgagc ggcctggccg gctcgaccct gcggaccgcg  600
cgcgagaccg tcggcgaagt ggccggcctg gtcccggccc tggcgggcac cgtgagccgg  660
gccttccgcg accagggcgg cccgctggcc ctgtcggcgc cgaagacccc cttcaacgtc  720
cccatcaccg cgcgccgcca gttcgccgcg cagtcgtggc cgctggaacg cctgcggctg  780
gtggccaagc tgtcggactc caccatcaac gacgtcgtgc tggccatgtc gtccggcgcg  840
ctgcggtcct acctggagga ccagaacgcc ctgccggacg accccctgat cgcgatggtc  900
ccggtgtccc tgaagagcca gcgcgaagcc gcgaccggca acaacatcgg cgtcctgatg  960
tgcaacctgg gcacccacct gcgggagccg gccgaccgcc tggaaccat ccggaccagc  1020
atgcgcgagg gcaaggaagc ctatggctcg atgaccgcga cccagatcct ggccatgtcc  1080
gcgctggggc ccgcgccgat cggcgccagc atgctgttcg gccataactc gcgcgtccgg  1140
ccgcccttca acctgatcat ctccaacgtg ccgggcccca gctcgccgct gtactggaac  1200
ggcgcccgcc tggacggat ctatccgctg agcgtccccg tggacggcca gggcctgaac  1260
atcacctgca cctcgaacga cgacatcatc tccttcggcg tcaccggctg ccggtccgcc  1320
gtgccggacc tgaagagcat ccccgcgcgc ctggccatg agctgcgggc cctggaacgc  1380
gcggtgggca tctga  1395
```

SEQ ID NO: 76          moltype = AA  length = 464
FEATURE                Location/Qualifiers
source                 1..464
                         mol_type = protein
                         organism = Rhodococcus opacus

```
SEQUENCE: 76
MPLPMSPLDS MFLLGESREH PMHVGGVEIF QLPEGADTYD MRAMLDRALA DGDGIVTPRL  60
AKRARSFSS LGQWSWETVD DIDLGHHIRH DALPAPGGEA ELMALCSRLH GSLLDRSRPL  120
WEMHLIEGLS DGRFAVYTKI HHAVADGVTA MKMLRNALSE NSDDRDVPAP WQPRGPRPQR  180
TPSSKGFSLS GLAGSTLRTA RETVGEVAGL VPALAGTVSR AFRDQGGPLA LSAPKTPFNV  240
PITGARQFAA QSWPLERLRL VAKLSDSTIN DVVLAMSSGA LRSYLEDQNA LPADPLIAMV  300
PVSLKSQREA ATGNNIGVLM CNLGTHLREP ADRLETIRTS MREGKEAYGS MTATQILAMS  360
ALGAAPIGAS MLFGHNSRVR PPFNLIISNV PGPSSPLYWN GARLDAIYPL SVPVDGQGLN  420
ITCTSNDDII SFGVTGCRSA VPDLKSIPAR LGHELRALER AVGI  464
```

-continued

```
SEQ ID NO: 77          moltype = DNA  length = 1407
FEATURE                Location/Qualifiers
source                 1..1407
                       mol_type = other DNA
                       organism = Rhodococcus opacus
SEQUENCE: 77
atggccccga ccgactccct gttcctgctg ggcgaatccc gcgagcaccc gatgcacgtg   60
ggcggcctgg cggtcttcac cccggcggag ggcagctcgg ccgcggacgt ccgcgccatg   120
ttcgacgccg cgctggtcgg cgaccgggtg gccgcgccgt tccgcaagcg cgcccgccgg   180
agcgtgacct cgctgggcca gtggggctgg gacaccctgc gcgacgacga ggtcgacctg   240
gaacaccatg tgcgccggga cgccctgccg cagccgggtg gcatggcgga actgatgacc   300
ctggtctccc gcctgcatgg caccctgctg gaccgcagcc ggccgctgtg ggagatgcac   360
ctgatcgaag gcctggccga cggccggtac gcggtgtata ccaagatcca ccatgccctg   420
gcggacggcg ccagcgcgat gcgcctgctg cgggactcga tgtccgagga cccgcatcgc   480
cggaacatgc cgaccccctg gcagccgcgc aaccccctgt cggccgtccc ggacgccggc   540
gtcgcggtga cccccggccc cggcagcgcc ctgcccgcga tggcctggga cgccgcgcgc   600
tccgccgcgg gcgaagtcgc cggcctgctg ccggccagcg tgggcaccgt ggaccgggcc   660
ctgcacggca agggcggcgc cctgtccctg accgcgccgc ataccctgtt caacgtcccc   720
atcagcggcg cccgccacgt ggccgcgcgg tcgttcccga tcgagcgcat ccggctgctg   780
gccaagcatg ccgacgcgac catcaacgac atcgtgctga ccatgtgcgc cggcaccctg   840
cgcgcgtacc tgcacacccg cgacgccctg ccggacaacc ccctgatcgc gatggtcccg   900
gtgagcctgc gcgcccccga aaccggcacc ggcgaccgcg ccctggcgg caaccgggtc   960
ggcgtgctga tgtgcaacct ggccacccac ctgccggacc ccgcgcatcg cctggagacc   1020
gtccggaact gcatgaacga aggcaaggcc gcgctgcagg ccatgtcgcc ggcgcaggtc   1080
ctggccatgt ccgcgctggg cgccgcgccg ctgggcgtga agatgttcct gggccgccgg   1140
ggccccctgc gcccgccctt caacgtcgtg atctcgaacg tggcgggccc gcgcaccccc   1200
ctgtactgga acggcgcccg gctggaatcc ctgtatccgc tgagcatccc caccaccggc   1260
caggccctga acatcacctg cacctccagc gacgaccaga tcgtcttcgg cctgaccggc   1320
tgccgccgga ccgtgccgga cctgcacccc atgctggacc agctggacgc ggagctggac   1380
ctgctggaaa ccgcggtcgg cctgtga                                       1407

SEQ ID NO: 78          moltype = AA  length = 468
FEATURE                Location/Qualifiers
source                 1..468
                       mol_type = protein
                       organism = Rhodococcus opacus
SEQUENCE: 78
MAPTDSLFLL GESREHPMHV GGLAVFTPAE GSSAADVRAM FDAALVGDRV AAPFRKRARR   60
SVTSLGQWGW DTLRDDEVDL EHHVRRDALP QPGGMAELMT LVSRLHGTLL DRSRPLWEMH   120
LIEGLADGRY AVYTKIHHAL ADGASAMRLL RDSMSEDPHR RNMPTPWQPR NPLSAVPDAG   180
VAVTPGPGSA LPAMAWDAAR SAAGEVAGLL PAALGTVDRA LHGKGGALSL TAPHTLFNVP   240
ISGARHVAAR SFPIERIRLL AKHADATIND IVLTMCAGTL RAYLHTRDAL PDNPLIAMVP   300
VSLRAPETGT GDRAPGGNRV GVLMCNLATH LPDPAHRLET VRNCMNEGKA ALQAMSPAQV   360
LAMSALGAAP LGVEMFLGRR GPLRPPFNVV ISNVAGPRTP LYWNGARLES LYPLSIPTTG   420
QALNITCTSS DDQIVFGLTG CRRTVPDLHP MLDQLDAELD LLETAVGL              468

SEQ ID NO: 79          moltype = DNA  length = 11299
FEATURE                Location/Qualifiers
misc_feature           1..11299
                       note = pCM132
source                 1..11299
                       mol_type = other DNA
                       organism = synthetic construct
SEQUENCE: 79
gacccttcc gacgctcacc gggctggttg ccctcgccgc tgggctggcg gccgtctatg    60
gccctgcaaa cgcgccagaa acgccgtcga agccgtgtgc gagacaccgc ggccgccggc   120
gttgtggata cctcgcggaa aacttggccc tcactgacag atgaggggcg gacgttgaca   180
cttgaggggc cgactcaccc ggcgcggcgt tgacagatga ggggcaggct cgatttcggc   240
cggcgacgtg gagctggcca gcctcgcaaa tcggcgaaaa cgcctgattt tacgcgagtt   300
tcccacagat gatgtggaca agcctgggga taagtgccct gcggtattga cacttgaggg   360
gcgcgactac tgacagatga ggggcgcgat ccttgacact tgaggggcag agtgctgaca   420
gatgaggggc gcaccattg acatttgagg ggctgtccac aggcagaaaa tccagcattt   480
gcaaggtttt ccgcccgttt ttcggccacc gctaaacctg cttttaacct gcttttaaac   540
caatatttat aaaccttgtt tttaaccagg gctgcgccct gtgcgcgtga ccgcgcacgc   600
cgaagggggg tgcccccct tctcgaaccc tcccggcccg ctaacgcggg cctcccatcc   660
ccccagggc tgcgccctc ggccgcgaac ggcctcaccc caaaaatggc agccaagctg   720
accacttctg cgctcggcc ttccggctgg ctggtttatt gctgataaat ctggagccgg   780
tgagcgtggg tctcgcggta tcattgcagc actggggcca gatggtaagc cctcccgtat   840
cgtagttatc tacacgacgg ggagtcaggc aactatggat gaacgaaata gacagatcgc   900
tgagataggt gcctcactga ttaagcattg gtaactgtca gaccaagttt actcatatat   960
actttagatt gatttaaaac ttcatttta atttaaaagg atctaggtga agatcctttt   1020
tgataatctc atgaccaaaa tcccttaacg tgagttttcg ttccactgag cgtcagaccc   1080
cgtagaaaag atcaaaggat cttcttgaga tcctttttt ctgcgcgtaa tctgctgctt   1140
gcaaacaaaa aaaccaccgc taccagcggt ggtttgtttg ccggatcaag agctaccaac   1200
tctttttccg aaggtaactg gcttcagcag agcgcagata ccaaatactg tccttctagt   1260
gtagccgtag ttaggccacc acttcaagaa ctctgtagca ccgcctacat acctcgctct   1320
gctaatcctg ttaccagtgg ctgctgccag tggcgataag tcgtgtctta ccgggttgga   1380
ctcaagacga tagttaccgg ataaggcgca gcggtcgggc tgaacggggg gttcgtgcac   1440
```

```
acagcccagc ttggagcgaa cgacctacac cgaactgaga tacctacagc gtgagctatg   1500
agaaagcgcc acgcttcccg aagggagaaa ggcggacagg tatccggtaa gcggcagggt   1560
cggaacagga gagcgcacga gggagcttcc agggggaaac gcctggtatc tttatagtcc   1620
tgtcgggttt cgccacctct gacttgagcg tcgatttttg tgatgctcgt cagggggcg    1680
gagcctatgg aaaaacgcca gcaacgcggc ctttttacgg ttcctggcct tttgctggcc   1740
ttttgctcac atgttctttc ctgcgttatc ccctgattct gtggataacc gtattaccgc   1800
ctttgagtga gctgataccg ctcgccgcag ccgaacgacc gagcgcagcg agtcagtgag   1860
cgaggaagcg gaagagcgcc caatacgcaa accgcctctc cccgcgcgtt ggccgattca   1920
ttaatgcagc tggcacgaca ggtttcccga ctggaaagcg ggcagtgagc gcaacgcaat   1980
taatgtgagt tagctcactc attaggcacc ccaggcttta cactttatgc ttccggctcg   2040
tatgttgtgt ggaattgtga gcggataaca atttccacaca ggaaacagct atgaccatga   2100
ttacgccaag cttgcatgcc tgcaggtcga ctctagagga tcaattcggc ttccaccgga   2160
attagcttga aatagtacat aatggatttc cttacgcgaa atacgggcag acatggcctg   2220
cccggttatt attatttttg acaccagacc aactggtaat ggtagcgacc ggcgctcagc   2280
tgtaattccg ccgatactga cgggctccag gagtcgtcgc caccaatccc catatggaaa   2340
ccgtcgatat tcagccatgt gccttcttcc gcgtgcagca gatggcgatg gctggtttcc   2400
atcagttgct gttgactgta gcggctgatg ttgaactgga agtcgccgcg ccactggtgt   2460
gggccataat tcaattcgcg cgtcccgcag cgcagaccgt tttcgctcgg gaagacgtac   2520
ggggtataca tgtctgacaa tggcagatcc cagcggtcaa aacaggcggc agtaaggcgg   2580
tcgggatagt tttcttgcgg ccctaatccg agccagttta cccgctctgc tacctgcgcc   2640
agctggcagt tcaggccaat ccgcgccgga tgcggtgtat cgctcgccac ttcaacatca   2700
acggtaatcg ccatttgacc actaccatca atccggtagg ttttccggct gataaataag   2760
gttttcccct gatgctgcca cgcgtgagcg gtcgtaatca gcaccgcatc agcaagtgta   2820
tctgccgtgc actgcaacaa cgctgcttcg gcctggtaat ggcccgccgc cttccagcgt   2880
tcgacccagg cgttagggtc aatgcgggtc gcttcactta cgccaatgtc gttatccagc   2940
ggtgcacggg tgaactgatc ggcgcagcggc gtcagcagtt gttttttatc gccaatccac   3000
atctgtgaaa gaaagcctga ctggcggtta aattgccaac gcttattacc cagctcgatg   3060
caaaaatcca tttcgctggt ggtcagatgc gggatggcgt gggacgcggc ggggagcgtc   3120
acactgaggt tttccgccag acgccactgc tgccaggcgc tgatgtgccc ggcttctgac   3180
catgcggtcg cgttcggttg cactacgcgt actgtgagcc agagttgccc ggcgctctcc   3240
ggctgcggta gttcaggcag ttcaatcaac tgtttacctt gtggagcgac atccagaggc   3300
acttcaccgc ttgccagcgg cttaccatcc agcgccacca tccagtgcag gagctcgtta   3360
tcgctatgac ggaacaggta ttcgctggtc acttcgatgg tttgcccgga taaacggaac   3420
tggaaaaact gctgctggtg ttttgcttcc gtcagcgctg gatgcggcgt gcggtcggca   3480
aagaccagac cgttcataca gaactggcga tcgttcggcg tatcgccaaa atcaccgccg   3540
taagccgacc acgggttgcc gttttcatca tatttaatca gcgactgatc cacccagtcc   3600
cagacgaagc cgccctgtaa acggggatac tgacgaaacg cctgccagta tttagcgaaa   3660
ccgccaagac tgttacccat cgcgtgggcg tattcgcaaa ggatcagcgg gcgcgtctct   3720
ccaggtagcg aaagccattt tttgatggac catttcggca cagccgggaa gggctggtct   3780
tcatccacgc gcgcgtacat cgggcaaata atatccggtgg ccgtggtgtc ggctccgccg   3840
ccttcatact gcaccgggcg ggaaggatcg acagatttga tccagcgata cagcgcgtcg   3900
tgattagcgc cgtggcctga ttcattcccc agcgaccaga tgatcacact cgggtgatta   3960
cgatccggct gcaccattcg cgttacgcgt tcgctcatcg ccggtagcca gcgcggatca   4020
tcggtcagac gattcattgg caccatgccg tgggtttcaa tattggcttc atccaccaca   4080
tacaggccgt agcggtcgca cagcgtgtac cacagcggat ggttcggata atgcgaacag   4140
cgcacggcgt taaagttgtt ctgcttcatc agcaggatat cctgcaccat cgtctgctca   4200
tccatgacct gaccatgcag aggatgatgc tcgtgacggt taacgcctcg aatcagcaac   4260
ggcttgccgt tcagcagcag cagaccattt tcaatccgca cctcgcggaa accgacatcg   4320
caggcttctg cttcaatcag cgtgccgtcg gcggtgtgca gttcaaccac cgcacgatag   4380
agattcggga tttcggcgct ccacagtttc gggttttcga cgttcagacg tagtgtgacg   4440
cgatccgcat aaccaccacg ctcatcgata atttcaccgc cgaaaggcgc ggtgccgctg   4500
gcgacctgcg tttcaccctg ccataaagaa actgttaccc gtaggtagtc acgcaactcg   4560
ccgcacatct gaacttcagc ctccagtaca gcgcggctga aatcatcatt aaagcgagtg   4620
gcaacatgga aatcgctgat ttgtgtagtc ggtttatgca gcaacgagac gtcacggaaa   4680
atgccgctca tccgccacat atcctgatct tccagataac tgccgtcact ccaacgcagc   4740
accatcaccg cgaggcggtt ttctccggcg cgtaaaaatg cgctcaggtc aaattcagac   4800
ggcaaacgac tgtcctggcc gtaaccgacc cagcgcccgt tgcaccacag atgaaacgcc   4860
gagttaacgc catcaaaaat aattcgcgtc tggccttcct gtagccagct ttcatcaaca   4920
ttaaatgtga gcgagtaaca acccgtcgga ttctccgtgg gaacaaacgg cggattgacc   4980
gtaatgggat aggttacgtt ggtgtagatg ggcgcatcgt aaccgtgcat ctgccagttt   5040
gaggggacga cgacagtatc ggcctcagga agatcgcact ccagccagct ttccggcacc   5100
gcttctggtg ccggaaacca ggcaaagcgc cattcgccat tcaggctgcg caactgttgg   5160
gaagggcgat cggtgcgggc ctcttcgcta ttacgccagc tggcgaaagg gggatgtgct   5220
gcaaggcgat taagttgggt aacgccaggg tttttcccgt cgacccgtaa tcttacgtca   5280
gtaacttcca cagtagttca ccacctttttc cctatagatc ttccgtgcag tttaagccga   5340
attgatcccc gggtaccgag ctcgaatcta gaattccctg ctttcctgat gcaaaaacga   5400
ggctagttta ccgtatctgt gggggatgg cttgtagata tgacgacagg aagagtttgt   5460
agaaacgcaa aaaggccatc cgtcaggatg gccttctgct taatttgatg cctggcagtt   5520
tatggcgggc gtcctgcccg ccaccctccg ggccgttgct tcgcaacgtt caaatccgct   5580
cccggcggat ttgtcctact caggagagcg ttcaccgaca aacaacagat aaaacgaaag   5640
gcccagtctt tcgactgagc cttttgtttt atttgatgcc tggcagttcc ctactctcgc   5700
atggggagac cccacactac catcggcgct acggcgtttc acttctgagt tcggcatggg   5760
gtcaggtggg accaccgcgc tactgccgcc aggcaaattc tgttttatca gaccgcttct   5820
gcgttctgat ttaatctgta tcaggctgaa aaattcactg tacaacgtg cgtctgat[?]   5880
tgactgggaa aaccctggcg ttacccaact taatcgcctt gcagcacatc cccctttcgc   5940
cagctggcgt aatagcgaag aggcccgcac cgatcgccct tcccaacagt tgcgcagcct   6000
gaatggcgaa tggcgcctga tgcggtattt tctccttacg catctgtgcg gtatttcaca   6060
ccgcatatgt tgcactctca gtacaatctg ctctgatgcc gcatagttaa gccagccccg   6120
acacccgcca cacccgctg acgcgccctg acgggcttgt ctgctcccgg catccgctta   6180
```

-continued

```
cagacaagct gtgaccgtct ccgggagctg catgtgtcag aggttttcac cgtcatcacc  6240
gaaacgcgcg agacgaaagg gcctcgtgat acgcctattt ttataggtta atgtcatgat  6300
aataatggtt tcttagcacc cttttctcggt ccttcaacgt tcctgacaac gagcctcctt  6360
ttcgccaatc catcgacaat caccgcgagt ccctgctcga acgctgcgtc cggaccggct  6420
tcgtcgaagg cgtctatcgc ggcccgcaac agcggcgaga agcggagcctg ttcaacggtg  6480
ccgccgcgct cgccggcatc gctgtcgccg gcctgctcct caagcacggc cccaacagtg  6540
aagtagctga ttgtcatcag cgcattgacg gcgtccccgg ccgaaaaacc cgcctcgcag  6600
aggaagcgaa gctgcgcgtc ggccgtttcc atctgcggtg cgcccggtcg cgtgccggca  6660
tggatgcgcg cgccatcgcg gtaggcgagc agcgcctgcc tgaagctgcg ggcattcccg  6720
atcagaaatg agcgccagtc gtcgtcggct ctcggcaccg aatgcgtatg attctccgcc  6780
agcatggctt cggccagtgc gtcgagcagc gcccgcttgt tcctgaagtg ccagtaaagc  6840
gccggctgct gaacccccaa ccgttccgcc agtttgcgtg tcgtcagacc gtctacgccg  6900
acctcgttca acaggtccag ggcggcacgg atcactgtat tcggctgcaa ctttgtcatg  6960
attgacactt tatcactgat aaacataata tgtccaccaa cttatcagtg ataaagaatc  7020
cgcgcgttca atcggaccag cggaggctgg tccggaggcc agacgtgaaa cccaacatac  7080
ccctgatcgt aattctgagc actgtcgcgc tcgacgctgt cggcatcggc ctgattatgc  7140
cggtgctgcc gggcctcctg cgcgatctgg ttcactcgaa cgacgtcacc gcccactatg  7200
gcattctgct ggcgctgtat gcgttggtgc aatttgcgtc cgcacctgtg ctgggcgcgc  7260
tgtcggatcg tttcgggcgg cggccaatct tgctcgtctc gctggccggc gccactgtcg  7320
actacgccat catggcgaca gcgcctttcc tttgggttct ctatatcggg cggatcgtgg  7380
ccggcatcac cggggcgact ggggcggtag ccggcgctta tattgccgat gacctgcagg  7440
ggggggggg cgctgaggtc tgcctcgtga agaaggtgtt gctgactcat accaggcctg  7500
aatcggccca tcatccagcc agaaagtgag ggagccacgg ttgatgagag ctttgttgta  7560
ggtggaccag ttggtgattt tgaacttttg ctttgccacg gaacggtctg cgttgtcggg  7620
aagatgcgtg atctgatcct tcaactcagc aaaagttcga tttattcaac aaagccgccg  7680
tcccgtcaag tcagcgtaat gctctgccag tgttacaacc aattaaccaa ttctgattag  7740
aaaaactcat cgagcatcaa atgaaactgc aatttattca tatcaggatt atcaatacca  7800
tatttttgaa aaagccgttt ctgtaatgaa ggagaaaact caccgaggca gttccatagg  7860
atggcaagat cctggtatcg gtctgcgatt ccgactcgtc caacatcaat acaacctatt  7920
aatttcccct cgtcaaaaat aaggttatca agtgagaaat caccatgagt gacgactgaa  7980
tccggtgaga atggcaaaag cttatgcatt tctttccaga cttgttcaac aggccagcca  8040
ttacgctcgt catcaaaatc actcgcatca accaaaccgt tattcattcg tgattgcgcc  8100
tgagcgagac gaaatacgcg atcgctgtta aaaggacaat tacaaacagg aatcgaatgc  8160
aaccggcgca ggaacactgc cagcgcatca acaatatttt cacctgaatc aggatattct  8220
tctaataccct ggaatgctgt tttcccgggg atcgcagtgg tgagtaacca tgcatcatca  8280
ggagtacgga taaaatgctt gatggtcgga agaggcataa attccgtcag ccagtttagt  8340
ctgaccatct catctgtaac atcattggca acgctacctt tgccatgttt cagaaacaac  8400
tctggcgcat cgggcttccc atacaatcga tagattgtcg cacctgattg cccgacatta  8460
tcgcgagccc atttatacccc atataaatca gcatccatgt tggaatttaa tcgcggcctc  8520
gagcaagacg tttcccgttg aatatggctc ataacacccc ttgtattact gtttatgtaa  8580
gcagacagtt ttattgttca tgatgatata ttttttatctt gtgcaatgta acatcagaga  8640
ttttgagaca caacgtggct ttccccccc ccctgcagg tccgacacgg ggatggatgg  8700
cgttcccgat catggtcctg cttgcttcgg gtggcatcgg aatgccggcg ctgcaagcaa  8760
tgttgtccag gcaggtggat gaggaacgtc aggggcagct gcaaggctca ctggcggcgc  8820
tcaccagcct gacctcgatc gtcggacccc tcctcttcac ggcgatctat gcggcttcta  8880
taacaacgtg gaacgggtgg gcatggattg caggcgctgc cctctacttg ctctgcctgc  8940
cggcgctgcg tcgcgggctt tggagcggcg cagggcaacg agcgatcgc tgatcgtgga  9000
aacgataggc ctatgccatg cgggtcaagg cgacttccgg caagctatac gcgccctaga  9060
attgtcaatt ttaatcctct gtttatcggc agttcgtaga gcgcgccgtg cgtcccgagc  9120
gatactgagc gaagcaagtg cgtcgagcag tgcccgcttg ttcctgaaat gccagtaaag  9180
cgctggctgc tgaacccca gccggaactg accccacaag gccctagcgt ttgcaatgca  9240
ccaggtcatc attgacccag gcgtgttcca ccaggccgct gcctcgcaac tcttcgcagg  9300
cttcgccgac ctgctcgcgc cacttcttca cgcgggtgga atccgatccg cacatgaggc  9360
ggaaggtttc cagcttgagc gggtacggct cccggtgcga gctgaaatag tcgaacatcc  9420
gtcgggccgt cggcgacagc ttgcggtact tctcccatat gaatttcgtg tagtggtcgc  9480
cagcaaacag cacgacgatt tcctcgtcga tcaggacctg gcaacgggac gttttcttgc  9540
cacggtccag gacgcggaag cggtgcagca gcgacaccga ttccaggtgc ccaacgcggt  9600
cggacgtgaa gcccatcgcc gtcgcctgta ggcgcgacag gcattcctcg gccttcgtgt  9660
aataccggcc attgatcgac cagcccaggt cctggcaaag ctcgtagaac gtgaaggtga  9720
tcggctcgcc gataggggtg cgcttcgcgt actccaacac ctgctgccac accagttcgt  9780
catcgtcggc ccgcagctcg acgccggtgt aggtgatctt cacgtccttg ttgacgtgga  9840
aaatgacctt gttttgcagc gcctcgcgcg ggatttctt gttgcgcgtg gtgaacaggg  9900
cagagcgggc cgtgtcgttt ggcatcgctc gcatcgtgtc cggccacggc gcaatatcga  9960
acaaggaaag ctgcatttcc tttgatctgct gcttcgtgtg tttcagcaac gcggcctgct  10020
tggcctcgct gacctgtttt gccaggtcct cgccggcggt ttttcgcttc ttggtcgtca  10080
tagttcctcg cgtgtcgatg gtcatcgact tcgccaaacc tgccgcctcc tgttcgagac  10140
gacgcgaacg ctccacggcg gccgatggcg cgggcagggc aggggagcc agttgcacgc  10200
tgtcgcgctc gatcttggcc gtagcttgct ggaccatcga gccgacggac tggaaggttt  10260
cgcggggcgac acgcatgacg gtgcggcttg cgatggtttc ggcatcctcg gcggaaaacc  10320
ccgcgtcgat cagttcttgc ctgtatgcct tccggtcaaa cgtccgattc attcaccctc  10380
cttgcgggat tgccccgact cacgccgggg caatgtgccc ttattcctga tttgacccgc  10440
ctggtgcctt ggtgtccaga taatccacct tatcggcaat gaagtcggtc ccgtagaccg  10500
tctggccgtc cttctcgtac ttggtattcc gaatcttgcc ctgcacgaat accagctccg  10560
cgaagtcgct cttcttgatg gagcgcatgg ggacgtgctt ggcaatcacg cgcacccccc  10620
ggccgttttta gcggctaaaa aagtcatggc tctgccctcg gcggaccac gcccatcatg  10680
accttgccaa gctcgtcctg cttctcttcg atcttcgcca gcagggcgag gatcgtggca  10740
tcaccgaacc gcgccgtgcg cgggtcgtcg gtgagccaga gtttcagcag gccgcccagg  10800
cggcccaggt cgccattgat gcgggccagc tcgcggacgt gctcatagtc cacgacgccc  10860
gtgatttgt agccctggcc gacggccagc aggtaggcct acaggctcat gccggccgcc  10920
```

```
gccgcctttt cctcaatcgc tcttcgttcg tctggaaggc agtacacctt gataggtggg    10980
ctgcccttcc tggttggctt ggtttcatca gccatccgct tgccctcatc tgttacgccg    11040
gcggtagccg gccagcctcg cagagcagga ttcccgttga gcaccgccag gtgcgaataa    11100
gggacagtga agaaggaaca cccgctcgcg ggtgggccta cttcacctat cctgcccggc    11160
tgacgccgtt ggatacacca aggaaagtct acacgaaccc tttggcaaaa tcctgtatat    11220
cgtgcgaaaa aggatggata taccgaaaaa atcgctataa tgaccccgaa gcagggttat    11280
gcagcggaaa agatccgtc                                                 11299

SEQ ID NO: 80           moltype = DNA  length = 7341
FEATURE                 Location/Qualifiers
misc_feature            1..7341
                        note = pJSvec
source                  1..7341
                        mol_type = other DNA
                        organism = synthetic construct SEQUENCE: 80
gacccttttcc gacgctcacc gggctggttg ccctcgccgc tgggctggcg gccgtctatg    60
gccctgcaaa cgcgccagaa acgccgtcga agccgtgtgc gagacaccgc gggcgccggc     120
gttgtggata cctcgcggaa aacttggccc tcactgacag atgaggggcg gacgttgaca     180
cttgaggggc cgactcaccc ggcgcggcgt tgacagatga ggggcaggct cgatttcggc     240
cggcgacgtg gagctggcca gcctcgcaaa tcggcgaaaa cgcctgattt tacgcgagtt     300
tcccacagat gatgtggaca agcctgggga taagtgccat gcggtattga cacttgaggg     360
gcgcgactac tgacagatga ggggcgcgat ccttgacact tgagggcag agtgctgaca      420
gatgaggggc gcacctattg acatttgagg ggctgtccac aggcagaaaa tccagcattt     480
gcaagggttt ccgcccgttt ttcggccacc gctaacctgt cttttaacct gcttttaaac     540
caatatttat aaaccttgtt tttaaccagg gctgcgccct gtgcgcgtga ccgcgcacgc     600
cgaaggggggg tgcccccct tctcgaaccc tcccggcccg ctaacgcggg cctccatcc     660
ccccaggggc tgcgcccctc ggccgcgaac ggcctcaccc caaaaatggc agccaagctg     720
accacttctg cgctcggccc ttccggctgg ctggtttatt gctgataaat ctggagccgg     780
tgagcgtggg tctcgcggta tcattgcagc actggggcca gatggtaagc cctcccgtat     840
cgtagttatc tacacgacgg ggagtcaggc aactatggat gaacgaaata gacagatcgc     900
tgagataggt gcctcactga ttaagcattg gtaactgtca gaccaagttt actcatatat     960
actttagatt gatttaaaac ttcatttta atttaaaagg atctaggtga agatcctttt     1020
tgataatctc atgaccaaaa tcccttaacg tgagttttcg ttccactgag cgtcagaccc     1080
cgtagaaaag atcaaaggat cttcttgaga tcctttttt ctgcgcgtaa tctgctgctt     1140
gcaaacaaaa aaaccaccgc taccagcggt ggtttgtttg ccggatcaag agctaccaac    1200
tctttttccg aaggtaactg gcttcagcag agcgcagata ccaaatactg tccttctagt    1260
gtagccgtag ttaggccacc acttcaagaa ctctgtagca ccgcctacat acctcgctct    1320
gctaatcctg ttaccagtgg ctgctgccag tggcgataag tcgtgtctta ccgggttgga    1380
ctcaagacga tagttaccgg ataaggcgca gcggtcgggc tgaacggggg gttcgtgcac    1440
acagcccagc ttggagcgaa cgacctacac cgaactgaga tacctacagc gtgagctatg    1500
agaaagcgcc acgcttcccg aagggagaaa ggcggacagg tatccggtaa gcggcagggt    1560
cggaacagga gagcgcacga gggagcttcc aggggaaac gcctggtatc tttatagtcc     1620
tgtcgggttt cgccacctct gacttgagcg tcgattttg tgatgctcgt caggggggcg    1680
gagcctatgg aaaaacgcca gcaacgcggc ctttttacgg ttcctggcct tttgctggcc    1740
ttttgctcac atgttctttc ctgcgttatc ccctgattct gtggataacc gtattaccgc    1800
ctttgagtga gctgataccg ctcgccgcag ccgaacgacc gagcgcagcg agtcagtgag    1860
cgaggaagcg gaagagcgcc caatacgcaa accgcctctc cccgcgcgtt ggccgattca    1920
ttaatgcagc tggcaggaag cggcgatggc ggagctgaat tacattccca accgcgtggc    1980
acaacaactg gcgggcaaac agtcgttgct gattggcgtt gccacctcca gtctggccct    2040
gcacgcgccg tcgcaaattg tcgcggcgat taaatctcgc gccgatcaac tgggtgccag    2100
cgtggtggtg tcgatggtag aacgaagcgg cgtcgaagcc tgtaaagcgg cggtgcacaa    2160
tcttctcgcg caacgcgtca gtgggctgat cattaactat ccgctggatg accaggatgc    2220
cattgctgtg gaagctgcct gcactaatgt tccggcgtta tttcttgatg tctctgacca    2280
gacacccatc aacagtatta ttttctccca tgaagacggt acgcgactgg gcgtggagca    2340
tctggtcgca ttgggtcacc agcaaatcgc gctgttagcg ggcccattaa gttctgtctc    2400
ggcgcgtctg cgtctggctg gctggcataa atatctcact cgcaatcaaa ttcagccgat    2460
agcggaacgg gaaggcgact ggagtgccat gtccggtttt caacaaacca tgcaaatgct    2520
gaatgagggc atcgttccca ctgcgatgct ggttgccaac gatcagatgg cgctgggcgc    2580
aatgcgcgcc attaccgagt ccgggctgcg cgttggtgcg gatatctcgg tagtgggata    2640
cgacgatacc gaagacagct catgttatat cccgccgtca accaccatca aacaggattt    2700
tcgcctgctg gggcaaacca gcgtggaccg cttgctgcaa ctctctcagg ccaggcggt     2760
gaagggcaat cagctgttgc ccgtctcact ggtgaaaaga aaaaccaccc tggcgcccaa    2820
tacgcaaacc gcctctcccc gcgcgttggc cgattcatta atgcagctgg cacgacaggt    2880
ttcccgactg gaaagcgggc agtgagcgca acgcaattaa tgtgagttag cgcgaattga    2940
tctggtttga cagcttatca tcgactgcac ggtgcaccaa tgcttctggc gtcaggcagc    3000
catcggaagc tgtggtatgg ctgtgcaggt cgtaaatcac tgcataattc gtgtcgctca    3060
aggcgcactc ccgttctgga taatgttttt tgcgccgaca tcataacggt tctggcaaat    3120
attctgaaat gagctgttga caattaatca tccggctcgt ataatgtgtg gaattgtgag    3180
cggataacaa tttcacacag aaacagcgc cgctgagaaa aagcgaagcg gcactgctct    3240
ttaacaattt atcagacaat ctgtgtgggc actcgaccgg aattatcgat taactttatt    3300
attaaaaatt aaagaggtat atattaatgt atcgattaaa taaggaggaa taaacccaga    3360
acgcagaagc ggtctgataa aacagaattt gcctggcggc agtagcgcgg tggtcccacc    3420
tgaccccatg ccgaactcag aagtgaaacg ccgtagcgcc gatggtagtg tggggtctcc    3480
ccatgcgaga gtagggaact gccaggcatc aaataaaacg aaaggctcag tcgaaagact    3540
gggcctttcg ttttatctgt tgtttgtcgg tgaacgctct cctgagtagg acaaatcttg    3600
taggtggacc agttggtgat tttgaacttt tgctttgcca cggaacggtc tgcgttgtcg    3660
ggaagatgcg tgatctgatc cttcaactca gcaaaagttc gatttattca acaaagccgc    3720
cgtcccgtca agtcagcgta atgctctgcc agtgttacaa ccaattaacc aattctgatt    3780
```

-continued

```
agaaaaactc atcgagcatc aaatgaaact gcaatttatt catatcagga ttatcaatac    3840
catatttttg aaaaagccgt ttctgtaatg aaggagaaaa ctcaccgagg cagttccata    3900
ggatggcaag atcctggtat cggtctgcga ttccgactcg tccaacatca atacaaccta    3960
ttaatttccc ctcgtcaaaa ataaggttat caagtgagaa atcaccatga gtgacgactg    4020
aatccggtga gaatggcaaa agcttatgca tttctttcca gacttgttca acaggccagc    4080
cattacgctc gtcatcaaaa tcactcgcat caaccaaacc gttattcatt cgtgattgcg    4140
cctgagcgag acgaaatacg cgatcgctgt taaaaggaca attacaaaca ggaatcgaat    4200
gcaaccggcg caggaacact gccagcgcat caacaatatt ttcacctgaa tcaggatatt    4260
cttctaatac ctggaatgct gtttttcccgg ggatcgcagt ggtgagtaac catgcatcat    4320
caggagtacg gataaaatgc ttgatggtcg gaagaggcat aaattccgtc agccagttta    4380
gtctgaccat ctcatctgta acatcattgg caacgctacc tttgccatgt ttcagaaaca    4440
actctggcgc atcgggcttc ccatacaatc gatagattgt cgcacctgat tgcccgacat    4500
tatcgcgagc ccatttatac ccatataaat cagcatccat gttggaattt aatcgcggcc    4560
tcgagcaaga cgtttcccgt tgaatatggc tcataacacc ccttgtatta ctgtttatgt    4620
aagcagacag ttttattgtt catgatgata tattttatc ttgtgcaatg taacatcaga    4680
gattttgaga cacaacgtgg ctttcccccc ccccctgca ggtccgacac ggggatggat    4740
ggcgttcccg atcatggtcc tgcttgcttc gggtggcatc ggaatgccgg cgctgcaagc    4800
aatgttgtcc aggcaggtgg atgaggaacg tcaggggcag ctgcaaggct cactggcggc    4860
gctcaccagc ctgacctcga tcgtcggacc cctcctcttc acggcggatc atgcggcttc    4920
tataacaacg tggaacgggt gggcatggat tgcaggcgct gccctctact tgctctgcct    4980
gccggcgctg cgtcgcgggc tttggagcgg cgcagggcaa cgagccgatc gctgatcgtg    5040
gaaacgatag gcctatgcca tgcgggtcaa ggcgacttcc ggcaagctat acgcgcccta    5100
gaattgtcaa ttttaatcct ctgtttatcg gcagttcgta gagcgcgccg tgcgtcccga    5160
gcgatactga gcgaagcaag tgcgtcgagc agtgcccgct tgttcctgaa atgccagtaa    5220
agcgctggct gctgaacccc cagccggaac tgaccccaca aggccctagc gtttgcaatg    5280
caccaggtca tcattgaccc aggcgtgttc caccaggccg ctgcctcgca actcttcgca    5340
ggcttcgccg acctgctcgc gccacttctt cacgcgggtg gaatccgatc cgcacatgag    5400
gcggaaggtt tccagcttga gcgggtacgg ctcccggtgc gagctgaaat agtcgaacat    5460
ccgtcgggcc gtcggcgaca gcttgcggta cttctcccat atgaatttcg tgtagtggtc    5520
gccagcaaac agcacgacga tttcctcgtc gatcaggacc tggcaacggg acgtttttctt    5580
gccacggtcc aggacgcgga agcggtgcag cagcgacacc gattccaggt gcccaacgcg    5640
gtcggacgtg aagcccatcg ccgtcgcctg taggcgcgac aggcattcct cggccttcgt    5700
gtaataccgg ccattgatcg accagcccag gtcctggcaa agctcgtaga acgtgaaggt    5760
gatcggctcg ccgatagggg tgcgcttcgc gtactccaac acctgctgcc acaccagttg    5820
gtcatcgtcg gcccgcagct cgacgccggt gtaggtgatc ttcacgtcct tgttgacgtg    5880
gaaaatgacc ttgttttgca gcgcctcgcg cgggattttc ttgttgcgcg tggtgaacag    5940
ggcagagcgg gccgtgtcgt ttggcatcgc tcgcatcgtg tccggccacg gcgcaatatc    6000
gaacaaggaa agctgcattt ccttgatctg ctgcttcgtg tgtttcagca acgcggcctg    6060
cttggcctcg ctgacctgtt ttgccaggtc ctcgccggcg gtttttcgct tcttggtcgt    6120
catagttcct cgcgtgtcga tggtcatcga cttcgccaaa cctgccgcct cctgttcgag    6180
acgacgcgaa cgctccacgg cggccgatgg cgcgggcagg gcaggggag ccagttgcac    6240
gctgtcgcgc tcgatcttgg ccgtagcttg ctggaccatc gagccgacgg actggaaggt    6300
ttcgcggggc gcacgcatga cggtgcggct tgcgatggtt tcggcatcct cggcggaaaa    6360
ccccgcgtcg atcagttctt gcctgtatgc cttccggtca aacgtccgat tcattcaccc    6420
tccttgcggg attgcccga ctcacgccgg ggcaatgtgc ccttattcct gatttgaccc    6480
gcctggtgcc ttggtgtcca gataatccac cttatcggca atgaagtcgg tcccgtagac    6540
cgtctggccg tccttctcgt acttggtatt ccgaatcttg ccctgcacga ataccagctc    6600
cgcgaagtcg ctcttcttga tggagcgcat ggggacgtgc ttggcaatca cgcgcacccc    6660
ccggccgttt tagcggctaa aaaagtcatg gctctgccct cgggcggacc acgcccatca    6720
tgaccttgcc aagctcgtcc tgcttctctt cgatcttcgc cagcagggcg aggatcgtgg    6780
catcaccgaa ccgcgccgtg cgcgggtcgt cggtgagcca gagtttcagc aggccgccca    6840
ggcggcccag gtcgccattg atgcgggcca gctcgcggac gtgctcatag tccacgacgc    6900
ccgtgatttt gtagccctgg ccgacggcca gcaggtaggc ctacaggctc atgccggccg    6960
ccgccgcctt ttcctcaatc gctcttcgtt cgtctggaag gcagtacacc ttgataggtg    7020
ggctgccctt cctggttggc ttggtttcat cagccatccg cttgccctca tctgttacgc    7080
cggcggtagc cggccagcct cgcagagcag gattccgtt gagcaccgcc aggtgcgaat    7140
aagggacagt gaagaaggaa cacccgctcg cgggtgggcc tacttcacct atcctgcccg    7200
gctgacgccg ttgatacac caaggaaagt ctacacgaac cctttggcaa aatcctgtat    7260
atcgtgcgaa aaaggatgga tataccgaaa aaatcgctat aatgacccg aagcagggtt    7320
atgcagcgga aaagatccgt c                                              7341
```

```
SEQ ID NO: 81            moltype = DNA  length = 10705
FEATURE                  Location/Qualifiers
misc_feature             1..10705
                         note = pMZT3
source                   1..10705
                         mol_type = other DNA
                         organism = synthetic construct
SEQUENCE: 81
tcaccctgtc gggcaatgcc gaggcattct ggcagcagcg cccccctggcc tgtagtggat    60
tacgtgccgg tctgttccat cctaccaccg gctattcact gccgctggcg gttgccgtgg    120
ccgaccgcct gagcgcactt gatgtcttta cgtcggcctc aattcaccag gctattaggc    180
attttgcccg cgagcgctgg cagcagcagc gcttttttccg catgctgaat cgcatgcgt    240
ttttagccgg acccgccgat tcacgctggc gggttatgca gcgttttat ggtttacctg    300
aagatttaat tgcccgtttt tatgcgggaa aactcacgct gaccgatcgg ctacgtattc    360
tgagcggcaa gccgcctgtt ccggtattag cagcattgca agccattatg acgactcatc    420
gttaagagac agaacgaagt gtgaccagaa cgcagaagcg gtctgataaa acagaatttg    480
cctgcggca gtagcgcggt ggtcccacct gaccccatgc cgaactcaga agtgaaacgc    540
cgtagcgccg atggtagtgt ggggtctccc catgcgagag tagggaactg ccaggcatca    600
```

-continued

```
aataaaacga aaggctcagt cgaaagactg ggcctttcgt tttatctgtt gtttgtcggt   660
gaacgctctc ctgagtagga caaatcttgt aggtggacca gttggtgatt ttgaactttt   720
gctttgccac ggaacggtct gcgttgtcgg gaagatgcgt gatctgatcc ttcaactcag   780
caaaagttcg atttattcaa caaagccgcc gtcccgtcaa gtcagcgtaa tgctctgcca   840
gtgttacaac caattaacca attctgatta gaaaaactca tcgagcatca aatgaaactg   900
caatttattc atatcaggat tatcaatacc atatttttga aaaagccgtt tctgtaatga   960
aggagaaaac tcaccgaggc agttccatag gatggcaaga tcctggtatc ggtctgcgat  1020
tccgactcgt ccaacatcaa tacaacctat taatttcccc tcgtcaaaaa taaggttatc  1080
aagtgagaaa tcaccatgag tgacgactga atccggtgag aatggcaaaa gcttatgcat  1140
ttctttccag acttgttcaa caggccagcc attacgctcg tcatcaaaat cactcgcatc  1200
aaccaaaccg ttattcattc gtgattgcgc ctgagcgaga cgaaatacgc gatcgctgtt  1260
aaaaggacaa ttacaaacag gaatcgaatg caaccggcgc aggaacactg ccagcgcatc  1320
aacaatattt tcacctgaat caggatattc ttctaatacc tggaatgctg tttttcccggg  1380
gatcgcagtg gtgagtaacc atgcatcatc aggagtacgg ataaaatgct tgatggtcgg  1440
aagaggcata aattccgtca gccagtttag tctgaccatc tcatctgtaa catcattggc  1500
aacgctacct ttgccatgtt tcagaaacaa ctctggcgca tcgggcttcc catacaatcg  1560
atagattgtc gcacctgatt gcccgacatt atcgcgagcc catttatacc catataaatc  1620
agcatccatg ttggaattta atcgcggcct cgagcaagac gtttcccgtt gaatatggct  1680
cataacaccc cttgtattac tgtttatgta agcagacagt tttattgttc atgatgatat  1740
attttttatct tgtgcaatgt aacatcagag attttgagac acaacgtggc tttcccccccc  1800
ccccctgcag gtccgacacg gggatggatg gcgttcccga tcatggtcct gcttgcttcg  1860
ggtggcatcg gaatgccggc gctgcaagca atgttgtcca ggcaggtgga tgaggaacgt  1920
caggggcagc tgcaaggctc actggcggcg ctcaccagcc tgacctcgat cgtcggaccc  1980
ctcctcttca cggcgatcta tgcggcttct ataacaacgt ggaacgggtg ggcatggatt  2040
gcaggcgctg ccctctactt gctctgcctg ccggcgctgc gtcgcgggct ttggagcggc  2100
gcagggcaac gagccgatcg ctgatcgtgg aaacgataag cctatgccat gcgggtcaag  2160
gcgacttccg gcaagctata cgcgccctag aattgtcaat tttaatcctc tgtttatcgg  2220
cagttcgtag agcgcgccgt gcgtcccgag cgatactgag cgaagcaagt gcgtcgagca  2280
gtgcccgctt gttcctgaaa tgccagtaaa gcgctggctg ctgaaccccc agccggaact  2340
gaccccacaa ggccctagcg tttgcaatgc accaggtcat cattgaccca ggcgtgttcc  2400
accaggccgc tgcctcgcaa ctcttcgcag gcttcgccga cctgctcgcg ccacttcttc  2460
acgcgggtgg aatccgatcc gcacatgagg cggaaggttt ccagcttgag cgggtacggc  2520
tcccggtgcg agctgaaata gtcgaacatc cgtcgggccg tcggcgacag cttgcggtac  2580
ttctcccata tgaatttcgt gtagtggtcg ccagcaaaca gcacgacgat ttcctcgtcg  2640
atcaggacct ggcaacggga cgttttcttg ccacggtcca ggacgcggaa gcggtgcagc  2700
agcgacaccg attccaggtg cccaacgcgg tcggacgtga agcccatcgc cgtcgcctgt  2760
aggcgcgaca ggcattcctc ggccttcgtg taataccggc cattgatcga ccagcccagg  2820
tcctggcaaa gctcgtagaa cgtgaaggtg atcggctcgc cgataggggt gcgcttcgcg  2880
tactccaaca cctgctgcca caccagttcg tcatcgtcgg cccgcagctc gacgccgggtg  2940
taggtgatct tcacgtcctt gttgacgtgg aaaatgacct tgttttgcag cgcctcgcgc  3000
gggattttct tgttgcgcgt ggtgaacagg gcagagcggg ccgtgtcgtt tggcatcgct  3060
cgcatcgtgt ccggccacgg cgcaatatcg aacaaggaaa gctgcatttc cttgatctgc  3120
tgcttcgtgt gtttcagcaa cgcggcctgc ttggcctcgc tgacctgttt tgccaggtcc  3180
tcgccggcgg tttttcgctt cttggtcgtc atagttcctc gcgtgtcgat ggtcatcgac  3240
ttcgccaaac ctgccgcctc ctgttcgaga cgacgcgaac gctccacggc ggccgatggc  3300
gcgggcaggg caggggagc cagttgcacg ctgtcgcgct cgatcttggc cgtagcttgc  3360
tggaccatcg agccgacgga ctggaaggtt tcgcggggac cacgcatgac ggtgcggctt  3420
gcgatggttt cggcatcctc ggcggaaaac cccgcgtcga tcagttcttg cctgtatgcc  3480
ttccggtcaa acgtccgatt cattcaccct ccttgcggga ttgccccgac tcacgccggg  3540
gcaatgtgcc cttattcctg atttgacccg cctggtgcct tggtgtccag ataatccacc  3600
ttatcggcaa tgaagtcggt cccgtagacc gtctggccgt ccttctcgta cttggtattc  3660
cgaatcttgc cctgcacgaa taccagctcc gcgaagtcgc tcttcttgat ggagcgcatg  3720
gggacgtgct tggcaatcac gcgcacccccc cggccgtttt agcggctaaa aaagtcatgg  3780
ctctgccctc gggcggacca cgcccatcat gaccttgcca agctcgtcct gcttctcttc  3840
gatcttcgcc agcagggcga ggatcgtggc atcaccgaac cgcgccgtgc gcgggtcgtc  3900
ggtgagccag agtttcagca ggccgcccag gcggcccagg tcgccattga tgcgggccag  3960
ctcgcggacg tgctcatagt ccacgacgcc cgtgattttg tagccctggc cgacggccag  4020
caggtaggcc tacaggctca tgccggccgc cgccgccttt tcctcaatcg ctcttcgttc  4080
gtctggaagg cagtacacct tgataggtgg gctgcccttc ctggttggct tggtttcatc  4140
agccatccgc ttgccctcat ctgttacgcc ggcggtagcc ggcagcctc gcagagcagg  4200
attcccgttg agcaccgcca ggtgcgaata agggacagtg aagaaggaac acccgctcgc  4260
gggtgggcct acttcaccta tcctgcccgg ctgacgccgt tggatacacc aaggaaagtc  4320
tacacgaacc ctttggcaaa atcctgtata tcgtgcgaaa aaggatggat ataccgaaaa  4380
aatcgctata atgaccccga agcagggtta tgcagcggaa aagatccgtc gacccctttcc  4440
gacgctcacc gggctggttg ccctcgccgc tgggctggcg gccgtctatg gccctgcaaa  4500
cgcgccagaa acgccgtcga agccgtgtgc gagacaccgc ggccgccggc gttgtggata  4560
cctcgcggaa aacttggccc tcactgacag atgaggggcg gacgttgaca cttgaggggc  4620
cgactcaccc ggcgcggcgt tgacagatga ggggcaggct cgatttcggc cggcgacgtg  4680
gagctggcca gcctcgcaaa tcggcgaaaa cgcctgattt tacgcgagtt tcccacagat  4740
gatgtggaca agcctgggga taagtgccct gcggtattga cacttgaggg gcgcgactac  4800
tgacagatga ggggcgcgat ccttgacact tgaggggcag agtgctgaca gatgaggggc  4860
gcacctattg acatttgagg ggctgtccac aggcagaaaa tccagcattt gcaagggttt  4920
ccgcccgttt ttcggccacc gctaacctgt cttttaacct gcttttaaac caatatttat  4980
aaaccttgtt tttaaccagg gctgcgccct gtgcgcgtga caggggattt gccaaggggc  5040
tgcccccct tctcgaaccc tcccggcccg ctaacgcggg cctccatc ccccagggc  5100
tgcgcccctc ggccgcgaac ggcctcaccc caaaaatggc agccaagctg accacttctg  5160
cgctcggccc ttccggctgg ctggtttatt gctgataaat ctggagcggg tgagcgtggg  5220
tctcgcggta tcattgcagc actggggcca gatggtaagc cctcccgtat cgtagttatc  5280
tacacgacgg ggagtcaggc aactatggat gaacgaaata gacagatcgc tgagataggt  5340
```

-continued

```
gcctcactga ttaagcattg gtaactgtca gaccaagttt actcatatat actttagatt   5400
gatttaaaac ttcattttta atttaaaagg atctaggtga agatcctttt tgataatctc   5460
atgaccaaaa tcccttaacg tgagtttcg ttccactgag cgtcagaccc cgtagaaaag   5520
atcaaaggat cttcttgaga tccttttttt ctgcgcgtaa tctgctgctt gcaaacaaaa   5580
aaaccaccgc taccagcggt ggtttgtttg ccggatcaag agctaccaac tctttttccg   5640
aaggtaactg gcttcagcag agcgcagata ccaaatactg tccttctagt gtagccgtag   5700
ttaggccacc acttcaagaa ctctgtagca ccgcctacat acctcgctct gctaatcctg   5760
ttaccagtgg ctgctgccag tggcgataag tcgtgtctta ccgggttgga ctcaagacga   5820
tagttaccgg ataaggcgca gcggtcgggc tgaacggggg gttcgtgcac acagcccagc   5880
ttggagcgaa cgacctacac cgaactgaga tacctacagc gtgagctatg agaaagcgcc   5940
acgcttcccg aagggagaaa ggcggacagg tatccggtaa gcggcagggt cggaacagga   6000
gagcgcacga gggagcttcc aggggggaaac gcctggtatc tttatagtcc tgtcgggttt   6060
cgccacctct gacttgagcg tcgatttttg tgatgctcgt caggggggcg gagcctatgg   6120
aaaaacgcca gcaacgcggc cttttttacgg ttcctggcct tttgctggcc ttttgctcac   6180
atgttctttc ctgcgttatc ccctgattct gtggataacc gtattaccgc ctttgagtga   6240
gctgataccg ctcgccgcag ccgaacgacc gagcgcagcg agtcagtgag cgaggaagcg   6300
gaagagcgcc caatacgcaa accgcctctc cccgcgcgtt ggccgattca ttaatgcagc   6360
tggcagccag cgcttcgtta atacagatgt aggtgttcca cagggtagcc agcagcatcc   6420
tgcgatgcag atccggaaca taatggtgca gggcgctgac tttatagcta gctcagccct   6480
tggtacaatg ctagcgagca accaacactt aaagaggaga aaatgtatcc gtttataagg   6540
acagcccgaa tgacggtctg cgcaaaaaaa cacgttcatc tcactcgcga tgctgcggag   6600
cagttactgg ctgatattga tcgacgcctt gatcagttat tgcccgtgga gggagaacgg   6660
gatgttgtgt gtgccgcgat gcgtgaaggt gcgctggcac cgggaaaacg tattcgcccc   6720
atgttgctgt tgctgaccgc ccgcgatctg ggttgcgctg tcagccatga cggattactg   6780
gatttggcct gtgcggtgga aatggtccac gcggcttcgc tgatccttga cgatatgccc   6840
tgcatgacg atgcgaagct gcggcgcgga cgccctacca ttcattctca ttacggagag   6900
catgtggcaa tactggcggc ggttgccttg ctgagtaaag cctttggcgt aattgccgat   6960
gcagatggcc tcacgccgct ggcaaaaaat cgggcggttt ctgaactgtc aaacgccatc   7020
ggcatgcaag gattggttca gggtcagttc aaggatctgt ctgaagggga taagccgcgc   7080
agcgctgaag ctattttgat gacgaatcac tttaaaacca gcacgctgtt ttgtgcctcc   7140
atgcagatgg cctcgattgt tgcgaatgcc tccagcgaag cgcgtgattg cctgcatcgt   7200
tttttcacttg atcttggtca ggcatttcaa ctgctggacg atttgaccga tggcatgacc   7260
gacaccggta aggatagcaa tcaggacgcc ggtaaatcga cgctggtcaa tctgttaggc   7320
cctaggcggg ttgaagaacg tctgagacaa catcttcatc ttgccagtga gcatctctct   7380
gcggcctgcc aacacgggca cgccactcaa cattttattc aggcctggtt tgacaaaaaa   7440
ctcgctgccg tcagttaaag gtctctagac aggatgtgtc acacaggaaa ccatgaaacc   7500
aactacggta attggtgcag gcttcggtgg cctggcactg gcaattcgtc tacaggctgc   7560
ggggatcccc gtcttactgc ttgaacaacg tgataaaccc ggcggtcggg cttatgtcta   7620
cgaggatacg gggtttacct ttgatgcagg cccgacggtt atcaccgatc ccagtgccat   7680
tgaagaactg tttgcactgg caggaaaaca gttaaaagag tatgtcgaac tgctgccggt   7740
tacgccgttt taccgcctgt gttgggagtc agggaaggtc tttaattacg ataacgatca   7800
aacccggctc gaagcgcaga ttcagcagtt taatccccgc gatgtcgaag gttatcgtca   7860
gtttctggac tattcacgcg cggtgtttaa agaaggctat ctgaagctcg gtactgtccc   7920
ttttttatcg ttcagagaca tgcttcgcgc cgcacctcaa ctggcgaaac tgcaggcatg   7980
gagaagcgtt tacagtaagg ttgccagtta catcgaagat gaacatctgc gccaggcgtt   8040
ttctttccac tcgctgttgg tgggcggcaa tcccttcgcc acctcatcca tttatacgtt   8100
gatacacgcg ctggagcgtg agtgggcgt ctggttccg cgtggcggca ccggcgcatt   8160
agttcagggg atgataaagc tgtttcagga tctgggtggg gaagtcgtgt aaaacgccag   8220
agtcagccat atggaaacga caggaaacaa gattgaagcc gtgcatttag aggacggtcg   8280
caggttcctg acgcaagccg tcgcgtcaaa tgcagatgtg gttcatacct atcgcgacct   8340
gttaacgcag caccctgccg cggttaagca gtccaacaaa ctgcagacta agcgtatgag   8400
taactctctg tttgtgctct attttggttt gaatcaccat catgatcagc tcgcgcatca   8460
cacggtttgt ttcggcccgc gttaccgcga actgattgac gagattttta atcatgatgg   8520
cctcgcagaa gacttctcac tttatctgca cgcgccctgt gtcacggatt cgtcactggc   8580
gcctgaaggt tgcggcagtt actatgtgtt ggcgccggtg ccgcatttag gcaccgcgaa   8640
cctcgactga acggttgagg ggccaaaact acgcgaccgt attttttgagt accttgagca   8700
gcattacatg cctggcttac ggagtcagct ggtcacgcac cagatgttta cgccgtttga   8760
ttttcgcgac cagcttaatg cctatcaggg ctcagccttt tctgtggagc ccgttcttac   8820
ccagagcgcc tggtttcggc cgcataaccg cgataaaacc attactaatc tctacctggt   8880
cggcgcaggc acgcatcccg gcgcaggcat tcctggcgtc atcggctcgg caaaagcgac   8940
agcaggtttg atgctggagg atctgattta agtgatcgtt gagtggtgaa cttaaagagg   9000
agaaatgaa taatccgtcg ttactcaatc atgcggtcga aacgatggca gttggctcga   9060
aaagttttgc gacagcctca aagttatttg atgcaaaaac ccggcgcagc gtactgatgc   9120
tctacgcctg gtgccgccat tgtgacgatg ttattgacga ccagacgctg ggcttccagg   9180
cccggcagcc tgccttacaa acgcccgaac aacgtctgat gcaacttgag atgaaaacgc   9240
gccaggccta tgcaggatcg cagatgcacg aaccggcgtt tgcggctttt caggaagtgg   9300
ctatggctca tgatatcgcc ccggcttacg cgtttgatca tctggaaggc ttcgccatgg   9360
atgtacgcga agcgcaatac agccaactgg acgatacgct gcgctattgc tatcacgttg   9420
caggcgttgt cggcttgatg atggcgcaaa tcatgggcgt acgggataac gccacgctgg   9480
accgcgcctg tgaccttggg ctggcatttc agttgaccaa tattgctcgc gatattgtgg   9540
acgatgcgca tgcggggccgc tgttatctgc cggcaagctg gctggagcat gaaggtctga   9600
acaaagagaa ttatgcggca cctgaaaacc gtcaggcgct gagccgtatc gcccgtcgtt   9660
tggtgcagga agcagaacct tactatttgt ctgccacagc gggcctggct gggttgcccc   9720
tgcgttcgac ctgggcaatc gctacggcga agcaggttta ccggaaaata ggtgtcaaag   9780
ttgaacaggc cggtcagcaa gcctgggatc agcggcagtc aacgaccacg cccgaaaaat   9840
taacgctgct gctggcgcc tctggtcagg cccttactc ccggatgcgg gctcatcctc   9900
cccgccctgc gcatctctgg cagcgcccgc tctaatcacg tagcaagctg acagtttaaa   9960
gaggagaaa tgggagcggc tatgcaaccg cattatgatc tgattctcgt gggggctgga   10020
ctcgcgaatg gccttatcgc cctgcgtctt cagcagcagc aacctgatat gcgtattttg   10080
```

```
cttatcgacg ccgcacccca ggcgggcggg aatcatacgt ggtcatttca ccacgatgat   10140
ttgactgaga gccaacatcg ttggatagct tcgctggtgg ttcatcactg gcccgactat   10200
caggtacgct ttcccacacg ccgtcgtaag ctgaacagcg gctacttctg tattacttct   10260
cagcgtttcg ctgaggtttt acagcgacag tttggcccgc acttgtggat ggataccgcg   10320
gtcgcagagg ttaatgcgga atctgttcgg ttgaaaaagg gtcaggttat cggtgcccgc   10380
gcggtgattg acgggcgggg ttatgcggca aactcagcac tgagcgtggg cttccaggcg   10440
tttattggcc aggaatggcg attgagccac ccgcatggtt tatcgtctcc cattatcatg   10500
gatgccacgg tcgatcagca aaatggttat cgcttcgtgt acagcctgcc gctctcgccg   10560
accagattgt taattgaaga cacgcactat atcgataatg cgacattaga tcctgaacgc   10620
gcgcggcaaa atatttgcga ctatgccgcg caacaggggt ggcagcttca gacattgctg   10680
cgtgaagaac agggcgcctt accca                                          10705

SEQ ID NO: 82            moltype = DNA  length = 1773
FEATURE                  Location/Qualifiers
source                   1..1773
                         mol_type = other DNA
                         organism = Methylosinus trichosporum
SEQUENCE: 82
atggccagaa aaatgaccgg agcggaaatg gtcgtcgaag ccctgaagga tcagggcgtc   60
gagattatct tcggctatcc cggcggcgcc gtgcttccga tctatgacgc gctcttccac   120
caggagaagg tgcagcacat tctcgtgcgc cacgagcagg gcgccgccca tgcggccgag   180
ggctatgcgc gctcctccgg caaggtcggc gtgctgctga tcacctccgg acccggcgcc   240
accaacacca tcaccggcct caccgatgcg ctgatggact ccattcccgt ggtctgcatc   300
accggccagt gccgacgca tctcatcggc tcggacgcct ttcaagagtg cgatacggtc   360
ggcatcaccc gtcactgcac caagcataat tatctggtga agagcgtcga cgatctgccg   420
cgcattctgc acgaggcctt ctatgtcgcc tcgagcgggc ggccgggccc tgtggtcatc   480
gacatcccca aggatgtgca attgccagc ggaacctata ccggcccgcg caacgtccat   540
cacaagacct atcagcccaa gctcgagggc gacacggagt ctatccgccg cgccgtgaag   600
atgatggccg ccgccaagcg gccgatcttc tacaccggcg gcggcgtcat caattccggt   660
cccgcggcct cgacgctgct gcgcgagctg gtgtcgctga ccggctttcc gatcacctcg   720
accttgatgg gcctcggcgc ctatccgggc tccggcccca attggctcgg catgctcggc   780
atgcacggca ccttcgaggc caataatgcg atgcatgatt gcgatctgat gatcgccgtc   840
ggcgcgcgtt cgacgatcg catcaccgga cggctcgacg ccttctcgcc cggctcgaag   900
aagatccaca tcgatatcga tcgctcctcg atcaataaga atgtgaagat cgatctgccg   960
atcgtcggcg actgcggcca tgtgctggag agtctggtgc gcgtctggcg ctccgaggcg   1020
atgcacgccg agaagcagcc gctcgacggc tggtggaaga cgatcgacca ttggcgcgag   1080
cgcaagtcgc tcgccttccg caattcggac aaggtgatca agccgcaata cgccgtgcag   1140
cggctctatg cgctcaccaa ggatcgcgat ccctacatca cgacggaagt cggccagcat   1200
cagatgtggg ccgcgcagca ttatcatttc gacgagccca atcgctggat gacttccggc   1260
gggctcggca ccatgggcta tggtctgccg gcggcgatcg gcgcgcagct cgcgcatccg   1320
aaatcgctgg tcgtcgacat cgccggcgag gcctcgatcc tgatgaacat tcaggagatg   1380
tcgacggcga tccaatatcg gctgccggtg aaggtgttca tcctcaacaa tgaatatatg   1440
ggcatggtgc gccagtggca ggagctgctg cacggcgggc gctactcgca ctcctattcg   1500
gaggcgctgc ccgatttcgt gaagctcgcc gaagccttcg ggggcaaggg catccgctgc   1560
tcggaccccg cggagctcga tagcgcgatt ctcgagatga tcgactatga cgggccggtg   1620
atcttcgatt gtctcgtcga gaaaaacgag aattgcttcc cgatgatccc gtcgggcaag   1680
gcgcataacg acatgctgct cgccgatctc ggcgacgacg ccggcgtcga gctcggctcg   1740
atcatcgacg agaagggcaa gatgctggtg tga                                1773

SEQ ID NO: 83            moltype = DNA  length = 1056
FEATURE                  Location/Qualifiers
source                   1..1056
                         mol_type = other DNA
                         organism = Methylosinus trichosporum
SEQUENCE: 83
atgtccacca aagcctatgc cgttgcgtcc gccgaggcgc tcttcggccc gctcgcgatc   60
gagcgccgcg cgctcgggcc cgaggatgta gagatcgaca tcctctattg cggcgtctgc   120
cattccgatc tgcacacggc gcgcagtgaa tggccgggca cgcgctaccc atgcgtcccg   180
ggccacgaga ttgtcggccg cgtcaccgct gtcgtgcgca aggtgacgaa attttcggtc   240
ggcgatctcg ccgcgtcgg ctgcatggtc gacagctgcc ggcgatgctt gtcctgcgac   300
gacgggctcg aacaatattg cgagcacggt ttcaccgcca cctataacgg cccgatctac   360
ggctcgggcg agaacacctt tggcggctat tcggagaaaa tcgtcgtcga cgcgcatttc   420
gtgctggcga tccaccattc tgagacgcag cttgccggag tcgcgccgct gctctgcgcc   480
ggcatcacca cttggtcgcc gctcaagcat tggggtgtcg gcccgggaaa atcggtcggc   540
atcgtcggca tcggcgggct cggccatatg ggggtcaagc tcgcccatgc gctcggcgcc   600
catgtcgtcg ccttcaccac ctcgccgtca aagcgcgacg cggccctcgc gctcggcgcc   660
gacgaggtcg tcgtctccac agatcctgcc gctatggcgg cgcgggcggg aagcctcgac   720
ttcattctcg atacggtcgc cgtcgcccat gacctcgacg cttatgtgaa tctgttgaag   780
cgcgatgcg ctctggtgct cgtcggcgtg ccggcgacgc cgcatccctc gccatcgacg   840
ggcgggttga tcttcaagcg gcgcaggtc gccggctcgc tgatcggcgg cgtaaaggag   900
acgcaggaga tgctcgactt ctgcgccgag cgcggcattg tcgcggacat agagacgatc   960
gccatgcagc agatcgagac cgcctatgcg cgcatgctga agaatgatgt gaaataccgc   1020
ttcgtcatcg acatggcgac gctgaaggcg gcgtga                             1056

SEQ ID NO: 84            moltype = DNA  length = 1029
FEATURE                  Location/Qualifiers
source                   1..1029
                         mol_type = other DNA
                         organism = Methylococcus capsulatus
```

-continued

```
SEQUENCE: 84
atgaaagctt gggtgatcga ccgaatcggc ccgctggact cgtcgcgaac tctgctacgc    60
gccaccgacc tcccggtgcc ggagcccggc cctggcgaaa tcctgctgca ggtggcggtt   120
tgcggcgtct gccacaccga aatcgacgag atcgagggcc gcaccgcgcc gccgcgcctg   180
ccggtcgtgc ccggacacca agcggtcggt cggatcggcg ctctcggctc cggcgtggcg   240
gaattcgctt tgggcgaccg cgtcggcgtg gcctggatct tttctgcctg cggagaatgc   300
gaattctgcc ggtcgggacg ggagaacctc tgtttcgcat tctgtgccac cgggcgcgat   360
gtcgacggcg gctacgccca gtacatgacc gtcccggcgg cctttgcttt ccgcattccg   420
gagggattca ccgatgccga agcggcgccg cttctgtgcg ccggcgccat cggttaccgt   480
tcgctcaatc tcagcgggct gaaaaacggc cagccgctgg ggctcaccgg gttcggggct   540
tccgcccatc tggtgctgat gatggcccgg taccggtttc ccgattcgga agtctatgtc   600
tttgcgcgtc atcccgagga gcgcgcgttc gcgctgcagc tgggcgcggt ctgggccggc   660
gacaccgcgg acattgctcc cgccccgctg gccgccatca tcgacacgac gccggcgtgg   720
aagccggtgg tcgcagcgct cgccaacctc gctcccggtg gccggctggt cgttaatgcg   780
atccgcaagg cgccggacga tcgcgcctgt ctcgccgaac tcgactatgc ccggcacttg   840
tggatggaac gggaaatcaa gtcggtcgcc aacgtggcgc gcagtgacgt ggccgggttc   900
ctggcgctgg cggcggaaat gggcatccgt cccgagacgg aggagtaccc gttcgaggat   960
gccgaccggg cgctgctcga cctcaagcaa cgccggattc gcggggcgaa ggtgttgcgg  1020
gtgacttga                                                          1029

SEQ ID NO: 85          moltype = DNA  length = 1068
FEATURE                Location/Qualifiers
source                 1..1068
                       mol_type = other DNA
                       organism = Methylococcus capsulatus
SEQUENCE: 85
atgcctacag ccaaagccta tgccgctttt tccgcagact cggcgctggc gccgttcgtc    60
ctgcagcggc gcgacccact gccccaggac atccgcatcg gaatcctgta ctgcggtgtc   120
tgccattccg acctgcacca ggcacgcaat gagtggaatg cgaccacata tccttgtgtg   180
ccaggccatg agatcgtcgg caaggtcctt gaagtcgtga gagtcgtgac gaagttcaag   240
cccggcgaca cggtcgcggt gggctgcatg gtggattcct gccggacctg cccgaactgc   300
gtggacgccc tggaacagca ctgcgagcac ggccccgtct tcacctacaa cagccccgat   360
ccgcacggcg gcggcatgac cttcggtggc tatgccgaga gcatcgtggt cgacgaggcc   420
ttcgtgctgc ggataccgga cggactggac ctcgcggccg ccgccccgct gttgtgcgcc   480
gggattacca cctattcgcc cctgcggcac tggaaagtgg gggcgggtca gcgggtcggg   540
gtcgtcggtc tgggtggact gggacacatg gcgctcaagt tcgcgcatac cttcggcgcc   600
gaaacggtgc tgttcacgac gacgccggac aaggcggagg atgcccgtcg gctgggagcg   660
gacgaggtcg tcgtgtcgag ggatcccgag gccatgcgcg ggcaggccgg ccggttcgat   720
ttcatcctcg acaccgtctc ggcgccccat gacatcgatc cctatctgaa cctgctgagg   780
cgggacggca cgctgaccct ggtcggcgta cctccgcaag gggtacaggt catgcccttc   840
agcctgatcg gcgggcgccg gcgactggct ggttcattga tcggcggcat ccgggaaacc   900
caggagatgc tggatttctg cggcgaacac ggcatcgtct gcgacatcga gctgattccg   960
atccaaggaa tcaacgacgc cttcgagcgc atgctcaaaa gcgacgtgaa ataccgtttc  1020
gtgatcgaca tggccgacgct gaacggggag tcgtccggag ggcgatga             1068

SEQ ID NO: 86          moltype = DNA  length = 1647
FEATURE                Location/Qualifiers
source                 1..1647
                       mol_type = other DNA
                       organism = Lactococcus lactis
SEQUENCE: 86
atgtacaccg tgggcgacta tctgctggac cggctgcatg aactgggcat cgaggaaatc    60
ttcggcgtcc ccggcgacta taacctgcag ttcctggacc agatcatcag ccgcaaggac   120
atgaagtggg tgggcaacgc caacgagctg aacgcctcgt acatggcgga cggctatgcc   180
cggaccaaga aggccgcggc cttcctgacc accttcggcg tcggcgaact gagcgccgtg   240
aacggcctgg cgggctcgta cgccgagaac ctgccggtcg tggaaatcgt cggctccccc   300
accagcaagg tgcagaacga gggcaagttc gtccaccata ccctggccga cggcgacttc   360
aagcacttca tgaagatgca tgaaccggtg accgcggccc gcaccctgct gaccgccgag   420
aacgcgaccg tcgaaatcga ccgcgtgctg agcgcgctgc tgaaggagcg gaagccggtc   480
tatatcaacc tgcccgtcga cgtggcggcc gcgaaggccg agaagccgtc cctgcccctg   540
aagaaggaaa accccacctc gaacacctcg gaccaggaga tcctgaacaa gatccaggaa   600
agcctgaaga acgccaagaa gccgatcgtg atcaccggcc acgagatcat ctcgttcggc   660
ctggaaaaca ccgtcaccca gttcatctcc aagaccaagc tgccgatcac caccctgaac   720
ttcggcaaga gctcggtgga cgagaccctg ccctcgttcc tgggcatcta caacggcaag   780
ctgtccgaac cgaacctgaa ggagttcgtg gaaagcgcgg acttcatcct gatgctgggc   840
gtcaagctga ccgactccag caccggcgcc ttcacccacc atctgaacga gaacaagatg   900
atctcgctga acatcgacga gggcaagatc ttcaacgaat ccatccagaa cttcgacttc   960
gaaagcctga tctcgtccct gctggacctg tccggcatcg agtacaaggg caagtatatc  1020
gacaagaagc aggaagactt cgtcccgagc aacgcgctga tgtcgcagga ccgcctgtgg  1080
caggccgtgg agaacctgac ccagagcaac gagaccatcg tcgcggaaca gggcacctcg  1140
ttcttcggcg ccagctcgat cttcctgaag ccgaagtcgc acttcatcgg ccagcccctg  1200
tggggctcca tcggctacac cttccccgcc gcgctgggct cgcagatcgc ggacaaggaa  1260
tcccggcatc tgctgttcat cggcgacggc agcctgcagc tgaccgtgca ggagctgggc  1320
ctggccatcc gcgaaaagat caacccgatc tgcttcatca tcaacaacga cggctatacc  1380
gtcgagcggg aaatccacgg cccgaaccag tcgtacaacg acatccccat gtggaactat  1440
tccaagctgc cggagagctt cggcgccacc gaggaacgcg tcgtgtccaa gatcgtccgg  1500
accgagaacg agttcgtcag cgtgatgaag gaagcccagg cggaccccaa ccggatgtac  1560
tggatcgagc tggtgctggc gaaggaagac gccccgaagg tcctgaagaa gatgggcaag  1620
ctgttcgccg aacagaacaa gagctga                                     1647
```

```
SEQ ID NO: 87            moltype = DNA  length = 1692
FEATURE                  Location/Qualifiers
source                   1..1692
                         mol_type = other DNA
                         organism = Saccharomyces cerevisiae
SEQUENCE: 87
atgtcggaaa tcaccctggg caagtacctg ttcgagcggc tgaagcaggt caacgtcaac   60
accatcttcg gcctgcccgg cgacttcaac ctgagcctgc tggacaagat ctacgaggtc  120
gacggcctgc gctgggccgg caacgcgaac gaactgaacg ccgcgtacgc cgcggacggc  180
tatgcccgga tcaagggcct gtcggtcctg gtgaccacct cggccgtggg cgagctgtcg  240
gccctgaacg gcatcgccgg ctcctacgcg gaacacgtcg gcgtgctgca tgtcgtgggc  300
gtcccgagca tctcggccca ggcgaagcag ctgctgctgc accataccct gggcaacggc  360
gacttcaccg tgttccaccg catgtccgcc aacatcagcg agaccacctc gatgatcacc  420
gacatcgcca ccgcgccgag cgaaatcgac cgcctgatcc ggaccacctt catcacccag  480
cggccgtcgt acctgggcct gcccgccaac ctggtcgacc tgaaggtgcc gggcagcctg  540
ctggagaagc ccatcgacct gtcgctgaag ccgaacgacc ccgaggccga aaaggaagtc  600
atcgacaccg tgctggaact gatccagaac agcaagaacc cggtcatcct gtccgacgcc  660
tgcgcgagcc gccacaacgt gaagaaggag acccagaagc tgatcgacct gacccagttc  720
ccggccttcg tcaccccct gggcaagggc tccatcgacg agcagcatcc gcggtacggc  780
ggcgtctatg tgggcaccct gagcaagcag gacgtcaagc aggccgtgga aagcgcggac  840
ctgatcctgt cggtgggcgc cctgctgtcc gacttcaaca cggctccttc cagctactcg  900
tataagacca agaacgtcgt ggagttccat tcggactacg tcaaggtgaa gaacgcgacc  960
ttcctgggcg tccagatgaa gttcgccctg cagaacctgc tgaaggtgat cccggacgtc 1020
gtgaagggct ataagtccgt cccggtgccc accaagaccc ccgccaacaa gggcgtcccg 1080
gcgtcgaccc ccctgaagca ggaatggctg tggaacgagc tgtccaagtt cctgcaggaa 1140
ggcgacgtga tcatctcgga gaccggcacc tccgcgttcg gcatcaacca gaccatcttc 1200
ccgaaggacg cctacggcat cagccaggtc ctgtggggct cgatcggctt caccaccggc 1260
gccaccctgg gcgccgcgtt cgccgcggag gaaatcgacc cgaacaagcg cgtcatcctg 1320
ttcatcggcg acggctccct gcagctgacc gtgcaggaaa tcagcaccat gatccggtcg 1380
ggcctgaagc cctacctgtt cgtgctgaac aacgacggct ataccatcga gaagctgatc 1440
cacggccgc atgcggaata caacgagatc cagacctggg accacctggc cctgctgccc 1500
gccttcggcc cgaagaagta tgaaaaccat aagatcgcca ccaccggcga gtgggacgcg 1560
ctgaccaccg actccgagtt ccagaagaac agcgtcatcc gcctgatcga gctgaagctg 1620
ccggtgttcg acgcccccga aagcctgatc aagcaggcgc agctgaccgc cgcgaccaac 1680
gccaagcagt ga                                                     1692

SEQ ID NO: 88            moltype = DNA  length = 1908
FEATURE                  Location/Qualifiers
source                   1..1908
                         mol_type = other DNA
                         organism = Saccharomyces cerevisiae
SEQUENCE: 88
atggccccg tcaccatcga gaagttcgtc aaccaggaag agcggcatct ggtgtccaac   60
cggagcgcga ccatcccgtt cggcgagtac atcttcaagc gcctgctgag catcgacacc  120
aagtcggtgt tcggcgtgcc gggcgacttc aacctgagcc tgctggagta cctgtatagc  180
ccctcggtcg aatcggccgg cctgcgctgg gtgggcaacc gcaacgaact gaacgccgcg  240
tacgccgcgg acggctactc ccggtatagc aacaagatcg gctgcctgat caccaccat  300
ggcgtcggcg aactgtcggc gctgaacggc atcgcgggct ccttcgccga aacgtgaag  360
gtcctgcaca tcgtgggcgt cgccaagtcg atcgactccc gcagctcgaa cttctcggac  420
cggaacctgc accatctggt cccgcagctg catgactcca acttcaaggg ccccaaccac  480
aaggtgtacc atgacatggt gaaggaccgc gtccgcgtgc ccgtggccta tctggaggac  540
atcgaaaccg cctgcgacca ggtggacaac gtcatccggg acatctacaa gtatagcaag  600
ccgggttaca tcttcgtccc cgcggacttc gccgacatgt ccgtgacctg cgacaacctg  660
gtgaacgtcc cgcgcatcag ccagcaggac tgcatcgtgt acccctccga aaaccagctg  720
agcgacatca tcaacaagat cacctcgtgg atctactcca gcaagacccc ggccatcctg  780
ggcgacgtcc tgaccgaccg gtatggcgtg agcaacttcc tgaacaagct gatctgcaag  840
accggcatct ggaacttctc gaccgtcatg ggcaagtcgg tgatcgacga tccaacccg  900
acctacatgg gccagtataa cggcaaggaa ggctgaagc aggtctacga gcacttcgaa  960
ctgtgcgacc tggtcctgca tttcggcgtg gacatcaacg agatcaacaa cggccactac 1020
accttcacct ataagccgaa cgcgaagatc atccagttcc atcccaacta catccgcctg 1080
gtggacaccc ggcagggcaa cgaacagatg ttcaagggca tcaacttcgc cccgatcctg 1140
aaggagctgt ataagcgcat cgacgtcagc aagctgtcgc tgcagtacga cagcaacgtg 1200
acccagtata ccaacgagac catgcggctg gaagacccca gcaacggcca gtcgtccatc 1260
atcacccagg tccacctgca gaagaccatg ccgaagttcc tgaacccggg cgacgtcgtg 1320
gtctgcgaga ccggctcctt ccagttcagc gtgcgcgact cgcgttccc gagccagctg 1380
aagtacatct cgcagggctt cttcctgtcc atcggcatgg ccctgcccgc cgcgctgggc 1440
gtcggcatcg cgatgcagga ccactcgaac gcccatatca acggcggcaa cgtgaaggaa 1500
gactacaagc cgcggctgat cctgttcgaa ggcgacgtcg agcgccagat gaccatccag 1560
gagctgtcca ccatcctgaa gtgcaacatc ccgctggaag tcatcatctg gaacaacaac 1620
ggctacacca tcgagcgcgc catcatgggc cccacccgga gctataacga cgtgatgtcg 1680
tggaagtgga ccaagctgtt cgaagcgttc ggcgacttcg acggcaagta caccaactcc 1740
accctgatcc agtgcccgag caagctggcc ctgaagctga ggaactgaa gaactcgaac 1800
aagcgctccg gcatcgagct gctggaagtc aagctgggcg agctggactt ccccgaacag 1860
ctgaagtgca tggtggaggc cgcggccctg aagcggaaca agaagtga             1908

SEQ ID NO: 89            moltype = DNA  length = 1047
FEATURE                  Location/Qualifiers
source                   1..1047
```

```
                     mol_type = other DNA
                     organism = Saccharomyces cerevisiae
SEQUENCE: 89
atgagcatcc ccgagaccca gaaggccatc atcttctacg agagcaacgg caagctggaa    60
cataaggaca tcccggtgcc caagcccaag ccgaacgaac tgctgatcaa cgtgaagtac   120
agcggcgtct gccacaccga cctgcacgcg tggcatggcg actggccgct gcccaccaag   180
ctgcccctgg tgggcggcca tgaaggcgcc ggcgtcgtgg tcggcatggg cgagaacgtc   240
aagggctgga agatcggcga ctacgcgggc atcaagtggc tgaacggcag ctgcatggcc   300
tgcgagtatt gcgaactggg caacgaatcg aactgcccgc acgcggacct gtccggctac   360
acccatgacg gcagcttcca ggagtatgcc accgcggacg ccgtgcaggc cggcgacatc   420
ccgcagggca ccgacctggc ggaggtggcc cccatcctgt gcgccggcat caccgtctac   480
aaggcgctga gagcgccaa cctgcgcgcg ggccattggg ccgcgatctc gggcgccgcc    540
ggtggcctgg gctccctggc cgtgcagtac gcgaaggcga tgggctaccg cgtcctgggc   600
atcgacggcg gtccgggcaa ggaagagctg ttcacctccc tgggcgacgg agtgttcatc   660
gacttcacca aggagaagga catcgtcagc gccgtggtca aggcgaccaa cggcggcgcc   720
cacggcatca tcaacgtgtc ggtctccgaa gccgcgatcg aggcgtcgac ccgctactgc   780
cgggccaacg gcaccgtggt cctggtgggc ctgcccgcgg gcgccaagtg cagctcggac   840
gtcttcaacc atgtggtcaa gagcatctcg atcgtgggct cgtatgtcgg caaccgcggc   900
gacacccgcg aggccctgga cttcttcgcc cgtggcctgg tcaagtcccc gatcaaggtg   960
gtcggcctgt ccagcctgcc cgagatctac gaaaagatgg agaagggcca gatcgccggc  1020
cgctatgtgg tcgacacctc caagtga                                       1047

SEQ ID NO: 90        moltype = DNA  length = 1692
FEATURE              Location/Qualifiers
source               1..1692
                     mol_type = other DNA
                     organism = Saccharomyces cerevisiae
SEQUENCE: 90
atgagcgaga tcaccctggg caagtacctg ttcgagcggc tgaagcaggt caacgtcaac    60
accgtcttcg gcctgcccgg cgacttcaac ctgagcctgc tggacaagat ctacgaggtc   120
gaaggcatgc gctgggcggg caacgccaac gagctgaacg ccgcgtacgc cgcggacggc   180
tatgcccgga tcaagggcat gtcgtgcatc atcaccacct tcggcgtggg cgagctgtcc   240
gccctgaacg gcatcgcggg cagctacgcc gaacacgtcg gcgtgctgca tgtcgtgggc   300
gtcccgagca tctcggccca ggcgaagcag ctgctgctgc accataccct gggcaacggc   360
gacttcaccg tgttccaccg catgtccgcg aacatcagcg agaccaccgc catgatcacc   420
gacatcgcca ccgcgccggc cgaaatcgac cgctgcatcc ggaccaccta cgtcacccag   480
cggcccgtgt atctgggcct gccggccaac ctggtcgacc tgaacgtgcc cgcgaagctg   540
ctgcagaccc cgatcgacat gtcgctgaag cccaacgacg ccgagtccga aaaggaagtc   600
atcgacacca tcctggcgct ggtcaaggac gccaagaacc cggtgatcct ggcggacgcc   660
tgctgctccc gccacgacgt caaggccgag accaagaagc tgatcgacct gacccagttc   720
cccgccttcg tgaccccgat gggcaagggc tccatcgacg aacagcatcc gcggtacggc   780
ggcgtctatg tgggcaccct gagcaagccc gaagtcaagg aagccgtgga aagcgccgac   840
ctgatcctgt cggtcggcgc cctgctgtcc gacttcaaca ccgctcctt cagctactcg    900
tataagacca agaacatcgt ggagttccac agcgaccaca tgaagatccg caacgccacc   960
ttccccggcg tccagatgaa gttcgtgctg cagaagctgc tgaccaccat cgccgacgcc  1020
gcgaagggct acaagccggt cgcggtgccc gcccggaccc cggcgaacgc cgcggtcccc  1080
gcctcgaccc cgctgaagca ggaatggatg tggaaccagc tgggcaactt cctgcaggaa  1140
ggcgacgtcg tgatcgcgga aaccggcacc tccgccttcg gcatcaacca gaccaccttc  1200
ccgaacaaca cctacggcat cagccaggtg ctgtggggct cgatcggctt caccaccggc  1260
gccaccctgg gcgccgcgtt cgccgcggag gaaatcgacc cgaagaagcg cgtcatcctg  1320
ttcatcggcg acggcaacct gcagctgacc gtgcaggaaa tctcgaccat gatccggttg  1380
ggcctgaagc cctacctgtt cgtcctgaac aacgacggct ataccatcga gaagctgatc  1440
cacggcccga aggcccagta caacgaaatc cagggctggg accatctgtc gctgctgccc  1500
accttcggcg ccaaggacta tgagacccat cgcgtggcga ccaccggcga atgggacaag  1560
ctgacccagg acaagtcgtt caacgacaac tccaagatcc ggatgatcga gatcatgctg  1620
cccgtcttcg acgcgccgca gaacctggtg gaacaggcca agctgaccgc cgcgaccaac  1680
gcgaagcagt ga                                                       1692

SEQ ID NO: 91        moltype = DNA  length = 3147
FEATURE              Location/Qualifiers
source               1..3147
                     mol_type = other DNA
                     organism = Saccharomyces cerevisiae
SEQUENCE: 91
atgaagtcgg aatacaccat cggccgctat ctgctggacc gcctgagcga gctgggcatc    60
cgccacatct tcggcgtccc cggcgactac aacctgtcgt tcctggacta catcatggag   120
tataagggca tcgactgggt cggcaactgc aacgaactga cgccggcta cgccgcggac    180
ggctatgccc gcatcaacgg catcggccgc atcctgacca ccttcggcgt cggcgagctg   240
tccgccatca acgccatcgc gggcgcctac gcggaacagg tgccggtcgt gaagatcccc   300
ggcatccca ccgccaaggt ccgcgacaac ggcctgtatg tgcaccatac cctgggcgac    360
ggccgcttcg accacttctt cgagatgttc cgggaagtca ccgtggccga ggcgctgctg   420
agcgaggaaa acgccgcgca ggaaatcgac cgcgtgctga tctcgtgctg cgccagaag    480
cggccggtcc tgatcaacct gcccatcgac gtgtacgaca gccgatcaa caagccgctg    540
aagcccctgc tggactatac catcagctcg aacaaggaag ccgtgttcgt cacc         600
gagatcgtgc cgatcatcaa ccgcgccaag aagcccgtca tcctggcgga ctacggcgtg   660
taccggtatc aggtccagca cgtgctgaag aacctggccg agaagaccgg cttccccggtc  720
gccaccctgt cgatgggcaa gggcgtgttc aacgaagccc atccgcagtt catcggcgtc   780
tacaacggca cgtgtccag ccctatctg cgccagcggg tcgacgaggc cgactgcatc     840
atctcggtcg gcgtgaagct gaccgactcc accaccggcg gcttctccca cggcttcagc   900
```

-continued

```
aagcgcaacg tgatccatat cgacccgttc tccatcaagg ccaagggcaa gaagtacgcg      960
cccatcacca tgaaggacgc cctgaccgaa ctgacctcga agatcgagca ccggaacttc     1020
gaagacctgg acatcaagcc gtacaagtcc gacaaccaga agtatttcgc gaaggagaag     1080
cccatcaccc agaagcgctt cttcgaacgg atcgcccatt tcatcaagga gaaggacgtc     1140
ctgctggcgg aacagggcac ctgcttcttc ggcgccagca ccatccagct gccgaaggac     1200
gcgaccttca tcggccagcc cctgtggggc tccatcggct acaccctgcc ggccctgctg     1260
ggcagccagc tggcggacca gaagcgtcgc aacatcctgc tgatcggcga cggcgccttc     1320
cagatgaccg cgcaggagat ctcgaccatg ctgcgcctgc agatcaagcc gatcatcttc     1380
ctgatcaaca acgacgcgta caccatcgag cgcgccatcc acggccggga acaggtgtac     1440
aacaacatcc agatgtggcg gtatcataac gtcccgaagg tgctgggccc caaggaatgc     1500
agcctgacct tcaaggtcca gtcggagacc gaactggaga aggccctgct ggtcgccgac     1560
aaggactgcg agcacctgat cttcatcgaa gtcgtgatgg accgctacga caagccggag     1620
cccctggaac gcctgtccaa gcggttcgcc aaccagaaca acggctatgc gcggatcaac     1680
ggcatcggcg ccattttaac caccttcggc gtgggcgagc tgagcgcgat caacgcgatc     1740
gccggcgcct acgcggagca ggtgccggtg gtcaaaatta ccggcatccc caccgcgaag     1800
gtgcgggaca acggcctgta cgtccatcac accctgggcg acggccggtt cgaccatttc     1860
ttcgaaatgt tccgggaggt gaccgtcgcc gaggcgctgc tgtcggaaga gaacgcggcc     1920
caggagatcg accgcgtcct gatcagctgc tggcggcaga agcccccgt gctgatcaac     1980
ctgccgatcg acgtctatga caagcccatc aacaagcccc tgaagccgct gctggactac     2040
accatctcgt ccaacaagga agccgcctgc gagttcgtca ccgaaatcgt ccccatcatc     2100
aaccgcgcga agaagccggt gatcctggcc gactatggcg tctatcggta tcaggtgcag     2160
catgtcctga agaacctggc cgaaaagacc ggcttcccg tggccaccct gagcatggac     2220
aagggcgtct tcaacgaggc gcaccccag ttcatcggcg tgtataacgg cgacgtgagc     2280
tcgccgtacc tgcggcagcg cgtggacgaa gccgactgca tcatcagcgt cggcgtcaag     2340
ctgaccgact cgaccaccgg cggcttctcg cacggcttct cgaagcggaa cgtcatccac     2400
atcgacccgt tctcgatcaa ggcgaagggc aagaagtatg cccgatcac catgaaggac     2460
gcgctgaccg aactgaccag caagatcgaa catcgcaact tcgaggacct ggacatcaag     2520
ccctacaagt cggacaacca gaagtacttc gccaaggaaa agccgattac tcagaagcgc     2580
ttcttcgagc gcatcgcgca cttcatcaag gaaaaggacg tcctgctggc cgagcaaggc     2640
acctgcttct tcggtgcgtc gaccatccag ctgcccaagg acgccacctt catcggccag     2700
ccgctgtggg gctcgatcgg ctataccctg cccgcgctgc tgggctccca gctggccgat     2760
caaaaacgtc gcaatatttt actgatcggc gacggcgcgt tccagatgac cgcccaggag     2820
atcagcacca tgctgcgggct gcagatcaag cccattatct tcctgattaa caacgacggc     2880
tataccatcg aacgggcgat ccacggccgc gagcaggtct ataataatat tcaaatgtgg     2940
cggtatcata atgtgcccaa ggtcctgggc ccgaaggaat gctcgctgac cttcaaggtg     3000
cagagcgaaa ccgagctgga aaaggccctg ctggtcgccg ataaggactg cgaacatctg     3060
atcttcatcg aggtggtcat ggaccggtat gacaagcccg aaccctggga acggctgagc     3120
aagcgcttcg cgaaccagaa caactga                                       3147
```

SEQ ID NO: 92        moltype = DNA   length = 35
FEATURE              Location/Qualifiers
misc_feature        1..35
                    note = JPS00082
source              1..35
                    mol_type = other DNA
                    organism = synthetic construct
SEQUENCE: 92
tgcaaggtac actgtcagaa cgcagaagcg gtctg                              35

SEQ ID NO: 93        moltype = DNA   length = 28
FEATURE              Location/Qualifiers
misc_feature        1..28
                    note = JPS00031
source              1..28
                    mol_type = other DNA
                    organism = synthetic construct
SEQUENCE: 93
ggtttattcc tccttattta atcgatac                                     28

SEQ ID NO: 94        moltype = DNA   length = 34
FEATURE              Location/Qualifiers
misc_feature        1..34
                    note = JPS00032
source              1..34
                    mol_type = other DNA
                    organism = synthetic construct
SEQUENCE: 94
aaggaggaat aaaccatggg cacggttgag cctg                              34

SEQ ID NO: 95        moltype = DNA   length = 33
FEATURE              Location/Qualifiers
misc_feature        1..33
                    note = GMV257
source              1..33
                    mol_type = other DNA
                    organism = synthetic construct
SEQUENCE: 95
cacatcctgt ctagatcagc cctcgccctt gac                               33

-continued

```
SEQ ID NO: 96          moltype = DNA   length = 58
FEATURE                Location/Qualifiers
misc_feature           1..58
                       note = JPS00118)
source                 1..58
                       mol_type = other DNA
                       organism = synthetic construct
SEQUENCE: 96
tctagacagg atgtgtcaca caggaaacca tgtcttatcc tgagaaattt gaaggtat        58

SEQ ID NO: 97          moltype = DNA   length = 41
FEATURE                Location/Qualifiers
misc_feature           1..41
                       note = JPS00119
source                 1..41
                       mol_type = other DNA
                       organism = synthetic construct
SEQUENCE: 97
acagtgtacc ttgcactagt ctgaaaattc tttgtcgtag c                          41

SEQ ID NO: 98          moltype = DNA   length = 70
FEATURE                Location/Qualifiers
misc_feature           1..70
                       note = ESG00087
source                 1..70
                       mol_type = other DNA
                       organism = synthetic construct
SEQUENCE: 98
gtgttggttg ctcgctagca ttgtaccaag ggctgagcta gctataaagt cagcgccctg      60
caccattatg                                                             70

SEQ ID NO: 99          moltype = DNA   length = 46
FEATURE                Location/Qualifiers
misc_feature           1..46
                       note = GMV251
source                 1..46
                       mol_type = other DNA
                       organism = synthetic construct
SEQUENCE: 99
gagcaaccaa cacttaaaga ggagaaaatg ggcacggttg agcctg                     46

SEQ ID NO: 100         moltype = DNA   length = 149
FEATURE                Location/Qualifiers
misc_feature           1..149
                       note = IDT gBlock synthesized rnpB
source                 1..149
                       mol_type = other DNA
                       organism = synthetic construct
SEQUENCE: 100
gctagcacta gtgatcacgt gcttaagccg gcttatcggt cagtttcacc tgatttacgt      60
aaaaacccgc ttcggcgggt ttttgctttt ggaggggcag aaagatgaat gactgtccac     120
gacgctatac ccaaaagaaa accggtacc                                       149

SEQ ID NO: 101         moltype = DNA   length = 35
FEATURE                Location/Qualifiers
misc_feature           1..35
                       note = JPS00161
source                 1..35
                       mol_type = other DNA
                       organism = synthetic construct
SEQUENCE: 101
gcctgataca gattattgta ggtggaccag ttggt                                 35

SEQ ID NO: 102         moltype = DNA   length = 34
FEATURE                Location/Qualifiers
misc_feature           1..34
                       note = JPS00162
source                 1..34
                       mol_type = other DNA
                       organism = synthetic construct
SEQUENCE: 102
ggtttattcc tccttgattt gtcctactca ggag                                  34

SEQ ID NO: 103         moltype = DNA   length = 34
FEATURE                Location/Qualifiers
misc_feature           1..34
                       note = JPS00163
source                 1..34
                       mol_type = other DNA
```

-continued

```
                          organism = synthetic construct
SEQUENCE: 103
aaggaggaat aaaccgctag cactagtgat cacg                                    34

SEQ ID NO: 104           moltype = DNA   length = 34
FEATURE                  Location/Qualifiers
misc_feature             1..34
                         note = JPS00164
source                   1..34
                         mol_type = other DNA
                         organism = synthetic construct
SEQUENCE: 104
taatctgtat caggcggtac cggttttctt ttgg                                    34

SEQ ID NO: 105           moltype = DNA   length = 34
FEATURE                  Location/Qualifiers
misc_feature             1..34
                         note = JPS00172
source                   1..34
                         mol_type = other DNA
                         organism = synthetic construct
SEQUENCE: 105
atcagactaa gccttgtgct taagccggct tatc                                    34

SEQ ID NO: 106           moltype = DNA   length = 51
FEATURE                  Location/Qualifiers
misc_feature             1..51
                         note = JPS00173
source                   1..51
                         mol_type = other DNA
                         organism = synthetic construct
SEQUENCE: 106
aaggaggaat aaaccgctag cactagtgat cacttgacgg ctagctcagt c                 51

SEQ ID NO: 107           moltype = DNA   length = 33
FEATURE                  Location/Qualifiers
misc_feature             1..33
                         note = JPS00174
source                   1..33
                         mol_type = other DNA
                         organism = synthetic construct
SEQUENCE: 107
tgaacaggtc tgacttcagt gctgcgccga ggc                                     33

SEQ ID NO: 108           moltype = DNA   length = 51
FEATURE                  Location/Qualifiers
misc_feature             1..51
                         note = JPS00176
source                   1..51
                         mol_type = other DNA
                         organism = synthetic construct
SEQUENCE: 108
agtcagacct gttcattaaa gaggagaaaa tgcagattta ctacgacaaa g                 51

SEQ ID NO: 109           moltype = DNA   length = 34
FEATURE                  Location/Qualifiers
misc_feature             1..34
                         note = JPS00177
source                   1..34
                         mol_type = other DNA
                         organism = synthetic construct
SEQUENCE: 109
aagtgttggt tgctctcagt tcttgctcgt gtcc                                    34

SEQ ID NO: 110           moltype = DNA   length = 45
FEATURE                  Location/Qualifiers
misc_feature             1..45
                         note = JPS00157
source                   1..45
                         mol_type = other DNA
                         organism = synthetic construct
SEQUENCE: 110
gagcaaccaa cacttaaaga ggagaaaatg accgacaagc acccc                        45

SEQ ID NO: 111           moltype = DNA   length = 33
FEATURE                  Location/Qualifiers
misc_feature             1..33
                         note = JPS00178
source                   1..33
```

-continued

```
                        mol_type = other DNA
                        organism = synthetic construct
SEQUENCE: 111
aaggcttagt ctgattcaga ggccgtcgtc ggt                                        33

SEQ ID NO: 112          moltype = DNA   length = 430
FEATURE                 Location/Qualifiers
misc_feature            1..430
                        note = IDT gBlock synthesized Me-AM1 PmxaF
source                  1..430
                        mol_type = other DNA
                        organism = synthetic construct
SEQUENCE: 112
atggtgcagg gcgcttcccg cttggtcggg ccgcttcgcg agggcccgtt gacgacaacg          60
gtgcgatggg tcccggcccc ggtcaagacg atgccaatac gttgcgacac tacgccttgg          120
cacttttaga attgccttat cgtcctgata agaaatgtcc gaccagctaa agacatcgcg          180
tccaatcaaa gcctagaaaa tataggcgaa gggacgctaa taagtctttc ataagaccgc          240
gcaaatctaa aaatatcctt agattcacga tgcggcactt cggatgactt ccgagcgagc          300
ctggaacctc agaaaaacgt ctgagagata ccgcgaggcc gaaaggcgag gcggttcagc          360
gaggagacgc aggatgagca ggtttgtgac atcagtctcg gccttggcgg ctagcgagca          420
accaacactt                                                                  430

SEQ ID NO: 113          moltype = DNA   length = 34
FEATURE                 Location/Qualifiers
misc_feature            1..34
                        note = JPS00169
source                  1..34
                        mol_type = other DNA
                        organism = synthetic construct
SEQUENCE: 113
agcgccctgc accattatgt tccggatctg catc                                       34

SEQ ID NO: 114          moltype = DNA   length = 46
FEATURE                 Location/Qualifiers
misc_feature            1..46
                        note = GMV00251
source                  1..46
                        mol_type = other DNA
                        organism = synthetic construct
SEQUENCE: 114
gagcaaccaa cacttaaaga ggagaaaatg ggcacggttg agcctg                          46

SEQ ID NO: 115          moltype = DNA   length = 32
FEATURE                 Location/Qualifiers
misc_feature            1..32
                        note = (PS00170
source                  1..32
                        mol_type = other DNA
                        organism = synthetic construct
SEQUENCE: 115
atggtgcagg gcgcttcccg cttggtcggg cc                                         32

SEQ ID NO: 116          moltype = DNA   length = 19
FEATURE                 Location/Qualifiers
misc_feature            1..19
                        note = JPS00171
source                  1..19
                        mol_type = other DNA
                        organism = synthetic construct
SEQUENCE: 116
aagtgttggt tgctcgcta                                                        19

SEQ ID NO: 117          moltype = DNA   length = 68
FEATURE                 Location/Qualifiers
misc_feature            1..68
                        note = JPS00153
source                  1..68
                        mol_type = other DNA
                        organism = synthetic construct
SEQUENCE: 117
accactcaac gatcagctag cactgtacct aggactgagc tagccgtcaa gtcagcgccc          60
tgcaccat                                                                    68

SEQ ID NO: 118          moltype = DNA   length = 48
FEATURE                 Location/Qualifiers
misc_feature            1..48
                        note = JPS00151
source                  1..48
                        mol_type = other DNA
```

```
                          organism = synthetic construct
SEQUENCE: 118
tgatcgttga gtggtttaaa gaggagaaaa tgcgtgaaac gatacctc                    48

SEQ ID NO: 119           moltype = DNA   length = 33
FEATURE                  Location/Qualifiers
misc_feature             1..33
                         note = JPS00154
source                   1..33
                         mol_type = other DNA
                         organism = synthetic construct
SEQUENCE: 119
aagtgttggt tgctctcagt gctgcgccga ggc                                    33

SEQ ID NO: 120           moltype = DNA   length = 33
FEATURE                  Location/Qualifiers
misc_feature             1..33
                         note = JPS00183
source                   1..33
                         mol_type = other DNA
                         organism = synthetic construct
SEQUENCE: 120
tgagctagct ataaagtgat cactagtgct agc                                    33

SEQ ID NO: 121           moltype = DNA   length = 55
FEATURE                  Location/Qualifiers
misc_feature             1..55
                         note = JPS00185
source                   1..55
                         mol_type = other DNA
                         organism = synthetic construct
SEQUENCE: 121
ttatagctag ctcagccctt ggtacaatgc tagctgatcg ttgagtggtt taaag           55

SEQ ID NO: 122           moltype = DNA   length = 35
FEATURE                  Location/Qualifiers
misc_feature             1..35
                         note = J23100
source                   1..35
                         mol_type = other DNA
                         organism = synthetic construct
SEQUENCE: 122
ttgacggcta gctcagtcct aggtacagtg ctagc                                  35

SEQ ID NO: 123           moltype = DNA   length = 35
FEATURE                  Location/Qualifiers
misc_feature             1..35
                         note = J23100 hybrid
source                   1..35
                         mol_type = other DNA
                         organism = synthetic construct
SEQUENCE: 123
ttgacggcta gctcagccct tggtacaatg ctagc                                  35

SEQ ID NO: 124           moltype = DNA   length = 35
FEATURE                  Location/Qualifiers
misc_feature             1..35
                         note = J23115
source                   1..35
                         mol_type = other DNA
                         organism = synthetic construct
SEQUENCE: 124
tttatagcta gctcagccct tggtacaatg ctagc                                  35

SEQ ID NO: 125           moltype = DNA   length = 22
FEATURE                  Location/Qualifiers
misc_feature             1..22
                         note = GMV00233
source                   1..22
                         mol_type = other DNA
                         organism = synthetic construct
SEQUENCE: 125
tgccagctgc attaatgaat cg                                                22

SEQ ID NO: 126           moltype = DNA   length = 45
FEATURE                  Location/Qualifiers
misc_feature             1..45
                         note = GMV00235
source                   1..45
```

-continued

```
                              mol_type = other DNA
                              organism = synthetic construct
SEQUENCE: 126
ttaatgcagc tggcagccag cgcttcgtta atacagatgt aggtg                        45

SEQ ID NO: 127          moltype = DNA   length = 52
FEATURE                 Location/Qualifiers
misc_feature            1..52
                        note = GMV00433
source                  1..52
                        mol_type = other DNA
                        organism = synthetic construct
SEQUENCE: 127
gatcgttgag tggtgaactt aaagaggaga aaatgggcac ggttgagcct gg              52

SEQ ID NO: 128          moltype = DNA   length = 19
FEATURE                 Location/Qualifiers
misc_feature            1..19
                        note = GMV00434
source                  1..19
                        mol_type = other DNA
                        organism = synthetic construct
SEQUENCE: 128
tgcattcgat tcctgtttg                                                     19

SEQ ID NO: 129          moltype = DNA   length = 19
FEATURE                 Location/Qualifiers
misc_feature            1..19
                        note = GMV00435
source                  1..19
                        mol_type = other DNA
                        organism = synthetic construct
SEQUENCE: 129
caggaatcga atgcaaccg                                                     19

SEQ ID NO: 130          moltype = DNA   length = 49
FEATURE                 Location/Qualifiers
misc_feature            1..49
                        note = GMV00436
source                  1..49
                        mol_type = other DNA
                        organism = synthetic construct
SEQUENCE: 130
gagcaaccaa cactcacaca ggaaaccatg catattacat acgatctgc                   49

SEQ ID NO: 131          moltype = DNA   length = 39
FEATURE                 Location/Qualifiers
misc_feature            1..39
                        note = GMV00437
source                  1..39
                        mol_type = other DNA
                        organism = synthetic construct
SEQUENCE: 131
gttcaccact caacgatctt aagcgtcaac gaaaccggt                              39

SEQ ID NO: 132          moltype = DNA   length = 69
FEATURE                 Location/Qualifiers
misc_feature            1..69
                        note = GMV00438
source                  1..69
                        mol_type = other DNA
                        organism = synthetic construct
SEQUENCE: 132
tgaacaggtc tgactgctag cattgtacca agggctgagc tagctataaa gatttgtcct       60
actcaggag                                                               69

SEQ ID NO: 133          moltype = DNA   length = 53
FEATURE                 Location/Qualifiers
misc_feature            1..53
                        note = GMV00439
source                  1..53
                        mol_type = other DNA
                        organism = synthetic construct
SEQUENCE: 133
agtcagacct gttcattaaa gaggagaaaa tgagcggaaa aaccctttac gac              53

SEQ ID NO: 134          moltype = DNA   length = 42
FEATURE                 Location/Qualifiers
misc_feature            1..42
```

-continued

```
                              note = GMV00440
source                        1..42
                              mol_type = other DNA
                              organism = synthetic construct
SEQUENCE: 134
aaggcttagt ctgattcaga cggcgcgcaa ggcggcgacg at                        42

SEQ ID NO: 135               moltype = DNA   length = 49
FEATURE                       Location/Qualifiers
misc_feature                  1..49
                              note = GMV00441
source                        1..49
                              mol_type = other DNA
                              organism = synthetic construct
SEQUENCE: 135
atcagactaa gcctttcaca caggaaacca tgcacgacag actgatcat               49

SEQ ID NO: 136               moltype = DNA   length = 35
FEATURE                       Location/Qualifiers
misc_feature                  1..35
                              note = GMV00442
source                        1..35
                              mol_type = other DNA
                              organism = synthetic construct
SEQUENCE: 136
ggtttattcc tcctttcaca catccccgac ttgcg                             35

SEQ ID NO: 137               moltype = DNA   length = 49
FEATURE                       Location/Qualifiers
misc_feature                  1..49
                              note = ESG00084
source                        1..49
                              mol_type = other DNA
                              organism = synthetic construct
SEQUENCE: 137
gagacagaac gaagtgtgac cagaacgcag aagcggtctg ataaaacag              49

SEQ ID NO: 138               moltype = DNA   length = 70
FEATURE                       Location/Qualifiers
misc_feature                  1..70
                              note = ESG00088
source                        1..70
                              mol_type = other DNA
                              organism = synthetic construct
SEQUENCE: 138
gtgttggttg ctcgctagca ctgtacctag gactgagcta gccgtcaagt cagcgccctg  60
caccattatg                                                          70

SEQ ID NO: 139               moltype = DNA   length = 10705
FEATURE                       Location/Qualifiers
misc_feature                  1..10705
                              note = pMZT37
source                        1..10705
                              mol_type = other DNA
                              organism = synthetic construct
SEQUENCE: 139
tcaccctgtc gggcaatgcc gaggcattct ggcagcagcg ccccctggcc tgtagtggat  60
tacgtgccgg tctgttccat cctaccaccg gctattcact gccgctggcg gttgccgtgg  120
ccgaccgcct gagcgcactt gatgtcttta cgtcggcctc aattcaccag gctattaggc  180
attttgcccg cgagcgctgg cagcagcagc gcttttccg catgctgaat cgcatgctgt  240
tttttagccgg acccgccgat tcacgctggc gggttatgca gcgttttat ggtttacctg   300
aagatttaat tgcccgtttt tatgcgggaa aactcacgct gaccgatcgg ctacgtattc  360
tgagcggcaa gccgcctgtt ccggtattag cagcattgca agccattatg acgactcatc  420
gttaagagac agaacgaagt gtgaccagaa cgcagaagcg gtctgataaa acagaatttg  480
cctggcggca gtagcgcggt ggtcccacct gaccccatgc cgaactcaga agtgaaacgc  540
cgtagcgccg atggtagtgt ggggtctccc catgcgagag tagggaactg ccaggcatca  600
aataaaacga aaggctcagt cgaaagactg ggcctttcgt tttatctgtt gtttgtcggt  660
gaacgctctc ctgagtagga caaatcttgt aggtggacca gttggtgatt ttgaactttt  720
gctttgccac ggaacggtct gcgttgtcgg gaagatgcgt gatctgatcc ttcaactcag  780
caaaagttcg atttattcaa caaagccgcc gtcccgtcaa gtcagcgtaa tgctctgcca  840
gtgttacaac caattaacca attctgatta gaaaaactca tcgagcatca aatgaaactg  900
caatttattc atatcaggat tatcaatacc atatttttga aaaagccgtt tctgtaatga  960
aggagaaaac tcaccgaggc agttccatag gatggcaaga tcctggtatc ggtctgcgat  1020
tccgactcgt ccaacatcaa tacaacctat taatttcccc tcgtcaaaaa taaggttatc  1080
aagtgagaaa tcaccatgag tgacgactga atccggtgag aatggcaaaa gcttatgcat  1140
ttctttccag acttgttcaa caggccagcc attacgctcg tcatcaaaat cactcgcatc  1200
aaccaaaccg ttattcattc gtgattgcgc ctgagcgaga cgaaatacgc gatcgctgtt  1260
aaaaggacaa ttacaaacag gaatcgaatg caaccggcgc aggaacactg ccagcgcatc  1320
aacaatattt tcacctgaat caggatattc ttctaatacc tggaatgctg ttttcccggg  1380
```

-continued

```
gatcgcagtg gtgagtaacc atgcatcatc aggagtacgg ataaaatgct tgatggtcgg   1440
aagaggcata aattccgtca gccagtttag tctgaccatc tcatctgtaa catcattggc   1500
aacgctacct ttgccatgtt tcagaaacaa ctctggcgca tcgggcttcc catacaatcg   1560
atagattgtc gcacctgatt gcccgacatt atcgcgagcc catttatacc catataaatc   1620
agcatccatg ttggaattta atcgcggcct cgagcaagac gtttcccgtt gaatatggct   1680
cataacaccc cttgtattac tgtttatgta agcagacagt tttattgttc atgatgatat   1740
attttatct tgtgcaatgt aacatcagag attttgagac acaacgtggc tttcccccc     1800
cccctgcag gtccgacacg gggatggatg gcgttcccga tcatggtcct gcttgcttcg    1860
ggtggcatcg gaatgccggc gctgcaagca atgttgtcca ggcaggtgga tgaggaacgt   1920
caggggcagc tgcaaggctc actggcggcg ctcaccagcc tgacctcgat cgtcggaccc   1980
ctcctcttca cggcgatcta tgcggcttct ataacaacgt ggaacgggtg ggcatggatt   2040
gcaggcgctg ccctctactt gctctgcctg ccggcgctgc gtcgcgggct ttggagcggc   2100
gcagggcaac gagccgatcg ctgatcgtgg aaacgatagg cctatgccat gcgggtcaag   2160
gcgacttccg gcaagctata cgcgccctag aattgtcaat tttaatcctc tgtttatcgg   2220
cagttcgtag agcgcgccgt gcgtcccgag cgatactgag cgaagcaagt gcgtcgagca   2280
gtgcccgctt gttcctgaaa tgccagtaaa gcgctggctg ctgaaccccc agccggaact   2340
gaccccacaa ggccctagcg tttgcaatgc accaggtcat cattgaccca ggcgtgttcc   2400
accaggccgc tgcctcgcaa ctcttcgcag gcttcgccga cctgctcgcg ccacttcttc   2460
acgcgggtgg aatccgatcc gcacatgagg cggaaggttt ccagcttgag cgggtacggc   2520
tcccggtgcg agctgaaata gtcgaacatc cgtcgggccg tcggcgacag cttgcggtac   2580
ttctcccata tgaatttcgt gtagtggtcg ccagcaaaca gcacgacgat ttcctcgtcg   2640
atcaggacct ggcaacggga cgttttcttg ccacggtcca ggacgcggaa gcggtgcagc   2700
agcgacaccg attccaggtg cccaacgcgg tcggacgtga agcccatcgc cgtcgcctgt   2760
aggcgcgaca ggcattcctc ggccttcgtg taataccggc cattgatcga ccagcccagg   2820
tcctggcaaa gctcgtagaa cgtgaaggtg atcggctcgc cgataggggt gcgcttcgcg   2880
tactccaaca cctgctgcca caccagttcg tcatcgtcag cccgcagctc gacgcgggtg   2940
taggtgatct tcacgtcctt gttgacgtgg aaaatgacct tgttttgcag cgcctcgcgc   3000
gggattttct tgttgcgcgt ggtgaacagg gcagagcggg ccgtgtcgtt tggcatcgct   3060
cgcatcgtgt ccggccacgg cgcaatatcg aacaaggaaa gctgcatttc cttgatctgc   3120
tgcttcgtgt gtttcagcaa cgccggcctgc ttggcctcgc tgacctgttt tgccaggtcc  3180
tcgccggcgg tttttcgctt cttggtcgtc atagttcctc gcgtgtcgat ggtcatcgac   3240
ttcgccaaac ctgccgcctc ctgttcgaga cgacgcgaac gctccacggc ggccgatggc   3300
gcgggcaggg caggggagc cagttgcacg ctgtcgcgct cgatcttggc cgtagcttgc    3360
tggaccatcg agccgacgga ctggaaggtt tcgcggggcg cacgcatgac ggtgcggctt   3420
gcgatggttt cggcatcctc ggcggaaaac cccgcgtcga tcagttcttg cctgtatgcc   3480
ttccggtcaa acgtccgatt cattcaccct ccttgcggga ttgccccgac tcacgccggg   3540
gcaatgtgcc cttattcctg atttgacccg cctggtgcct tggtgtccag ataatccacc   3600
ttatcggcaa tgaagtcggt cccgtagacc gtctggccgt ccttctcgta cttggtattc   3660
cgaatcttgc cctgcacgaa taccagctcc gcgaagtcgc tcttcttgat ggagcgcatg   3720
gggacgtgct tggcaatcac gcgcaccccc cggccgtttt agcggctaaa aaagtcatgg   3780
ctctgccctc gggcggacca cgcccatcat gaccttgcca agctcgtcct gcttctcttc   3840
gatcttcgcc agcagggcga ggatcgtggc atcaccgaac cgcgccgtgc gcgggtcgtc   3900
ggtgagccag agtttcagca ggccgcccag gcggcccaag tcgccattga tgcgggccag   3960
ctcgcggacg tgctcatagt ccacgacgcc cgtgattttg tagccctggc cgacggccag   4020
caggtaggcc tacaggctca tgccggccgc cgccgccttt tcctcaatcg ctcttcgttc   4080
gtctggaagg cagtacacct tgataggtgg gctgcccttc ctggttggct tggtttcatc   4140
agccatccgc ttgccctcat ctgttacgcc ggcggtaacc gcgagagcagg              4200
attcccgttg agcaccgcca ggtgcgaata agggacagtg aagaaggaac acccgctcgc   4260
gggtgggcct acttcaccta tcctgcccgg ctgacgccgt tggatacacc aaggaaagtc   4320
tacacgaacc ctttggcaaa atcctgtata tcgtgcgaaa aaggatggat ataccgaaaa   4380
aatcgctata atgaccccga agcaggggtta tgcagcggaa aagatccgtc gacccctttcc  4440
gacgctcacc gggctggttg ccctcgccgc tgggctggcg gccgtctatg gccctgcaaa   4500
cgcgccagaa acgccgtcga agccgtgtgc gagacaccgc ggccgccggc gttgtggata   4560
cctcgcggaa aacttggccc tcactgacag atgaggggcg gacgttgaca cttgaggggc   4620
cgactcaccc ggcgcggcgt tgacagatga ggggcacgct cgatttcggc cggcgacgtg   4680
gagctggcca gcctcgcaaa tcggcgaaaa cgcctgattt tacgcgagtt tcccacagat   4740
gatgtggaca agcctgggga taagtgccct gcggtattga cacttgaggg gcgcgactac   4800
tgacagatga ggggcgcgat ccttgacact tgaggggcag agtgctgaca gatgaggggc   4860
gcacctattg acatttgagg ggctgtccac aggcagaaaa tccagcattt gcaagggttt   4920
ccgcccgttt ttcggccacc gctaacctgt cttttaacct gcttttaaac caatatttat   4980
aaaccttgtt tttaaccagg ctgcgccct gtgcgcgtga ccgcgcacgc cgaagggggg    5040
tgccccccct tctcgaaccc tcccggcccg ctaacgcggg cctccatccc cccaggggc     5100
tgcgcccctc ggccgcgaac ggcctcaccc caaaaatggc agccaagctg accacttctg   5160
cgctcggccc ttccggctgg ctggtttatt gctgataaat ctggagccgg tgagcgtggg   5220
tctcgcggta tcattgcagc actggggcca gatggtaagc cctcccgtat cgtagttatc   5280
tacacgacgg ggagtcaggc aactatggat gaacgaaata gacagatcgc tgagataggt   5340
gcctcactga ttaagcattg gtaactgtca gaccaagttt actcatatat actttagatt   5400
gatttaaaac ttcatttta atttaaaagg atctaggtga agatccttt tgataatctc     5460
atgaccaaaa tcccttaacg tgagttttcg ttccactgag cgtcagaccc cgtagaaaag   5520
atcaaaggat cttcttgaga tcctttttt ctgcgcgtaa tctgctgctt gcaaacaaaa    5580
aaaccaccgc taccagcggt ggtttgtttg ccggatcaag agctaccaac tctttttccg   5640
aaggtaactg gcttcagcag agcgcagata ccaaatactg tccttctagt gtagccgtag   5700
ttaggccacc acttcaagaa ctctgtagca ccgcctacat acctcgctct gctaatcctg   5760
ttaccagtgg ctgctgccaa tggcgataag tcgtgtctta ccgggttgga ctcaagacga   5820
tagttaccgg ataaggcgca gcggtcgggc tgaacggggg gttcgtgcac acagcccagc   5880
ttggagcgaa cgacctacac cgaactgaga tacctacagc gtgagctatg agaaagcgcc   5940
acgcttcccg aagggagaaa ggcggacagg tatccggtaa gcggcagggt cggaacagga   6000
gagcgcacga gggagcttcc aggggggaaac gcctggtatc tttatagtcc tgtcgggttt   6060
cgccacctct gacttgagcg tcgatttttg tgatgctcgt caggggggcg gagcctatgg   6120
```

-continued

```
aaaaacgcca gcaacgcggc cttttttacgg ttcctggcct tttgctggcc ttttgctcac    6180
atgttctttc ctgcgttatc ccctgattct gtggataacc gtattaccgc ctttgagtga    6240
gctgataccg ctcgccgcag ccgaacgacc gagcgcagcg agtcagtgag cgaggaagcg    6300
gaagagcgcc caatacgcaa accgcctctc cccgcgcgtt ggccgattca ttaatgcagc    6360
tggcagccag cgcttcgtta atacagatgt aggtgttcca cagggtagcc agcagcatcc    6420
tgcgatgcag atccggaaca taatggtgca gggcgctgac ttgacggcta gctcagtcct    6480
aggtacagtg ctagcgagca accaacactt aaagaggaga aaatgtatcc gtttataagg    6540
acagcccgaa tgacggtctg cgcaaaaaaa cacgttcatc tcactcgcga tgctgcggag    6600
cagttactgg ctgatattga tcgacgcctt gatcagttat tgcccgtgga gggagaacgg    6660
gatgttgtgg gtgccgcgat gcgtgaaggt gcgctggcac cgggaaaacg tattcgcccc    6720
atgttgctgt tgctgaccgc ccgcgatctg ggttgcgctg tcagccatga cggattactg    6780
gatttggcct gtgcggtgga aatggtccac gcggcttcgc tgatccttga cgatatgccc    6840
tgcatggacg atgcgaagct gcggcgcgga cgccctacca ttcattctca ttacggagag    6900
catgtggcaa tactggccgc ggttgccttg ctgagtaaag cctttggcgt aattgccgat    6960
gcagatggcc tcacgccgct ggcaaaaaat cgggcggttt ctgaactgtc aaacgccatc    7020
ggcatgcaag gattggttca gggtcagttc aaggatctgt ctgaagggga taagccgcgc    7080
agcgctgaag ctattttgat gacgaatcac tttaaaacca gcacgctgtt ttgtgcctcc    7140
atgcagatgg cctcgattgt tgcgaatgcc tccagcgaag cgcgtgattg cctgcatcgt    7200
ttttcacttg atcttggtca ggcatttcaa ctgctggacg atttgaccga tggcatgacc    7260
gacaccggta aggatagcaa tcaggacgcc ggtaaatcga cgctggtcaa tctgttaggc    7320
cctagggcgg ttgaagaacg tctgagacaa catcttcatc ttgccagtga gcatctctct    7380
gcggcctgcc aacacgggca cgccactcaa cattttattc aggcctggtt tgacaaaaaa    7440
ctcgctgccg tcagttaaag gtctctagac aggatgtgtc acacaggaaa ccatgaaacc    7500
aactacggta attggtgcag gcttcggtgg cctggcactg gcaattcgtc tacaggctgc    7560
ggggatcccc gtcttactgc ttgaacaacg tgataaaccc ggcggtcggg cttatgtcta    7620
cgaggatcag gggtttacct ttgatgcagg cccgacggtt atcaccgatc ccagtgccat    7680
tgaagaactg tttgcactgg caggaaaaca gttaaaagac tatgtcgaac tgctgccggt    7740
tacgccgttt taccgcctgt gttgggagtc agggaaggtc tttaattacg ataacgatca    7800
aacccggctc gaagcgcaga ttcagcagtt taatccccgc gatgtcgaag gttatcgtca    7860
gtttctggac tattcacgcg cggtgtttaa agaaggctat ctgaagctcg gtactgtccc    7920
ttttttatcg ttcagagaca tgcttcgcgc cgcacctcaa ctggcgaaac tgcaggcatg    7980
gagaagcgtt tacagtaagg ttgccagtta catcgaagat gaacatctgc gccaggcgtt    8040
ttctttccac tcgctgttgg tgggcggcaa tcccttcgcc acctcatcca tttatacgtt    8100
gatacacgcg ctggagcgtg agtggggcgt ctggtttccg cgtggcggca ccggcgcatt    8160
agttcagggg atgataaagc tgtttcagga tctgggtggt gaagtcgtgt taaacgccag    8220
agtcagccat atggaaacga caggaaacaa gattgaagcc gtgcatttag aggacggtcg    8280
caggttcctg acgcaagccg tcgcgtcaaa tgcagatgtg gttcatacct atcgcgacct    8340
gttaagccag caccctgccg cggttaagca gtccaacaaa ctgcagacta agcgtatgag    8400
taactctctg tttgtgctct attttggttt gaatcaccat catgatcagc tcgcgcatca    8460
cacggtttgt ttcggcccgc gttaccgcga actgattgac gagatttta atcatgatgg    8520
cctcgcagaa gacttctcac tttatctgca cgcgccctgt gtcacggatt cgtcactggc    8580
gcctgaaggt tgcggcagtt actatgtgtt ggcgccggtg ccgcatttag gcaccgcgaa    8640
cctcgactga acggttgagg ggccaaaact acgcgacctg attttttgagt accttgagca    8700
gcattacatg cctggcttac ggagtcagct ggtcacgcac cagatgttta cgccgtttga    8760
ttttcgcgac cagcttaatg cctatcaggg ctcagccttt tctgtggagc ccgttcttac    8820
ccagagcgcc tggtttcggc cgcataaccg cgataaaacc attactaatc tctacctggt    8880
cggcgcaggc acgcatcccg gcgcaggcat tcctggcgtc atcggctcgg caaaagcgac    8940
agcaggtttg atgctggagg atctgattta agtgatcgtc gagtggtgaa cttaaagagg    9000
agaaatgaa taatccgtcg ttactcaatc atgcggtcga aacgatggca gttggctcga    9060
aaagttttgc gacagcctca aagttatttg atgcaaaaac ccggcgcagc gtactgatgc    9120
tctacgcctg gtgccgccat tgtgacgatg ttattgacga ccagacgctg ggcttccagg    9180
cccggcagcc tgccttacaa acgcccgaac aacgtctgat gcaacttgag atgaaaacgc    9240
gccaggccta tgcaggatcg cagatgcacg aaccggcgtt tgcggctttt caggaagtgg    9300
ctatggctca tgatatcgcc ccggcttacg cgtttgatca tctggaaggc ttcgccatgg    9360
atgtacgcga agcgcaatac agccaactgg acgataccgct gcgctattgc tatcacgttg    9420
caggcgttgt cggcttgatg atggcgcaaa tcatggcgca cgggataac gccacgctgg    9480
accgcgcctg tgaccttggg ctggcatttc agttgaccaa tattgctcgc gatattgtgg    9540
acgatgcgca tgcgggccgc tgttatctgc cggcaagctg gctggagcat gaaggtctga    9600
acaaagagaa ttatgcggca cctgaaaacc gtcaggcgct gagccgtatc gcccgtcgtt    9660
tggtgcagga agcagaacct tactatttgt ctgccacagc gggcctggct gggttgcccc    9720
tgcgttcggc ctgggcaatc gctacggcga agcaggttta ccggaaaata ggtgtcaaag    9780
ttgaacaggc cggtcagcaa gcctgggatc agcggcagtc aacgaccacg cccgaaaaat    9840
taacgctgct gctggccgcc tctggtcagg cccttacttc ccggatgcgg gctcatcctc    9900
cccgccctgc gcatctctgg cagcgcccgc tctaatcacg tagcaagctg acagtttaaa    9960
gaggagaaaa tgggagcggc tatgcaaccg cattatgatc tgattctcgt ggggctgga   10020
ctcgcgaatg gccttatcgc cctgcgtctt cagcagcagc aacctgatat gcgtattttg   10080
cttatcgacg ccgcacccca ggcggcgggg aatcatacgt ggtcatttca ccacgatgat   10140
ttgactgaga gccaacatcg ttggatagct tcgctggtgg ttcatcactg gcccgactat   10200
caggtacgct ttcccacacg ccgtcgtaag ctgaacagcg gctacttctg tattacttct   10260
cagcgtttcg ctgaggtttt acagcgacag tttggcccgc acttgtggat ggataccgcg   10320
gtcgcagagg ttaatgcgga atctgttcgg ttgaaaaagg gtcaggttat cggtgcccgc   10380
gcggtgattg acgggcgggg ttatgcggca aactcagcac tgagcgtggg cttccaggcg   10440
tttattggcc aggaatggcg attgagccac ccgcatggtt tatcgtctcc cattatcatg   10500
gatgccacgg tcgatcagca aaatggttat cgcttcgtgt acagcctgcc tctcgcgtca   10560
accagattgt taattgaaga cacgcactat atcgataatg cgacattaga tcctgaacgc   10620
gcgcggcaaa atatttgcga ctatgccgcg caacagggtt ggcagcttca gacattgctg   10680
cgtgaagaac agggcgcctt accca                                          10705
```

SEQ ID NO: 140          moltype = DNA   length = 411

```
FEATURE               Location/Qualifiers
misc_feature          1..411
                      note = MaFAR-g1
source                1..411
                      mol_type = other DNA
                      organism = synthetic construct
SEQUENCE: 140
gagcaaccaa cacttaaaga ggagaaaatg gcgacccagc agcagcagaa cggcgcctcg   60
gcgagcggcg tcctggaaca gttgcgcggg aagcatgtcc tgataaccgg taccaccggt  120
ttccttggca aggtagtcct ggaaaagctg atccgcacag tcccggacat cggcggcatc  180
cacctcctga tccggggcaa caagaggcat ccggccgccc gtgaacggtt cttgaacgag  240
atcgccagca gttcggtctt cgagcgtctg cgccacgacg acaacgaggc cttcgaaacc  300
ttcctggaag aaagggtgca ctgtataacc ggagaggtca ccgagagtcg tttcggcctt  360
accccggagc gcttccgcgc gctggcgggt caggtggacg ccttcatcaa t           411

SEQ ID NO: 141       moltype = DNA   length = 465
FEATURE               Location/Qualifiers
misc_feature          1..465
                      note = MaFAR-g2
source                1..465
                      mol_type = other DNA
                      organism = synthetic construct
SEQUENCE: 141
gacgccttca tcaattcggc cgcctccgtc aacttccgcg aggaactgga caaggcgctg   60
aagatcaata cgctgtgcct ggagaatgtc gcggcccttg ctgaactcaa cagtgcgatg  120
gcggtcatcc aggtttcgac ctgctacgtt aacggcaagg atagcgggca gatcaccgaa  180
tcggtcatca agcccgcggg ggagtccatc ccgcgtagca ccgatgggta ctatgaaatc  240
gaagaattgg tgcacctgct gcaggacaaa atcagcgatg tgaaggcccg atactccggg  300
aaggttctgg aaaaaaaatt ggtggaccta ggcatccggg aagccaataa ctacgggtgg  360
agcgatacat ataccttcac caagtggctg ggcgaacagc tcctcatgaa ggccctgagc  420
ggcagatcgc tgaccatcgt gcggccgtcg atcatcgagt cggca                  465

SEQ ID NO: 142       moltype = DNA   length = 374
FEATURE               Location/Qualifiers
misc_feature          1..374
                      note = MaFAR-g3
source                1..374
                      mol_type = other DNA
                      organism = synthetic construct
SEQUENCE: 142
atcatcgagt cggcattgga agagcccagc ccggggtgga ttgaaggcgt caaggtcgcc   60
gatgccatca tactggccta cgcgagggag aaggtatcgc tctttcctgg caagcggagc  120
ggcatcatcg acgtcatccc agtggatctg gtggccaatt cgatcattct gtccctgggc  180
gaggcgctct ccggttcggg ccagcggcgt atctatcagt gctgcagcgg cggctcgaac  240
cccatctccc tcgggaagtt catcgactat ctgatggcgg aggcgaagac caactacgcg  300
gcctacgatc agctgttcta ccgccgcccc accaagccgt tcgtggccgt caaccgcaaa  360
ctcttcgacg tcgt                                                    374

SEQ ID NO: 143       moltype = DNA   length = 376
FEATURE               Location/Qualifiers
misc_feature          1..376
                      note = MaFAR-g4
source                1..376
                      mol_type = other DNA
                      organism = synthetic construct
SEQUENCE: 143
actcttcgac gtcgtcgtgg gcggcatgcg ggtcccgctc tcgatcgcgg gcaaagccat   60
gcgcctggcg ggacaaaacc gcgaactgaa ggtcctgaag aatctggata cgacccggtc  120
cctggccacc attttcgggt tctacaccgc tccggactac atctttcgca atgacagcct  180
gatggccctg gcctcgcgca tgggcgagct ggaccgcgtg ttgttccccg ttgacgcccg  240
tcagatcgac tggcagctgt atctgtgcaa aatccacctc ggcgggctga atcggtacgc  300
gctcaaggaa cgtaagctgt actcgctccg ggccgccgac actcgcaaga aggcagcctg  360
agagacagaa cgaagt                                                  376

SEQ ID NO: 144       moltype = DNA   length = 47
FEATURE               Location/Qualifiers
misc_feature          1..47
                      note = GMV410
source                1..47
                      mol_type = other DNA
                      organism = synthetic construct
SEQUENCE: 144
gagcaaccaa cacttaaaga ggagaaaatg cgccccctgc accccat                47

SEQ ID NO: 145       moltype = DNA   length = 47
FEATURE               Location/Qualifiers
misc_feature          1..47
                      note = GMV411
source                1..47
```

-continued

```
                              mol_type = other DNA
                              organism = synthetic construct
SEQUENCE: 145
gagcaaccaa cacttaaaga ggagaaaatg cgcctgctga ccgccgt                47

SEQ ID NO: 146          moltype = DNA   length = 47
FEATURE                 Location/Qualifiers
misc_feature            1..47
                        note = GMV412
source                  1..47
                        mol_type = other DNA
                        organism = synthetic construct
SEQUENCE: 146
gagcaaccaa cacttaaaga ggagaaaatg tccgtgatgt ccccgac                47

SEQ ID NO: 147          moltype = DNA   length = 47
FEATURE                 Location/Qualifiers
misc_feature            1..47
                        note = GMV413
source                  1..47
                        mol_type = other DNA
                        organism = synthetic construct
SEQUENCE: 147
gagcaaccaa cacttaaaga ggagaaaatg ccggtcaccg actccat                47

SEQ ID NO: 148          moltype = DNA   length = 47
FEATURE                 Location/Qualifiers
misc_feature            1..47
                        note = GMV414
source                  1..47
                        mol_type = other DNA
                        organism = synthetic construct
SEQUENCE: 148
gagcaaccaa cacttaaaga ggagaaaatg gccccgaccg actccct                47

SEQ ID NO: 149          moltype = DNA   length = 47
FEATURE                 Location/Qualifiers
misc_feature            1..47
                        note = GMV415
source                  1..47
                        mol_type = other DNA
                        organism = synthetic construct
SEQUENCE: 149
gagcaaccaa cacttaaaga ggagaaaatg cccctgccga tgtcccc                47

SEQ ID NO: 150          moltype = DNA   length = 35
FEATURE                 Location/Qualifiers
misc_feature            1..35
                        note = GMV416
source                  1..35
                        mol_type = other DNA
                        organism = synthetic construct
SEQUENCE: 150
acttcgttct gtctctcagt tggcggtctt gatgt                             35

SEQ ID NO: 151          moltype = DNA   length = 35
FEATURE                 Location/Qualifiers
misc_feature            1..35
                        note = ACTTCGTTCTGTCTCTCACGGGGCCAGCTTCTTCA
source                  1..35
                        mol_type = other DNA
                        organism = synthetic construct
SEQUENCE: 151
acttcgttct gtctctcacg gggccagctt cttca                             35

SEQ ID NO: 152          moltype = DNA   length = 35
FEATURE                 Location/Qualifiers
misc_feature            1..35
                        note = GMV418
source                  1..35
                        mol_type = other DNA
                        organism = synthetic construct
SEQUENCE: 152
acttcgttct gtctctcagg tgccgctcgc ggcca                             35

SEQ ID NO: 153          moltype = DNA   length = 35
FEATURE                 Location/Qualifiers
misc_feature            1..35
                        note = GMV419
```

-continued

```
source                  1..35
                        mol_type = other DNA
                        organism = synthetic construct
SEQUENCE: 153
acttcgttct gtctctcaca gcagggccgc ttcca                        35

SEQ ID NO: 154          moltype = DNA   length = 35
FEATURE                 Location/Qualifiers
misc_feature            1..35
                        note = GMV420
source                  1..35
                        mol_type = other DNA
                        organism = synthetic construct
SEQUENCE: 154
acttcgttct gtctctcaca ggccgaccgc ggttt                        35

SEQ ID NO: 155          moltype = DNA   length = 35
FEATURE                 Location/Qualifiers
misc_feature            1..35
                        note = GMV421
source                  1..35
                        mol_type = other DNA
                        organism = synthetic construct
SEQUENCE: 155
acttcgttct gtctctcaga tgcccaccgc gcgtt                        35

SEQ ID NO: 156          moltype = DNA   length = 1149
FEATURE                 Location/Qualifiers
source                  1..1149
                        mol_type = other DNA
                        organism = Saccharomyces cerevisiae
SEQUENCE: 156
atgcgggcgc tggcgtattt caagaagggc gacatccatt tcaccaacga catccccgg   60
ccggagatcc agaccgacga cgaagtgatc atcgacgtct cctggtgcgg catctgcggc  120
agcgacctgc acgagtacct ggacggcccc atcttcatgc cgaaggacgg cgaatgccac  180
aagctgagca cgccgcgct gccctggcg atgggccatg agatgtcggg catcgtctcc  240
aaagtggggcc cgaaggtgac caaggtcaaa gtgggcgacc acgtcgtggt cgacgccgcg  300
agctcgtgcg ccgacctgca ctgctggccc cattccaagt tctataacag caagccgtgc  360
gacgcctgcc agcgcggctc ggagaacctg tgcacccatg cgggcttcgt cggcctggcc  420
gtgatcagcg gcggcttcgc cgaacaggtg tccgtgtcgc agcaccatat catccccggtc  480
cccaaggaga tccccctgga cgtcgccgcc ctggtcgagc cgctgtccgg cacctggcac  540
gccgtgaaga tctccggctt caagaagggc tccagcgccc tggtcctggg cgcgggcccc  600
atcggcctgt gcaccatcct ggtgctgaag ggcatgggcc gtcgaagat cgtcgttcc  660
gagatcgccg aacgtcgcat cgagatggcg aagaagctgg gcgtcgaagt gttcaacccg  720
agcaagcacg gccataagtc gatcgagatc ctgcgggggcc tgaccaagtc ccacgacggc  780
ttcgactaca gctatgactg ctcgggcatc caggtcacct tcgaaaccag cctgaaggcc  840
ctgaccttca agggcaccgc caccaacatc gcggtcgggg gcccgaaagtc cgtgccgttc  900
cagccgatgg acgtcaccct gcaggagaag gtgatgaccg gctcgatcgg ctacgtcgtg  960
gaagacttcg aggaagtcgt gcgcgccatc cataacggcg acatcgcgat ggaggactgc 1020
aagcagctga tcaccggcaa gcagcggatc gaggacggct gggaaaaggg cttccaggag 1080
ctgatggacc acaaggaatc caacgtgaag atcctgctga ccccgaacaa ccacggcgaa 1140
atgaagtga                                                    1149

SEQ ID NO: 157          moltype = AA   length = 382
FEATURE                 Location/Qualifiers
source                  1..382
                        mol_type = protein
                        organism = Saccharomyces cerevisiae
SEQUENCE: 157
MRALAYFKKG DIHFTNDIPR PEIQTDDEVI IDVSWCGICG SDLHEYLDGP IFMPKDGECH   60
KLSNAALPLA MGHEMSGIVS KVGPKVTKVK VGDHVVVDAA SSCADLHCWP HSKFYNSKPC  120
DACQRGSENL CTHAGFVGLG VISGGFAEQV VVSQHHIIPV PKEIPLDVAA LVEPLSVTWH  180
AVKISGFKKG SSALVLGAGP IGLCTILVLK GMGASKIVVS EIAERRIEMA KKLGVEVFNP  240
SKHGHKSIEI LRGLTKSHDG FDYSYDCSGI QVTFETSLKA LTFKGTATNI AVWGPKPVPF  300
QPMDVTLQEK VMTGSIGYVV EDFEEVVRAI HNGDIAMEDC KQLITGKQRI EDGWEKGFQE  360
LMDHKESNVK ILLTPNNHGE MK                                       382

SEQ ID NO: 158          moltype = DNA   length = 47
FEATURE                 Location/Qualifiers
misc_feature            1..47
                        note = GMV00268
source                  1..47
                        mol_type = other DNA
                        organism = synthetic construct
SEQUENCE: 158
gagcaaccaa cacttaaaga ggagaaaatg cgggcgctgg cgtattt            47

SEQ ID NO: 159          moltype = DNA   length = 35
FEATURE                 Location/Qualifiers
```

-continued

```
misc_feature            1..35
                        note = GMV00271
source                  1..35
                        mol_type = other DNA
                        organism = synthetic construct
SEQUENCE: 159
acttcgttct gtctctcact tcatttcgcc gtggt                                    35

SEQ ID NO: 160          moltype = DNA  length = 990
FEATURE                 Location/Qualifiers
source                  1..990
                        mol_type = other DNA
                        organism = Escherichia coli
SEQUENCE: 160
atgcatatta catacgatct gccggttgct attgatgaca ttattgaagc gaaacaacga        60
ctggctgggc gaatttataa aacaggcatg cctcgctcca actatttttag tgaacgttgc      120
aaaggtgaaa tattcctgaa gtttgaaaat atgcagcgta cgggttcatt taaaattcgt      180
ggcgcattta ataaattaag ttcactgacc gatgcggaaa aacgcaaagg cgtggtggcc      240
tgttctgcgg gcaaccatgc gcaagggggt tccctctcct gcgcgatgct gggtatcgac      300
ggtaaagtgg tgatgccaaa aggtgcgcca aaatccaaag tagcggcaac gtgcgactac      360
tccgcagaag tcgttctgca tggtgataac ttcaacgaca ctatcgctaa agtgagcgaa      420
attgtcgaaa tggaaggccg tatttttatc ccaccttacg atgatccgaa agtgattgct      480
ggccagggaa cgattggtct ggaaattatg gaagatctct atgatgtcga taacgtgatt      540
gtgccaattg gtggtggcgg tttaattgct ggtattgcgg tggcaattaa atctattaac      600
ccgaccattc gtgttattgg cgtacagtct gaaaacgttc acggcatggc ggcttctttc      660
cactccggag aaataaccac gcaccgaact accggcaccc tggcgggatgg ttgtgatgtc      720
tcccgcccgg gtaatttaac ttacgaaatc gttcgtgaat tagtcgatga catcgtgctg      780
gtcagcgaag acgaaatcag aaacagtatg attgccttaa ttcagcgcaa taaagtcgtc      840
accgaaggcg caggcgctct ggcatgtgct gcattattaa gcggtaaatt agaccaatat      900
attcaaaaca gaaaaaccgt cagtattatt ccggcggca atatcgatct ttctcgcgtc      960
tctcaaatca ccggtttcgt tgacgcttaa                                       990

SEQ ID NO: 161          moltype = AA  length = 329
FEATURE                 Location/Qualifiers
source                  1..329
                        mol_type = protein
                        organism = Escherichia coli
SEQUENCE: 161
MHITYDLPVA IDDIIEAKQR LAGRIYKTGM PRSNYFSERC KGEIFLKFEN MQRTGSFKIR        60
GAFNKLSSLT DAEKRKGVVA CSAGNHAQGV SLSCAMLGID GKVVMPKGAP KSKVAATCDY      120
SAEVVLHGDN FNDTIAKVSE IVEMEGRIFI PPYDDPKVIA GQGTIGLEIM EDLYDVDNVI      180
VPIGGGGLIA GIAVAIKSIN PTIRVIGVQS ENVHGMAASF HSGEITTHRT TGTLADGCVD      240
SRPGNLTYEI VRELVDDIVL VSEDEIRNSM IALIQRNKVV TEGAGALACA ALLSGKLDQY      300
IQNRKTVSII SGGNIDLSRV SQITGFVDA                                        329

SEQ ID NO: 162          moltype = AA  length = 590
FEATURE                 Location/Qualifiers
source                  1..590
                        mol_type = protein
                        organism = Methylosinus trichosporium
SEQUENCE: 162
MARKMTGAEM VVEALKDQGV EIIFGYPGGA VLPIYDALFH QEKVQHILVR HEQGAAHAAE        60
GYARSSGKVG VLLVTSGPGA TNTITGLTDA LMDSIPVVCI TGQVPTHLIG SDAFQECDTV      120
GITRHCTKHN YLVKSVDDLP RILHEAFYVA SSGRPGPVVI DIPKDVQFAS GTYTGPRNVH      180
HKTYQPKLEG DTESIRRAVK MMAAAKRPIF YTGGGVINLG PAASTLLREL VSLTGFPITS      240
TLMGLGAYPG SGPNWLGMLG MHGTFEANNA MHDCDLMIAV GARFDDRITG RLDAFSPGSK      300
KIHIDIDRSS INKNVKIDLP IVGDCGHVLE SLVRVWRSEA MHAEKQPLDG WWKTIDHWRE      360
RKSLAFRNSD KVIKPQYAVQ RLYALTKDRD PYITTEVGQH QMWAAQHYHF DEPNRWMTSG      420
GLGTMGYGLP AAIGAQLAHP KSLVVDIAGE ASILMNIQEM STAIQYRLPV KVFILNNEYM      480
GMVRQWQELL HGGRYSHSYS EALPDFVKLA EAFGGKGIRC SDPAELDSAI LEMIDYDGPV      540
IFDCLVEKNE NCFPMIPSGK AHNDMLLADL GDDAGVELGS IIDEKGKMLV                  590

SEQ ID NO: 163          moltype = AA  length = 351
FEATURE                 Location/Qualifiers
source                  1..351
                        mol_type = protein
                        organism = Methylosinus trichosporium
SEQUENCE: 163
MSTKAYAVAS AEALFGPLAI ERRALGPEDV EIDILYCGVC HSDLHTARSE WPGTRYPCVP        60
GHEIVGRVTA VGAKVTKFSV GDLAAVGCMV DSCRRCLSCD DGLEQYCEHG FTATYNGPIY      120
GSGENTFGGY SEKIVVDAHF VLAIHHSETQ LAGVAPLLCA GITTWSPLKH WGVGPGKSVG      180
IVGIGGLGHM GVKLAHALGA HVVAFTTSPS KRDAALALGA DEVVSTDPA AMAARAGSLD      240
FILDTVAVAH DLDAYVNLLK RDGALVLVGV PATPHPSPSA GGLIFKRRQV AGSLIGGVKE      300
TQEMLDFCAE RGIVADIETI AMQQIETAYA RMLKNDVKYR FVIDMATLKA A               351

SEQ ID NO: 164          moltype = AA  length = 342
FEATURE                 Location/Qualifiers
source                  1..342
                        mol_type = protein
```

-continued

```
                          organism = Methylococcus capsulatus
SEQUENCE: 164
MKAWVIDRIG PLDSSRTLLR ATDLPVPEPG PGEILLQVAV CGVCHTEIDE IEGRTAPPRL   60
PVVPGHQAVG RIAALGSGVA EFALGDRVGV AWIFSACGEC EFCRSGRENL CFAFCATGRD  120
VDGGYAQYMT VPAAFAFRIP EGFTDAEAAP LLCAGAIGYR SLNLSGLKNG QPLGLTGFGA  180
SAHLVLMMAR YRFPDSEVYV FARHPEERAF ALQLGAVWAG DTADIAPAPL AAIIDTTPAW  240
KPVVAALANL APGGRLVVNA IRKAPDDRAC LAELDYARHL WMEREIKSVA NVARSDVAGF  300
LALAAAEMGIR PETEEYPFED ADRALLDLKQ RRIRGAKVLR VT                     342

SEQ ID NO: 165          moltype = AA  length = 355
FEATURE                 Location/Qualifiers
source                  1..355
                        mol_type = protein
                        organism = Methylococcus capsulatus
SEQUENCE: 165
MPTAKAYAAF SADSALAPFV LQRRDPLPQD IRIGILYCGV CHSDLHQARN EWNATTYPCV   60
PGHEIVGKVL EVGRSVTKFK PGDTVAVGCM VDSCRTCPNC VDALEQHCEH GPVFTYNSPD  120
PHGGGMTFGG YAESIVVDEA FVLRIPDGLD LAAAAPLLCA GITTYSPLRH WKVGAGQRVG  180
VVGLGGGLGHM ALKFAHTFGA ETVLFTTTPD KAEDARRLGA DEVVVSRDPE AMARQAGRFD  240
FILDTVSAPH DIDAYLNLLR RDGTLTLVGV PPQGVQVMPF SLIGGRRRLA GSLIGGIRET  300
QEMLDFCGEH GIVCDIELIP IQGINDAFER MLKSDVKYRF VIDMATLNGE SSGGR        355

SEQ ID NO: 166          moltype = AA  length = 548
FEATURE                 Location/Qualifiers
source                  1..548
                        mol_type = protein
                        organism = Lactococcus lactis
SEQUENCE: 166
MYTVGDYLLD RLHELGIEEI FGVPGDYNLQ FLDQIISRKD MKWVGNANEL NASYMADGYA   60
RTKKAAAFLT TFGVGELSAV NGLAGSYAEN LPVVEIVGSP TSKVQNEGKF VHHTLADGDF  120
KHFMKMHEPV TAARTLLTAE NATVEIDRVL SALLKERKPV YINLPVDVAA AKAEKPSLPL  180
KKENPTSNTS DQEILNKIQE SLKNAKKPIV ITGHEIISFG LENTVTQPIS KTKLPITTLN  240
FGKSSVDETL PSFLGIYNGK LSEPNLKEFV ESADFILMLG VKLTDSSTGA FTHHLNENKM  300
ISLNIDEGKI FNESIQNFDF ESLISSLLDL SGIEYKGKYI DKKQEDFVPS NALLSQDRLW  360
QAVENLTQSN ETIVAEQGTS FFGASSIFLK PKSHFIGQPL WGSIGYTFPA ALGSQIADKE  420
SRHLLFIGDG SLQLTVQELG LAIREKINPI CFIINNDGYT VEREIHGPNQ SYNDIPMWNY  480
SKLPESFGAT EERVVSKIVR TENEFVSVMK EAQADPNRMY WIELVLAKED APKVLKKMGK  540
LFAEQNKS                                                            548

SEQ ID NO: 167          moltype = AA  length = 563
FEATURE                 Location/Qualifiers
source                  1..563
                        mol_type = protein
                        organism = Saccharomyces cerevisiae
SEQUENCE: 167
MSEITLGKYL FERLKQVNVN TIFGLPGDFN LSLLDKIYEV DGLRWAGNAN ELNAAYAADG   60
YARIKGLSVL VTTFGVGELS ALNGIAGSYA EHVGVLHVVG VPSISAQAKQ LLLHHTLGNG  120
DFTVFHRMSA NISETTSMIT DIATAPSEID RLIRTTFITQ RPSYLGLPAN LVDLKVPGSL  180
LEKPIDLSLK PNDPEAEKEV IDTVLELIQN SKNPVILSDA CASRHNVKKE TQKLIDLTQF  240
PAFVTPLGKG SIDEQHPRYG GVYVGTLSKQ DVKQAVESAD LILSVGALLS DFNTGSFSYS  300
YKTKNVVEFH SDYVKVKNAT FLGVQMKFAL QNLLKVSVPV PTKTPANKGV  360
ASTPLKQEWL WNELSKFLQE GDVIISETGT SAFGINQTIF PKDAYGISQV LWGSIGFTTG  420
ATLGAAFAAE EIDPNKRVIL FIGDGSLQLT VQEISTMIRW GLKPYLFVLN NDGYTIEKLI  480
HGPHAEYNEI QTWDHLALLP AFGAKKYENH KIATTGEWDA LTTDSEFQKN SVIRLIELKL  540
PVFDAPESLI KQAQLTAATN AKQ                                          563

SEQ ID NO: 168          moltype = AA  length = 635
FEATURE                 Location/Qualifiers
source                  1..635
                        mol_type = protein
                        organism = Saccharomyces cerevisiae
SEQUENCE: 168
MAPVTIEKFV NQEERHLVSN RSATIPFGEY IFKRLLSIDT KSVFGVPGDF NLSLLEYLYS   60
PSVESAGLRW VGTCNELNAA YAADGYSRYS NKIGCLITTY GVGELSALNG IAGSFAENVK  120
VLHIVGVAKS IDSRSSNFSD RNLHHLVPQL HDSNFKGPNH KVYHDMVKDR VACSVAYLED  180
IETACDQVDN VIRDIYKYSK PGYIFVPADF ADMSVTCDNL VNVPRISQQD CIVYPSENQL  240
SDIINKITSW IYSSKTPAIL GDVLTDRYGV SNFLNKLICK TGIWNFSTVM GKSVIDESNP  300
TYMGQYNGKE GLKQVYEHFE LCDLVLHFGV DINEINNGHY TFTYKPNAKI IQFHPNYIRL  360
VDTRQGNEQM FKGINFAPIL KELYKRIDVS KLSLQYDSNV TQYTNETMRL EDPTNGQSSI  420
ITQVHLQKTM PKFLNPGDVV VCETGSFQFS VRDFAFPSQL KYISQGFFLS IGMALPAALG  480
VGIAMQDHSN AHINGGNVKE DYKPRLILFE GDGAAQMTIQ ELSTILKCNI PLEVIIWNNN  540
GYTIERAIMG PTRSYNDVMS WKWTKLFEAF GDFDGKYTNS TLIQCPSKLA LKLEELKNSN  600
KRSGIELLEV KLGELDFPEQ LKCMVEAAAL KRNKK                            635

SEQ ID NO: 169          moltype = AA  length = 348
FEATURE                 Location/Qualifiers
source                  1..348
                        mol_type = protein
                        organism = Saccharomyces cerevisiae
```

```
SEQUENCE: 169
MSIPETQKAI IFYESNGKLE HKDIPVPKPK PNELLINVKY SGVCHTDLHA WHGDWPLPTK 60
LPLVGGHEGA GVVVGMGENV KGWKIGDYAG IKWLNGSCMA CEYCELGNES NCPHADLSGY 120
THDGSFQEYA TADAVQAAHI PQGTDLAEVA PILCAGITVY KALKSANLRA GHWAAISGAA 180
GGLGSLAVQY AKAMGYRVLG IDGGPGKEEL FTSLGGEVFI DFTKEKDIVS AVVKATNGGA 240
HGIINVSVSE AAIEASTRYC RANGTVVLVG LPAGAKCSSD VFNHVVKSIS IVGSYVGNRA 300
DTREALDFFA RGLVKSPIKV VGLSSLPEIY EKMEKGQIAG RYVVDTSK               348

SEQ ID NO: 170          moltype = AA  length = 563
FEATURE                 Location/Qualifiers
source                  1..563
                        mol_type = protein
                        organism = Saccharomyces cerevisiae
SEQUENCE: 170
MSEITLGKYL FERLKQVNVN TVFGLPGDFN LSLLDKIYEV EGMRWAGNAN ELNAAYAADG 60
YARIKGMSCI ITTFGVGELS ALNGIAGSYA EHVGVLHVVG VPSISAQAKQ LLLHHTLGNG 120
DFTVFHRMSA NISETTAMIT DIATAPAEID RCIRTTYVTQ RPVYLGLPAN LVDLNVPAKL 180
LQTPIDMSLK PNDAESEKEV IDTILALVKD AKNPVILADA CCSRHDVKAE TKKLIDLTQF 240
PAFVTPMGKG SIDEQHPRYG GVYVGTLSKP EVKEAVESAD LILSVGALLS DFNTGSFSYS 300
YKTKNIVEFH SDHMKIRNAT FPGVQMKFVL QKLLTTIADA AKGYKPVAVP ARTPANAAVP 360
ASTPLKQEWM WNQLGNFLQE GDVVIAETGT SAFGINQTTF PNNTYGISQV LWGSIGFTTG 420
ATLGAAFAAE EIDPKKRVIL FIGDGSLQLT VQEISTMIRW GLKPYLFVLN NDGYTIEKLI 480
HGPKAQYNEI QGWDHLSLLP TFGAKDYETH RVATTGEWDK LTQDKSFNDN SKIRMIEIML 540
PVFDAPQNLV EQAKLTAATN AKQ                                          563

SEQ ID NO: 171          moltype = AA  length = 1048
FEATURE                 Location/Qualifiers
source                  1..1048
                        mol_type = protein
                        organism = Clostridium acetobutylicum
SEQUENCE: 171
MKSEYTIGRY LLDRLSELGI RHIFGVPGDY NLSFLDYIME YKGIDWVGNC NELNAGYAAD 60
GYARINGIGA ILTTFGVGEL SAINAIAGAY AEQVPVVKIT GIPTAKVRDN GLYVHHTLGD 120
GRFDHFFEMF REVTVAEALL SEENAAQEID RVLISCWRQK RPVLINLPID VYDKPINKPL 180
KPLLDYTISS NKEAACEFVT EIVPIINRAK KPVILADYGV YRYQVQHVLK NLAEKTGFPV 240
ATLSMGKGVF NEAHPQFIGV YNGDVSSPYL RQRVDEADCI ISVGVKLTDS TTGGFSHGFS 300
KRNVIHIDPF SIKAKGKKYA PITMKDALTE LTSKIEHRNF EDLDIKPYKS DNQKYFAKEK 360
PITQKRFFER IAHFIKEKDV LLAEQGTCFF GASTIQLPKD ATFIGQPLWG SIGYTLPALL 420
GSQLADQKRR NILLIGDGAF QMTAQEISTM LRLQIKPIIF LINNDGYTIE RAIHGREQVY 480
NNIQMWRYHN VPKVLGPKEC SLTFKVQSET ELEKALLVAD KDCEHLIFIE VVMDRYDKPE 540
PLERLSKRFA NQNNGYARIN GIGAILTTFG VGELSAINAI AGAYAEQVPV VKITGIPTAK 600
VRDNGLYVHH TLGDGRFDHF FEMFREVTVA EALLSEENAA QEIDRVLISC WRQKRPVLIN 660
LPIDVYDKPI NKPLKPLLDY TISSNKEAAC EFVTEIVPII NRAKKPVILA DYGVYRYQVQ 720
HVLKNLAEKT GFPVATLSMG KGVFNEAHPQ FIGVYNGDVS SPYLRQRVDE ADCIISVGVK 780
LTDSTTGGFS HGFSKRNVIH IDPFSIKAKG KKYAPITMKD ALTELTSKIE HRNFEDLDIK 840
PYKSDNQKYF AKEKPITQKR FFERIAHFIK EKDVLLAEQG TCFFGASTIQ LPKDATFIGQ 900
PLWGSIGYTL PALLGSQLAD QKRRNILLIG DGAFQMTAQE ISTMLRLQIK PIIFLINNDG 960
YTIERAIHGR EQVYNNIQMW RYHNVPKVLG PKECSLTFKV QSETELEKAL LVADKDCEHL 1020
IFIEVVMDRY DKPEPLERLS KRFANQNN                                     1048

SEQ ID NO: 172          moltype = DNA  length = 645
FEATURE                 Location/Qualifiers
source                  1..645
                        mol_type = other DNA
                        organism = Methylococcus capsulatus
SEQUENCE: 172
atggcaagac cattgattca gctcgccctg gacacgctgg acatcccgca gaccctgaag 60
ctcgcaagcc tcaccgcgcc ctatgtcgat atcttcgaaa tcggcacccc cagcatcaag 120
cacaacggca tcgccctggt gaaggagttc aaaaaacgct tccccaacaa gctgctcctg 180
gtcgacctca aaaccatgga cgccggtgaa tacgaagcca cccccttctt cgccgccggc 240
gccgacatca ccaccgtcct cggcgtcgca ggactggcca ccatcaaggg cgtcatcaac 300
gccgccaaca agcacaacgc cgaggtccag gtcgacctga tcaacgtccc cgacaaggcc 360
gcctgcgccc gtgagtccgc caaggccggc gcccagatcg tcggcatcca caccggcctc 420
gacgcccagg ccgccggcca gacccccttc gccgacctcc aggccatcgc caagctcggc 480
ctccccgtcc gcatctccgt cgccggcggc atcaaggcct ccaccgccca acaggtcgtc 540
aaaaccggtg ccaacatcat cgtcgtcgga gccgccatct acggcgccgc ctcccccgcc 600
gatgccgcgc gcgaaatcta cgaacaggtc gtcgccgctt ccgcc               645

SEQ ID NO: 173          moltype = AA  length = 215
FEATURE                 Location/Qualifiers
source                  1..215
                        mol_type = protein
                        organism = Methylococcus capsulatus
SEQUENCE: 173
MARPLIQLAL DTLDIPQTLK LASLTAPYVD IFEIGTPSIK HNGIALVKEF KKRFPNKLLL 60
VDLKTMDAGE YEATPFFAAG ADITTVLGVA GLATIKGVIN AANKHNAEVQ VDLINVPDKA 120
ACARESAKAG AQIVGIHTGL DAQAAGQTPF ADLQAIAKLG LPVRISVAGG IKASTAQQVV 180
KTGANIIVVG AAIYGAASPA DAAREIYEQV VAASA                             215
```

-continued

```
SEQ ID NO: 174        moltype = DNA   length = 531
FEATURE               Location/Qualifiers
source                1..531
                      mol_type = other DNA
                      organism = Methylococcus capsulatus
SEQUENCE: 174
atgcatcaga aactgatcat agacaaaatc tccggcatcc tcgccgccac cgatgccggc  60
tatgatgcaa aactgactgc catgctcgac caggcctccc gcatcttcgt cgcgggggcc 120
ggccggtcgg ggctggtcgc caagttcttc gccatgcgcc tcatgcacgg cggctatgac 180
gtcttcgtcg tcggcgaaat cgtcaccccc agcatccgca agggcgactt gctgatcgtg 240
atctccggct ccggtgaaac cgaaaccatg ctcgccttca ccaaaaaagc caaggagcag 300
ggcgcctcca tcgccctcat ctccacccgc gacagctcct ccctcggcga cctcgccgac 360
tccgtcttcc gcatcggctc cccagagctc ttcggaaaag tcgtcggcat gcccatgggc 420
accgtcttcg agctctccac cctcctcttc ctcgaggcca ccatctctca catcatccac 480
gagaaaggca tccccgaaga agaaatgaga actcgtcacg ccaacctgga a           531

SEQ ID NO: 175        moltype = AA   length = 177
FEATURE               Location/Qualifiers
source                1..177
                      mol_type = protein
                      organism = Methylococcus capsulatus
SEQUENCE: 175
MHQKLIIDKI SGILAATDAG YDAKLTAMLD QASRIFVAGA GRSGLVAKFF AMRLMHGGYD  60
VFVVGEIVTP SIRKGDLLIV ISGSGETETM LAFTKKAKEQ GASIALISTR DSSSLGDLAD 120
SVFRIGSPEL FGKVVGMPMG TVFELSTLLF LEATISHIIH EKGIPEEEMR TRHANLE     177
```

BIOLOGICAL PRODUCTION OF MULTI-CARBON COMPOUNDS FROM METHANE

CROSS-REFERENCE TO RELATED APPLICATION

This application claims priority benefit of U.S. provisional Application No. 61/782,830, filed Mar. 14, 2013, which is hereby incorporated by reference in its entirety.

REFERENCE TO AN ELECTRONIC SEQUENCE LISTING

The contents of the electronic sequence listing (35016-001C4.xml; Size: 304,171 bytes; and Date of Creation: May 27, 2024) are herein incorporated by reference in its entirety.

BACKGROUND OF THE INVENTION

Field of the Invention

The present invention is generally related to the fields of molecular biology and methods of producing metabolically engineered microorganisms which utilize methane feed-stocks for the biological production of bio-fuels and bio-chemicals such as 1-butanol, isobutanol, fatty alcohols, fatty acid esters, 2,3-butanediol and the like.

Background Art

Traditional fossil fuels (e.g., gasoline, diesel, kerosene and the like) and numerous chemicals (e.g., for use in pharmaceuticals, solvents, fertilizers, pesticides, plastics and the like) are derived (and refined from) non-renewable petroleum (oil) resources. Current estimates suggest that the world's supply of non-renewable petroleum will likely be exhausted somewhere between the years 2045 and 2065 (U.S. Department of the Interior, U.S. Geological Survey World Petroleum Assessment, 2000), with concomitant extensions or reductions of these estimates dependent on variables such as increased (or reduced) global demand, more efficient petroleum refining processes, more efficient use of energy and products derived from petroleum and the discovery of new petroleum sources/reserves.

Independent of any current or future methods contemplated to mitigate petroleum consumption, there is no debate that the world's supply of petroleum is a finite and a constantly diminishing (non-renewable) energy source. Thus, to meet the ever increasing global demands for energy consumption, renewable, biologically produced fuels (i.e., "bio-fuels" and "bio-diesel") have become an area of intense research, capital investment and government intervention.

For example, the U.S. "Energy Policy Act" of 2005 (42 USC, Title XV "Ethanol and Motor Fuels", § 1501-§ 1533; enacted into law Aug. 8, 2005), sets forth parameters and definitions of "renewable fuels", and established the "minimum ethanol" volume to gasoline volume blending requirements (presently E10: 10% ethanol: 90% gasoline), with E15 (15% ethanol: 85% gasoline) enacted as law and being "phased-in" across the U.S. The Energy Policy Act defines "renewable fuel" as a "motor vehicle fuel produced from grain, starch, oil-seeds, vegetable, animal, or fish materials including fats, greases, and oils, sugarcane, sugar beets, sugar components, tobacco, potatoes, or other biomass; or a natural gas produced from a biogas source, including a landfill, sewage waste treatment plant, feedlot, or other place where decaying organic material is found; and is used to replace or reduce the quantity of fossil fuel present in a fuel mixture used to operate a motor vehicle. The term "renewable fuel" includes (a) cellulosic biomass ethanol and waste derived ethanol; and (b) biodiesel, and any blending components derived from renewable fuel".

In addition to the current E10 ethanol/gasoline blends and ongoing adoption of E15 ethanol/gasoline blends, ethanol volumes of up to E85 (i.e., 85% ethanol: 15% gasoline) are also presently being utilized in "flex-fuel" vehicles (i.e., vehicles with engines and fuel systems capable of combusting and delivering, respectively, 85% ethanol blended gasoline) and it is estimated that the production of E85 fuel will only continue to increase as the supply (i.e., production) of "flex-fuel" vehicles increase. However, an inherent limitation of "ethanol" blended fuels (due to the decreased or lower "energy content" of ethanol relative to gasoline) is that increasing the percentage of ethanol blended into gasoline reduces the overall fuel economy of the vehicle (e.g., fuel economy of vehicles operating on E85 is about 25-30% less than vehicles operating on E10 gasoline blends). This limitation of ethanol's total energy content has further facilitated research and development of alternative bio-fuel blending additives (e.g., terpenoid hydrocarbons, n-butanol, isobutanol and the like) to replace bio-ethanol. Also predicated on the assumption of a finite, diminishing supply of non-renewable petroleum resources, research in the areas of biologically derived (hereinafter, "bio-based") chemicals (e.g., for use in pharmaceuticals, solvents, fertilizers, pesticides, plastics and the like) are being pursued, wherein these "bio-based" chemicals are contemplated as a means for reducing or eliminating their equivalents traditionally derived from petroleum feed stocks.

A considerable topic of ongoing debate is whether the ethanol fuel provisions of the Energy Policy Act of 2005 (and similar policies of other countries) have reduced (or will reduce) dependence on foreign oil/petroleum sources and/or have mitigated (or will mitigate) greenhouse gas emissions (two perceived benefits of the Act). For example, bio-fuels such as ethanol were initially seen as a solution to energy and environmental problems (i.e., considered carbon neutral) because the carbon dioxide emitted when ethanol is combusted is equivalent to the carbon dioxide absorbed from the atmosphere when the ethanol feed stock crop is grown (e.g., corn ethanol, sugarcane ethanol, cellulosic ethanol from switchgrass, etc.).

A recent study by economists at Oregon State University (Jaeger & Egelkraut, 2011) suggests however, that once additional factors/consequences are considered, such as (a) the use of fossil fuels to produce bio-fuel feedstocks and transport bio-fuels, (b) the use of nitrogen fertilizers to grow bio-fuel feedstocks and (c) that growing bio-fuel feedstock crops often pushes food production onto previously unfarmed land (which typically requires clearing tress and heavy tilling of the land), the perceived environmental benefits of ethanol derived bio-fuels may be lost. Likewise, another recent study on the environmental impact of bio-fuel production concludes that high corn and soybean prices, prompted largely by the demand for bio-fuel feedstocks (and partly by government incentives to use them as fuels instead of food), are driving one of the most important land cover/land use change events in recent US history; the accelerated conversion of grassland to cropland in the US Corn Belt (Wright and Wimberly, 2013).

The shift from petroleum based diesel fuel as a (transportation) energy source (e.g., used in automobiles, trucks and other heavy equipment) to renewable bio-diesel fuels is another source of scientific and policy disagreement similar to the arguments set forth above with regard to ethanol bio-fuels. Bio-diesel is generally made from plant oils or animal fats (triacylglycerides) by transesterification with methanol or ethanol, resulting in fatty acid methyl esters and fatty acid ethyl esters. However, the limited supply of bioresources to obtain triacylglycerides has become a major bottleneck for bio-diesel production, the primary reason being that vegetable oil feedstocks are also food sources and their planting is geographically limited.

There is therefore a pressing need in the art for novel methods of producing bio-fuel, bio-diesel and bio-based chemical compositions which reduce the world's dependence/utilization of petroleum products, ameliorate ongoing depletion of arable food source "farmland" currently being diverted to grow bio-fuel feedstocks and generally improve the environmental footprint of future bio-fuel, bio-diesel and bio-based chemical compositions.

As mentioned previously above, ethanol is currently the most abundant bio-fuel produced, but due to certain limitations (e.g., low energy content, high water solubility, incompatibility/corrosive with many fuel systems), ethanol based bio-fuels may not be the best option to meet future energy demands. Butanol, in comparison, has several advantages over ethanol as a bio-fuel, such as its high blending compatibility with gasoline, its low solubility in water allow it to be stored and distributed using the existing petrochemical infrastructure, it has a much higher energy content than ethanol (thereby improving fuel economy) and has a lower vapor pressure than ethanol blends, which is important in reducing evaporative hydrocarbon emissions. Isobutanol has the same advantages as butanol, with the additional advantage of having a higher octane number due to its branched carbon chain, and it is also useful as a commodity chemical.

Various methods for producing renewable bio-fuel, bio-diesel and other bio-based chemicals are known and described in the art. For example, traditional fermentation and distillation methods for producing and extracting bio-ethanol from starch or sugar rich biomass (e.g., corn) and the hydrolysis, fermentation and distillation methods of producing bio-ethanol from ligno-cellulosic biomass are well known in the art (Rudolph et al., 2009; Kim et al, 2013; Philips et al., 2013). The production of bio-diesel via extraction and esterification of vegetable oils, used cooking oils and animal fats using alcohols is also well known in the art (Saka & Kusdiana, 2001).

In more recent efforts, researchers have started to look at alternative methods for producing bio-fuels, bio-diesel and bio-based chemicals. For example, methods for producing bio-fuels such as butanol and isobutanol in various microorganisms such as *Escherichia coli* (Atsumi et al., 2010), *Clostridium acetobutylicum* (Jang et al., 2012) and *Saccharomyces cerevisiae* (Avalos et al., 2013) have been described in the art. Furthermore, the complete biosynthetic pathway for isobutanol production has been engineered in yeast (see, U.S. Pat. Nos. 8,232,089; 7,993,889) and bacteria (see, U.S. Patent Publication No. 2011/0301388). Similarly, de novo biosynthesis of bio-diesel using genetically engineered *E. coli* has been described in the art (Xingye et al., 2011; Yangkai et al., 2011).

However, each of the methods set forth above (i.e., traditional biomass fermentation methods and engineered biological/microorganism methods) for producing bio-fuel, bio-diesel, bio-based chemicals and the like, are limited by the choice of feedstock (or substrate) used to produce the end product (e.g., bio-ethanol, bio-butanol, bio-diesel, etc.). For example, the growth substrates utilized by each of the microorganisms set forth above (i.e., *E. coli, C. acetobutylicum* and *S. cerevisiae*) are dependent, in one way or another, on substrate feedstocks derived from crop-based food sources (e.g., glucose (growth) substrates fed to microorganisms are derived from plant sources).

Thus, as set forth previously, there is an ongoing need in the art for novel methods of producing bio-fuel, bio-diesel and bio-based chemical compositions, which not only reduce dependence/utilization of petroleum products, but also ameliorate the ongoing depletion of arable food source "farmland" currently being diverted to grow bio-fuel feedstocks and generally improve the environmental footprint of future bio-fuel, bio-diesel and bio-based chemical compositions.

Methane ($CH_4$) has great value as a chemical feedstock for the production of chemicals and food additives, due to its widespread availability, abundant supply and low price (Kidnay et al., 2011). Methane, in the form of natural gas, can be obtained from shale gas, oil drilling, municipal solid waste, biomass gasification/conversion, and methanogenic archaea. Wellhead natural gas varies in composition from about 40% to 95% methane, wherein the other components include ethane, propane, butane, pentane, and heavier hydrocarbons, along with hydrogen sulfide, carbon dioxide, helium and nitrogen. The proportion of methane in the gas feedstock can be increased by gas conditioning, which can produce natural gas consisting of 85-95% (v/v) methane (U.S. Pat. No. 4,982,023).

Current industrial methods for utilizing methane from natural gas include the Fischer-Tropsch process for converting methane into ethylene, steam-methane reforming from methane synthesis gas, as well as direct conversion from methane to methanol using inorganic catalysts (Veazey, 2012; Alayon et al., 2012; U.S. Pat. No. 4,982,023). Although the economics of syngas-to-liquids and methanol-to-gasoline from natural gas have become more favorable, these thermochemical methods for methane conversion still suffer from serious drawbacks (Arakawa et al., 2001). For example: (1) industrial plant construction requires high capital expenditure, (2) operating costs are high, (3) thermochemical conversion plants require elevated temperatures (150° C. to 300° C.) and high pressures (tens of atmospheres), which add to capital and operational costs, (4) the gas-to-liquids process is not always selective in producing liquid fuel and chemical products, further requiring expensive distillation costs and (5) the inorganic catalysts required for producing methanol and other products are susceptible to poisoning by contaminants in the process stream, and therefore the gas streams must be cleaned and the catalysts periodically replaced.

Certain embodiments of the present invention, as set forth below (see, "Detailed Description"), are directed to methods for biosynthetic production of multi-carbon compounds such as fuels (bio-fuels) and chemicals (bio-based) from methane. It is contemplated herein that the methods according to the present invention, using biological catalysts or biocatalysts (e.g., a genetically modified host microorganism) provide a number of economic advantages over current "industrial" methods for utilizing methane from natural gas. These advantages include (1) lower processing temperatures and pressures; (2) high selectivity for the reactions and (3) renewability, all of which lead to substantially lower capital and operational expenses.

A number of microorganisms, including bacteria and yeast, use single-carbon (C1) substrates as their sole source of carbon. These methylotrophs or C1-metabolizers can convert carbon compounds that do not contain carbon-carbon bonds, such as methane ($CH_4$) or methanol ($CH_3OH$) into biomass (Gellissen et al., 2005; Trotsenko & Murrell, 2008; Chistoserdova et al., 2009; Schrader et al., 2009; Chistoserdova, 2011). With regard to methane utilization, one particularly important group of bacteria known as the methanotrophs, the "obligate" members of which convert methane into methanol ($CH_3OH$), formaldehyde ($H_2C=O$), formic acid (HCOOH) and ultimately $CO_2$ by sequential enzymatic oxidation (Hanson & Hanson, 1996; Trotsenko & Murrell, 2008; Rosenzweig & Ragsdale, 2011 (a); Rosenzweig & Ragsdale 2011 (b)). Certain "facultative" methanotrophs (e.g., from the genus *Methylocella*) can also be cultivated using methane, methanol or methylamines as growth substrates (Dunfield et al., 2003; Rosenzweig & Ragsdale, 2011 (a); Rosenzweig & Ragsdale 2011 (b); Semrau et al., 2011).

The initial step of methane oxidation to methanol in methanotrophs is carried out by the enzyme methane monooxygenase (MMO) (Hakemian & Rosensweig, 2007; Rosenzweig & Ragsdale, 2011 (b)). Methane monooxygenase (MMO) activity is expressed in two different forms: a particulate form (pMMO), which contains copper and is membrane-bound (Culpepper & Rosenzweig, 2012), and a soluble form (sMMO), which contains iron and is expressed when copper becomes limiting (Murrel et al., 2000; Hakemian & Rosenzweig, 2007; Tinberg & Lippard, 2007). The second step of converting methanol to formaldehyde is catalyzed by the enzyme methanol dehydrogenase (MDH), another membrane-bound enzyme (Anthony & Williams, 2003). From this point, the formaldehyde can be dissimilated into formate (by formaldehyde dehydrogenase) and carbon dioxide (by formate dehydrogenase). The dissimilation reactions generate reducing equivalents for the cell, but do not directly contribute to the production of biomass or other multi-carbon products, since the carbon is released as $CO_2$. In some methanotrophs, however, carbon dioxide can be fixed through the serine pathway and/or the Calvin-Benson-Bassham cycle (see below), both of which depend on methane consumption to support growth (Stanley & Dalton, 1982; Chistoserdova et al., 2005). Among the oxidized C1 products that can be generated in the above described reactions, formaldehyde is the most important product (or imtermediate), as it serves as a metabolite that can be "fixed" into multi-carbon compounds via its introduction (or assimilation) into a central metabolism pathway of the host microorganism.

For example, the assimilation of the carbon in the formaldehyde formed can occur via various metabolic routes (Hanson & Hanson, 1996; Yurimoto et al., 2005; Yurimoto et al., 2009; Trotsenko & Murrell, 2008; Rosenzweig & Ragsdale, 2011 (a); Rosenzweig & Ragsdale, 2011 (b)). For example, the Type I methanotrophs, which are members of the Gammaproteobacteria, use the ribulose monophosphate (RuMP) pathway (see, Hanson & Hanson, 1996). The Type II methanotrophs, which are members of the Alphaproteobacteria, utilize the serine pathway (Hanson & Hanson, 1996). The bacterium *Methylococcus capsulatus*, strain Bath, however, uses elements of both these pathways, and is sometimes referred to as a "Type X" methanotroph (Hanson & Hanson, 1996; Chistoserdova et al., 2005). *Methylococcus capsulatus* (Bath), also expresses the enzymes needed to fix carbon dioxide via the Calvin-Benson-Bassham cycle (Chistoserdova et al., 2005).

Turnover of these pathways (i.e., Type I, Type II or Type X) ultimately supplies multi-carbon intermediates for other pathways of central metabolism. For example, the 3-phospho-glyceraldehyde generated by the RuMP cycle can be converted into pyruvate, and the 2-phospho-glycerate generated by the serine cycle can eventually be converted into phosphoenolpyruvate, oxaloacetate and acetyl-CoA, among other intermediates.

Substantial efforts have been expended over the past 40 years to exploit methanotrophs for chemical production and transformations on an industrial scale. However, to date there are still significant deficiencies and unmet needs in the art for improved host microorganisms which can utilize "non-traditional" carbon sources such as oxidized single-carbon compounds (e.g., methane, methanol or formaldehyde) and produce industrial, commercially relevant, multi-carbon compounds such as ethanol, n-butanol, sec-butanol, isobutanol, tert-butanol, fatty alcohols, fatty acid methyl esters, 2,3-butanediol and the like.

The present invention fulfills a need in the art for improved host microorganisms (which can utilize methane as a sole-carbon source in the production of multi-carbon compounds) for use in the biological production of bio-fuels and bio-based chemical compositions. The metabolically engineered host microorganisms and methods of producing the same, as set forth in the present invention, further address a long felt need in the art to reduce dependence/consumption of petroleum products and mitigate the depletion of farmland currently being diverted to grow bio-fuel and bio-based chemical feedstocks.

SUMMARY OF THE INVENTION

The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

Thus, in certain embodiments, the invention is directed to a method for producing isobutanol from a methane substrate comprising the steps of (a) providing a methanotrophic host microorganism that metabolizes methane ($CH_4$) to methanol ($CH_3OH$) and methanol to formaldehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway; and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In another embodiment, the ALS polypeptide comprises an amino acid sequence having at least 90% sequence homology to SEQ ID NO:2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO:8 and the ADH polypeptide comprises an amino acid sequence having at least 90% sequence homology to SEQ ID NO:10. In other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments a method for producing isobutanol from a methane substrate further comprises the step of recovering the isobutanol produced.

In another embodiment, the invention is directed to a method for producing isobutanol from a methane substrate comprising the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In certain other embodiments, the ALS polypeptide comprises an amino acid sequence having at least 90% sequence homology to SEQ ID NO: 2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO: 8 and the ADH polypeptide comprises an amino acid sequence having at least 90% sequence homology to SEQ ID NO:10. In another embodiment, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments, the methane monooxygenase (MMO) is a soluble MMO of Enzyme Class EC 1.14.13.25 or a particulate MMO of Enzyme Class 1.14.18.3. In certain embodiments, the MMO comprises an amino acid sequence comprising at least 90% sequence homology to a particulate methane monooxygenase (pMMO) selected from the group consisting of SEQ ID NO:12, SEQ ID NO: 14, SEQ ID NO: 16, SEQ ID NO: 18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO: 32 and SEQ ID NO:34. In other embodiments a method for producing isobutanol from a methane substrate further comprises the step of recovering the isobutanol produced.

In another embodiment, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 4.1.1.72, and EC 1.1.1.1. In yet other embodiments, the one or more polynucleotide ORFs introduced in step (b) encode a 1-butanol pathway polypeptide selected from the group consisting of L-threonine ammonia lyase, 2-ethylmalate synthase, isopropylmalate isomerase, 3-isopropylmalate dehydratase, 3-isopropylmalate dehydrogenase, 2-ketoacid decarboxylase (KDC) and alcohol dehydrogenase (ADH). In another embodiment, the L-threonine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyralde-hyde to 1-butanol. In another embodiment, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO:58, the isopropylmalate isomerase comprises an amino acid sequence having at least 90% sequence homology to SEQ ID NO: 60 and SEQ ID NO:62, a 3-isopropylmalate dehy-drogenase comprises an amino acid sequence having at least 90% sequence homology to SEQ ID NO:64, the KDC comprises an amino acid sequence having at least 90% sequence homology to SEQ ID NO:8 and the ADH com-prises an amino acid sequence having at least 90% sequence homology to SEQ ID NO: 10. In certain other embodiments, the one or more polynucleotide ORFs introduced in step (b) encode the complete 1-butanol pathway comprising L-threo-nine ammonia lyase, 2-ethylmalate synthase, isopropyl-malate isomerase, 3-isopropylmalate dehydrogenase, 2-ke-toacid decarboxylase (KDC) and alcohol dehydrogenase (ADH). In other embodiments a method for producing 1-butanol from a methane substrate further comprises the step of recovering the 1-butanol produced.

In another embodiment, the invention is directed to a method for producing 1-butanol from a methane substrate comprising the steps of (a) providing a non-methanotroph host microorganism which has been genetically engineered to express a methane monooxygenase (MMO), (b) introduc-ing into the host and expressing at least one polynucleotide open reading frame (ORF), under the control of suitable regulatory sequences, wherein the at least one polynucle-otide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous metha-nol dehydrogenase (MDH) polypeptide catalyzes the sub-strate to product conversion of methanol to formaldehyde and the formaldehyde produced is converted to pyruvate through an endogenous RuMP or serine pathway, wherein the host metabolizes pyruvate to produce 1-butanol. In certain embodiments, the one or more polynucleotide ORFs introduced in step (b) encode an 1-butanol pathway poly-peptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-bu-tanol pathway polypeptide selected from the group consist-ing of L-threonine ammonia lyase, 2-ethylmalate synthase, isopropylmalate isomerase, 3-isopropylmalate dehydroge-nase, 2-ketoacid decarboxylase (KDC) and alcohol dehy-drogenase (ADH). In yet other embodiments, the L-threo-nine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethyl-malate; the isopropylmalate isomerase catalyzes the sub-strate to product conversion of 2-ethylmalate to 3-ethyl-malate; the 3-isopropylmalate dehydrogenase catalyzes the substrate to product conversion of 3-ethylmalate to 2-ke-tovalerate, $CO_2$ and NADH; the KDC catalyzes the substrate to product conversion of 2-ketovalerate to butryaldehyde and the ADH catalyzes the substrate to product conversion of butyraldehyde to 1-butanol. In other embodiments, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO: 58, the isopropylmalate isomerase comprises an amino acid sequence having at least 90% sequence homology to SEQ ID NO:60 and SEQ ID NO:62, a 3-iso-propylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In another embodiment, the methane monooxygenase (MMO) is a soluble MMO of Enzyme Class EC 1.14.13.25 or a particu-late MMO of Enzyme Class 1.14.18.3. In certain other embodiments, the MMO comprises an amino acid sequence comprising at least 90% sequence homology to a particulate methane monooxygenase (pMMO) selected from the group consisting of SEQ ID NO: 12, SEQ ID NO: 14, SEQ ID NO: 16, SEQ ID NO:18, SEQ ID NO:20 and SEQ ID NO: 22 or at least 90% sequence homology to a soluble methane monooxygenase (sMMO) selected from the group consist-ing of SEQ ID NO:24, SEQ ID NO:26, SEQ ID NO:28, SEQ ID NO:30, SEQ ID NO:32 and SEQ ID NO:34. In other embodiments a method for producing 1-butanol from a methane substrate further comprises the step of recovering the 1-butanol produced.

In certain other embodiments, the invention is directed to a method for producing fatty alcohols from a methane substrate comprising the steps of (a) providing a methano-trophic host microorganism that metabolizes methane ($CH_4$) to methanol ($CH_3OH$) and methanol to formaldehyde ($H_2C{=}O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol. In one embodiment, the FAR polypeptide is further defined as a polypeptide from Enzyme Class EC 1.2.1.50. In another embodiment, the FAR poly-peptide catalyzes the substrate to product conversion of fatty acetyl-CoA to a fatty alcohol. In yet other embodiments, the FAR polypeptide comprises an amino acid sequence having at least 90% sequence homology to SEQ ID NO:66. In other embodiments a method for producing fatty alcohols from a methane substrate further comprises the step of recovering the fatty alcohol produced.

In certain other embodiments, the invention is directed to a method for producing a fatty alcohol from a methane substrate comprising the steps of (a) providing a non-methanotroph host microorganism which has been geneti-cally engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RuMP or serine pathway and the host metabolizes acetyl-CoA to produce a fatty alcohol. In certain embodiments, the FAR polypeptide cata-lyzes the substrate to product conversion of fatty acetyl-CoA to a fatty alcohol. In certain other embodiments, the FAR polypeptide comprises an amino acid sequence comprising at least 90% sequence homology to SEQ ID NO: 66. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO: 12, SEQ ID NO:14, SEQ ID NO: 16, SEQ ID NO: 18, SEQ ID NO: 20 and SEQ ID NO:22 or at least 90% sequence homology to a soluble methane monooxygenase (sMMO) selected from the group consisting of SEQ ID NO:24, SEQ ID NO: 26, SEQ ID NO:28, SEQ ID NO:30, SEQ ID NO:32 and SEQ ID NO:34. In other embodiments a method for producing fatty alcohols from a methane substrate further comprises the step of recovering the fatty alcohol produced.

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C{=}O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester. In certain embodiments, the WES polypeptide is further defined as a polypeptide from Enzyme Class EC 2.3.1.75. In another embodiment, the WES polypeptide catalyzes the substrate to product conversion of fatty acyl-CoA and alcohols to fatty acid esters. In other embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In other embodiments a method for producing fatty acid esters from a methane substrate further comprises the step of recovering the fatty acid esters produced.

In another embodiment, the invention is directed to a method for producing a fatty acid ester from a methane substrate comprising the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester. In certain embodiments, the WES polypeptide catalyzes the substrate to product conversion of fatty acyl-CoA and alcohols to fatty acid esters. In certain other embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO: 12, SEQ ID NO:14, SEQ ID NO: 16, SEQ ID NO: 18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing fatty acid esters from a methane substrate further comprises the step of recovering the fatty acid esters produced.

In certain other embodiments, the invention is directed to a method for producing 2,3-butanediol from a methane substrate comprising the steps of (a) providing a methanotrophic host microorganism that metabolizes methane ($CH_4$) to methanol ($CH_3OH$) and methanol to formaldehyde ($H_2C{=}O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol. In certain embodiments, the (2R,3R)-2,3-butanediol dehydrogenase (BDH1) has at least 90% sequence homology to a BDH1 polypeptide of SEQ ID NO:157. In other embodiments, the polynucleotide ORF comprises a nucleotide sequence of SEQ ID NO:156. In other embodiments a method for producing 2,3-butanediol from a methane substrate further comprises the step of recovering the 2,3-butanediol produced.

In certain embodiments, a methanotroph host microorganism of the invention is selected from genus consisting of *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* and *Methyloacidophilum.* In other embodiments, the methanotroph host microorganism is selected from the phylum Verrucomicrobia. In another embodiment, the methanotroph host is *Methylococcus capsulatus,* strain Bath.

In certain other embodiments, a non-methanotroph host microorganism of the invention is a yeast microorganism or bacterial microorganism. In certain embodiments, the non-methanotroph yeast microorganism is selected from *Saccharomyces cerevisiae, Hansenuela polymorpha, Pichia pastoris* and *Kluyveromyces lactis.* In one particular embodiment, the yeast microorganism is *Pichia pastoris.*

In certain other embodiments, a non-methanotrophic bacterial microorganism of the invention is *Pseudomonas putida, Cupriavidus metallidurans* or *Rhodobacter sphaeroides.*

In other embodiments, recovering the isobutanol produced according to the methods of the invention is a process selected from distillation, liquid extraction, flash evaporation, membrane separation and phase separation.

In other embodiments, recovering the 1-butanol produced according to the methods of the invention is a process selected from distillation, liquid extraction, flash evaporation, membrane separation and phase separation.

In another embodiment, recovering the fatty alcohol produced according to the methods of the invention is a process selected from flash evaporation, membrane separation, centrifugation and phase separation.

In certain other embodiments, recovering the fatty acid ester produced according to the methods of the invention is a process selected from flash evaporation, membrane separation, centrifugation and phase separation.

In another embodiment, recovering the 2,3-butanediol produced according to the methods of the invention is a process selected from steam stripping, solvent extraction, aqueous two-phase extraction, reactive extraction and pervaporation.

In certain other embodiments, a methane substrate is provided as a dry natural gas, as a wet natural gas or as a biogas.

In other embodiments, the host microorganism is grown by a batch process, a fed-batch process or a continuous perfusion process.

In another embodiment, the fatty alcohol composition produced according to the methods of the invention comprises a carbon chain of about 5 to about 40 carbon atoms. In certain embodiments, the fatty alcohol comprises a carbon chain of 8 to 22 carbon atoms.

In another embodiment, the fatty acid ester composition produced according to the methods of the invention has a fatty acid moiety comprising a carbon chain of about 5 to about 40 carbon atoms. In one particular embodiment, the fatty acid moiety comprises a carbon chain of 8 to 22 carbon atoms.

In yet other embodiments, the fatty acid ester composition produced according to the methods of the invention has an alcohol moiety comprising a carbon chain of about 5 to about 40 carbon atoms. In one particular embodiment, the alcohol moiety comprises a chain of 8 to 22 carbon atoms.

In yet other embodiments, a non-methanotroph host microorganism of the invention is further engineered to express an exogenous methanol dehydrogenase (MDH). In certain embodiments, the MDH is a polypeptide from Enzyme Class 1.14.18.3. In other embodiments, the MDH comprises an amino acid sequence having at least 90% sequence homology to a MDH polypeptide selected from the group consisting of SEQ ID NO:36, SEQ ID NO:38, SEQ ID NO:40, SEQ ID NO:42, SEQ ID NO:44, SEQ ID NO:46, SEQ ID NO: 48, SEQ ID NO:50, SEQ ID NO:52 and SEQ ID NO:54.

In other embodiments, the invention is directed to a substantially purified isobutanol composition produced according to the methods of the invention.

In another embodiment, the invention is directed to a substantially purified 1-butanol composition produced according to the methods of the invention.

In other embodiments, the invention is directed to a substantially purified fatty alcohol composition produced according to the methods of the invention.

In another embodiment, the invention is directed to a substantially purified fatty acid ester composition produced according to the methods of the invention.

In other embodiments, the invention is directed to a substantially purified 2,3-butanediol composition produced according to the methods of the invention.

In yet other embodiments, the invention is directed to an isobutanol producing methanotroph host microorganism manufactured according to the steps of (a) providing a methanotrophic host microorganism that metabolizes methane ($CH_4$) to methanol ($CH_3OH$) and methanol to formaldehyde ($H_2C\!=\!O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol.

In another embodiment, the invention is directed to an isobutanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol.

In yet other embodiments, the invention is directed to a 1-butanol producing methanotroph host microorganism manufactured according to the steps of (a) providing a methanotrophic host microorganism that metabolizes methane ($CH_4$) to methanol ($CH_3OH$) and methanol to formaldehyde ($H_2C\!=\!O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol.

In other embodiments, the invention is directed to a 1-butanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce 1-butanol.

In another embodiment, the invention is directed to a fatty alcohol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol.

In other embodiments, the invention is directed to a fatty alcohol producing non-methanotroph host microorganism manufactured according to the steps of (a) providing a non-methanotroph host microorganism which has been genetically engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RuMP or serine pathway and the host metabolizes acetyl-CoA to produce a fatty alcohol.

In another embodiment, the invention is directed to a fatty acid ester producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester.

In certain other embodiments, the invention is directed to a fatty acid ester producing non-methanotroph host microorganism manufactured according to the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester.

In certain other embodiments, the invention is directed to a 2,3-butanediol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol.

BRIEF DESCRIPTION OF THE DRAWINGS

Certain embodiments of the invention are illustrated in the drawings, in which.

DETAILED DESCRIPTION OF THE INVENTION

Figure 1:
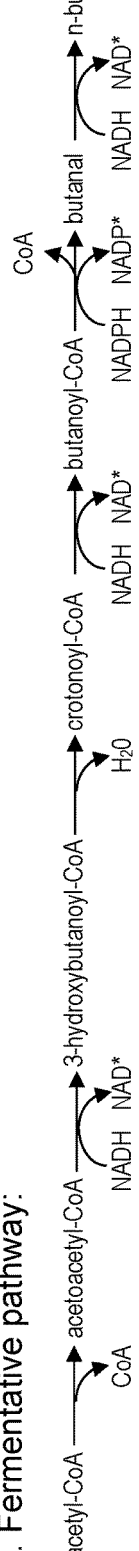
FIG. 1 depicts five pathways for the biosynthetic production of n-butanol (1-butanol) and one pathway for the biosynthetic production of isobutanol.
Figure 1:
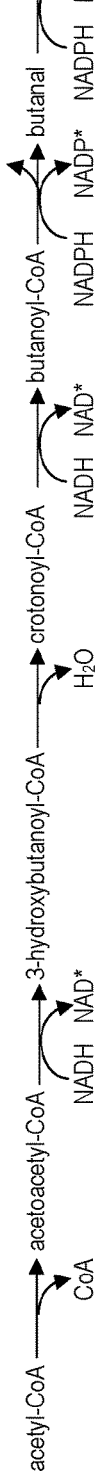
Figure 1:
Figure 1:
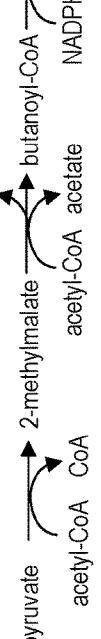
Figure 1:

Unless defined otherwise, all technical and scientific terms used herein have the same meaning as commonly understood to one of ordinary skill in the art to which this disclosure pertains. Although methods and materials similar or equivalent to those described herein can be used in the practice of the disclosed methods and compositions, the exemplary methods, devices and materials are described herein.

In certain embodiments, the present invention is directed to host microorganisms metabolically engineered to produce multi-carbon compounds. Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications, including, but not limited to their use in fuels (e.g., bio-fuel, bio-diesel) and bio-based chemicals. The present invention addresses a number of commercial, industrial and environmental needs in the art related to the production of multi-carbon compounds.

As set forth herein, the metabolically engineered host microorganisms of the present invention utilize methane ($CH_4$) as their sole carbon source (i.e., the host microorganism does not require plant based feedstocks for growth and energy) and ameliorate much of the ongoing depletion of arable food source "farmland" currently being diverted to grow bio-fuel feedstocks, and as such, improve the environmental footprint of future bio-fuel, bio-diesel and bio-based chemical compositions. Furthermore, use of the metabolically engineered host microorganisms set forth in the present invention (which utilize methane as the sole carbon source) mitigate current industry practices and methods of producing multi-carbon compounds from petroleum or petroleum-derived feedstocks.

Thus, in certain embodiments of the invention, a host microorganism is genetically engineered to produce multi-carbon compounds. As is known in the art, methanotrophic organisms are able to metabolize methane as their primary source of carbon and energy, can grow aerobically or anaerobically, and require single-carbon compounds (e.g., methane, $CH_4$; methanol, $CH_3OH$ and/or formaldehyde, $H_2C{=}O$) to survive. In particular embodiments, a host microorganism of the invention is a methanotroph. As defined herein, a "methanotroph", a "methanotrophic" or a "methanophile" host microorganism of the invention is a "prokaryotic microorganism which can metabolize methane as its primary source of carbon and energy".

In other embodiments, the host microorganism of the invention is a non-methanotrophic microorganism genetically engineered to metabolize methane as its only source of carbon and energy. As defined herein, a "non-methanotroph" host microorganism of the invention is a host microorganism which "cannot metabolize (or utilize) methane as its sole carbon source", until the "non-methanotroph" host microorganism has been genetically modified or engineered according to the methods of the present invention. As further defined herein, a "non-methanotroph" host microorganism of the invention includes any prokaryotic and eukaryotic microbial species which comprise a complete or partial "endogenous ribulose monophosphate (RuMP) pathway, a serine pathway or a mixed RuMP/serine pathway" (e.g., see RuMP, serine and mixed (Type X) pathways described below). In certain embodiments, a "non-methanotroph" host microorganism of the invention includes prokaryotic and eukaryotic microbial species from the Domains Archaea, Bacteria and Eucarya, wherein the Domain Eucarya includes yeast, filamentous fungi, protozoa, algae or higher Protista. The terms "microbial" and "microbes" are used interchangeably with the term "microorganism".

As defined herein, the phrase "providing a methanotrophic host microorganism that metabolizes methane to methanol and metabolizes methanol to formaldehyde" refers to an "endogenous enzymatic activity encoded by one or more endogenous genes of the methanotroph host microorganism". For example, an endogenous enzyme (or polypeptide) encoded by one or more endogenous genes of a methanotroph host microorganism include a methane monooxygenase (MMO) enzyme (which metabolizes (or converts) methane to methanol) and a methanol dehydrogenase (MDH) enzyme (which metabolizes (or converts) methanol to formaldehyde). Stated another way, the phrase "providing a methanotrophic host microorganism that metabolizes methane to methanol and metabolizes methanol to formaldehyde" does not require the introduction of exogenous (or heterologous) genes encoding single-carbon (C1) oxidizing enzymes (or polypeptides), as such enzymes and the activity thereof are inherent (endogenous) attributes of a methanotrophic host microorganism of the invention.

Furthermore, as is known in the art, a "methanotrophic host microorganism" of the invention comprises endogenous genes encoding at least a Type I methanotroph RuMP pathway and/or a Type II methanotroph serine pathway. In general, Type I methanotrophs (e.g., *Methylomonas, Methylomicrobium, Methylobacter*, Methylocaldum, *Methylosphaera*) assimilate formaldehyde produced (i.e., from the oxidation of methane to methanol and methanol to formaldehyde), using the ribulose monophosphate pathway (RuMP), whereas Type II methanotrophs (e.g., *Methylocystis* and *Methylosinus*) assimilate formaldehyde produced (i.e., from the oxidation of methane to methanol and methanol to formaldehyde), using the serine pathway. Lastly, the genus *Methylococcus* are known to comprise a combination of characteristics of both Type I methanotroph (RuMP) pathway and Type II methanotroph (serine) pathway.

The ribulose monophosphate pathway (RuMP) was originally identified in methanotrophic bacteria, as described above. However, more recent genome sequence analysis of various microorganisms have revealed that the key enzymes of the RuMP pathway (e.g., 3-hexulose-6-phosphate (HPS), 6-phsopho-3-hexuloisomerase (PHI)) are widely distributed (i.e., endogenous) among "non-methanotrophic" bacteria and archaeal genomes (Orita et al., 2006).

As defined herein, the phrases "recombinant host microorganism", "genetically engineered host microorganism", "engineered host microorganism" and "genetically modified host microorganism" may be used interchangeably and refer to host microorganisms that have been genetically modified to (a) express one or more exogenous polynucleotides, (b) over-express one or more endogenous and/or one or more exogenous polynucleotides, such as those included in a vector, or which have an alteration in expression of an endogenous gene or (c) knock-out or down-regulate an endogenous gene. In addition, certain genes may be physically removed from the genome (e.g., knock-outs) or they may be engineered to have reduced, altered or enhanced activity.

The terms "engineer", "genetically engineer" or "genetically modify" refer to any manipulation of a microorganism that results in a detectable change in the microorganism, wherein the manipulation includes, but is not limited to, introducing non-native metabolic functionality via heterologous (exogenous) polynucleotides or removing native-functionality via polynucleotide deletions, mutations or knock-outs. The term "metabolically engineered" generally involves rational pathway design and assembly of biosynthetic genes (or ORFs), genes associated with operons, and control elements of such polynucleotides, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

As defined herein, the term "introducing", as used in phrases such as "introducing into the methanotroph host" or "introducing into the non-methanotroph host" at least one polynucleotide open reading frame (ORF) or a gene thereof or a vector thereof includes methods known in the art for introducing polynucleotides into a cell, including, but not limited to transformation (e.g., calcium chloride, electroporation), transduction, transfection, conjugation and the like.

The phrases "metabolically engineered microorganism" and "modified microorganism" are used interchangeably herein, and refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide (i.e., relative to the wild-type nucleic acid or polypeptide sequence). Mutations include, for example, point mutations, substitutions, deletions, or insertions of single or multiple residues in a polynucleotide (or the encoded polypeptide), which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In certain embodiments, a portion of a genetically modified microorganism's genome may be replaced with one or more heterologous (exogenous) polynucleotides. In some embodiments, the mutations are naturally-occurring. In other embodiments, the mutations are the results of artificial selection pressure. In still other embodiments, the mutations in the microorganism genome are the result of genetic engineering.

The term "expression" or "expressed" with respect to a gene sequence, an ORF sequence or polynucleotide sequence, refers to transcription of the gene, ORF or polynucleotide and, as appropriate, translation of the resulting mRNA transcript to a protein. Thus, as will be clear from the context, expression of a protein results from transcription and translation of the open reading frame sequence. The level of expression of a desired product in a host microorganism may be determined on the basis of either the amount of corresponding mRNA that is present in the host, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press, 1989). Protein encoded by a selected sequence can be quantitated by various methods (e.g., by ELISA, by assaying for the biological activity of the protein, or by employing assays that are independent of such activity, such as western blotting or radioimmunoassay, using antibodies that are recognize and bind reacting the protein).

The term "endogenous", as used herein with reference to polynucleotides (and the polypeptides encoded therein), indicates polynucleotides and polypeptides that are expressed in the organism in which they originated (i.e., they are innate to the organism). In contrast, the terms "heterologous" and "exogenous" are used interchangeably, and as defined herein with reference to polynucleotides (and the polypeptides encoded therein), indicates polynucleotides and polypeptides that are expressed in an organism other than the organism from which they (i.e., the polynucleotide or polypeptide sequences) originated or where derived.

The term "feedstock" is defined as a raw material or mixture of raw materials supplied to a microorganism, or fermentation process, from which other products can be made. For example, as set forth in the present invention, a methane carbon source or a methanol carbon source or a formaldehyde carbon source, either alone or in combination, are feedstocks for a microorganism that produces a bio-fuel or bio-based chemical in a fermentation process. However, in addition to a feedstock (e.g., a methane substrate) of the invention, the fermentation media contains suitable minerals, salts, cofactors, buffers and other components, known to those skilled in the art, suitable for the growth of the cultures and promotion of the enzymatic pathways necessary for multi-carbon compound production.

The term "substrate" refers to any substance or compound that is converted, or meant to be converted, into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material (e.g., methane), but also intermediate and end product metabolites used in a pathway associated with a metabolically engineered microorganism as described herein.

The term "fermentation" or "fermentation process" is defined as a process in which a host microorganism is cultivated in a culture medium containing raw materials, such as feedstock and nutrients, wherein the microorganism converts raw materials, such as a feedstock, into products.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, including DNA, RNA, ORFs, analogs and fragments thereof.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

It is understood that the polynucleotides described herein include "genes" and that the nucleic acid molecules described herein include "vectors" or "plasmids". Accordingly, the term "gene", refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon-optimized" as it refers to genes or coding regions of nucleic acid molecules (or ORFs) for transformation of various hosts, refers to the alteration of codons in the gene or coding regions of the nucleic acid molecules to reflect the typical codon usage of the host organism without altering the polypeptide encoded by the DNA.

The term "operon" refers to two or more genes which are transcribed as a single transcriptional unit from a common promoter. In certain embodiments, the genes, polynucleotides or ORFs comprising the operon are contiguous genes. It is understood that transcription of an entire operon can be modified (i.e., increased, decreased, or eliminated) by modifying the common promoter. Alternatively, any gene, polynucleotide or ORF, or any combination thereof in an operon can be modified to alter the function or activity of the encoded polypeptide. The modification can result in an increase or a decrease in the activity or function of the encoded polypeptide. Further, the modification can impart new activities on the encoded polypeptide.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The term "homolog", as used with respect to an original enzyme, polypeptide, gene or polynucleotide (or ORF encoding the same) of a first family or species, refers to distinct enzymes, genes or polynucleotides of a second family or species, which are determined by functional, structural or genomic analyses to be an enzyme, gene or polynucleotide of the second family or species, which corresponds to the original enzyme or gene of the first family or species. Most often, "homologs" will have functional, structural or genomic similarities. Techniques are known by which homologs of an enzyme, gene or polynucleotide can readily be cloned using genetic probes and PCR. Identity of cloned sequences as "homologs" can be confirmed using functional assays and/or by genomic mapping of the genes.

A polypeptide (or protein or enzyme) has "homology" or is "homologous" to a second polypeptide if the nucleic acid sequence that encodes the polypeptide has a similar sequence to the nucleic acid sequence that encodes the second polypeptide. Alternatively, a polypeptide has homology to a second polypeptide if the two proteins have "similar" amino acid sequences. Thus, the terms "homologous proteins" or "homologous polypeptides" is defined to mean that the two polypeptides have similar amino acid sequences. In certain embodiments of the invention, polynucleotides and polypeptides homologous to one or more polynucleotides and/or polypeptides set forth in Table 1 may be readily identified using methods known in the art for sequence analysis and comparison.

A homologous polynucleotide or polypeptide sequence of the invention may also be determined or identified by BLAST analysis (Basic Local Alignment Search Tool) or similar bioinformatic tools, which compare a query nucleotide or polypeptide sequence to a database of known sequences. For example, a search analysis may be done using BLAST to determine sequence identity or similarity to previously published sequences, and if the sequence has not yet been published, can give relevant insight into the function of the DNA or protein sequence.

Bioconversion of Methane to Multi-Carbon Compounds

In general, the conversion of methane ($CH_4$) to multi-carbon compounds such as isobutanol (($CH_3$)$_2$CHCH$_2$OH), 1-butanol or n-butanol ($CH_3CH_2CH_2CH_2OH$), ethanol ($CH_3CH_2OH$), fatty alcohols, fatty acid esters, 2,3-butanediol and the like, using a "methanotrophic host microorganism", requires at least the following three steps, all of which are innate (or endogenous) with respect to methanotrophic organisms: (1) a methane ($CH_4$) substrate is oxidized to methanol ($CH_3OH$) via a methane monooxygenase (MMO) (e.g., particulate methane monooxygenase (pMMO) or soluble methane monooxygenase (sMMO)), (2) the methanol ($CH_3OH$) is oxidized to formaldehyde ($H_2C{=}O$) via methanol dehydrogenase (MDH) and (3) the formaldehyde ($H_2C{=}O$) produced in step (2) above is assimilated into a central metabolism pathway (e.g., see type I (RuMP) and type II (serine) pathways described below).

In certain embodiments of the invention, a host microorganism is a methanotroph, which endogenously expresses a methane monooxygenase (MMO) enzyme and a methanol dehydrogenase (MDH) enzyme. In other embodiments of the invention, a host microorganism of the invention is a "non-methanotrophic" prokaryotic microorganism (e.g., a non-methanotrophic bacteria or archaea) or a eukaryotic microorganism (e.g., fungi and algae) engineered to utilize a methane substrate (as sole carbon source) for growth and energy. Thus, in certain embodiments of the invention, a "non-methanotrophic" microorganism is engineered to express (or over-express) an exogenous methane monooxygenase (MMO), an enzyme requisite to metabolize methane to methanol. The non-methanotroph host microorganisms of the invention comprise an endogenous dehydrogenase (MDH) enzyme, which converts methanol to formaldehyde. However, in certain embodiments, the "non-methanotroph" microorganism is further engineered to express an exogenous methanol dehydrogenase (MDH) enzyme, which converts methanol to formaldehyde. The expression of the exogenous MDH enzyme in a non-methanotroph host is not a strict requirement for the utilization of the methane substrate, but it is contemplated in certain embodiments, that the introduction and expression of an exogenous MDH in a non-methanotroph host thereof may facilitate, under certain growth conditions, the production of one or more multi-carbon compounds of the invention.

As mentioned briefly above with regard to methanotrophic host organisms, there are at least two known pathways (i.e., the ribulose monophosphate (RuMP) pathway and the serine pathway; Hanson & Hanson, 1996) for the assimilation of formaldehyde into central metabolism. In the Type I methanotroph RuMP pathway, formaldehyde combines with ribulose-5-phosphate to form hexulose-6-phosphate (catalyzed via hexulose-6-phosphate synthase), the hexulose-6-phosphate is then isomerized to fructose-6-phosphate (catalyzed via hexulose phosphate isomerase), which is an intermediate of a central metabolic pathway (i.e., glycolysis pathway). In the type II methanotroph serine pathway, formaldehyde reacts with tetrahydrofolate (THF) to form methylene-THF, the methylene-THF is then transferred to L-glycine to form L-serine, and finally the L-serine is transferred to glyoxylate to form hydroxypyruvate. The hydroxypyruvate formed is subsequently converted to 2-phosphoglycerate (catalyzed via hydroxypruvate reductase), which is an central metabolism intermediate of the glycolytic pathway.

Likewise, as mentioned briefly above, an endogenous pathway, which functions similarly (or analogous) to the ribulose monophosphate (RuMP) pathway in methanotrophs is also present in "non-methanotrophic" prokaryotes (Orita et al., 2006), wherein formaldehyde is fixed with ribulose 5-phosphate to form hexulose-6-phosphate (catalyzed via hexulose-6-phosphate synthase (HPS)) and then isomerized to fructose-6-phosphate (catalyzed via hexulose phosphate isomerase (PHI)), which is an intermediate of a central metabolic pathway. Thus, in certain preferred embodiments, a "non-methanotrophic" host microorganism of the invention comprises an endogenous RuMP pathway or an endogenous pathway analogous to the RuMP pathway. As defined herein, a pathway analogous to the RuMP pathway comprises at least a gene, polynucleotide or ORF encoding an enzyme having hexulose-6-phosphate synthase (HPS) activity from enzyme class EC 4.1.2.43 and at least a gene, polynucleotide or ORF encoding a an enzyme having hexulose phosphate isomerase (PHI) activity from enzyme class 5.3.1.27.

In other embodiments, wherein a "non-methanotrophic" host microorganism genome does not encode endogenous enzymes having HPS and PHI activity, the non-methanotroph host microorganism is genetically modified to express HPS and PHI enzymes. Thus, in certain embodiments, a gene, polynucleotide or ORF encoding a hexulose-6-phosphate synthase (HPS) is provided, wherein the gene, polynucleotide or ORF encodes a HPS polypeptide of enzyme class EC 4.1.2.43. In other embodiments, a gene, polynucleotide or ORF encoding a hexulose-6-phosphate synthase (HPS) is provided, wherein the gene, polynucleotide or ORF encodes a HPS polypeptide having at least 90% sequence homology to a *M. capsulatus* (Bath) HPS polypeptide of SEQ ID NO:173. In other embodiments, a gene, polynucleotide or ORF encoding a hexulose phosphate isomerase (PHI) is provided, wherein the gene, polynucleotide or ORF encodes a PHI polypeptide of enzyme class EC 5.3.1.27. In other embodiments, a gene, polynucleotide or ORF encoding a hexulose phosphate isomerase (PHI) is provided, wherein the gene, polynucleotide or ORF encodes a *M. capsulatus* (Bath) PHI polypeptide having at least 90% sequence homology to a PHI (also referred to as a sugar isomerase (SIS) domain) polypeptide of SEQ ID NO:175.

Once the formaldehyde has been assimilated into a central metabolic pathway of the methanotroph or non-methanotroph host organism (as described above), the fourth and final step for producing multi-carbon compounds from a methane substrate as described in steps (1)-(3) above, is the introduction of one or more nucleic acids into the host microorganism, wherein the one or more nucleic acids introduced encode one or more enzymes of a relevant multi-carbon compound pathway. Independent of the compound to be produced according to the present invention (e.g., isobutanol, 1-butanol, ethanol, fatty alcohols, fatty acid methyl esters, 2,3-butanediol and the like), any multi-carbon pathway introduced into a host microorganism must utilize a central metabolic molecule (e.g., pyruvate, acetyl-CoA, methionine and oxobutyrate) previously assimilated and introduced into the metabolic pathway through steps (1)-(3) described above. Stated another way, a salient feature of the present invention is the ability of the host microorganism to utilize methane (as a sole carbon source for growth and energy) and to produce multi-carbon compounds (via engineered metabolic pathways introduced therein), without the need for additional or supplemental carbon sources such as carbohydrates.

As defined herein, a relevant "multi-carbon compound pathway", includes, but is not limited to, a 1-butanol pathway (which includes, but is not limited to, a fermentative 1-butanol pathway, a thiobutanoate pathway, a ketoacid pathway and a methylmalate pathway), an isobutanol path-way, a fatty alcohol pathway, a fatty acid methyl ester pathway and a 2,3-butanediol pathway. A "multi-carbon compound pathway" as further defined herein, may include one specific enzyme from the pathway, multiple enzymes from the pathway or all of the enzymes of the pathway. It will be understood by a person of skill in the art, that the selection of one or more specific pathway enzymes (and nucleic acids encoding the same) may be dependent on the host microorganism (e.g., certain methanotroph hosts or "non-methanotroph" hosts may endogenously encode and express one or more enzymes of a given pathway).

For example, FIG. 1 depicts five representative 1-butanol (i.e., n-butanol) pathways (pathways 1-5), wherein one or more nucleic acids encoding one or more enzymes of any of these pathways may be introduced into a methanotroph (or non-methanotroph) host microorganism and be expressed (or over-expressed) therein to yield 1-butanol. Similarly, FIG. 1 depicts an isobutanol pathway (pathway 6), wherein one or more nucleic acids encoding one or more enzymes of the isobutanol pathway may be introduced into a methano-troph (or non-methanotroph) host microorganism and expressed (or over expressed) therein to yield isobutanol. Further contemplated herein, is the introduction into a methanotroph (or non-methanotroph) host microorganism a combination of nucleic acids encoding one or more enzymes from a 1-butanol pathway and one or more enzymes from an isobutanol pathway.

As depicted in FIG. 1, at least five pathways are known to exist for converting one or more of these metabolic precur-sors into n-butanol (i.e., 1-butanol). The first synthesis pathway is the classical fermentative n-butanol pathway. Beginning with acetyl-CoA, this six step pathway requires three NADH and one NADHPH, but loses no carbon atoms to by-products formed. The second n-butanol synthesis pathway is the fermentative pathway, but using NADPH instead of NADH as the electron donor for the final con-version of butanal to n-butanol. The third potential n-butanol pathway is the thiobutanoate pathway, which begins with L-methionine, which is subsequently deaminated and then converted to n-butanol in two additional steps that involve loss of carbon dioxide ($CO_2$) and a sulfur(S) atom by an unknown mechanism. The fourth n-butanol pathway is the ketoacid pathway, which starting from L-threonine, n-buta-nol is synthesized in four steps, involving both reduction of $NAD^+$ and oxidation of NADH, while losing two $CO_2$. The fifth n-butanol synthesis pathway is the methylmalate path-way, which begins by combining pyruvate with acetyl-CoA to form citramalate (methylmalate), a reaction known to be catalyzed by LeuA in many bacteria, followed by conversion to butanoyl-CoA, which is then converted to n-butanol using the final two reactions of the fermentative pathway. Like-wise, as depicted in FIG. 1, at least one isobutanol pathway is known in the art for synthesizing isobutanol from pyru-vate, wherein the five-step pathway loses two carbon atoms as $CO_2$ per molecule of isobutanol synthesized.

Thus, in certain embodiments, the present invention is directed to a method for producing isobutanol from a methane substrate comprising the steps of (a) providing a methanotrophic host microorganism that metabolizes meth-ane ($CH_4$) to methanol ($CH_3OH$) and methanol to formal-dehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobu-tanol pathway; (c) feeding the methanotroph host of step (b)

a methane substrate under suitable growth conditions, wherein the host metabolizes methane to formaldehyde as set forth in step (a), wherein the formaldehyde is converted to pyruvate by means of an endogenous RuMP pathway or a serine pathway and the host metabolizes pyruvate to produce isobutanol, and (d) optionally recovering the isobu-tanol produced.

In one particular embodiment, the one or more polynucle-otide ORFs introduced in step (b) encode an isobutanol pathway polypeptide thereof selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reduc-toisomerase (KARI), dihydroxy-acid dehydratase (DHAD), ketoacid decarboxylase (KDC) and alcohol dehydrogenase (ADH). In certain embodiments, the ALS polypeptide cata-lyzes the substrate to product conversion of pyruvate to acetolactate; the KARI polypeptide catalyzes the substrate to product conversion of acetolactate to 2,3-dihydroxyisovaler-ate; the DHAD polypeptide catalyzes the substrate to prod-uct conversion of 2,3-dihydroxyisovalerate to ketoisovaler-ate; the KDC polypeptide catalyzes the substrate to product conversion of ketoisovalerate to isobutryaldehyde and ADH polypeptide catalyzes the substrate to product conversion of isobutyraldehyde to isobutanol. In other embodiments, the ALS polypeptide comprises an amino acid sequence com-prising at least 90% sequence homology to SEQ ID NO:2, the KARI polypeptide comprises an amino acid sequence comprising at least 90% sequence homology to SEQ ID NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO: 8 and the ADH polypeptide comprises an amino acid sequence comprising at least 90% sequence homology to SEQ ID NO:10. In yet other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In certain embodiments, the ORFs encoding the complete isobutanol pathway are comprised in one operon, two operons or three operons, wherein each operon may comprise the same promoter or a different promoter, wherein the same or different promoters may be constitutive or inducible.

In certain embodiments, a methanotroph host microor-ganism is modified or genetically engineered to express one or more enzymes of a metabolic pathway capable of pro-ducing n-butanol, isobutanol, fatty (or aliphatic long chain) alcohols, fatty acid methyl esters and the like. In particular embodiments, a methanotroph of the invention is selected from genera consisting of *Methylobacter, Methylomicro-bium, Methylomonas, Methylocaldum, Methylococcus, Methylosoma, Methylosarcina, Methylothermus, Methylo-halobius, Methylogaea, Methylovulum, Crenothrix, Clono-thrix, Methylosphaera, Methylocapsa, Methylocella, Meth-ylosinus, Methylocystis* and *Methyloacidophilum.* In other embodiments, the methanotroph is from the phylum Verru-comicrobia. Previously published work has shown that several species within these taxa can be genetically trans-formed by introducing DNA constructs on plasmid vectors (Stafford et al., 2003), or by integrating them into the bacterial chromosome (Welander & Summons, 2012). Thus, a vector construct of the invention will typically comprise the pathway genes or polynucleotide ORFs, which are initially constructed and cloned into *E. coli* to generate sufficient quantities of the vector, and then the vectors are subsequently transformed into the host microorganism for expression.

In other embodiments, the invention is directed to a method for producing isobutanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce isobutanol, and (d) optionally recovering the isobutanol produced. Methods for heterologous expression of pMMO genes have been described in Gou et al. (2006). Methods for heterologous expression of sMMO genes have been described in Lloyd et al. (1999). Suitable microbial hosts for heterologous expression include microorganisms that have the ability to process methanol and formaldehyde, that have multiple heterotrophic growth modes, and/or that can assemble complex membranes and metalloprotein complexes. Such organisms include methylotrophic yeasts (e.g., *Pichia pastoris*) as well as bacteria such as *Pseudomonas putida, Cupriavidus metallidurans* and *Rhodobacter sphaeroides*.

In certain embodiments, the one or more polynucleotide ORFs introduced in step (b) above, encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol.

In one particular embodiment, the ALS polypeptide comprises an amino acid sequence comprising at least 90% sequence homology to SEQ ID NO:2, the KARI polypeptide comprises an amino acid sequence comprising at least 90% sequence homology to SEQ ID NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO: 8 and the ADH polypeptide comprises an amino acid sequence comprising at least 90% sequence homology to SEQ ID NO:10. In certain other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO: 28), mmoZ (SEQ ID NO:30), mmoD (SEQ ID NO:32) or mmoC (SEQ ID NO:34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxal (SEQ ID NO:42), mxaR (SEQ ID NO:44), mxaA (SEQ ID NO:46), mxaC (SEQ ID NO:48), mxaK (SEQ ID NO:50), mxaL (SEQ ID NO: 52) or mcaD (SEQ ID NO:54).

In other embodiments, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol, and (d) optionally recovering the 1-butanol produced. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO: 10. In one particular embodiment, the one or more polynucleotide ORFs introduced in step (b) encode the complete 1-butanol pathway comprising an L-threonine ammonia-lyase, a 2-ethylmalate synthase, an isopropylmalate isomerase, a 3-isopropylmalate dehydrogenase, a KDC and an ADH.

In other embodiments, the invention is directed to a method for producing 1-butanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce 1-butanol, and (d) optionally recovering the 1-butanol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO: 12), pmoA subunit 1 (SEQ ID NO:14), pmoB subunit 1 (SEQ ID NO: 16) or a pMMO of operon 2 comprising pmoC subunit 2 (SEQ ID NO: 18), pmoA subunit 2 (SEQ ID NO: 20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO: 34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxal (SEQ ID NO:42), mxaR (SEQ ID NO:44), mxaA (SEQ ID NO:46), mxaC (SEQ ID NO:48), mxaK (SEQ ID NO:50), mxaL (SEQ ID NO: 52) or mcaD (SEQ ID NO:54).

In one particular embodiment, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butyraldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In one particular embodiment, the one or more polynucleotide ORFs introduced in step (b) encode the complete 1-butanol pathway comprising an L-threonine ammonia-lyase, a 2-ethylmalate synthase, an isopropylmalate isomerase, a 3-isopropylmalate dehydrogenase, a KDC and an ADH.

In certain other embodiments, the invention is directed to a method for producing fatty alcohols from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR); (c) feeding the methanotroph host of step (b) a methane substrate under suitable growth conditions, wherein the host metabolizes methane to formaldehyde as set forth in step (a), wherein the formaldehyde is converted to acetyl- CoA by means of an endogenous type I RuMP pathway or a type II serine pathway and the host metabolizes acetyl-CoA to produce a fatty alcohol, and (d) recovering the fatty alcohol produced. In certain embodiments, the FAR polypeptide is further defined as a polypeptide from Enzyme Class EC 1.2.1.50. In yet other embodiments, the FAR polypeptide catalyzes the substrate to product conversion of fatty acetyl-CoA to a fatty alcohol. In another embodiment, a FAR polypeptide comprises an amino acid sequence having at least 90% sequence homology to SEQ ID NO:66.

In still other embodiments, the invention is directed to a method for producing a fatty alcohol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing a polynucleotide open reading frame (ORF), under the control of suitable regulatory sequences, wherein the polynucleotide ORF encodes a fatty-acyl-CoA reductase (FAR), (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol, and (d) optionally recovering the fatty alcohol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO: 20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO: 34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxal (SEQ ID NO:42), mxaR (SEQ ID NO:44), mxaA (SEQ ID NO:46), mxaC (SEQ ID NO:48), mxaK (SEQ ID NO:50), mxaL (SEQ ID NO: 52) or mcaD (SEQ ID NO:54).

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES); (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty-acyl-CoA and alcohols to produce a fatty acid ester, and (d) recovering the fatty acid ester produced. In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid esters. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO: 74, SEQ ID NO: 76 and SEQ ID NO: 78.

In another embodiment, the invention is directed to a method for producing a fatty acid ester from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing at least one polynucleotide open reading frame (ORF), under the control of suitable regulatory sequences, wherein the at least one polynucleotide ORF encodes a wax ester synthase; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, wherein the formaldehyde is converted to acetyl-CoA by means of an endogenous RuMP or serine pathway and the host metabolizes fatty-acyl-CoA and alcohols to produce a fatty acid ester, and (d) recovering the fatty acid ester produced.

In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid ester. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO: 74, SEQ ID NO: 76 and SEQ ID NO: 78.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO: 18), pmoA subunit 2 (SEQ ID NO: 20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO: 34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO: 52) or mcaD (SEQ ID NO:54).

Figure 9:
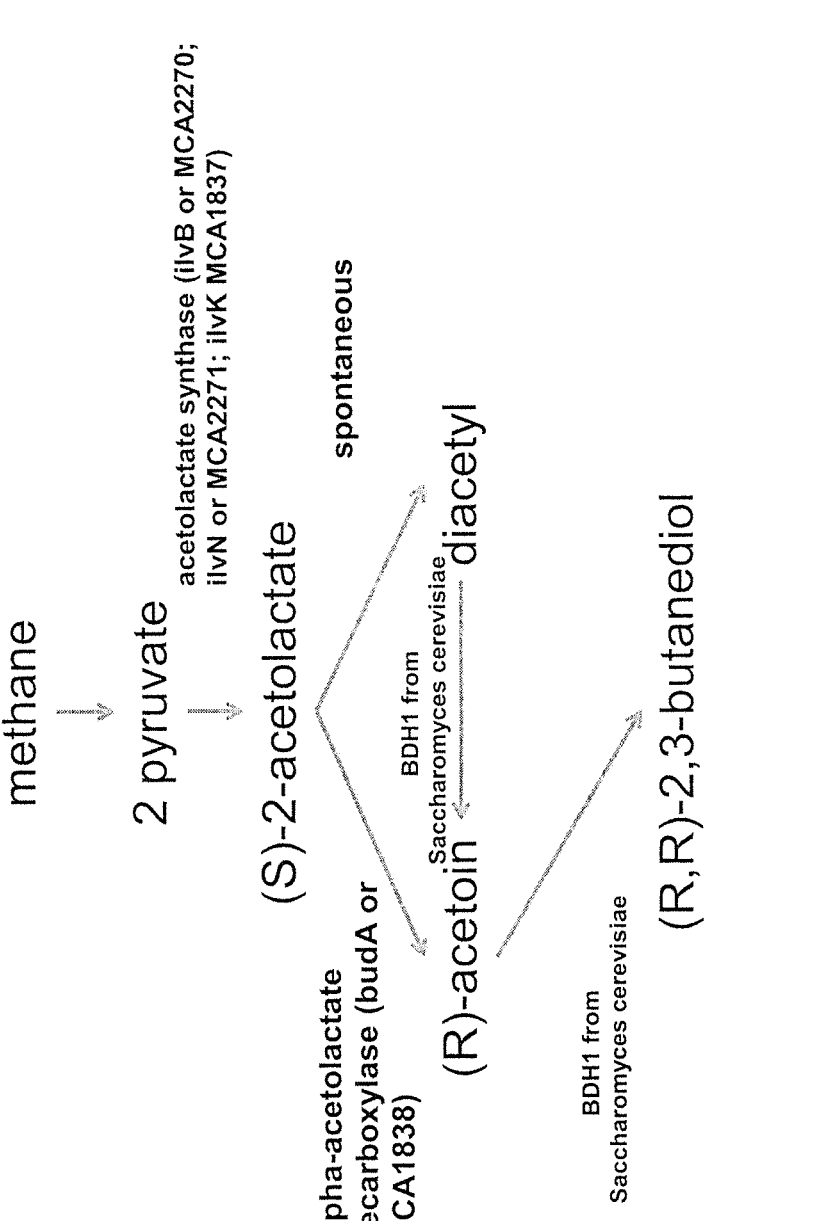
FIG. 9 shows an engineered pathway for 2,3-butanediol production from methane using a heterologously expressed BDH1 enzyme from *Saccharomyces cerevisiae*.

In certain other embodiments, the invention is directed to methods of producing 2,3-butanediol from a methane substrate. The compound 2,3-butanediol (a four-carbon diol) is an important intermediate for the chemical industry. At the commercial scale, 2,3-butanediol is mainly produced or generated from petroleum, where it serves as a precursor for the production of various commodity and specialty chemicals, such as the solvent methyl ethyl ketone (MEK), gamma-butyrolactone (GBL) and 1,3-butadiene. The biological production of 2,3-butanediol from methane requires engineering the native (or endogenous) metabolism of methanotrophs to take advantage of their endogenous production of (R)-acetoin (FIG. 9). The compound (R)-acetoin is produced in methanotrophs from two molecules of pyruvate, which are ultimately derived from methane. By introducing and expressing a single gene (SEQ ID NO:156) encoding a (2R,3R)-2,3-butanediol dehydrogenase (BDH1) from *Saccharomyces cerevisiae* in a suitable microbial expression host (such as *M. capsulatus* (Bath)), the (R)-acetoin is converted into 2,3-butanediol. Thus, in certain embodiments, a host microorganism of the invention is genetically modified to express an exogenous (2R,3R)-2,3-butanediol dehydrogenase (BDH1) having at least 90% sequence homology to a BDH1 polypeptide of SEQ ID NO:157.

General methods for gene synthesis and DNA cloning, as well as vector and plasmid construction, are well known in the art, and are described in a number of publications (Lipps, 2008; Peccoud, 2012; Ausubel et al., 2002). More specifically, techniques such as digestion and ligation-based cloning, as well as in vitro and in vivo recombination methods, can be used to assemble DNA fragments encoding a polypeptide that catalyzes a substrate to product conversion into a suitable vector. These methods include restriction digest cloning, sequence- and ligation-independent Cloning (SLIC) (Li & Elledge, 2012), Golden Gate cloning (Engler et al., 2009), Gibson assembly (Gibson et al., 2009), and the like (Merryman & Gibson, 2012; Wang et al., 2012). Some of these methods can be automated and miniaturized for high-throughput applications (Yehezkel et al., 2011; Ma et al., 2012).

In certain embodiments, the cloning procedures use in vitro homologous recombination, to insert DNA fragments into a vector (e.g., the In-Fusion kit from Clontech Laboratories, Inc. (Mountain View, CA)). For example, (1) the recipient vector is linearized by a restriction digest and purified; (2) PCR primers that are complementary to the fragment to be cloned and that are complementary (with 15-base pair extensions) to the ends of the linearized vector are used to amplify the insert, using high-fidelity polymerase; (3) the size of the PCR amplicon is verified by agarose gel electrophoresis; (4) the PCR product is purified by a spin-column; (5) the In-Fusion reaction is run according to the manufacturer's instructions; (6) competent *E. coli* cells are transformed with 2.5 μL of the reaction products; (7) positive transformants are selected from colonies grown on antibiotic selection medium and transferred to individual liquid cultures with the appropriate antibiotic; (8) the cells are harvested after overnight growth at 37° C. with 200 rpm shaking and (9) the plasmid DNA is extracted and analyzed for the correct insert.

The plasmid vector is chosen so that it will be capable of replicating in both an *E. coli* host (for cloning and amplification) and a methanotrophic or non-methanotrophic host microorganism (for metabolic pathway expression). The plasmid can be transferred from the *E. coli* donor cell to the recipient cell via bacterial conjugation. In addition, the vector contains a promoter sequence upstream of the one or more polynucleotide ORFs that are to be expressed. The promoter sequence can be included as part of the insert so that it can be adjusted and tested for each new construct. Broad-host-range (bhr) vectors for different gram-negative bacterial hosts have been described in the literature (Marx & Lidstrom, 2001). These vectors typically contain the following components: (1) an origin of replication that is functional in *E. coli* (colE1); (2) an oriV/IncP origin of replication for the non-*E. coli* host; (3) an oriT/IncP origin of transfer, which is needed for transferring a bacterial plasmid from a bacterial host such as *E. coli* to the recipient during bacterial conjugation; (4) a traJ' gene, which codes for a transcriptional activator that initiates production of the proteins needed for conjugative transfer; and (5) a trfA, the replication initiation protein gene of plasmid RK2 which binds to a activates oriV.

Figure 2:
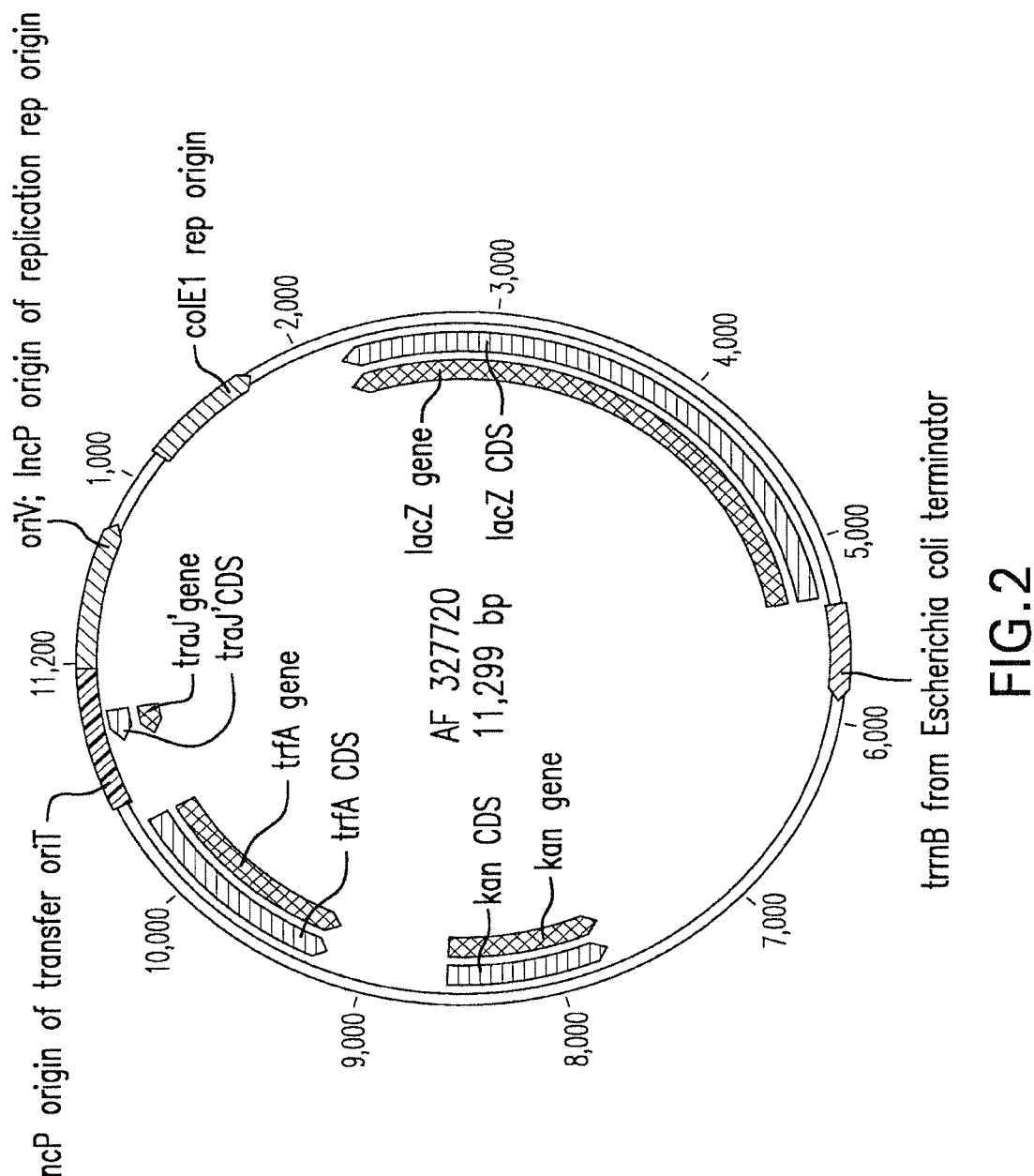
FIG. 2 depicts a vector map of the broad host range expression plasmid pCM 132. The vector map shows the following components: (1) an origin of replication that is functional in *E. coli* (colE1); (2) an oriV/IncP origin of replication for the non-*E. coli* microbial host; (3) an oriT/IncP origin of transfer, which is needed for transferring a bacterial plasmid from a bacterial host such as *E. coli* to the recipient during bacterial conjugation; (4) a traJ gene, which codes for a transcriptional activator that initiates production of the proteins needed for conjugative transfer; (5) a trfA gene, the replication initiation protein gene of plasmid RK2 which binds to and activates oriV; (6) a lacZ (beta-galactosidase) gene for identifying plasmids with DNA inserts based on colony color using indolyl-galactoside-based substrates; and (7) a kanamycin resistance gene (kan). Genes of interest are inserted into the polylinker region that lies between the rrnB transcription terminator and the 5'-end of the lacZ gene.

In one embodiment, the conjugative bhr plasmid is based on pCM132 (GenBank Accession No. AF327720, SEQ ID NO:79) (Marx & Lidstrom, 2001), which has been engineered to contain a kanamycin resistance gene for plasmid selection and a lacZ (beta-galactosidase) gene for identifying plasmids with DNA inserts based on colony color using indolyl-galactoside-based substrates. Genes (or polynucleotide ORFs thereof) of interest can be inserted into the polylinker region that lies between the rrnB transcription terminator and the 5'-end of the lacZ gene (e.g., see, FIG. 2).

Figure 3:
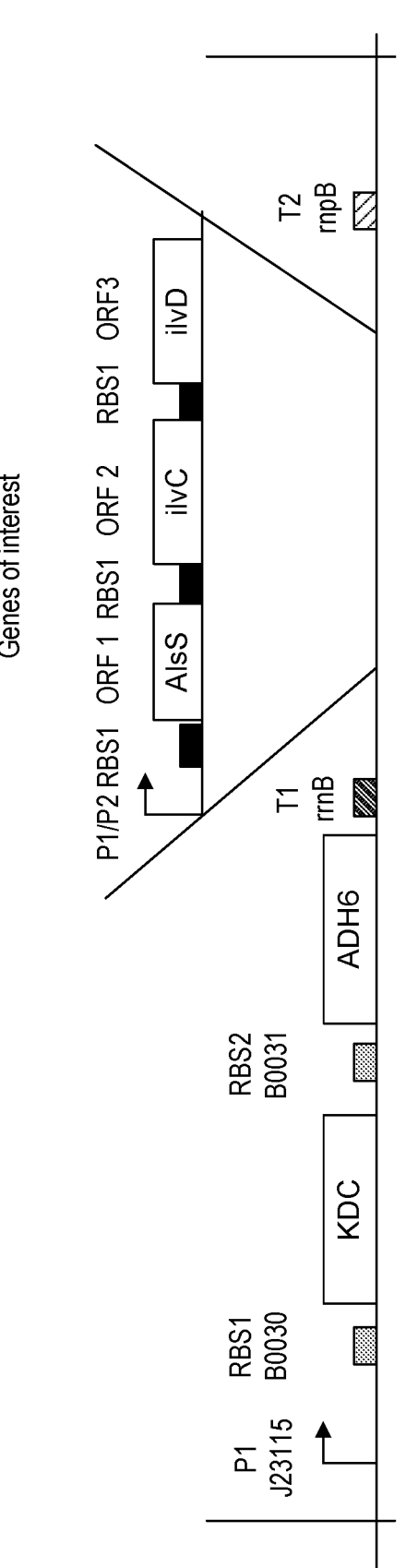
FIG. 3 shows a schematic diagram of component DNA arrangements for cloning into an expression vector.

Typical gene cassettes for expressing an engineered metabolic pathway in a host microorganism such as a methanotroph are shown in FIG. 3. The cassette comprises one or more open reading frames (ORFs) which encode the enzymes of the introduced pathway, a promoter for directing transcription of the downstream ORF(s) within the operon, ribosome binding sites for directing translation of the mRNAs encoded by the individual ORF(s), and a transcriptional terminator sequence. Due to the modular nature of the various components of the expression cassette, one can create combinatorial permutations of these arrangements by substituting different components at one or more of the positions. One can also reverse the orientation of one or more of the ORFs to determine whether any of these alternate orientations improve the product yield.

In one embodiment, the plasmids generated as part of the present invention are based on the broad-host-range expression vector pCM132 (Marx & Lidstrom, 2001). In this embodiment, the use of the Clontech (catalog no. 639647) InFusion HD Cloning System kit is one example of how to construct plasmids, but is not meant to limit or exclude other methods that are known in the art, including Gibson assembly, yeast in vivo recombination, PCR Splicing by Overlap Extension, or any combination of these with standard molecular biology techniques.

In certain embodiments of the invention, the plasmids of interest are generated in a modular fashion such that various modules, including suitable regulatory sequences, can be easily assembled or replaced as needed and are amenable to scaled-up, high-throughput assembly. The plasmids are designed to consist of multiple linear modules: a vector backbone and one or more vector inserts. The 5' and 3' ends of individual modules have overlapping sequence homology to the ends of adjacent modules within the designed plasmid. The overlapping homology between the modules allows them to be assembled into a circular plasmid using the Clontech InFusion HD Cloning System kit or other assembly method known in the art. Primers were designed to introduce homologous ends to the PCR-amplified products to facilitate assembly.

Vector backbones of the invention contain the components of the plasmid that will remain constant. In certain embodiments, the broad-host range vector pCM132 is modified to produce vector backbones for the plasmids (vectors) of the invention. The pCM132 vector, further described below in the Examples section, consists of the following components: trrnB terminator, kanamycin resistance gene, trfA, IncP oriT, IncP oriV, colE1 ori, and lacZ. This parental vector was modified to replace lacZ with a vector insert that contains promoter sequence(s) to produce plasmids pJSvec (SEQ ID NO: 80) and pMZT3 (SEQ ID NO: 81). In certain embodiments of the invention, vector backbones were PCR-amplified with the NEB Phusion master mix (M0531L) according to the manufacturer's instructions, unless specified otherwise.

The general rationale or procedure for selecting the appropriate ORFs for a given pathway was to examine a list of pathway-relevant genes as specified in the literature. Using this set of pathway-relevant genes as a target, BLAST searches were run, looking for genes in three groups: (1) similar genes found in microbial hosts that are phylogenetically close to the ones already listed in the literature, (2) similar genes found in microbes that are phylogenetically distant from the microbial host of the targeted gene, and (3) homologs that are similar to the target gene but that are found in the wild-type methanotroph or non-methanotroph organism that is to be used as the expression host. An example of the above strategy would be to target the kivD gene (encoding alpha-ketoisovalerate decarboxylase) from *Lactococcus lactis*: the first group would contain genes from species similar to *L. lactis*, including *Lactococcus* itself; the second group would be genes similar to kivD, but found in organisms phylogenetically distant from *L. lactis*; and finally the last group would include a kivD gene in a microbe of interest, specifically, *Methylococcus capsulatus* (Bath). Thus, in certain embodiments of the invention, the exemplary polynucleotide and polypeptide sequences set forth in Table 1 are used to identify similar or homologous polynucleotide, genes, ORFs and polypeptides found in microbial hosts that are (1) phylogenetically close to the ones already listed, (2) found in microbes that are phylogenetically distant from the microbial host of the targeted sequence, and (3) homologs that are similar to the target gene but that are found in the wild-type methanotroph or non-methanotroph organism that is to be used as the expression host.

For example, genes encoding similar proteins or polypeptides to those of the invention may isolated directly by using all or a portion of a nucleic acid (e.g., see Table 1, below) or a primer sequence (e.g., see Table 2, below) as DNA hybridization probes to screen libraries from any desired microorgansim using methodology well known to those skilled in the art. Specific oligonucleotide probes based upon these nucleic acid sequences can be designed and synthesized by methods known in the art (Sambrook et al., 1989; Ausubel et al., 1987). Moreover, the entire sequence can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Alternatively a nucleic acid sequence of the invention may be employed as a hybridization reagent for the identification of homologs. The basic components of a nucleic acid hybridization test include a probe, a sample suspected of containing the gene or gene fragment of interest, and a specific hybridization method. Probes are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. base. Hybridization methods are well defined and know in the art.

An important component of these engineered operons is the promoter sequence. The promoter must be chosen based on its compatibility with the transcriptional machinery of the host organism, as well as its ability to tune the desired level of gene expression (e.g., high or low). For example, one may introduce the strong pmxaF or pmmoX promoters from a methanotroph to generate high expression levels in a methanotrophic or non-methanotroph host. Alternatively, one can introduce a promoter from the Anderson promoter collection, which is a library of constitutive sigma70 bacterial promoters (http://partsregistry.org/Promoters/Catalog/Anderson; Registry of Standard Biological Parts), such as J23100 (strong) or J23115 (weak), to modulate expression of different ORFs or combinations of ORFs. Inducible promoters, whose activity is controlled by the addition of exogenous small molecule activators, such as IPTG, arabinose or salicylate, can also be used to provide temporal control of gene expression. However, regardless of the choice of promoter, its effect on host expression must be empirically tested in vivo to be certain of its effectiveness for achieving the desired level of expression.

These different combinatorial permutations of the cassette can be synthesized, cloned and expressed in the target host organism (via chemical transformation, electroporation, or conjugation of the DNA) so that the production of a multi-carbon product can be compared. The best candidate or candidates can then be further engineered to provide additional improvements in product yield by repeating the design-build-test cycle.

In one embodiment, the host microorganism for expressing the plasmid is a methanotroph, and plasmid vector(s) containing the metabolic pathway expression cassettes are readily mobilized into these organisms via conjugation. Various methods for bacterial conjugation are known in the art, and one of the most widely used methods takes advantage of a strain of E. coli S17-1, which has an RP4 plasmid (with the RK2 tra genes for transfer of genetic material) inserted into the chromosome for mobilizing oriT (RP4)-carrying plasmids (Simon et al. 1983; Simon, 1984).

The transfer of plasmid containing RP4-mob from E. coli to methanotrophs, as further described in the Examples section, was based on the conjugation methods described previously (Martin & Murrell, 1995; Ali, 2006). A 10 ml overnight E. coli S17-1λ pir culture, containing RP4-mob plasmid, was collected on a 0.2 μm pore-size nitrocellulose filter (Millipore). The E. coli donor strain was washed twice with 50 ml NMS. A 50 ml methanotroph culture grown to mid exponential phase ($A_{540}$ of 0.2-0.5) was also collected on the same filter and washed again with 50 mL NMS medium. The filter was placed on an NMS agar plate containing 0.02% (w/v) proteose peptone and incubated for 24 hours at 30° C. with methane except for M. capsulatus, which was incubated at 37° C. for 24 hours.

Following incubation, the cells were washed with 10 ml NMS and collected by centrifugation (7,000×g for 10 min) before re-suspending the cells in 1 ml NMS. Aliquots (50-100 μl) of the cells were spread onto NMS plates containing selective antibiotics and incubated at the appropriate temperature. Colonies typically formed on the plates after 8-12 days. (Note: the E. coli S17-1λ pir strain has chromosomally integrated conjugal transfer functions, thus allowing transfer of plasmid to occur by means of a bi-parental mating without a helper plasmid). Transconjugants can also be purified by serial cultivation in liquid medium containing the appropriate antibiotics for selection, followed by plating onto selective NMS agar plates to obtain single colonies.

In an alternative method for expressing metabolic pathway genes in a microbial host, the biosynthetic pathway genes are inserted directly into the chromosome. Methods for chromosomal modification include both non-targeted and targeted deletions and insertions. For example, non-targeted insertions can be achieved by using transposon mutagenesis to make insertion mutants or gene "knockouts" in vitro using the EZ-Tn5<KAN-2> Insertion Kit (Epicentre). Briefly, the procedure is as follows, according to the manufacturer: Preparation: prepare 0.2 μg of recombinant DNA for the EZ-Tn5<KAN-2> insertion reaction. Day 1: perform the 2-hour in vitro EZ-Tn5<KAN-2> insertion reaction; transform competent recA-E. coli with 1 μl of the reaction mix and select for kanamycin-resistant transposon insertion clones on kanamycin plates overnight. Day 2: prepare DNA from kanamycin-resistant colonies, (and optionally map the EZ-Tn5<KAN-2> Transposon insertion sites and optionally (DNA) sequence chosen clones bi-directionally using the unlabeled forward and reverse transposon-specific primers supplied in the kit.

For targeted modifications, various methods have been developed based on RecA-dependent homologous recombination (Hamilton et al., 1989; Link et al., 1997; Posfai et al., 1999). However, using antibiotic resistance markers for deletion/insertion is limited by the number of different antibiotics that can be used in a given target organism. For this reason, markerless insertion methods have been developed. For example, Yu et al. (2008) describe a deletion procedure in which expression of the A-Red recombinase genes (gam, bet and exo) and the I-SceI endonuclease gene are controlled by tightly regulated promoters ParaB and PrhaB. Arabinose and rhamnose added to cultures to induce ParaB and PrhaB are used and depleted by the bacteria. Thus, by changing the carbon source in the medium from arabinose to rhamnose in bacteria that contain the pREDI plasmid, one can replace a targeted genomic region with a markerless deletion cassette and subsequently delete the selection markers that were introduced.

Sun et al. (2008) also describe methods for sequence-specific insertion or deletion of genes within a bacterial genome. This method permits multiple markerless insertions and scarless deletions in the targeted genome. In the Sun et al. method, a target gene can be deleted in two steps. In the first step, a linear DNA fragment is created that carries the cat (chloramphenicol resistance) gene and sacB (a levansucrase gene that confers sensitivity to sucrose). The fragment is flanked by long (500 bp) regions of DNA that are homologous to the regions that flank the targeted deletion site. The DNA fragment is electroporated into the host cell, which already contains plasmid pKD46, a vector containing the genes for λ Red recombination. Homologous recombination then directs the replacement of the targeted gene. Medium containing chloramphenicol is used to select for cells that contain the desired insertion or deletion. In the second step, a second DNA fragment that contains the desired deletion or insertion is electroporated into host cells that contain the pKD46 plasmid. By plating the resulting cells on medium containing sucrose, one can select for transformants in which the cat-sacB cassette has been replaced. These candidates are also screened for sensitivity to chloramphenicol, and the deletion can be confirmed by PCR and sequencing. By repeating the process, multiple deletions and/or insertions can be achieved. The pKD46 plasmid can then be removed by culturing the cells at 37 C. Thus, by using various genes encoding the isobutanol, butanol, fatty alcohol and fatty acid ester biosynthetic pathways, these pathways can be inserted into the genome of a methanotroph (or non-methanotroph), and unwanted genes (e.g., genes that encode for enzymes that produce competing products) can be removed.

U.S. Patent Publication No. 2006/0057726 describes using sacB gene and the pGP704 suicide vector to engineer markerless insertions into single carbon (C1) metabolizing bacteria. Yomantas et al. (2010) describes methods for markerless substitutions in the genome of the methylotrophic bacterium Methylophilus methylotrophus.

Several methanotroph strains were evaluated according to the present invention as potential hosts for pathway engineering. Of the well characterized methanotroph strains, Methylosinus trichosporium OB3b (NCIMB 11131) and Methylococcus capsulatus str. Bath (NCIMB 11853) were examined for their case of transformability (via conjugation), growth rate, and suitability for industrial fermentation. Both strains can be cultivated in liquid or agar containing Nitrate Mineral Salts (NMS) medium (Whittenbury et al., 1970; Bowman, 2000). Although both strains were found to transform with approximately equal efficiency, Methylococcus capsulatus (Bath) has the advantage of growing about twice as fast as M. trichosporium (ca. 24-30 to reach saturation in shake flask growth). In addition, the ability of M. capsulatus (Bath) to grow more readily at 45° C. is an advantage in industrial cultivation, since this relatively high temperature will impede the growth of other potentially contaminating microorganisms. Furthermore, the complete genome sequence of M. capsulatus (Bath) has been published (Ward et al., 2004), and as such, manipulation of its genome via genetic engineering is readily available to one of skill in the art. Thus, in certain embodiments, M. capsulatus (Bath) is used as a model organism for further development of genetically modified host microorganisms.

Following conjugation, positive methanotroph trans-conjugants were purified on NMS agar containing the appropriate antibiotic selection (e.g., 15 µg/ml kanamycin for selecting the plasmid and counter-selecting the untransformed methanotroph host cells, and 10 µg/ml for counter-selecting the *E. coli* donor cells). Alternatively, transconjugants can be purified by serial cultivation in liquid medium containing the appropriate antibiotics for selection, followed by plating onto selective NMS agar plates to obtain single colonies. Colonies were used to inoculate small (5-10 ml) starter cultures in liquid NMS medium containing, for example, 15 µg/ml kanamycin in 125-ml flasks. The flasks were stoppered with tight-fitting Suba Seals to create a closed atmosphere inside the flasks. A volume of gas corresponding to 20% of the total volume of the flask and composed of 95% methane and 5% carbon dioxide was injected via a sterile syringe and 23-gauge needle into each flask. Flasks were shaken at 200 rpm and 45° C. When these cultures achieved an optical density of $A_{540}>0.5$ (after about 24 hours), a 1:100 dilution of these cells was used to inoculate 125 ml (or larger volume) cultures, and the same growth protocol was followed. Growth in shake flasks is most robust when the liquid volume is maintained at about 5-10% of the nominal volume of the flask so that good aeration of the liquid is achieved. These flasks were then used for the subsequent assays of product formation. In certain examples related to 2-KIV feeding experiments, only the ketoacid intermediate was added along with the methane and $CO_2$ at the zero time point.

After approximately 72 hours of growth, the cultures were harvested for analysis by gas chromatography. The sealed flasks were first chilled for at least 1 hour on ice, to concentrate any volatile organic compounds from the vapor phase into the liquid phase. After opening the flasks, an aliquot of the culture was diluted 1:2 with ethyl acetate in a clean 50 ml tube to extract and concentrate the isobutanol, butanol, fatty alcohols or fatty acid esters. After vortexing or shaking (and centrifugation to separate the phases), a small volume of the organic layer (approximately 1 ml) was filtered through a 0.2 µm PTFE filter, and 1 µl of the purified extract was then injected into an Agilent 7890A GC equipped with a Leap Technologies (Carrboro, NC) CombiPAL autosampler for analysis. Appropriate purified standards were included to generate a standard curve and determine the concentration of the targeted product. Each measurement included a positive control and a negative control (e.g., a wild-type sample or other appropriate background control) with each sample set. Additional details of the methods used for the specific products are given in the Examples section. Strains with the highest levels of production were designated for further scale-up in 1-10 liter fermentors.

During the analysis of the engineered host strains, unexpectedly high levels of isobutanol and butanol consumption (up to 30 mM after 72 hours of growth) was observed even in wild-type cultures of *M. capsulatus* (Bath), and therefore it was important to find mutant strains that can produce these products at a rate that is greater than their inherent rate of consumption. In certain embodiments of the invention, the competing alcohol dehydrogenase and alcohol oxidase activities are identified, and reduced or eliminated by gene knockouts, as described above.

For initial fermentation scale-up in the 1-10 liter range, methods similar to those described in Theisen et al. (2005) and U.S. Pat. No. 4,594,324 can be used, with specific modifications for *M. capsulatus* (Bath). A fermentation system such as the Sartorius-Stedim Biostat A plus system (Goettingen, Germany) can be used, or other equivalent fermentation systems and methods for methanotroph fermentation (e.g., see Jiang et al., 2010). An Applikon ADI 1030 Bio Controller and ADI 1035 BioConsole (Applikon Biotechnology Inc., Foster City, CA) can also be used for the 10 liter vessel.

The starting inoculum is created by inoculating a large colony of *M. capsulatus* (Bath) containing the desired plasmid from a plate culture into 10 ml of sterile NMS medium containing kanamycin, as described above. After 24 to 48 hours, when the optical density ($A_{540}$) of the culture is greater than 0.5, five starter flasks of NMS medium are inoculated at 1:100 dilution. The liquid volumes in these starter inocula can range in size from 20 ml each for a 1 liter fermentor to 200 ml each for a 10 liter fermentor (i.e., about a 10% inoculum).

After autoclaving the NMS medium in the fermentor vessel, the phosphate salts portion of the NMS medium and the kanamycin (both sterilized) are added to the vessel. The same inlet can be used to inject the starter cultures. Air is supplied as oil-free compressor air, and the methane carbon source is supplied from a pre-mixed tank (Airgas) containing 95% methane and 5% $CO_2$. The air and methane are mixed to 15-20% methane using equipment that is rated intrinsically safe or explosion proof to eliminate the possibility of sparking or static electricity, which could lead to an explosion. The gas flow rate depends on the fermentor size and culture density, but a value of 0.75 liters per minute for 10 liters is typical. The gas mixture is fed into the fermentor, and the entire culture is mixed with an impeller rotating at approximately 200 rpm for agitation, the rate of which may be increased during growth. For maintenance of the culture pH at 6.8, 0.1 M HCl or 1 M NaOH is added as needed. The temperature is maintained at 45° C. by a thermostatic jacket. The effluent gas is fed through a water-jacketed condenser to reduce liquid loss at 45° C., and vented to a fume hood.

The fermentation is monitored (via pH and dissolved oxygen probes) and controlled using Sartorius BioPAT MFCS bioprocess control software (Sartorius Corp, Bohemia, NY). A dissolved oxygen concentration below 1% saturation with air (typically 0.2-0.3%) is desirable to avoid wasting methane. Periodically, small samples of the fermentation broth are removed by sterile transfer and used to measure the optical density of the culture. These samples can also be used to monitor product formation using the methods described above and in the Examples section. Purity of the culture can also be checked by plating a small sample onto R2A agar, which allows most organisms other than methanotrophs to grow. Cultures achieve an optical density ($A_{540}$) of greater than 9 after about 48 hours. For *M. capsulatus* (Bath), 1 ml of culture with $A_{540}$ equal to 1 corresponds to about 0.23-0.25 mg of dry weight of biomass. When the maximum cell density or product concentration is achieved, the culture can be harvested and analyzed.

For large-scale commercial fermentation, a system based on the fermentor design employed by Norferm (Norefem, AS; Stavanger, Norway) for production of single-cell protein can be used (Bothe et al., 2002; EP 1419234; U.S. Publication No. 2009/0263877). The largest system has a total volume of 300 m$^3$ (300,000 liters) and an annual production capacity of 10,000 tons of biomass (van Laere et al., 2005). Publications such as EP 1419234, U.S. Publication No. 2009/0263877 and Villadsen (2012), and references therein, describe a loop reactor and bioprocess methods for culturing methanotrophs at the commercial scale. The advantage of this design is that nutrient gases such as methane and oxygen are supplied to the system in such a way that exposure of the cells to nutrient-depleted culture medium or to unduly high concentrations of nutrient gases is minimized.

However, when using "wet" natural gas as a nutrient feedstock, the problem of acetate and propionate toxicity (resulting from the oxidation of ethane and propane, respectively) may need to be addressed (Bothe et al., 2002; Eiteman & Altman, 2006). A genetic approach is to eliminate (knock-out) or knock-down the ethanol and propanol dehydrogenases and acetaldehyde/propionaldehyde dehydrogenases that convert the ethanol and propanol to the corresponding acids. Another approach is to introduce the genes for acetate assimilation from an organism that can use it as a carbon source, such as E. coli (Wolfe, 2005). For example, AMP-ACS (acetate: CoA ligase [AMP forming]; EC 6.2.1.1) catalyzes the conversion of acetate and ATP to an enzyme-bound acetyladenylate (acetyl-AMP) and pyrophosphate. In a subsequent step, it reacts the acetyl-AMP with CoASH (CoenzymeA-SH) to acetyl-CoA and free AMP. Similarly, AMP-ACS can activate and assimilate propionate (Wolfe, 2005). In this way, the two potentially harmful organic acids are converted into the useful intermediate, acetyl-CoA. These genes can be cloned and expressed in a methanotroph host by the methods described above.

Another aspect of the commercial production of multi-carbon compounds from methane using the present invention involves recovering and purifying the desired product from the fermentation broth. The method to be used depends on the physico-chemical properties of the product and the nature and composition of the fermentation medium and cells. For example, U.S. Pat. No. 8,101,808 describes methods for recovering C3-C6 alcohols from fermentation broth using continuous flash evaporation and phase separation processing. Thus, the biologically produced multi-carbon compounds of the invention may be isolated from the fermentation medium using methods known in the art for Acetone-butanol-ethanol (ABE) fermentations For example, solids may be removed from the fermentation medium by centrifugation, filtration, decantation, wherein the multi-carbon compounds of the invention may be isolated from the fermentation medium using methods such as distillation, azeotropic distillation, liquid-liquid extraction, adsorption, gas stripping, membrane evaporation, or pervaporation.

In certain embodiments the invention, the fermentation process produces greater than about 7% (v/v) concentration of the desired multi-carbon product in the fermentation broth, and the product is separated from the rest of the medium using membrane separation technology to achieve about a 12% or greater concentration of the product, at which point relatively small molecules (such as isobutanol) can be further purified by phase separation in an integrated system (Hickey & Slater, 1990; Neel, 1995; Hägg, 1998; Liu et al., 2011). Continuous recovery of the product from the fermentation medium has the advantage of possibly reducing the toxicity effects of the multi-carbon products.

For longer-chain alcohols, such as fatty alcohols, U.S. Pat. No. 8,268,599 describes methods for separating these components from the aqueous phase of the fermentation by bi-phasic separation, whereby the immiscibility of the product compounds with the fermentation broth allows the organic phase to be collected and removed. This separation can also reduce the toxic effects of the product on the host microbial cells.

U.S. Publication No. 2007/0251141 describes methods for recovering fatty acid methyl esters (FAMEs) from a liquid suspension by adding urea and creating a phase separation whereby the saturated and unsaturated FAMEs can be recovered separately. Membrane separation methods can also be applied to purifying fatty acid ester products such as biodiesel (Saleh, 2011).

In certain embodiments, a methane substrate of the invention is provided or obtained from a natural gas source, wherein the natural gas is "wet" natural gas or "dry" natural gas. Natural gas is referred to as "dry" natural gas when it is almost pure methane, having had most of the other commonly associated hydrocarbons removed. When other hydrocarbons are present, the natural gas is referred to as "wet". Wet natural gas typically comprises about 70-90% methane, about 0-20% ethane, propane and butane (combined total), about 0-8% $CO_2$, about 0-5% N2, about 0-5% $H_2S$ and trace amounts of oxygen, helium, argon, neon and xenon. In certain other embodiments, a methane substrate of the invention is provided or obtained from methane emissions, or methane off-gases, which are generated by a variety of natural and human-influenced processes, including anaerobic decomposition in solid waste landfills, enteric fermentation in ruminant animals, organic solids decomposition in digesters and wastewater treatment operations, and methane leakage in fossil fuel recovery, transport, and processing systems.

Table 1 below, provides exemplary polynucleotide and polypeptide sequences for implementing various embodiments of the present invention. These sequences are not meant to limit or exclude the use of other polynucleotide sequences encoding polypeptides or enzymes useful for producing multi-carbon compounds according to the present invention. For example, one of skill in the art can search gene sequence databases (or genome databases) and/or protein sequence databases (e.g., via BLAST or other sequence search algorithms) to identify homologous polynucleotides encoding one or more enzyme activities based on the reference sequences set forth in Table 1. Alternatively, a homologous polynucleotide may be isolated directly by using all or a portion of a nucleic acid sequence set forth in Table 1 (or a primer sequence set forth below in Table 2) as DNA hybridization probes to screen libraries from any desired microorgansim and/or PCR amplify a desired polynucleotide sequence using methodology well known to those skilled in the art.

TABLE 1

Exemplary Nucleic Acid and Polypeptide Sequences Described in the Invention

| Pathway or Reaction | Gene Name | Nucleic acid SEQ | Enzyme Name | Polypeptide SEQ ID | Organism |
|---|---|---|---|---|---|
| isobutanol | MCA1837 | SEQ ID NO: 1 | ALS | SEQ ID NO: 2 | M. capsulatus, Bath |
| isobutanol | MCA2272 | SEQ ID NO: 3 | KARI | SEQ ID NO: 4 | M. capsulatus, Bath |
| isobutanol | MCA2082 | SEQ ID NO: 5 | DHAD | SEQ ID NO: 6 | M. capsulatus, Bath |
| isobutanol | MCA0996 | SEQ ID NO: 7 | KDC | SEQ ID NO: 8 | M. capsulatus, Bath |
| isobutanol | YMR318C | SEQ ID NO: 9 | ADH | SEQ ID NO: 10 | S. cerevisiae |

TABLE 1-continued

Exemplary Nucleic Acid and Polypeptide Sequences Described in the Invention

| Pathway or Reaction | Gene Name | Nucleic acid SEQ | Enzyme Name | Polypeptide SEQ ID | Organism |
|---|---|---|---|---|---|
| isobutanol | MtKDC | SEQ ID NO: 82 | KDC | SEQ ID NO: 162 | *M. trichosporium* |
| isobutanol | MtADH | SEQ ID NO: 83 | ADH | SEQ ID NO: 163 | *M. trichosporium* |
| isobutanol | McADH-2a | SEQ ID NO: 84 | ADH | SEQ ID NO: 164 | *M. capsulatus*, Bath |
| isobutanol | McADH-2b | SEQ ID NO: 85 | ADH | SEQ ID NO: 165 | *M. capsulatus*, Bath |
| Isobutanol | LlkivD | SEQ ID NO: 86 | KDC | SEQ ID NO: 166 | *L. lactis* |
| Isobutanol | ScPDC6 | SEQ ID NO: 87 | KDC | SEQ ID NO: 167 | *S. cerevisiae* |
| Isobutanol | ScARO10 | SEQ ID NO: 88 | KDC | SEQ ID NO: 168 | *S. cerevisiae* |
| Isobutanol | ScADH2 | SEQ ID NO: 89 | ADH | SEQ ID NO: 169 | *S. cerevisiae* |
| Isobutanol | ScPDC1 | SEQ ID NO: 90 | KDC | SEQ ID NO: 170 | *S. cerevisiae* |
| isobutanol | CaPDC | SEQ ID NO: 91 | KDC | SEQ ID NO: 171 | *C. acetobutylicum* |
| $CH_4$ to $CH_3OH$ | MCA1798 | SEQ ID NO: 11 | pmoC subunit 1 | SEQ ID NO: 12 | *M. capsulatus*, Bath |
| $CH_4$ to $CH_3OH$ | MCA1797 | SEQ ID NO: 13 | pmoA subunit 1 | SEQ ID NO: 14 | *M. capsulatus*, Bath |
| $CH_4$ to $CH_3OH$ | MCA1796 | SEQ ID NO: 15 | pmoB subunit 1 | SEQ ID NO: 16 | *M. capsulatus*, Bath |
| $CH_4$ to $CH_3OH$ | MCA2855 | SEQ ID NO: 17 | pmoC subunit 2 | SEQ ID NO: 18 | *M. capsulatus*, Bath |
| $CH_4$ to $CH_3OH$ | MCA2854 | SEQ ID NO: 19 | pmoA subunit 2 | SEQ ID NO: 20 | *M. capsulatus*, Bath |
| $CH_4$ to $CH_3OH$ | MCA2853 | SEQ ID NO: 21 | pmoB subunit 2 | SEQ ID NO: 22 | *M. capsulatus*, Bath |
| $CH_4$ to $CH_3OH$ | MCA1194 | SEQ ID NO: 23 | mmoX | SEQ ID NO: 24 | *M. capsulatus*, Bath |
| $CH_4$ to $CH_3OH$ | MCA1195 | SEQ ID NO: 25 | mmoY | SEQ ID NO: 26 | *M. capsulatus*, Bath |
| $CH_4$ to $CH_3OH$ | MCA1196 | SEQ ID NO: 27 | mmoB | SEQ ID NO: 28 | *M. capsulatus*, Bath |
| $CH_4$ to $CH_3OH$ | MCA1198 | SEQ ID NO: 29 | mmoZ | SEQ ID NO: 30 | *M. capsulatus*, Bath |
| $CH_4$ to $CH_3OH$ | MCA1199 | SEQ ID NO: 31 | mmoD | SEQ ID NO: 32 | *M. capsulatus*, Bath |
| $CH_4$ to $CH_3OH$ | MCA1200 | SEQ ID NO: 33 | mmoC | SEQ ID NO: 34 | *M. capsulatus*, Bath |
| $CH_3OH$ to $H_2CO$ | MCA0779 | SEQ ID NO: 35 | mxaF | SEQ ID NO: 36 | *M. capsulatus*, Bath |
| $CH_3OH$ to $H_2CO$ | MCA0780 | SEQ ID NO: 37 | mxaJ | SEQ ID NO: 38 | *M. capsulatus*, Bath |
| $CH_3OH$ to $H_2CO$ | MCA0781 | SEQ ID NO: 39 | mxaG | SEQ ID NO: 40 | *M. capsulatus*, Bath |
| $CH_3OH$ to $H_2CO$ | MCA0782 | SEQ ID NO: 41 | mxaI | SEQ ID NO: 42 | *M. capsulatus*, Bath |
| $CH_3OH$ to $H_2CO$ | MCA0783 | SEQ ID NO: 43 | mxaR | SEQ ID NO: 44 | *M. capsulatus*, Bath |
| $CH_3OH$ to $H_2CO$ | MCA0785 | SEQ ID NO: 45 | mxaA | SEQ ID NO: 46 | *M. capsulatus*, Bath |
| $CH_3OH$ to $H_2CO$ | MCA0786 | SEQ ID NO: 47 | mxaC | SEQ ID NO: 48 | *M. capsulatus*, Bath |
| $CH_3OH$ to $H_2CO$ | MCA0787 | SEQ ID NO: 49 | mxaK | SEQ ID NO: 50 | *M. capsulatus*, Bath |
| $CH_3OH$ to $H_2CO$ | MCA0788 | SEQ ID NO: 51 | mxaL | SEQ ID NO: 52 | *M. capsulatus*, Bath |
| $CH_3OH$ to $H_2CO$ | MCA0789 | SEQ ID NO: 53 | mxaD | SEQ ID NO: 54 | *M. capsulatus*, Bath |
| 1-butanol | MCA0354 | SEQ ID NO: 55 | Threonine-ammonia-lyase | SEQ ID NO: 56 | *M. capsulatus*, Bath |
| 1-butanol | MCA2275 | SEQ ID NO: 57 | 2-ethylmalate synthase | SEQ ID NO: 58 | *M. capsulatus*, Bath |
| 1-butanol | MCA2065 | SEQ ID NO: 59 | Isopropyl malate dehydratase, large subunit | SEQ ID NO: 60 | *M. capsulatus*, Bath |
| 1-butanol | MCA2064 | SEQ ID NO: 61 | Isopropyl malate dehydratase, small subunit | SEQ ID NO: 62 | *M. capsulatus*, Bath |
| 1-butanol | VIMSS17191 | SEQ ID NO: 160 | tdcB | SEQ ID NO: 161 | *E. coli* |
| 1-butanol | MCA0996 | SEQ ID NO: 7 | KDC | SEQ ID NO: 8 | *M. capsulatus*, Bath |
| 1-butanol | YMR318C | SEQ ID NO: 9 | ADH | SEQ ID NO: 10 | *S. cerevisiae* |
| 1-butanol | MtKDC | SEQ ID NO: 82 | KDC | SEQ ID NO: 162 | *M. trichosporium* |
| 1-butanol | MtADH | SEQ ID NO: 83 | ADH | SEQ ID NO: 163 | *M. trichosporium* |
| 1-butanol | McADH-2a | SEQ ID NO: 84 | ADH | SEQ ID NO: 164 | *M. capsulatus*, Bath |
| 1-butanol | McADH-2b | SEQ ID NO: 85 | ADH | SEQ ID NO: 165 | *M. capsulatus*, Bath |
| 1-butanol | LlkivD | SEQ ID NO: 86 | KDC | SEQ ID NO: 166 | *L. lactis* |
| 1-butanol | ScPDC6 | SEQ ID NO: 87 | KDC | SEQ ID NO: 167 | *S. cerevisiae* |
| 1-butanol | ScARO10 | SEQ ID NO: 88 | KDC | SEQ ID NO: 168 | *S. cerevisiae* |
| 1-butanol | ScADH2 | SEQ ID NO: 89 | ADH | SEQ ID NO: 169 | *S. cerevisiae* |
| 1-butanol | ScPDC1 | SEQ ID NO: 90 | KDC | SEQ ID NO: 170 | *S. cerevisiae* |
| 1-butanol | CaPDC | SEQ ID NO: 91 | KDC | SEQ ID NO: 171 | *C. acetobutylicum* |
| Fatty alcohol | FAR | SEQ ID NO: 65 | FAR | SEQ ID NO: 66 | *M. algicola* |
| Fatty acid ester | Ab-wax-dgaT | SEQ ID NO: 67 | wax-dgaT | SEQ ID NO: 68 | *A. baylyi* |
| Fatty acid ester | Psyc_0223 | SEQ ID NO: 69 | PaWES | SEQ ID NO: 70 | *P. arcticus* |
| Fatty acid ester | ROP_02100 | SEQ ID NO: 71 | RoWES1 | SEQ ID NO: 72 | *R. opacus* |
| Fatty acid ester | ROP_13050 | SEQ ID NO: 73 | RoWES2 | SEQ ID NO: 74 | *R. opacus* |
| Fatty acid ester | ROP_54550 | SEQ ID NO: 75 | RoWES3 | SEQ ID NO: 76 | *R. opacus* |
| Fatty acid ester | ROP_26950 | SEQ ID NO: 77 | RoWES4 | SEQ ID NO: 78 | *R. opacus* |
| 2,3-butanediol | YAL060W | SEQ ID NO: 156 | Bdh1 | SEQ ID NO: 157 | *S. cerevisiae* |
| RuMP | MCA3049 | SEQ ID NO: 160 | HPS | SEQ ID NO: 161 | *M. capsulatus*, Bath |
| RuMP | MCA3050 | SEQ ID NO: 162 | HPS/PHI | SEQ ID NO: 163 | *M. capsulatus*, Bath |

TABLE 2

Plasmid, Primer, Promoter and Gene Fragment
Sequences Described in the Invention

| Name | Nucleic acid SEQ ID |
| --- | --- |
| pCM132 | SEQ ID NO: 79 |
| pJSvec | SEQ ID NO: 80 |
| pMZT3 | SEQ ID NO: 81 |
| JPS00082 | SEQ ID NO: 92 |
| JPS00031 | SEQ ID NO: 93 |
| JPS00032 | SEQ ID NO: 94 |
| GMV257 | SEQ ID NO: 95 |
| JPS00118 | SEQ ID NO: 96 |
| JPS00119 | SEQ ID NO: 97 |
| ESG00087 | SEQ ID NO: 98 |
| GMV251 | SEQ ID NO: 99 |
| rnpB | SEQ ID NO: 100 |
| JPS00161 | SEQ ID NO: 101 |
| JPS00162 | SEQ ID NO: 102 |
| JPS00163 | SEQ ID NO: 103 |
| JPS00164 | SEQ ID NO: 104 |
| JPS00172 | SEQ ID NO: 105 |
| JPS00173 | SEQ ID NO: 106 |
| JPS00174 | SEQ ID NO: 107 |
| JPS00176 | SEQ ID NO: 108 |
| JPS00177 | SEQ ID NO: 109 |
| JPS00157 | SEQ ID NO: 110 |
| JPS00178 | SEQ ID NO: 111 |
| Me-AM1 PmxaF | SEQ ID NO: 112 |
| JPS00169 | SEQ ID NO: 113 |
| GMV00251 | SEQ ID NO: 114 |
| JPS00170 | SEQ ID NO: 115 |
| JPS00171 | SEQ ID NO: 116 |
| JPS00153 | SEQ ID NO: 117 |
| JPS00151 | SEQ ID NO: 118 |
| JPS00154 | SEQ ID NO: 119 |
| JPS00183 | SEQ ID NO: 120 |
| JPS00185 | SEQ ID NO: 121 |
| J23100 | SEQ ID NO: 122 |
| J23100 hybrid | SEQ ID NO: 123 |
| J23115 | SEQ ID NO: 124 |
| GMV00233 | SEQ ID NO: 125 |
| GMV00235 | SEQ ID NO: 126 |
| GMV00433 | SEQ ID NO: 127 |
| GMV00434 | SEQ ID NO: 128 |
| GMV00435 | SEQ ID NO: 129 |
| GMV00436 | SEQ ID NO: 130 |
| GMV00437 | SEQ ID NO: 131 |
| GMV00438 | SEQ ID NO: 132 |
| GMV00439 | SEQ ID NO: 133 |
| GMV00440 | SEQ ID NO: 134 |
| GMV00441 | SEQ ID NO: 135 |
| GMV00442 | SEQ ID NO: 136 |
| ESG00084 | SEQ ID NO: 137 |
| ESG00088 | SEQ ID NO: 138 |
| pMZT37 | SEQ ID NO: 139 |
| MaFAR-g1 | SEQ ID NO: 140 |
| MaFAR-g2 | SEQ ID NO: 141 |
| MaFAR-g3 | SEQ ID NO: 142 |
| MaFAR-g4 | SEQ ID NO: 143 |
| GMV410 | SEQ ID NO: 144 |
| GMV411 | SEQ ID NO: 145 |
| GMV412 | SEQ ID NO: 146 |
| GMV413 | SEQ ID NO: 147 |
| GMV414 | SEQ ID NO: 148 |
| GMV415 | SEQ ID NO: 149 |
| GMV416 | SEQ ID NO: 150 |
| GMV417 | SEQ ID NO: 151 |
| GMV418 | SEQ ID NO: 152 |
| GMV419 | SEQ ID NO: 153 |
| GMV420 | SEQ ID NO: 154 |
| GMV421 | SEQ ID NO: 155 |
| GMV422 | SEQ ID NO: 158 |
| GMV423 | SEQ ID NO: 159 |

EXAMPLES

The present invention is further defined in the following Examples. It should be understood that these examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Biosynthetic Production of Isobutanol from Methane

Initial experiments were performed to confirm and validate enzymatic activity of isobutanol pathway enzymes at the relatively high temperatures (i.e., 45° C.) requisite for growth of one preferred methanotroph host organism, *Methylococcus capsulatus* (Bath). Thus, in this example, the methanotroph *M. capsulatus* was engineered in the first series of experiments to overexpress two isobutanol pathway enzymes, ketoacid decarboxylase (KDC) and alcohol dehydrogenase (ADH), prior to introducing the full complement of five isobutanol pathway enzymes (Atsumi et al., 2010) into *M. capsulatus*. Following the functional validation of KDC and ADH activity in *M. capsulatus* (set forth below), the complete five-gene isobutanol pathway was introduced into *M. capsulatus*, the results of which are set forth below.
Gene Selection, Synthesis and Cloning For the two-gene (isobutanol) pathway experiments (and for the downstream section of the five-gene isobutanol pathway set forth below), ketoacid decarboxylase (KDC) and alcohol dehydrogenase (ADH) genes were amplified by colony PCR from *Methylosinus trichosporium* (strain: OB3b, National Collection of Industrial, Food and Marine Bacteria (NCIMB) Accession No: 11131) and *Methylococcus capsulatus* (Bath). The *Methylosinus trichosporium* gene, MtKDC, encoding KDC is set forth in SEQ ID NO: 82, *Methylosinus trichosporium* gene, MtADH, encoding ADH is set forth in SEQ ID NO: 83. The *Methylococcus capsulatus* (Bath) gene, McKDC, encoding KDC is set forth in SEQ ID NO:7, the *Methylococcus capsulatus* (Bath) genes, McADH-2a and McADH-2b, encoding two ADH2 homologs, are set forth in SEQ ID NO:84 and SEQ ID NO:85, respectively.

Other KDC and ADH genes such as L1KIVD: *Lactococcus lactis* KDC (SEQ ID NO: 86); ScPDC6: *Saccharomyces cerevisiae* PDC6 (SEQ ID NO:87); ScARO10: *S. cerevisiae* ARO10 (SEQ ID NO:88); ScADH2: *S. cerevisiae* ADH2 (SEQ ID NO:89); ScPDC1: *S. cerevisiae* PDC1 (SEQ ID NO:90); CaPDC: *Clostridium acetobutylicum* PDC (SEQ ID NO:91) were codon optimized for expression in *M. capsulatus* and de novo synthesized by GenScript (Piscataway, NJ). Various KDC and ADH combinations were cloned with a constitutive promoter (J23115) or inducible (Ptrc) promoter into plasmid pCM132 (Accession No. AF327720; SEQ ID NO:79) with the Clontech In-Fusion kit (Mountain View, CA). A gene for the ds-Red protein was used as a control. Plasmids were transformed into *E. coli* S17-1 for conjugation.
Vector Inserts Vector inserts contain the DNA fragments that are to be carried in the plasmid. The vector inserts were designed as exchangeable parts to the vector backbone described above. In one embodiment of the 2-gene pathway example, the plasmids were designed to contain two inserts made up of *Methylococcus capsulatus* KDC (MCA0996; SEQ ID NO:7) and *Saccharomyces cerevisiae* ADH6 (YMR318C; SEQ ID NO:9) genes. Both genes were amplified from genomic DNA of their respective hosts, with the primers described above in Tables 2 and below in Table 3.

TABLE 3

Plasmid insert modules, templates and primers

| Plasmid | PCR rxn: | Vector Backbone | Insert 1 | Insert 2 | Insert 3 |
|---|---|---|---|---|---|
| pJS0025 | template | pJSvec | MCA0996 (*M. capsulatus* DNA) | YMR318C (*S. cerevisiae* DNA) | — |
|  | primer 1 | JPS0082 | JPS0032 | JPS00118 | — |
|  | primer 2 | JPS0031 | GMV00257 | JPS00119 | — |
| pGMV145 | template | pMZT3 | MCA0996 (*M. capsulatus* DNA) | YMR318C (*S. cerevisiae* DNA) | — |
|  | primer 1 | JPS0082 | GMV00251 | JPS00118 | — |
|  | primer 2 | ESG00087 | GMV00257 | JPS00119 | — |
| pJS034 | template | pGMV145 | IDT gBlock synthesized rnpB DNA | — | — |
|  | primer 1 | JPS00161 | JPS00163 | — | — |
|  | primer 2 | JPS00162 | JPS00164 | — | — |
| pJS041 pJS041n | template | pJS034 | MCA1837 (*M. capsulatus* DNA) | MCA2272 (*M. capsulatus* DNA) | MCA2082 (*M. capsulatus* DNA) |
|  | primer 1 | JPS00162 | JPS00173 | JPS00176 | JPS00157 |
|  | primer 2 | JPS00172 | JPS00174 | JPS00177 | JPS00178 |
| pJS048 | template | pJS034 | IDT gBlock synthesized Me-AM1 PmxaF DNA | — | — |
|  | primer 1 | JPS00169 | JPS00170 | — | — |
|  | primer 2 | GMV251 | JPS00171 | — | — |
| pJS038 | template | pGMV145 | MCA1837 (*M. capsulatus* DNA) | — | — |
|  | primer 1 | JPS00153 | JPS00151 | — | — |
|  | primer 2 | GMV251 | JPS00154 | — | — |
| pJS042 pJS042n | template | pJS048 | pJS038 | — | — |
|  | primer 1 | JPS00162 | JPS00173 | — | — |
|  | primer 2 | JPS00172 | JPS00178 | — | — |
| pJS050 | template | pJS041n | pJS041n | — | — |
|  | primer 1 | JPS00183 | JPS00174 | — | — |
|  | primer 2 | JPS00176 | JPS00185 | — | — |

The modular parts (i.e., vector backbone and vector inserts) were PCR amplified (as listed in Table 3) with NEB Phusion master mix (New England Biolabs; Ipswich, MA) according to the manufacturer's instructions and in vitro assembled with the Clontech InFusion HD Cloning System kit (Clontech; Mountain View, CA) according to the manufacturer's instructions to generate circular plasmid listed below.

The in vitro assembled plasmids (2 µl of the InFusion reaction) were transformed into chemically competent NEB Turbo *E. coli* cells, screened by colony PCR, purified, and subsequently sequence verified.

The plasmid pJSvec (SEQ ID NO:80) served as the template for the vector backbone with an inducible promoter and consisted of the pCM132 cloning vector (SEQ ID NO:79), lacIq, and the IPTG-inducible pTrc promoter.

The plasmid pMZT3 (SEQ ID NO:81) served as the template for the vector backbone with a constitutive promoter and consisted of the pCM132 (SEQ ID NO:79) cloning vector and *E. coli* J23115 promoter (SEQ ID NO:124).

The plasmid pJS0025 was designed to express *M. capsulatus* KDC (MCA0996; SEQ ID NO:7) and *S. cerevisiae* ADH6 (YMR 318C; SEQ ID NO:9) from the inducible promoter.

The plasmid pGMV145 was designed to express *M. capsulatus* KDC (MCA0996; SEQ ID NO:7) and *S. cerevisiae* ADH6 (YMR 318C; SEQ ID NO:9) from the constitutive promoter.

The plasmid pJS034 introduced a second terminator sequence into pGMV145. The pGMV145 vector backbone was PCR amplified with primers JPS00161 (SEQ ID NO:101)/JPS00162 (SEQ ID NO:102) and KOD mastermix. The insert contained DNA sequence for rnpB (SEQ ID NO:100) synthesized as a gBlock from Integrated DNA Technologies (Coralville, IA) and amplified with JPS00163 (SEQ ID NO:103)/JPS00164 (SEQ ID NO:104) primers.

Expression of the Full Five-Gene Pathway for Methane-to-Isobutanol Conversion

In order to synthesize isobutanol from methane (i.e., via pyruvate), without the need to exogenously supply a ketoacid intermediate, the pJS041 and pJS041n plasmids were designed to express all five isobutanol pathway genes: (1) *M. capsulatus* KDC (MCA0996; SEQ ID NO:7) and (2) *S. cerevisiae* ADH6 (YMR318C; SEQ ID NO:9) from the J23115 constitutive promoter (SEQ ID NO:124), and (3) *M. capsulatus* ilvK (MCA1837; SEQ ID NO: 1), (4) *M. capsulatus* ilvC (MCA2272; SEQ ID NO:3), and (5) *M. capsulatus* ilvD (MCA2082; SEQ ID NO:5) from the J23100 constitutive promoter (see, FIG. 3). Plasmid pJS041n contains the canonical J23100 promoter sequence (5'-TTGACGGCTAGCTCAGTCCTAGGTACAGTGCTAGC-3'; SEQ ID NO:122), and plasmid pJS041 contains a modified J23100 promoter sequence (5'-TTGACGGCTAGCTCAGCCCTTGGTACAATGCTAGC-3'; SEQ ID NO:123), which represents a hybrid fusion of the J23100 and J23115 (SEQ ID NO:124) promoters that arose during the process of cloning and generating the plasmid in *E. coli* (Table 3). This mutated construct was retained and tested to see whether the promoter mutations might impart improved production of isobutanol in the microbial expression host (e.g., *M. capsulatus* (Bath)).

TABLE 4

Sequence comparison between the "hybrid"
promoters in plasmids pJS041 and pJS042 and
the canonical promoters J23115 and J23100

| J23115 (SEQ ID NO: 124) | TTTATAGCTAGCTCAGCC CTTGGTACAATGCTAGC |
|---|---|
| pJS041-hybrid (SEQ ID NO: 123) | TTGACGGCTAGCTCAGCC CTTGGTACAATGCTAGC |
| J23100 (SEQ ID NO: 122) | TTGACGGCTAGCTCAGTC CTAGGTACAGTGCTAGC |

The pJS048 plasmid replaced the J23100 promoter with the MxaF promoter (SEQ ID NO: 112) from *Methylobacterium extorquens* AM-1 in pJS034.

The pJS050 plasmid was designed to express five genes: *M. capsulatus* KDC (MCA0996; SEQ ID NO:7) and *S. cerevisiae* ADH6 (YMR318C; SEQ ID NO:9) from the J23115 constitutive promoter and *M. capsulatus* ilvK (MCA1837; SEQ ID NO:1), *M. capsulatus* ilvC (MCA2272; SEQ ID NO:3), and *M. capsulatus* ilvD (MCA2082; SEQ ID NO: 5) from the J23115 constitutive promoter.

Conjugations

The method for conjugal transfer of RP4-mob-containing plasmids into *M. trichosporium* and *M. capsulatus* (Bath) was based on the method described previously (Martin & Murrell, 1995; Stafford et. al., 2003). Briefly, 10 ml of a 16 hour culture of *E. coli* S17-1 carrying the plasmid was collected on a sterile 47 mm, 0.2 μm pore-size, nitrocellulose filter (Millipore). The cells were washed with 50 ml NMS medium without antibiotic. A fresh 50 ml culture of the *M. trichosporium* or *M. capsulatus* (Bath) recipient grown to an optical density ($A_{540}$) of 0.2-0.4 (mid-exponential phase of growth) was collected on the same filter as the *E. coli* S17-1 host cells. The cells were washed with 50 ml NMS and the filter was placed on an NMS agar plate supplemented with 0.02% (w/v) Proteose Peptone (Difco Laboratories, Detroit, MI) and incubated for 24 hours at 30° C. (for *M. trichosporium*) or 37° C. (*M. capsulatus* (Bath)) in the presence of 20-25% methane ($CH_4$) (v/v) in air. After incubation, the cells from the conjugation plate were washed from the filter with 10 ml of NMS, pelleted by centrifugation at 7,000×g, and re-suspended in 1 ml of NMS. 150 μl aliquots were spread onto selective NMS plates containing 10 μg/ml nalidixic acid to select against *E. coli* and 15 μg/ml kanamycin for plasmid selection and incubated at 30° C. or 45° C. for *M. trichosporium* or *M. capsulatus*, respectively. The remaining cells were grown in NMS liquid containing 10 μg/ml nalidixic acid and 15 μg/ml kanamycin (Sigma, St. Louis, MO) as a secondary selection process. Cells grown in liquid selection were serially passaged three times, before spreading onto selective NMS plates for clone isolation.

*M. capsulatus* Growth Conditions

From a saturated starter culture, *M. capsulatus* (Bath) cells were diluted 1:100 into 10 ml of fresh NMS containing 15 μg/ml kanamycin in a 125-ml shake flask. For ketoacid feeding experiments, cultures were treated with 1 g/L 2-ketovalerate (CAS #1821 Feb. 9) or 8 g/L 2-ketoisovalerate (CAS #3715-19-5) with or without the inducer, 0.1 mM isopropylthiogalactoside (IPTG). The flasks were closed with Suba-seals, injected with 20-25% $CH_4$ (v/v) in air, and incubated at 45° C. for 0-120 hours.

Extraction of Alcohols from the Growth Medium

1. Isobutanol production: The shake-flask samples were prepared for extraction by cooling them on ice for 1 hour, which ensures that the volatile organic compounds (VOC's) in the vapor phase were not lost to the atmosphere after the Suba-seal is opened.

2. If extracting from a 9-10 ml culture, all of the culture was transferred to a 50 ml tube. For samples with high isobutanol productions (e.g., pGMV 145), 10 ml of ethyl acetate was added for extraction. For samples with low isobutanol production, only 3 ml of ethyl acetate was used. Once ethyl acetate was added to the cultures, they were subjected to either vortexing (1-2 minutes) or shaking at room temperature (for 1 hour) for efficient extraction.

3. The tubes were then centrifuged at 4000 rpm for 20 minutes in an Eppendorf 5810 centrifuge equipped with an A-4-81 rotor.

4. One (1) ml of the organic layer was then filtered (0.2 μm PTFE membrane) and transferred to 2 ml glass Agilent gas chromatography vials for analysis.

GC-FID Analysis for Isobutanol

The extracted alcohol compounds were quantified with the Agilent 7890A gas chromatograph (GC) with flame ionization detector and PAL auto-sampler. An HP InnoWax capillary column (30 m, 0.32-mm internal diameter, 0.25-mm film thickness; Agilent Technologies, Santa Clara, CA) was used to separate the alcohols. The GC oven temperature was initially set at 35° C. for 1 minute and ramped at rate of 10° C./minute until 85° C. was reached and held for 1 minute. A second temperature ramp of 80° C./minute up to 240° C. was performed and held for 2 minutes. Hydrogen gas was the carrier gas used with 9.3 psi constant inlet pressure. The inlet and detector were maintained at 240° C. A 1 μl sample was injected in split injection mode with a 25:1 split ratio.

Figure 4:
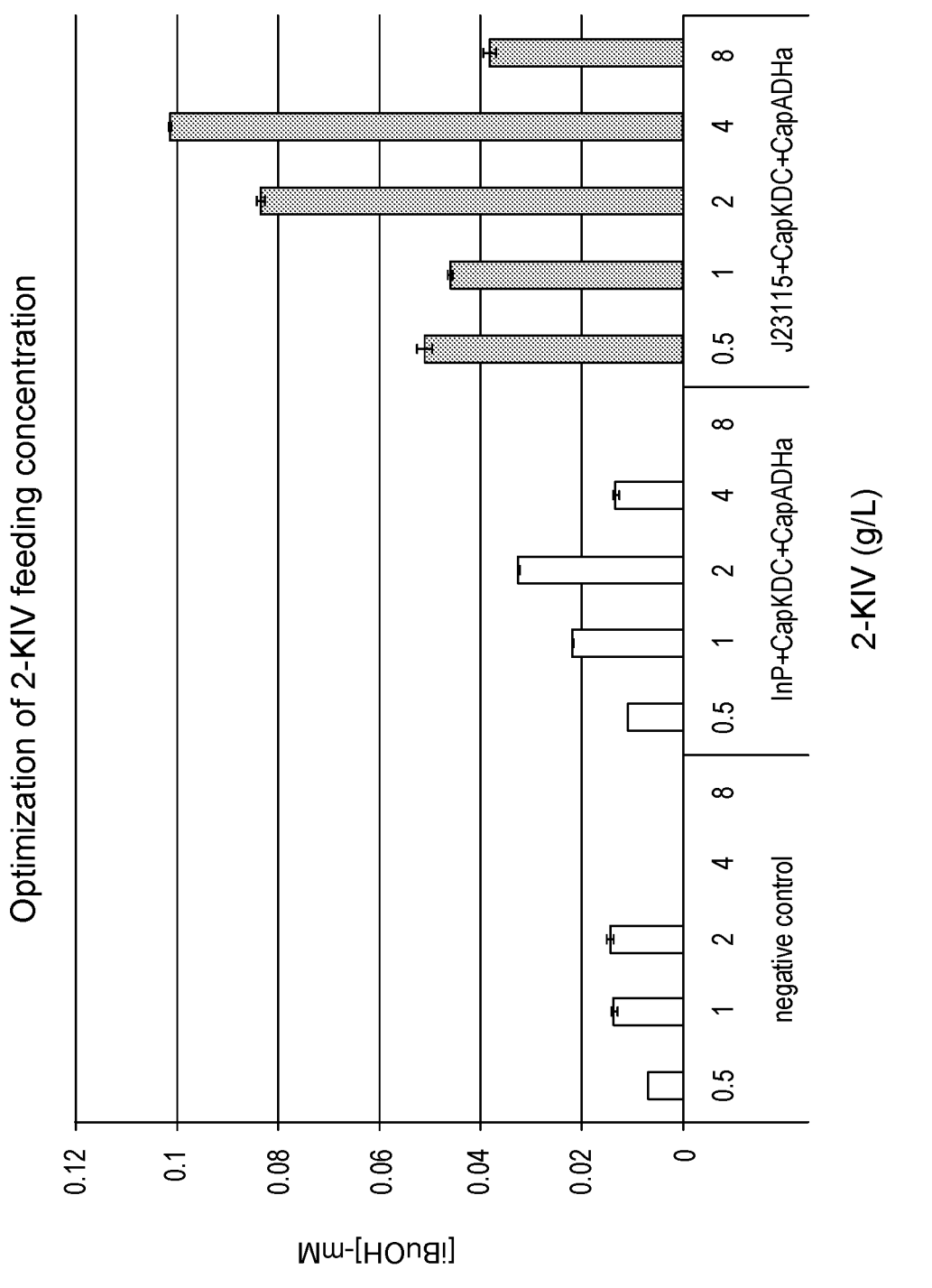
FIG. 4 shows the optimization of the 2-ketoisovalerate (2-KIV) concentration fed to various engineered host strains expressing the two-gene (isobutanol) pathway.
Figure 5:
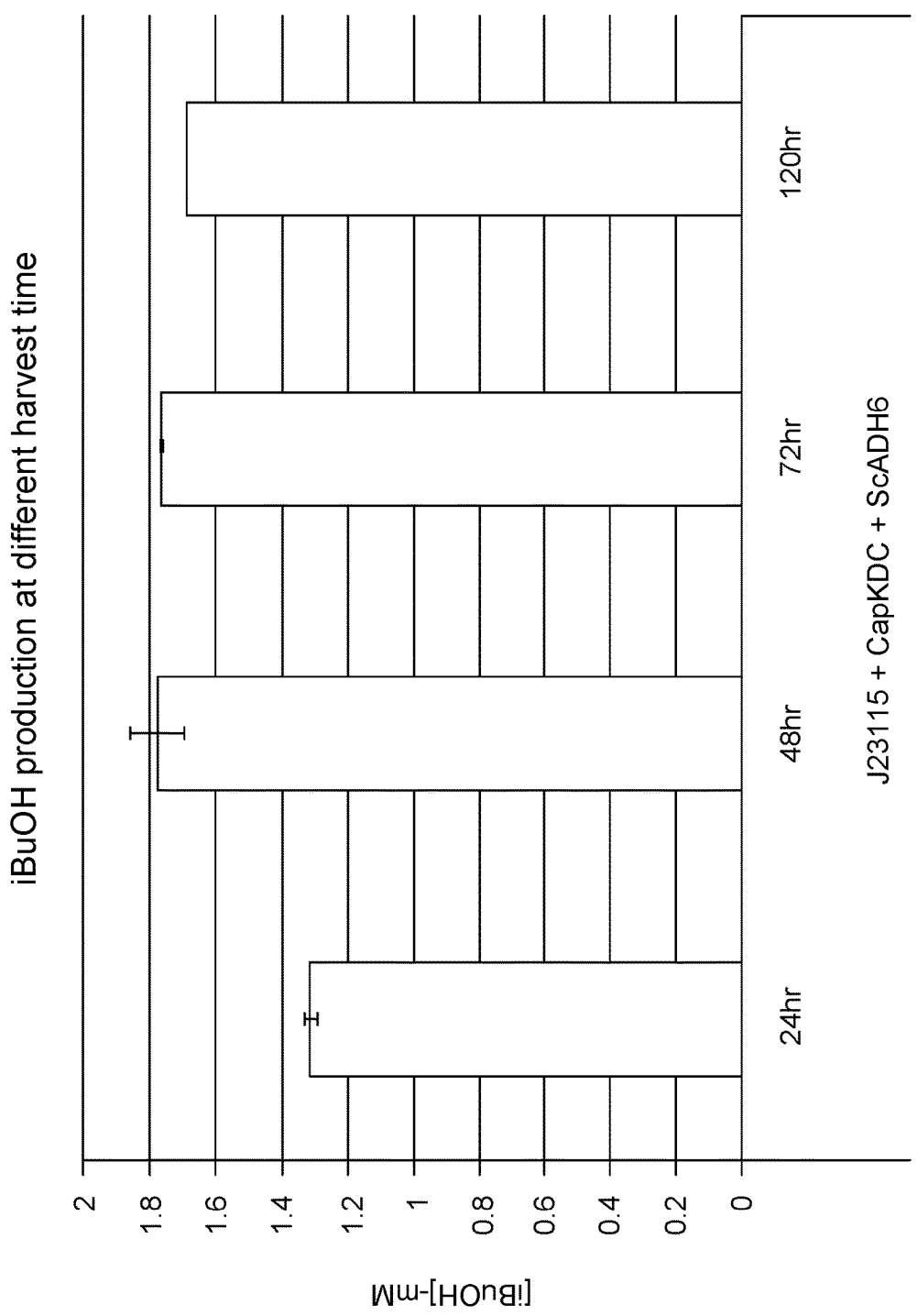
FIG. 5 shows the measured production of isobutanol in an *M. capsulatus* strain expressing plasmid pGMV145 (containing: promoter J23115, the gene for *M. capsulatus* (Bath) 2-ketoisovalerate decarboxylase (CapKDC) and the gene for *S. cerevisiae* alcohol dehydrogenase (ScADH6)), harvested at different time intervals after 2-KIV addition.
Figure 6:
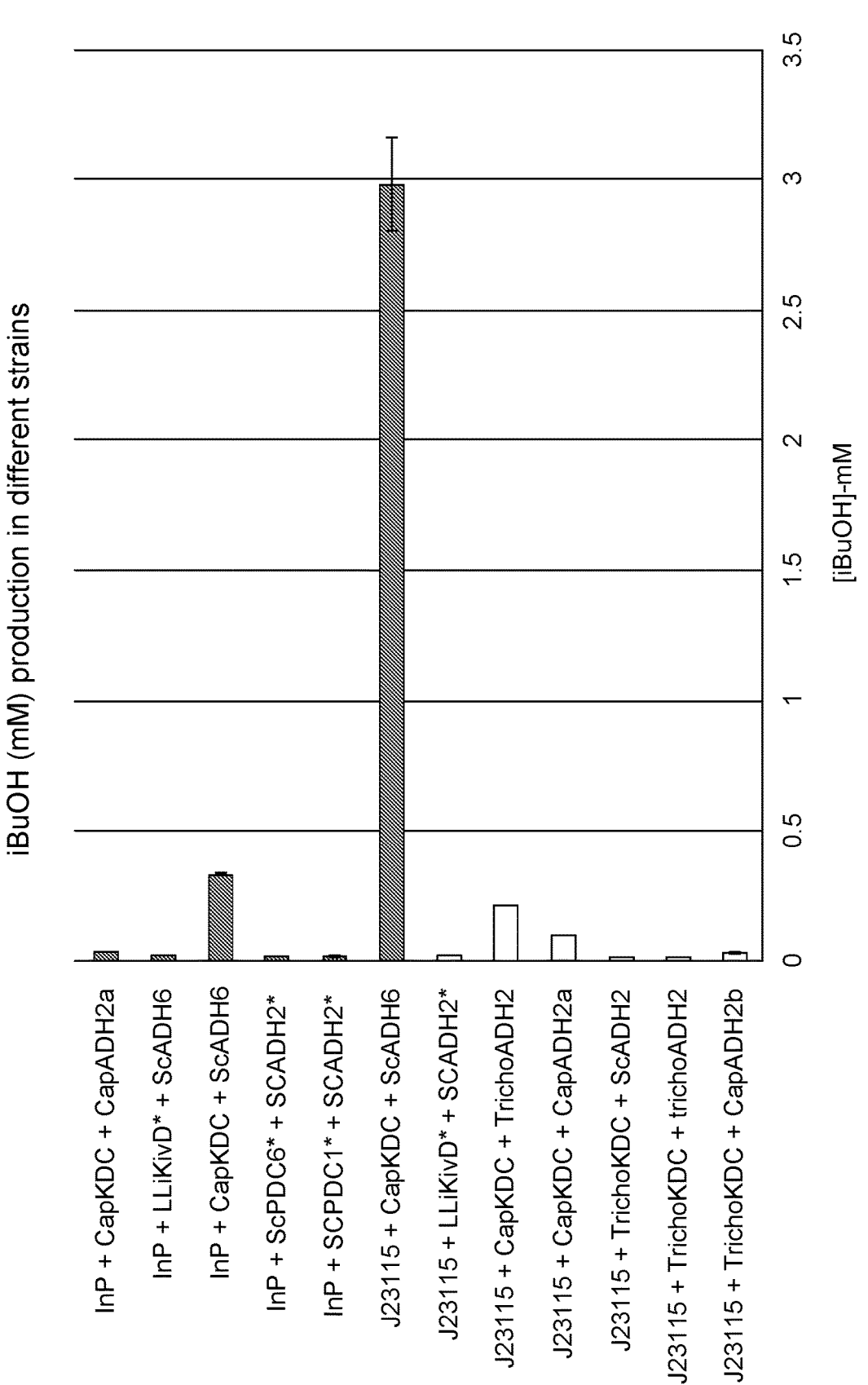
FIG. 6 is a comparison of isobutanol production after 2-KIV feeding in various engineered host strains expressing different combinations of two genes (i.e., isobutanol pathway genes) and with different promoters.

When the two-gene KDC/ADH pathway was expressed in *M. capsulatus* and the isobutanol production was measured (using exogenous 2-KIV feeding), the following results were observed. A concentration of 2-KIV greater than about 4 g/L had a toxic effect on growth, wherein a 2-KIV concentration of about 2 g/L yielded the best results (FIG. 4). Peak isobutanol production occurred about 48-72 hours after 2-KIV feeding (FIG. 5). *E. coli* promoters function in *M. capsulatus*, but not equally well. Constitutive promoters yielded better results than inducible promoters, but the optimal constitutive promoter will typically depend on the individual construct to be used. For example, J23115 was observed to work best for *M. capsulatus* KDC and *M. capsulatus* ADH (data not shown). Lastly, different host strains require slightly different concentrations of 2-KIV to maximize isobutanol production.

Figure 7:
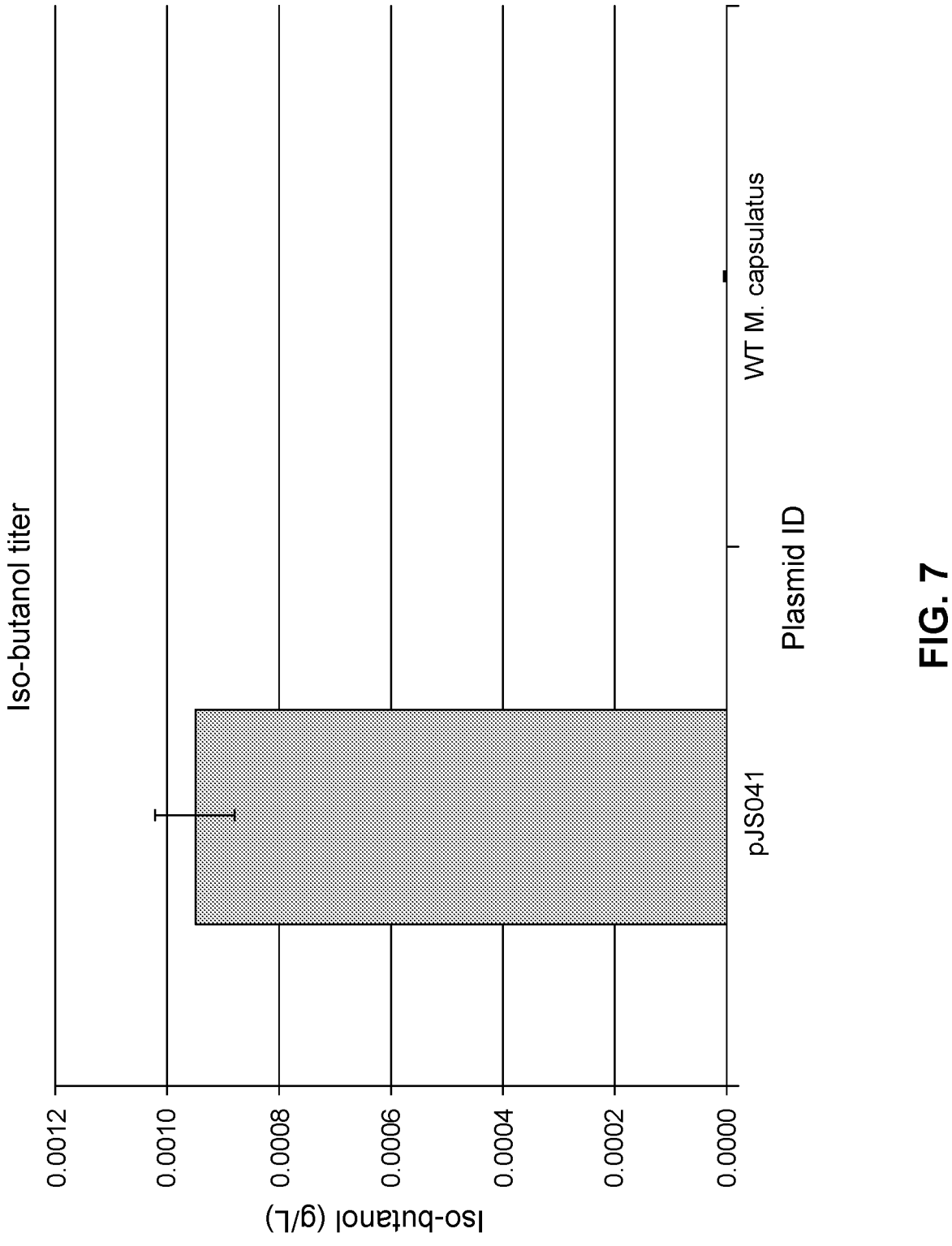
FIG. 7 compares production of isobutanol in the wild-type *M. capsulatus* str. Bath (no plasmid) and an engineered strain (pJS041) expressing the five-gene (isobutanol) pathway.

The best two-gene combination with a constitutive promoter (J23115; SEQ ID NO: 124) was *M. capsulatus* KDC and *S. cerevisiae* ADH6 (plasmid pGMV145), wherein harvesting after 48-72 hours produced the most isobutanol (FIG. 7). The vector construct using pGMV145, having constitutive promoter J23115, a CapKDC gene (MCA0996; SEQ ID NO: 7), and a ScADH6 gene (YMR318C; SEQ ID NO:9), produced the most isobutanol after 2-KIV feeding, which was about 3 mM (or about 0.22 g/L).

When the complete five-gene isobutanol pathway was introduced into a host strain, plasmid pJS041 yielded the highest levels of isobutanol production, with a measured titer of about 0.001 g/liter (FIG. 7), compared to no detectable production in the wild-type strain.

In certain embodiments, the production of isobutanol from methane substrate in a host strain (i.e., expressing the five-gene isobutanol pathway, e.g. via plasmid pJS041) is further optimized by genetic manipulations described above, as well as by cultivating the host strain in a fermentor culture with continuous $CH_4$ perfusion, instead of batch addition of $CH_4$ to the culture medium (as was done for the shake flasks experiments). In other embodiments, the production of increased isobutanol titers from methane in a host strain is further optimized via manipulations to the fermentation process (batch fed or perfusion), such as feeding additional media components as they are depleted (phosphate, nitrate, etc.) and maintaining the pH by continuously adding acid or base.

Example 2

Biosynthetic Production of 1-Butanol from Methane

A ketoacid pathway analogous to that described in Example 1, but designed to produce 1-butanol (n-butanol) is engineered in a single carbon (C1) metabolizing microbial host, such as *M. capsulatus* (Bath). In this example, L-threonine (which is ultimately generated from methane via phosphoenolpyruvate) is first de-aminated to 2-ketobutyrate (2-oxobutanoate) by the action of threonine dehydratase (also referred to in the art as threonine ammonia-lyase (EC 4.3.1.19) encoded by the genes ilvA or tdcB) (Shen & Liao, 2008). The tdcB gene product has the biotechnological advantage that the enzyme is a catabolic enzyme, and is not feedback inhibited by L-valine or L-isoleucine (Guillouet et al., 1999).

In the second reaction step, the reaction catalyzed by leuA (encoding isopropylmalate synthase/2-ethylmalate synthase (EC 2.3.3.6)) combines 2-ketobutyrate, acetyl-CoA, and $H_2O$ to create (R)-2-ethylmalate. In the third reaction step, the gene product of leuC and leuD (encoding the two subunits of isopropylmalate isomerase) converts 2-ethylmalate into 3-ethylmalate. In the fourth reaction step, the gene product of leuB (encoding the enzyme 3-isopropylmalate dehydrogenase) converts 3-ethylmalate into 2-ketovalerate). At this stage, the same two enzymes used in the previous example, KDC (acting as a 2-ketovalerate decarboxylase) and ADH2 (alcohol dehydrogenase), are used to convert 2-ketovalerate into 1-butanol.

An alternate pathway (the citramalate pathway) from phosphoenolpyruvate and pyruvate to 2-ketobutyrate has also been described for making 1-butanol (Atsumi & Liao, 2008).

As described, above, the plasmids generated in this study are based on the broad-host-range pCM132 (Accession No. AF327720, SEQ ID NO:79) cloning vector described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO: 139).

Vector Inserts

Vector inserts contain DNA to be added to a vector backbone. The inserts were designed as exchangeable (modular) parts to the vector and in this example consist of *Methylococcus capsulatus* KDC (MCA0996; SEQ ID NO:7), leuA (MCA2275; SEQ ID NO: 57), leuCDB (MCA2063; SEQ ID NO:63, MCA2064; SEQ ID NO:61 and MCA2065; SEQ ID NO:59), *Saccharomyces cerevisiae* ADH6 (YMR318C; SEQ ID NO:9), and *M. capsulatus* ilvA (MCA0354; SEQ ID NO:55) or *E. coli* tdcB (SEQ ID NO:160) genes. The genes were amplified from genomic DNA of their respective hosts with the primers described in Table 5.

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 μl of the InFusion reaction) were transformed into chemically competent NEB Turbo *E. coli* cells, screened for by colony PCR, purified, and subsequently sequence verified.

The pGMV145 plasmid was designed to express *M. capsulatus* KDC (MCA0996; SEQ ID NO:7) and *S. cerevisiae* ADH6 (YMR318C; SEQ ID NO:9) from the constitutive promoter.

The pJS034 plasmid introduced a second terminator sequence into pGMV145. The pGMV145 vector backbone was PCR amplified with primers JPS00161 (SEQ ID NO: 101)/JPS00162 (SEQ ID NO:102) and KOD mastermix. The insert was rnpB DNA synthesized as a gBlock from IDT and amplified with JPS00163 (SEQ ID NO: 103)/JPS00164 (SEQ ID NO:104) primers.

The pGMV165 plasmid was designed to express 3 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV166 plasmid was designed to express 3 genes: *E. coli* tdcB (SEQ ID NO: 160), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV167 plasmid was designed to express 7 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter and *M. capsulatus* leuCDB (MCA2063; SEQ ID NO:63, MCA2064; SEQ ID NO:61 and MCA2065; SEQ ID NO:59) and *M. capsulatus* leuA (MCA2275; SEQ ID NO: 57) from second J23115 (SEQ ID NO:124) constitutive promoter.

The pGMV168 plasmid was designed to express 7 genes: *E. coli* tdcB (SEQ ID NO: 160), *M. capsulatus* KDC (MCA0996; SEQ ID NO:7) and *S. cerevisiae* ADH6 (YMR318C; SEQ ID NO:9) from the J23115 constitutive promoter and *M. capsulatus* leuCDB (MCA2063; SEQ ID NO:63, MCA2064; SEQ ID NO:61 and MCA2065; SEQ ID NO: 59) and leuA (MCA2275; SEQ ID NO:57) from a second J23115 constitutive promoter.

Host strains modified with these plasmids were grown on methane as described in the examples above, harvested, extracted, and analyzed for 1-butanol production.

TABLE 5

| | | Modules | | | |
|---|---|---|---|---|---|
| | | Insert Modules, Templates and Primers for 1-Butanol Production | | | |
| Plasmid | PCR rxn: | Vector backbone | Insert 1 | Insert 2 | Insert 3 |
| pGMV145 | template | pMZT3 | MCA0996 (*M. capsulatus* DNA) | YMR318C (*S. cerevisiae* DNA) | — |
| | primer 1 | JPS0082 | GMV00251 | JPS00118 | — |
| | primer 2 | ESG00087 | GMV00257 | JPS00119 | — |
| pJS034 | template | pGMV145 | IDT gBlock synthesized rnpB DNA | — | — |
| | primer 1 | JPS00161 | JPS00163 | — | — |
| | primer 2 | JPS00162 | JPS00164 | — | — |
| pGMV165 | template | pJS034 | pJS034 | MCA0354 (*M. capsulatus* DNA) | — |
| | primer 1 | GMV435 | GMV433 | GMV431 | — |
| | primer 2 | ESG000087 | GMV434 | GMV432 | — |
| pGMV166 | template | pJS034 | pJS034 | tdcB (*E. coli* DNA) | — |
| | primer 1 | GMV435 | GMV433 | GMV436 | — |
| | primer 2 | ESG000087 | GMV434 | GMV437 | — |
| pGMV167 | template | pGMV165 | pGMV165 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |
| pGMV168 | template | pGMV166 | pGMV166 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |

Example 3

Biosynthetic Production of Fatty Alcohols from Methane

Conversion of methane to diesel components requires engineering the native metabolism of methanotrophs. The two principal native pathways that can be engineered for increased production of diesel components are the fatty acid pathway and isoprenoid pathway. In the current example, the invention describes the use of the fatty acid pathway for synthesis of diesel (wax ester) components.

Fatty acids are an important source of energy and adenosine triphosphate (ATP) for many cellular organisms. Excess fatty acids, glucose, and other nutrients can be stored efficiently as fat. All cell membranes are built up of phospholipids, each of which contains fatty acids. Fatty acids are also used for protein modification. Fatty acid synthesis is the creation of fatty acids from acetyl-CoA and malonyl-CoA precursors through action of enzymes called fatty acid synthases. Fatty acid chain length and degree of saturation depends on the host microorganism. With regard to *M. capsulatus* (Bath), the primary fatty acids are C16 with saturated or mono unsaturated carbon chains.

The conversion of methane to diesel components requires the over-expression of specific heterologous (exogenous) enzymes within a methanotroph (or non-methanotroph) host microorganism, wherein the over-expression of specific heterologous (exogenous) enzymes can divert the flux from native fatty acid synthesis to compounds of interest. Key intermediates of the fatty acid pathway are the fatty acyl-ACP molecules. Thus, the over-expression of specific heterologous enzymes in a host microorganism divert the flux from acyl-ACP to diesel components such as fatty acids, fatty alcohols, fatty esters and derivatives thereof. Thus, in certain embodiments, a host microorganism has been engineered to over-express specific enzymes such as a fatty acyl ACP reductase (FAR), a fatty acyl CoA reductase (CAR) and wax ester synthases (WES) for diverting flux from native compounds to compounds of interest. Active expression of these enzymes results in the conversion of methane to diesel components via FARs, CARs and WES enzymes cloned and expressed in a host microorganism (e.g., *M. capsulatus* (Bath)).

A biosynthetic pathway analogous to that described in Example 1, but designed to produce fatty alcohols can be engineered in a (C1) metabolizing host microorganism, such as *M. capsulatus*. In this example, fatty acyl-CoA (which is ultimately generated from methane via pyruvate) is converted directly into fatty alcohols by the heterologous over-expression of a fatty-acyl-CoA reductase (FAR).

Construction of Methanotroph Plasmids for Fatty Alcohol Production

As described, above, the plasmids generated in this study are based on the broad-host-range pCM132 (Accession No. AF327720) cloning vector (SEQ ID NO:79) described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO: 139).

Vector Inserts

Vector inserts contain DNA to be added to the vector backbone. The inserts were designed as exchangeable (modular) parts to the vector and in this embodiment consist of the following components. In this example, the plasmids were designed to contain one insert: *Marinobacter algicola*

Figure 8:
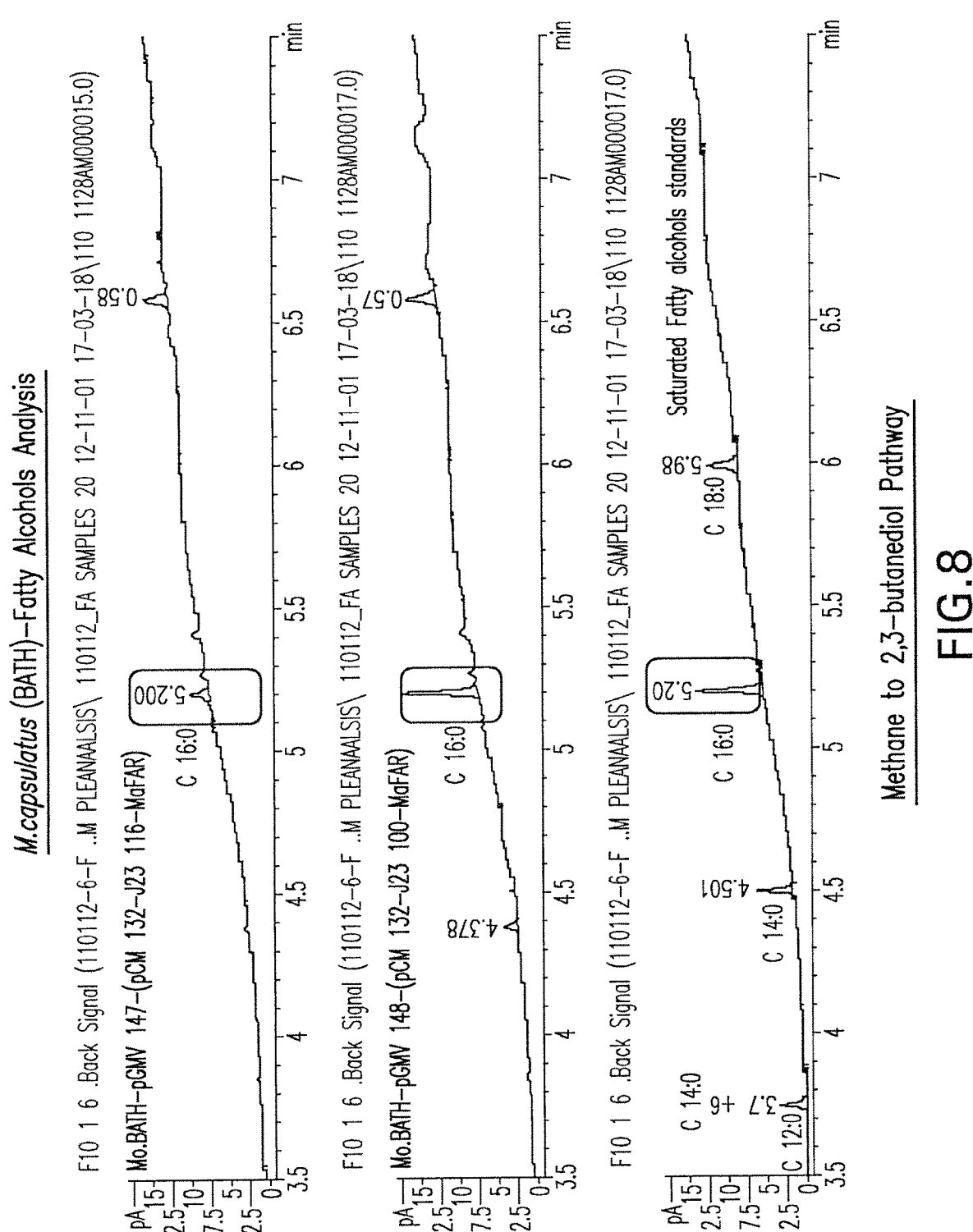
FIG. 8 is a gas chromatography (GC) analysis of fatty acid alcohol production by various engineered strains of *M. capsulatus* (Bath). The GC peak at about 5.2 minutes corresponds to a C16:0 fatty alcohol standard.

Gas chromatography results after various host strains were grown on methane in shake flasks, extracted, and analyzed as described above, are set forth in FIG. 8. The results indicate that the host strain containing plasmid pGMV148 produced C16:0 alcohol (a fatty alcohol) when grown on methane. The host strain containing plasmid pGMV147 produced only a trace amount of fatty alcohol.

TABLE 6

| Insert Modules, Templates and Primers for Fatty Alcohol Production | | | | | | |
|---|---|---|---|---|---|---|
| | | | Modules | | | |
| Plasmid | PCR rxn: | Vector backbone | Insert 1 | Insert 2 | Insert 3 | Insert 4 |
| pGMV147 | template | pMZT3 | MaFAR-g1 | MaFAR-g2 | MaFAR-g3 | MaFAR-g4 |
| | primer 1 | ESG00084 | — | — | — | — |
| | primer 2 | ESG00087 | — | — | — | — |
| pGMV148 | template | pMZT37 | MaFAR-g1 | MaFAR-g2 | MaFAR-g3 | MaFAR-g4 |
| | primer 1 | ESG00084 | — | — | — | — |
| | primer 2 | ESG00088 | — | — | — | — | fatty acid reductase (MaFAR; SEQ ID NO:65), also known as a fatty acyl-CoA reductase. The MaFAR gene was codon optimized and synthesized as a series of 4 gBlocks from Integrated DNA Technologies (Coralville, IA). The synthesized DNA was designed to include pivot regions to allow proper assembly by InFusion.

Assembly of the Constructs

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 μl of the InFusion reaction) were transformed into chemically competent NEB Turbo *E. coli* cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV147 plasmid was designed to express *M. algicola* FAR gene (SEQ ID NO: 65) from the J23115 constitutive promoter (SEQ ID NO:124). The modules of this plasmid included the PCR amplified pMZT3 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

The pGMV148 plasmid was designed to express *M. algicola* FAR gene (SEQ ID NO: 65) from the J23110 constitutive promoter (SEQ ID NO:122). The modules of this plasmid included the PCR amplified pMZT37 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

Example 4

Biosynthetic Production of Fatty Acid Methyl Esters from Methane

Construction of Methanotroph Plasmids for Fatty Acid Ester (Wax Ester) Production The plasmids generated in this example are based on the broad-host-range pCM132 (Accession no. AF327720, SEQ ID NO: 79) cloning vector described by Marx & Lidstrom (2001). In this embodiment, the use of the Clontech (catalogue no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids and pMZT3 and pMZT37.

Vector Inserts

Vector inserts contain DNA to be added to a vector backbone. The inserts were designed as exchangeable (modular) parts to the vector and in this embodiment consist of a wax ester synthase (WES) derived from *Acinetobacter* sp. ADP1 (SEQ ID NO:67), *Psychrobacter arcticum* 273-4 (SEQ ID NO:69) or *Rhodococcus opcaus* B4 (SEQ ID NO: 71, SEQ ID NO:73, SEQ ID NO:75 or SEQ ID NO:77). The WES genes were codon-optimized and synthesized by GenScript.

Assembly of the Constructs

The modular parts (vector backbone and vector insert) were PCR amplified as listed in Table 7 with NEB Phusion master mix according to the manufacturer's instructions and in vitro assembled with the Clontech InFusion HD Cloning System kit according to the manufacturer's instructions to generate circular plasmid. The in vitro assembled plasmids (2 μl of the InFusion reaction) were transformed into chemically competent NEB Turbo *E. coli* cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV153 plasmid was designed to express *Acinetobacter* sp. ADP1 WES gene (wax-dgaT; SEQ ID NO:67) from the J23115 constitutive promoter. The modules of this plasmid included the PCR amplified pMZT3 vector backbone and the codon-optimized synthesized gene.

The pGMV154 plasmid was designed to express *Psychrobacter arcticum* 273-4 WES gene (Psyc_0223; SEQ ID NO:69) from the J23115 constitutive promoter. The modules of this plasmid included the PCR amplified pMZT3 vector backbone and the codon-optimized synthesized gene.

The pGMV155 plasmid was designed to express *Rhodococcus opcaus* B4 WES gene (ROP_02100; SEQ ID NO:71) from the J23115 constitutive promoter. The modules of this plasmid included the PCR amplified pMZT3 vector backbone and the codon-optimized synthesized gene.

The pGMV156 plasmid was designed to express *Rhodococcus opcaus* B4 WES gene (ROP_13050; SEQ ID NO:73) from the J23115 constitutive promoter. The modules of this plasmid included the PCR amplified pMZT3 vector backbone and the codon-optimized synthesized gene.

The pGMV157 plasmid was designed to express *Rhodococcus opcaus* B4 WS gene (ROP_26950; SEQ ID NO:77) from the J23115 constitutive promoter. The modules of this plasmid included the PCR amplified pMZT3 vector backbone and the codon-optimized synthesized gene.

The pGMV158 plasmid was designed to express *Rhodococcus opcaus* B4 WES gene (ROP_54550; SEQ ID NO:75) from the J23115 constitutive promoter. The modules of this plasmid included the PCR amplified pMZT3 vector backbone and the codon-optimized synthesized gene.

The pGMV159 plasmid was designed to express *Acinetobacter* sp. ADP1 WES gene (wax-dgaT; SEQ ID NO:67) from the J23100 constitutive promoter. The modules of this plasmid included the PCR amplified pMZT3 vector backbone and the codon-optimized synthesized gene.

The pGMV160 plasmid was designed to express *Psychrobacter arcticum* 273-4 WES gene (Psyc_0223; SEQ ID NO:69) from the J23100 constitutive promoter. The modules of this plasmid included the PCR amplified pMZT3 vector backbone and the codon-optimized synthesized gene.

The pGMV161 plasmid was designed to express *Rhodococcus opcaus* B4 WES gene (ROP_02100; SEQ ID NO:71) from the J23100 constitutive promoter. The modules of this plasmid included the PCR amplified pMZT3 vector backbone and the codon-optimized synthesized gene.

The pGMV162 plasmid was designed to express *Rhodococcus opcaus* B4 WES gene (ROP_13050; SEQ ID NO:73) from the J23100 constitutive promoter. The modules of this plasmid included the PCR amplified pMZT3 vector backbone and the codon-optimized synthesized gene.

The pGMV163 plasmid was designed to express *Rhodococcus opcaus* B4 WES gene (ROP_26950; SEQ ID NO:77) from the J23100 constitutive promoter. The modules of this plasmid included the PCR amplified pMZT3 vector backbone and the codon-optimized synthesized gene.

The pGMV164 plasmid was designed to express *Rhodococcus opcaus* B4 WES gene (ROP_54550; SEQ ID NO:75)

from the J23100 constitutive promoter. The modules of this plasmid included the PCR amplified pMZT3 vector backbone and the codon-optimized synthesized gene.

Strains modified with these plasmids are grown on methane as described in the examples above, harvested, extracted, and analyzed for fatty acid ester production.

TABLE 7

Insert Modules, Templates and Primers for Fatty Acid Ester Production

| Plasmid | PCR rxn: | Vector backbone | Insert |
|---------|----------|-----------------|--------|
| pGMV153 | template | pMZT3 | pUC57-AbWS (WS-dgaT) |
| | primer 1 | ESG00084 | GMV410 |
| | primer 2 | ESG00087 | GMV416 |
| pGMV154 | template | pMZT3 | pUC57-PaWS (Psyc_0223) |
| | primer 1 | ESG00084 | GMV411 |
| | primer 2 | ESG00087 | GMV417 |
| pGMV155 | template | pMZT3 | pUC57-RoWS (ROP_02100) |
| | primer 1 | ESG00084 | GMV412 |
| | primer 2 | ESG00087 | GMV418 |
| pGMV156 | template | pMZT3 | pUC57-RoWS (ROP_13050) |
| | primer 1 | ESG00084 | GMV413 |
| | primer 2 | ESG00087 | GMV419 |
| pGMV157 | template | pMZT3 | pUC57-RoWS (ROP_26950) |
| | primer 1 | ESG00084 | GMV414 |
| | primer 2 | ESG00087 | GMV420 |
| pGMV158 | template | pMZT3 | pUC57-RoWS (ROP_54550) |
| | primer 1 | ESG00084 | GMV415 |
| | primer 2 | ESG00087 | GMV421 |
| pGMV159 | template | pMZT37 | pUC57-AbWS (WS-dgaT) |
| | primer 1 | ESG00084 | GMV410 |
| | primer 2 | ESG00088 | GMV416 |
| pGMV160 | template | pMZT37 | pUC57-PaWS (Psyc_0223) |
| | primer 1 | ESG00084 | GMV411 |
| | primer 2 | ESG00088 | GMV417 |
| pGMV161 | template | pMZT37 | pUC57-RoWS (ROP_02100) |
| | primer 1 | ESG00084 | GMV412 |
| | primer 2 | ESG00088 | GMV418 |
| pGMV162 | template | pMZT37 | pUC57-RoWS (ROP_13050) |
| | primer 1 | ESG00084 | GMV413 |
| | primer 2 | ESG00088 | GMV419 |
| pGMV163 | template | pMZT37 | pUC57-RoWS (ROP_26950) |
| | primer 1 | ESG00084 | GMV414 |
| | primer 2 | ESG00088 | GMV420 |
| pGMV164 | template | pMZT37 | pUC57-RoWS (ROP_54550) |
| | primer 1 | ESG00084 | GMV415 |
| | primer 2 | ESG00088 | GMV421 |

Example 5

Biosynthetic Production of 2,3-Butanediol from Methane

The four-carbon (C4) diol 2,3-butanediol is an important intermediate for the chemical industry. At the commercial scale, it is mostly generated from petroleum. It serves as a precursor for the production of various commodity and specialty chemicals, such as the solvent methyl ethyl ketone (MEK), gamma-butyrolactone (GBL), and 1,3-butadiene. The potential production of these downstream commercial products amounts to about 32 million tons per year, with a value of about $43 billion (Köpke et al., 2011).

Biological production of 2,3-butanediol from methane requires engineering the native (or endogenous) metabolism of methanotrophs to take advantage of their endogenous production of (R)-acetoin (FIG. 9). (R)-acetoin is produced in methanotrophs from two molecules of pyruvate, which are ultimately derived from methane. By introducing and expressing the gene (SEQ ID NO: 156) encoding (2R,3R)-

2,3-butanediol dehydrogenase (BDH1) from *Saccharomyces cerevisiae* in a suitable microbial expression host (such as *M. capsulatus* (Bath)), (R)-acetoin is converted into 2,3-butanediol.

Construction of Methanotroph Plasmids for 2,3-Butanediol Production

As described, above, the plasmids generated in this study are based on the broad-host-range pCM132 (Accession no. AF327720, SEQ ID NO: 79) cloning vector described by Marx & Lidstrom (2001). In this embodiment, the use of the Clontech (catalogue 639647) InFusion HD Cloning System kit is one example of how to construct plasmids, but is not meant to limit or exclude other methods that are known in the art. Sequences for the ORF and PCR primers are presented below in Table 1.

Vector Backbones

Vector backbones contain the components of the plasmid that will remain constant. The broad-host range pCM132 vector was modified to produce vector backbones for the plasmids in this example. The pCM132 vector consists of the following components: trrnB terminator, kanamycin resistance gene, trfA, IncP oriT, IncP oriV, colE1 ori, and lacZ. This parental vector has been modified to replace lacZ with a vector insert that contains promoter sequence to produce plasmid pMZT3, which was used for this example.

Vector Inserts

Vector inserts contain DNA to be added to the vector backbone. The inserts were designed as exchangeable (modular) parts to the vector, and in this embodiment consists of the components listed in Table 1 and Table 8. In this example, the plasmids were designed to contain one insert: *Saccharomyces cerevisiae* (R,R)-butanediol dehydrogenase (Standard name: Bdh1p (EC 1.1.1.4); SEQ ID NO:156; Systematic gene name: YAL060W).

The BDH1 gene (SEQ ID NO:156) was codon optimized and synthesized by Integrated DNA Technologies (Coralville, IA).

Assembly of the Constructs

The modular parts (vector backbone and vector insert) were PCR amplified as listed in Table 8 with NEB Phusion master mix according to the manufacturer's instructions and in vitro assembled with the Clontech InFusion HD Cloning System kit according to the manufacturer's instructions to generate circular plasmid. The in vitro assembled plasmids (2 µl of the InFusion reaction) were transformed into chemically competent NEB Turbo *E. coli* cells, screened for by colony PCR, purified, and subsequently sequence verified.

Plasmid pMZT3 served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO: 137)/ESG00087 (SEQ ID NO:98).

The pGMV111 plasmid was designed to express the *S. cerevisiae* BDH1 gene (SEQ ID NO: 156) from the J23115 constitutive promoter. The modules of this plasmid included the PCR amplified pMZT3 vector backbone and the ScBDH1 insert amplified from the shuttle vector pUC57-ScBDH1 template using primers GMV268 (SEQ ID NO: 158)/GMV271 (SEQ ID NO:159). The plasmid was conjugated from *E. coli* donor strain S17-1 into the *M. capsulatus* (Bath) recipient as described above Example 1. The transconjugant strain was purified by repeated rounds of antibiotic selection using kanamycin and naladixic acid to remove the parent cells, as described in Example 1 above. Cells expressing the pGMV111 plasmid were cultivated in liquid NMS medium in sealed shake flasks in the presence of 20% methane at 45° C. as described above in Example 1, for about 72 hours with 200 rpm shaking. For UPLC analysis, proteins and other debris were separated from the 2,3-butanediol in the growth medium using 2% (wt/vol.) 5-sulfosalicylic acid and centrifugation as described in Köpke et al. (2011). Extracted samples can be analyzed using a BioRad (Hercules, CA) Fast Acid column on a Waters (Milford, MA) Acquity H-class UPLC equipped with a #2414 Refractive Index Detector. Other conditions are as follows: the mobile phase is 5 mM $H_2SO4$, the flow rate is 0.4 ml/min, the column is maintained at 40 C, and the product is detected at 410 nm.

Methods for the processing of biologically produced 1,3-propanediol and 2,3-butanediol are further described by Xiu & Zeng, 2008.

For GC analysis, the 2,3-butanediol can be extracted from the culture medium with ethyl acetate, as described in Xiao et al., (2012). The extracted sample is analyzed on an Agilent (Santa Clara, CA) 7890A GC equipped with a Leap Technologies CombiPAL autosampler and a flame ionization detector. Either an Agilent HP-INNOWax or HP-5 MS GC column can be used to separate the components according to the method of Xiao et al. (2012). Alternatively, the samples can be analyzed on a Waters Acquity H-Class UPLC equipped with a Waters 2414 Refractive Index detector using a method similar to that of Köpke et al. (2011). A BioRad (Hercules, CA) Fast Acid Column operated at 40° C. with a flow rate of 0.4 ml/minute and a 5 mM $H_2SO4$ mobile phase can be used to perform the separation. Samples for either GC or UPLC can be quantitated against a series of known concentrations of purified (D-(–)-, L-(+)-, and meso-) 2,3-butanediol standards (Sigma, St. Louis, MO).

At the industrial fermentation scale, the 2,3-butanediol product can be extracted from the fermentation medium using one of the following methods: steam stripping, solvent extraction, aqueous two-phase extraction, reactive extraction, and pervaporation. These methods are described in Xiu & Zeng (2008).

TABLE 8

| Plasmid | PCR reaction: | Modules | |
| | | Vector backbone | Insert |
|---|---|---|---|
| pGMV111 | template | pMZT3 | pUC57-ScBDH1 |
| | primer 1 | ESG00084 | GMV268 |
| | primer 2 | ESG00087 | GMV271 |

Following is a list of citations for application.

U.S. Pat. No. 4,594,324
U.S. Pat. No. 4,982,023
U.S. Pat. No. 6,576,449
U.S. Pat. No. 6,660,507
U.S. Pat. No. 6,767,744
U.S. Pat. No. 6,818,424
U.S. Pat. No. 6,969,595
U.S. Pat. No. 7,026,464
U.S. Pat. No. 7,851,188
U.S. Pat. No. 7,910,342
U.S. Pat. No. 7,943,362
U.S. Pat. No. 7,977,084
U.S. Pat. No. 7,993,889
U.S. Pat. No. 8,017,375
U.S. Pat. No. 8,030,021
U.S. Pat. No. 8,101,808

U.S. Pat. No. 8,158,404
U.S. Pat. No. 8,232,089
U.S. Pat. No. 8,263,373
U.S. Pat. No. 8,268,599
U.S. Pat. No. 8,283,143
U.S. Pat. No. 8,349,587
U.S. Publication No. 2006/0057726
U.S. Publication No. 2007/0251141
U.S. Publication No. 2009/0263877
U.S. Publication No. 2010/0274033
U.S. Publication No. 2011/0301388
U.S. Publication No. 2012/0009640
European Patent No. EP 1419234
European Patent No. EP 1328639
European Patent No. EP 1416808
European Patent No. EP 1625204
European Patent No. EP 1694854
European Patent No. EP 2464722
European Patent No. EP 306466
European Patent No. EP 418187
PCT Publication No. WO 2001/60974
Alayon et al., "Catalytic Conversion of Methane to Methanol Using Cu-Zeolites", *Chimia,* 66:668-674, 2012.
Ali, H., "Development of Genetic Tools in Methanotrophs and the Molecular Regulation of Methane Monooxygenase", Ph.D. Thesis, Univ. of Warwick, Coventry, U.K., 2006.
Anthony, C. and Williams, P., "The structure and mechanism of methanol dehydrogenase", *Biochim. Biophys. Acta.,* 1647:18-23, 2003.
Arakawa et al., "Catalysis research of relevance to carbon management: progress, challenges, and opportunities", *Chem. Rev.,* 101:953-996, 2001.
Atsumi, S. et al., "Engineering the isobutanol biosynthetic pathway in *Escherichia coli* by comparison of three aldehyde reductase/alcohol dehydrogenase genes", *Appl. Microbiol.* Biotechnology, 85:651-657, 2010.
Ausubel et al., "Current Protocols in Molecular Biology", pub. by Greene Publishing Assoc. and Wiley-*Interscience,* 1987.
Ausubel, F. M., Brent, R., Kingston, R. E., Moore, D. D., Seidman, J. G., Smith, J. A., and Struhl, K., eds., *Short Protocols in Molecular Biology, Fifth Edition.* Wiley, 2002.
Avalos et al., "Compartmentalization of Metabolic Pathways in Yeast Mitochondria Improves the Production of Branched-Chain Alcohols", *Nature Biotechnology,* Advanced Online Publication, Feb. 17, 2013, pages 1-7, doi: 10.1038/nbt.2509.
Bothe et al., "Heterotrophic bacteria growing in association with *Methylococcus capsulatus* (Bath) in a single cell protein production process", *Appl. Microbiol. Biotechnol.,* 59:33-39, 2002.
Bothe, H., Jensen, K. M., Mergel, A., Larsen, J., Jorgensen, C., Bothe, H. and Jorgensen, L., "Heterotrophic bacteria growing in association with *Methylococcus capsulatus* (Bath) in a single cell protein production process", *Appl. Microbiol. Biotechnol.* 59:33-39, 2002.
Bowman, J., "The methanotrophs—the families Methylococcaceae and Methylocystaceae", In: *The Prokaryotes* (Dworkin, M., ed.). Springer Verlag, New York, 2000 (http://link.springer-ny.com/link/service/books/10125).
Chistoserdova et al., "A genomic view of methane oxidation by aerobic bacteria and anaerobic archaea", *Genome Biol.,* 6:208, 2005.

Chistoserdova et al., "The Expanding World of Methylotrophic Metabolism", *Annu. Rev. Microbiol.,* 63:477-499, 2009.
Chistoserdova, L., "Modularity of methylotrophy, revisited", *Environ. Microbiol.,* 13:2603-2622, 2011.
Culpepper, M. A. and Rosenzweig, A. C., "Architecture and active site of particulate methane monooxygenase", *Crit. Rev. Biochem. Mol. Biol.,* 47:483-492, 2012.
Dunfield et al., "Methane oxidation by an extremely acidophilic bacterium of the phylum Verrucomicrobia", *Nature* 450:879-882, 2007.
Dunfield et al., "*Methylocella silvestris* sp. nov., a novel methanotroph isolated from an acidic forest cambisol" *Int. J. Syst. Evol. Microbiol.,* 53:1231-1239, 2003.
Eiteman, M. A. and Altman, E., "Overcoming acetate in *Escherichia coli* recombinant protein fermentations", *Trends Biotechnol.* 24:53-536, 2006.
Engler et al., "Golden Gate Shuffling: A One-Pot DNA Shuffling Method Based on Type IIs Restriction Enzymes", *PLOS One* 4: e5553, 2009.
Gellissen et al., "New yeast expression platforms based on methylotrophic *Hansenula polymorpha* and *Pichia pastoris* and on dimorphic Arxula adeninivorans and *Yarrowia lipolytica*—a comparison", *FEMS Yeast Res.,* 5:1079-1096, 2005.
Gibson et al., "Enzymatic assembly of DNA molecules up to several hundred kilobases", *Nature Methods* 6:343-345, 2009.
Gou et al., "Functional expression of the particulate methane mono-oxygenase gene in recombinant *Rhodococcus erythropolis*", *FEMS Microbiol. Lett.* 263:136-141, 2006.
Guillouet et al., "Expression of the *Escherichia coli* Catabolic Threonine Dehydratase in *Corynebacterium glutamicum* and Its Effect on Isoleucine Production", *Appl. Environ. Microbiol.* 65:3100-3107, 1999.
Hägg, M. B., "Membranes in Chemical Processing—A Review of Applications and Novel Developments, Separation and Purification Methods", *Separ. Purif. Meth.* 27:51-168, 1998.
Hakemian A. S. and Rosenzweig, A. C, "The biochemistry of methane oxidation", *Annu. Rev. Biochem.* 76:223-241, 2007.
Hamilton, C. M., Aldea, M., Washburn, B. K., Babitzke, P. & Kushner, S. R., "New method for generating deletions and gene replacements in *E. coli*", *J. Bacteriol.* 171:4617-4622, 1989. Hanson, R. S. and Hanson, T. E., "Methanotrophic bacteria", *Microbiol. Rev.,* 60:439-471, 1996.
Hickey, P. J. and Slater, C. S., "The selective recovery of alcohols from fermentation broths by pervaporation", *Separ. Purif. Meth.* 19:93-115, 1990.
Jaeger, W. K. and Egelkraut, T. M., "Biofuel Economics in a Setting of Multiple Objectives and Unintended Consequences", *Renewable and Sustainable Energy Reviews,* 15 (9): 4320, 2011. Jang, Y. S. et al., "Enhanced Butanol Production Obtained by Reinforcing the Direct Butanol-Forming Route in *Clostridium acetobutylicum*", *mBio,* 3 (5): 1-9, 2012.
Jiang, H., Chen, Y., Jiang, P., Zhang, C., Smith, T. J., Xing, X.-H. and Murrell, J. C., "Methanotrophs: Multifunctional bacteria with promising applications in environmental bioengineering", *Biochem. Eng. J.* 49:277-288, 2010.
Kidnay et al., "Fundamentals of Natural Gas Processing", Second Edition, 2011 (Dekker *Mechanical Engineering*). CRC Press, Boca Raton.

Kim, S., Baek, S. H. and Hahn, J. S., "Cellulosic ethanol production using a yeast consortium displaying a mini-cellulosome and beta-glucosidase", *Microb Cell Fact.*, 12 (1): 14, 2013.

Kopke et. al., "2,3-Butanediol Production by Acetogenic Bacteria, an Alternative Route to Chemical Synthesis, Using Industrial Waste Gas", *Appl. Environ. Microbiol.*, 77:5467-5475, 2011.

Li, M. Z. and Elledge, S. J., "SLIC: a method for sequence- and ligation-independent cloning", *Methods Mol. Biol.* 852:51-59, 2012.

Link, A. J., Phillips, D. and Church, G. M., "Methods for generating precise deletions and insertions in the genome wild-type *Escherichia coli*: applications to open reading frame characterization", *J. Bacteriol.* 179:6228-6237, 1997.

Lipps, G., ed. "Plasmids: Current Research and Future Trends", *Caister Academic Press*, Norfolk, England, U. K., 2008.

Liu, G., Hou D., Wei, W., Xiangli, F. and Jin, W., "Pervaporation separation of butanol-water mixtures using polydimethylsiloxane/ceramic composite membrane', *Chin. J. Chem. Eng.* 19:40-44, 2011.

Lloyd et al., "Heterologous expression of soluble methane monooxygenase genes in methanotrophs containing only particulate methane monooxygenase", *Arch. Microbiol.* 171:364-370, 1999.

Ma et al., "DNA synthesis, assembly and applications in synthetic biology", *Curr. Opin. Chem. Biol.* 16:1-8, 2012.

Martin, H. and Murrell, J. C., "Methane monooxygenase mutants of *Methylosinus trichosporium* constructed by marker-exchange mutagenesis", *FEMS Microbiol. Lett.* 127:243-248, 1995.

Marx, C. J. & Lidstrom, M. E., "Development of improved versatile broad-host-range vectors for use in methylotrophs and other Gram-negative bacteria", *Microbiology* 147:2065-2075, 2001.

Merryman, C. and Gibson, D. G., "Methods and applications for assembling large DNA constructs", *Metabol. Eng.* 14:196-204, 2012.

Murrel et al., "Molecular biology and regulation of methane monooxygenase", *Arch. Microbiol.*, 173:325-332, 2000.

Neel, J., "*Pervaporation" In: Membrane Science and Technology*, 1995 (Noble, R. D. & Stern, S. A., eds.) Elsevier Science, Amsterdam, The Netherlands.

Orita et al., "The Ribulose Monophosphate Pathway Substitutes for the Missing Pentose Phosphate Pathway in the Archaeon *Thermococcus kodakaraensis"*, *J. Bacteriology*, 188 (13): 4698-4704, 2006.

Peccoud, J., ed. "Gene Synthesis: Methods and Protocols" (Methods in Molecular Biology, Vol. 852). Humana Press, New York, 2012.

Phillips, R. B., Jameel, H, and Chang, H. M., "Integration of pulp and paper technology with bioethanol production", *Biotechnol Biofuels*, 6 (1): 13, 2013.

Posfai, G., Kolisnychenko, V., Bereczki, Z. and Blattner, F. R., "Markerless gene replacement in *Escherichia coli* stimulated by a double-strand break in the chromosome", *Nucleic Acids Res.* 27:4409-4415, 1999.

Rosenzweig, A. C. and Ragsdale, S. W. "Methods in Methane Metabolism", *Part B: Methanotrophy. Methods Enzymol.*, 495:1-309, 2011 (b).

Rosenzweig, A. C. and Ragsdale, S. W., "Methods in Methane Metabolism", *Part A. Methods Enzymol.*, 494:1-373, 2011 (a).

Rudolf, A., Karhumaa, K. and Hahn-Hagerdal, B., "Ethanol Production from Traditional and Emerging Raw Materials", *Yeast Biotechnology: Diversity and Applications*, Chapter 23, pages 489-513, 2009.

Saka, S. and Kusdiana, D., "Biodiesel fuel from rapeseed oil as prepared in supercritical methanol", *Fuel*, 80:225, 2001.

Saleh, J., "A Membrane Separation Process for Biodiesel Purification', *Ph.D. Thesis*, 2011, University of Ottawa, Canada.

Sambrook et al., Molecular Cloning: A Laboratory Manual, Cold Spring Harbor Laboratory Press, 1989.

Sambrook, J., Fritsch, E. F. and Maniatis, T., "*Molecular Cloning: A Laboratory Manual*"; Cold Spring Harbor Laboratory Press, Cold Spring Harbor, 1989.

Schrader et al., "Methanol-based industrial biotechnology: current status and future perspectives of methylotrophic bacteria", *Trends Biotechnol.*, 27:107-115, 2009.

Semrau et al., "Facultative methanotrophy: false leads, true results, and suggestions for future research", *FEMS Microbiol. Lett.*, 323:1-12, 2011.

Shen, C. R. and Liao, J. C., "Metabolic engineering of *Escherichia coli* for 1-butanol and 1-propanol production via the keto-acid pathways", *Metab. Eng.* 10:312-320, 2008.

Silhavy, et al., "Experiments with Gene Fusions", *Cold Spring Harbor Laboratory*, Cold Spring Harbor, N.Y. 1984, Simon R. "High frequency mobilization of Gram-negative bacterial replicons by the in vitro constructed Tn5-mob transposons", *Mol. Gen. Genet.* 196:413-420, 1984.

Simon, R., Priefer, U. and Puhler, A. "A Broad Host Range Mobilization System for In Vivo Genetic Engineering: Transposon Mutagenesis in Gram Negative Bacteria", *Nature Biotechnology* 1:784-791, 1983.

Stafford et al., "rpoN, mmoR and mmoG, genes involved in regulating the expression of soluble methane monooxygenase in *Methylosinus trichosporium* OB3b", *Microbiol.* 149:1771-1784, 2003.

Stanley, S. H. and Dalton, H., "Role of ribulose-1,5-biphosphate carboxylase/oxygenase in *Methylococcus capsulatus"*, *J. Gen. Microbiol.*, 128:2927-2935, 1982.

Sun, W., Wang, S. and Curtis III, R., "Highly efficient method for introducing successive multiple scarless gene deletions and markerless gene insertions into the *Yersinia pestis* chromosome", *Appl. Environ. Microbiol.* 74:4241-4245, 2008.

Theisen et al., "Regulation of methane oxidation in the facultative methanotroph *Methylocella silvestris* BL2", *Mol. Microbiol.* 58:682-692, 2005.

Tinberg, C. E. and Lippard, S. J., "Dioxygen activation in soluble methane monooxygenase", *Acc. Chem. Res.*, 44:280-288, 2007.

Trotsenko, Y. A. and Murrell, J. C., "Metabolic Aspects of Aerobic Obligate Methanotrophy", *Adv. Appl. Microbiol.*, 63:183-229, 2008.

U.S. Department of the Interior, U.S. Geological Survey World Petroleum Assessment, 2000, U.S. Geological Survey Digital Data Series-DDS-60 (URL: http://pubs. usgs-.gov/dds/dds-060/)

van Laere, V., van Batenburg, O. & Huizing, H. J., "InnoFisk1: Feasibility study into a new concept for sustainable aquaculture on board of a ship", *Innovation Network Rural Areas and Agricultural Systems*, 2005.

Veazey, M. W., "*GTL Tech Converts Methane to Ethylene without Fischer Tropsch"*, *Rigzone*. Apr. 10, 2012 (http://www.rigzone.com/news/article.asp?a_id=116784)

Wang et al., "Available methods for assembling expression cassettes for synthetic biology", *Appl. Microbiol. Biotechnol.* 93:1853-1863, 2012.

Ward, N., Larsen, Ø., Sakwa, J., et al., *PLOS Biol.* 2: e303, 2004.

Welander, P. V. and Summons, R. E., "Discovery, taxonomic distribution, and phenotypic characterization of a gene required for 3-methylhopanoid production", *Proc. Natl. Acad. Sci.,* 109:12905-12910, 2012.

Whittenbury, R., Phillips, K. C. and Wilkinson, J. F., "Enrichment, isolation and some properties of methane-utilizing bacteria", *J. Gen. Microbiol.* 61:205-218, 1970.

Wolfe, A. J., "The acetate switch", *Microbiol. Mol. Biol. Rev.* 69:12-50, 2005.

Wright, C. K. and Wimberly, M. C., "Recent Land Use Change in the Western Corn Belt Threatens Grasslands and Wetlands", *Proceedings of the National Academy of Sciences—Early Edition*, February 19, pg. 1-6, 2013; DOI: 10.1073/pnas.1215404110.

Xiao et al., "Thermophilic fermentation of acetoin and 2,3-butanediol by a novel *Geobacillus* strain", *Biotechnol. for Biofuels* 5:88, 2012.

Xingye et al., "In vitro Reconstitution and Steady-State analysis of the Fatty Acid Synthase from *Escherichia coli*", *Proceedings of the National Academy of Sciences*, 10 (8): 18643-18648, 2011.

Xiu, Z.-L. and Zeng, A.-P., "Present state and perspective of downstream processing of biologically produced 1,3-propanediol and 2,3-butanediol", *Appl. Microbiol. Biotechnol.* 78:917-926, 2008.

Yangkai et al., "De novo Biosynthesis of Biodiesel by *Escherichia coli* in Optimized Fed-Batch Cultivation", *PLOS ONE,* 6 (5): 1-7, 2011.

Yehezkel et al., "Computer-aided high-throughput cloning of bacteria in liquid medium", *Biotechniques* 50:124-127, 2011.

Yomantas, Y. A., Tokmakova, I. L., Gorshkova, N. V., Abalakina, E. G., Kazakova, S. M., Gak, E. R. and Mashko, S. V., "Aromatic amino acid auxotrophs constructed by recombinant marker exchange in *Methylophilus methylotrophus* AS1 cells expressing the aroP-encoded transporter of *Escherichia coli*", *Appl. Environ. Microbiol.* 76:75-83, 2010.

Yu, B. J., Kang, K. H., Lee, J. H., Sung, B. H., Kim, M. S. and Kim, S. C., "Rapid and efficient construction of markerless deletions in the *Escherichia coli* genome", *Nucleic Acids Res.* 36: e84, 2008.

Yurimoto, H., Katoh, N. and Sakai, Y., "Assimilation, dissimilation, and detoxification of formaldehyde, a central metabolic intermediate of methylotrophic metabolism", *Chem Rec.,* 5:367-375, 2005.

Yurimoto, H., Katoh, N. and Sakai, Y., "Genomic organization and biochemistry of the ribulose monophosphate pathway and its application in biotechnology", *Appl Microbiol Biotechnol.,* 84:407-416, 2009.

What is claimed is:

1. A genetically modified methanotroph comprising a heterologous polynucleotide encoding for an acetolactate synthase (ALS), wherein the acetolactate synthase can catalyze the conversion of pyruvate to acetolactate and comprises an amino acid sequence having at least 90% sequence homology to SEQ ID NO: 2, and wherein said genetically modified methanotroph is capable of converting formaldehyde to pyruvate through a type I RuMP pathway or a type II serine pathway.

2. The genetically modified methanotroph of claim 1, wherein the genetically modified methanotroph further comprises a heterologous polynucleotide encoding a ketoacid decarboxylase (KDC), wherein the ketoacid decarboxylase can catalyze the conversion of ketoisovalerate to isobutryaldehyde.

3. The genetically modified methanotroph of claim 2, wherein the genetically modified methanotroph further comprises a heterologous polynucleotide encoding a ketol-acid reductoisomerase (KARI), a heterologous polynucleotide encoding a dihydroxy-acid dehydratase (DHAD), and a heterologous polynucleotide encoding an alcohol dehydrogenase (ADH); wherein the ketol-acid reductoisomerase can catalyze the conversion of acetolactate to 2,3-dihydroxyisovalerate; wherein the dihydroxy-acid dehydratase can catalyze the conversion of 2,3-dihydroxyisovalerate to ketoisovalerate; and wherein the alcohol dehydrogenase can catalyze the conversion of isobutyraldehyde to isobutanol.

4. The genetically modified methanotroph of claim 3, wherein the genetically modified methanotroph further comprises a heterologous polynucleotide encoding an alcohol dehydrogenase (ADH), wherein the ketoacid decarboxylase can catalyze the conversion of isobutyraldehyde to isobutanol.

5. The genetically modified methanotroph of claim 4, wherein the ketoacid decarboxylase (KDC) comprises an amino acid sequence having at least 90% sequence homology to SEQ ID NO: 8.

6. The genetically modified methanotroph of claim 1, wherein the genetically modified methanotroph further comprises a heterologous polynucleotide encoding a ketol-acid reductoisomerase (KARI), heterologous polynucleotide encoding a dihydroxy-acid dehydratase (DHAD), and a heterologous polynucleotide encoding a ketoacid decarboxylase (KDC), and a heterologous polynucleotide encoding an alcohol dehydrogenase (ADH); wherein the acetolactate synthase can catalyze the conversion of pyruvate to acetolactate and comprises an amino acid sequence having at least 90% sequence homology to SEQ ID NO: 2; wherein the ketol-acid reductoisomerase can catalyze the conversion of acetolactate to 2,3-dihydroxyisovalerate and comprises an amino acid sequence having at least 90% sequence homology to SEQ ID NO: 4; wherein the dihydroxy-acid dehydratase can catalyze the conversion of 2,3-dihydroxyisovalerate to ketoisovalerate and comprises an amino acid sequence having at least 90% sequence homology to SEQ ID NO: 6; wherein the ketoacid decarboxylase can catalyze the conversion of ketoisovalerate to isobutryaldehyde and comprises an amino acid sequence having at least 90% sequence homology to SEQ ID NO: 8; and wherein the alcohol dehydrogenase can catalyze the conversion of isobutyraldehyde to isobutanol and comprises an amino acid sequence having at least 90% sequence homology to SEQ ID NO: 10.

7. The genetically modified methanotroph of claim 6, wherein the genetically modified methanotroph further comprises a polynucleotide sequence encoding for the alcohol dehydrogenase (ADH) and a promoter, wherein said promoter can direct the expression of the alcohol dehydrogenase in the genetically modified methanotroph.

8. The genetically modified methanotroph of claim 2, wherein the genetically modified methanotroph further comprises a polynucleotide sequence encoding for the ketoacid decarboxylase (KDC), the alcohol dehydrogenase (ADH), and a promoter, wherein said promoter can direct the expression of the ketoacid decarboxylase and the alcohol dehydrogenase (ADH) in the genetically modified methanotroph.

9. The genetically modified methanotroph of claim 3, wherein the genetically modified methanotroph further comprises a polynucleotide sequence encoding for the acetolactate synthase (ALS), the ketol-acid reductoisomerase (KARI), the dihydroxy-acid dehydratase (DHAD), the ketoacid decarboxylase (KDC), the alcohol dehydrogenase (ADH) and a promoter, wherein said promoter can direct the expression of the acetolactate synthase (ALS), the ketol-acid reductoisomerase (KARI), the dihydroxy-acid dehydratase (DHAD), the ketoacid decarboxylase (KDC), and the alcohol dehydrogenase (ADH) in the genetically modified methanotroph.

10. The genetically modified methanotroph of claim 9, wherein said promoter is constitutive.

11. The genetically modified methanotroph of claim 9, wherein said promoter is inducible.

12. The genetically modified methanotroph of claim 1, wherein said genetically modified methanotroph is from the genus *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum.*

13. The genetically modified methanotroph of claim 1, wherein said genetically modified methanotroph is from the genus *Methylococcus.*

14. The genetically modified methanotroph of claim 13, wherein said genetically modified methanotroph is from the species *Methylococcus capsulatus.*

15. The genetically modified methanotroph of claim 13, wherein said genetically modified methanotroph is from the strain *Methylococcus capsulatus* strain Bath.

16. A method of making a multi-carbon compound comprising:

(a) contacting a genetically modified methanotroph with a multi-carbon product precursor comprising a heterologous polynucleotide encoding for an acetolactate synthase (ALS), wherein the ALS can catalyze the conversion of pyruvate to acetolactate and comprises an amino acid sequence having at least 90% sequence homology to SEQ ID NO: 2, and wherein said genetically modified methanotroph is capable of converting formaldehyde to pyruvate through a type I RuMP pathway or a type II serine pathway; and (b) growing said genetically modified methanotroph in conditions to produce a multi-carbon compound.

17. The method of claim 16, wherein said multi-carbon product precursor is methane.

18. The method of claim 16 wherein said multi-carbon compound is isobutanol.

19. The method of claim 16 wherein said multi-carbon compound is 1-butanol.

20. A genetically modified methanotroph capable of converting methane to a multi-carbon product comprising a heterologous polynucleotide encoding for an acetolactate synthase (ALS), wherein the ALS can catalyze the conversion of pyruvate to acetolactate and comprises an amino acid sequence having at least 90% sequence homology to SEQ ID NO: 2, and wherein said genetically modified methanotroph is capable of converting formaldehyde to pyruvate through a type I RuMP pathway or a type II serine pathway.

* * * * *